(12) United States Patent
Khurana et al.

(10) Patent No.: US 12,303,892 B2
(45) Date of Patent: *May 20, 2025

(54) DEVICES AND METHODS FOR ANALYZING BIOLOGICAL SAMPLES

(71) Applicant: Cellanome, Inc., Foster City, CA (US)

(72) Inventors: Tarun Kumar Khurana, Palo Alto, CA (US); Ali Agah, Palo Alto, CA (US); Yir-Shyuan Wu, Palo Alto, CA (US); Filiz Gorpe Yasar, Palo Alto, CA (US)

(73) Assignee: Cellanome, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/776,193

(22) Filed: Jul. 17, 2024

(65) Prior Publication Data
US 2024/0367167 A1    Nov. 7, 2024

Related U.S. Application Data

(63) Continuation of application No. 18/593,787, filed on Mar. 1, 2024, now Pat. No. 12,151,242, which is a continuation of application No. 18/219,545, filed on Jul. 7, 2023, now Pat. No. 12,030,047, which is a continuation of application No. PCT/US2022/011720, filed on Jan. 7, 2022.

(60) Provisional application No. 63/253,500, filed on Oct. 7, 2021, provisional application No. 63/135,463, filed on Jan. 8, 2021.

(51) Int. Cl.
| C12Q 1/68 | (2018.01) |
| B01L 3/00 | (2006.01) |
| C12Q 1/6869 | (2018.01) |
| C12Q 1/6874 | (2018.01) |
| G01N 33/543 | (2006.01) |
| G01N 33/68 | (2006.01) |

(52) U.S. Cl.
CPC ... *B01L 3/502715* (2013.01); *B01L 3/502707* (2013.01); *B01L 3/502761* (2013.01); *C12Q 1/6869* (2013.01); *C12Q 1/6874* (2013.01); *G01N 33/54386* (2013.01); *G01N 33/6842* (2013.01); *B01L 2200/0647* (2013.01); *B01L 2200/12* (2013.01); *B01L 2300/0663* (2013.01); *B01L 2300/0883* (2013.01); *B01L 2300/12* (2013.01); *B01L 2300/163* (2013.01); *B01L 2300/18* (2013.01); *C12Q 2600/158* (2013.01); *G01N 2570/00* (2013.01)

(58) Field of Classification Search
CPC .................................................. C12Q 1/6869
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 4,942,124 A | 7/1990 | Church |
| 4,965,188 A | 10/1990 | Mullis et al. |
| 5,126,022 A | 6/1992 | Soane et al. |
| 5,168,038 A | 12/1992 | Tecott et al. |
| 5,210,015 A | 5/1993 | Gelfand et al. |
| 5,367,066 A | 11/1994 | Urdea et al. |
| 5,399,491 A | 3/1995 | Kacian et al. |
| 5,498,392 A | 3/1996 | Wilding et al. |
| 5,587,128 A | 12/1996 | Wilding et al. |
| 5,700,642 A | 12/1997 | Monforte et al. |
| 5,739,386 A | 4/1998 | Holmes |
| 5,830,655 A | 11/1998 | Monforte et al. |
| 5,854,033 A | 12/1998 | Lizardi |
| 5,858,195 A | 1/1999 | Ramsey |
| 5,925,517 A | 7/1999 | Tyagi et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,060,288 A | 5/2000 | Adams et al. |
| 6,090,592 A | 7/2000 | Adams et al. |
| 6,174,670 B1 | 1/2001 | Wittwer et al. |
| 6,312,134 B1 | 11/2001 | Jain et al. |

(Continued)

FOREIGN PATENT DOCUMENTS

| EP | 3145689 B1 | 1/2020 |
| EP | 3450471 B1 | 12/2020 |

(Continued)

OTHER PUBLICATIONS

Albrecht et al, Photo- and electropatterning of hydrogel-encapsulated living cell arrays. LabChip, 5: 111-118 (2005).
Attayek et al, An array-based platform to select, release and capture EBV-infected cells based on intercellular adhesion. Anal. Chem., 87(24): 12281-12289 (2015).
Attayek et al, Identification and isolation of antigen-specific cytotoxic T lymphocytes with an automated microraft sorting system. Intergr. Biol. (Camb.), 8(12): 1208-1220 (2016).
Bose et al, Scalable microfluidics for single-cell RNA printing and sequencing. Genome Biology, 16: 120 (2015).

(Continued)

*Primary Examiner* — Kenneth R Horlick
(74) *Attorney, Agent, or Firm* — Wilson Sonsini Goodrich & Rosati.

(57) ABSTRACT

Described herein are systems and methods for analyzing biological samples. Including a method for processing an analyte, comprising providing a fluidic device comprising the analyte and one or more polymer precursors; selecting a discrete area within said fluidic device; providing an energy source in optical communication with fluidic device; and selectively supplying a unit of energy generated from the energy source to the fluidic device to generate a polymer matrix within the fluidic device, wherein the polymer matrix is within the discrete area or adjacent to the discrete area.

28 Claims, 49 Drawing Sheets

(56) References Cited

U.S. PATENT DOCUMENTS

| | | |
|---|---|---|
| 6,399,952 B1 | 6/2002 | Maher et al. |
| 6,514,706 B1 | 2/2003 | Von Kalle et al. |
| 6,569,627 B2 | 5/2003 | Wittwer et al. |
| 6,613,525 B2 | 9/2003 | Nelson et al. |
| 6,787,308 B2 | 9/2004 | Balasubramanian et al. |
| 6,960,437 B2 | 11/2005 | Enzelberger et al. |
| 7,097,809 B2 | 8/2006 | Van et al. |
| 7,276,381 B2 | 10/2007 | Kitagawa |
| 7,425,431 B2 | 9/2008 | Church et al. |
| 7,771,949 B2 | 8/2010 | Kramer |
| 7,824,854 B2 | 11/2010 | Arai et al. |
| 8,173,080 B2 | 5/2012 | Lebl et al. |
| 8,778,849 B2 | 7/2014 | Bowen et al. |
| 8,822,647 B2 | 9/2014 | Jensen |
| 8,900,828 B2 | 12/2014 | Smith et al. |
| 8,906,684 B2 | 12/2014 | Bhatia et al. |
| 8,921,073 B2 | 12/2014 | Reed et al. |
| 9,057,097 B2 | 6/2015 | Piepenburg et al. |
| 9,068,155 B2 | 6/2015 | Allbritton et al. |
| 9,169,513 B2 | 10/2015 | Shen et al. |
| 9,367,049 B2 | 6/2016 | Jariwala et al. |
| 9,476,080 B2 | 10/2016 | Li et al. |
| 9,487,745 B2 | 11/2016 | Wang et al. |
| 9,512,422 B2 | 12/2016 | Barnard et al. |
| 9,561,622 B2 | 2/2017 | Das et al. |
| 9,593,365 B2 | 3/2017 | Frisen et al. |
| 9,631,092 B2 | 4/2017 | Bowman et al. |
| 9,758,578 B2 | 9/2017 | Fujino et al. |
| 9,765,291 B2 | 9/2017 | Allbritton et al. |
| 9,963,666 B2 | 5/2018 | Allbritton et al. |
| 10,011,872 B1 | 7/2018 | Belgrader et al. |
| 10,072,257 B2 | 9/2018 | Bhatia et al. |
| 10,260,039 B2 | 4/2019 | Bhatia et al. |
| 10,351,819 B2 | 7/2019 | Hribar et al. |
| 10,385,335 B2 | 8/2019 | McGall |
| 10,423,071 B2 | 9/2019 | Hribar |
| 10,464,307 B2 | 11/2019 | Chung et al. |
| 10,570,447 B2 | 2/2020 | Ronaghi et al. |
| 10,661,275 B2 | 5/2020 | Levner et al. |
| 11,003,071 B2 | 5/2021 | Hribar et al. |
| 11,046,926 B2 | 6/2021 | Allbritton et al. |
| 11,065,620 B2 | 7/2021 | Levner et al. |
| 11,085,036 B2 | 8/2021 | Norberg et al. |
| 11,137,385 B2 | 10/2021 | Khurana et al. |
| 11,143,638 B2 | 10/2021 | Khurana et al. |
| 11,180,752 B2 | 11/2021 | Wu et al. |
| 11,554,370 B2 | 1/2023 | Khurana et al. |
| 11,612,890 B2 * | 3/2023 | Kurz ............... C12M 23/16 422/502 |
| 2003/0096239 A1 | 5/2003 | Gunderson et al. |
| 2003/0175824 A1 | 9/2003 | Pishko et al. |
| 2003/0186226 A1 | 10/2003 | Brennan et al. |
| 2004/0106728 A1 | 6/2004 | McGall et al. |
| 2004/0219214 A1 | 11/2004 | Gravett et al. |
| 2005/0084912 A1 | 4/2005 | Poponin |
| 2005/0208465 A1 | 9/2005 | Arai et al. |
| 2006/0110722 A1 | 5/2006 | Beebe et al. |
| 2010/0292931 A1 | 11/2010 | Wang et al. |
| 2012/0148552 A1 | 6/2012 | Jensen |
| 2012/0202263 A1 | 8/2012 | Blakely et al. |
| 2012/0270209 A1 | 10/2012 | Shah et al. |
| 2012/0316086 A1 | 12/2012 | Lin et al. |
| 2013/0123988 A1 | 5/2013 | Jariwala et al. |
| 2013/0288368 A1 | 10/2013 | June et al. |
| 2014/0080717 A1 | 3/2014 | Li et al. |
| 2014/0134142 A1 | 5/2014 | Smith et al. |
| 2014/0314795 A1 | 10/2014 | Riddell et al. |
| 2015/0119280 A1 | 4/2015 | Srinivas et al. |
| 2015/0159204 A1 | 6/2015 | Drmanac et al. |
| 2016/0060621 A1 | 3/2016 | Agresti et al. |
| 2016/0138086 A1 | 5/2016 | Seelig et al. |
| 2016/0177030 A1 | 6/2016 | Sugiura et al. |
| 2016/0208308 A1 | 7/2016 | Cohen et al. |
| 2016/0221262 A1 | 8/2016 | Das et al. |
| 2016/0375143 A1 | 12/2016 | Gunatillake et al. |
| 2017/0087766 A1 | 3/2017 | Chung et al. |
| 2017/0312368 A1 | 11/2017 | Ashley et al. |
| 2018/0113114 A1 | 4/2018 | Lütolf et al. |
| 2019/0017107 A1 | 1/2019 | Light et al. |
| 2019/0106667 A1 | 4/2019 | Hribar |
| 2019/0136170 A1 | 5/2019 | Allbritton et al. |
| 2019/0256817 A1 | 8/2019 | Gebhart et al. |
| 2019/0360121 A1 | 11/2019 | Fan et al. |
| 2020/0080046 A1 | 3/2020 | Gebhart et al. |
| 2020/0122137 A1 | 4/2020 | Jung et al. |
| 2020/0139696 A1 | 5/2020 | Chung et al. |
| 2020/0216895 A1 | 7/2020 | Khurana et al. |
| 2020/0362334 A1 | 11/2020 | Regev et al. |
| 2020/0399428 A1 | 12/2020 | Kleine-Brüggeney et al. |
| 2021/0018503 A1 | 1/2021 | Varadarajan et al. |
| 2021/0079386 A1 | 3/2021 | Kaper et al. |
| 2021/0172856 A1 | 6/2021 | Zhao |
| 2021/0246495 A1 | 8/2021 | Hosokawa et al. |
| 2021/0405019 A1 | 12/2021 | Khurana et al. |
| 2022/0003728 A1 | 1/2022 | Khurana et al. |
| 2022/0025447 A1 | 1/2022 | Tentori et al. |
| 2022/0033893 A1 | 2/2022 | Lan et al. |
| 2022/0034867 A1 | 2/2022 | Butler et al. |
| 2022/0143603 A1 | 5/2022 | Khurana et al. |
| 2022/0219170 A1 | 7/2022 | Khurana et al. |
| 2023/0001413 A1 | 1/2023 | Khurana et al. |
| 2023/0348974 A1 | 11/2023 | Khurana et al. |

FOREIGN PATENT DOCUMENTS

| | | |
|---|---|---|
| EP | 3836887 B1 | 7/2024 |
| GB | 2315700 A | 2/1998 |
| JP | H04262799 A | 9/1992 |
| KR | 20210103010 A | 8/2021 |
| NL | 2017834 | 5/2018 |
| WO | WO-9919717 A1 | 4/1999 |
| WO | WO-0224322 A2 | 3/2002 |
| WO | WO-2004006840 A2 | 1/2004 |
| WO | WO-2005074569 A2 | 8/2005 |
| WO | WO-2006125458 A1 | 11/2006 |
| WO | WO-2010132795 A2 | 11/2010 |
| WO | WO-2014031997 A1 | 2/2014 |
| WO | WO-2015010019 A1 | 1/2015 |
| WO | WO-2015179572 A1 | 11/2015 |
| WO | WO-2017048993 A1 | 3/2017 |
| WO | WO-2017075265 A1 | 5/2017 |
| WO | WO-2018097715 A1 | 5/2018 |
| WO | WO-2018172726 A1 | 9/2018 |
| WO | WO-2019028047 A1 | 2/2019 |
| WO | WO-2019028166 A1 | 2/2019 |
| WO | WO-2019157529 A1 | 8/2019 |
| WO | WO-2019203728 A1 | 10/2019 |
| WO | WO-2020047002 A1 | 3/2020 |
| WO | WO-2020120442 A2 | 6/2020 |
| WO | WO-2020190509 A1 | 9/2020 |
| WO | WO-2021108499 A1 | 6/2021 |
| WO | WO-2021122579 A1 | 6/2021 |
| WO | WO-2022013094 A1 | 1/2022 |
| WO | WO-2022015600 A2 | 1/2022 |
| WO | WO-2022150659 | 7/2022 |
| WO | WO-2022150659 A1 | 7/2022 |
| WO | WO-2022261507 | 12/2022 |
| WO | WO-2022261507 A1 | 12/2022 |
| WO | WO-2023183327 A1 | 9/2023 |
| WO | WO-2023196603 A1 | 10/2023 |
| WO | WO-2023225366 A1 | 11/2023 |
| WO | WO-2023240207 A1 | 12/2023 |
| WO | WO-2024020398 A1 | 1/2024 |
| WO | WO-2024092056 A1 | 5/2024 |
| WO | WO-2024145393 A1 | 7/2024 |

OTHER PUBLICATIONS

Brock, S.L., Nanostructures and Nanomaterials: Synthesis, Properties and Applications By Guozhang Cao (University of Washington). Imperial College Press (distributed by World ScientificPublis): London. 445 pages, (2004).

Burdick et al, Moving from static to dynamic complexity in hydrogel design. Nature Communications. 3:1269, pp. 1-8 (2012).

(56) References Cited

OTHER PUBLICATIONS

Caliari et al. A practical guide to hydrogels for cell culture. Nature Methods. 13(5):405-414 (2016).
Cha et al, Structural reinforcement of cell-laden hydrogels with microfabricated three dimensional scaffolds, Biomaterial Science. 2(5):703-709 (2014).
Cheng, J., & Kricka, L.J. Biochip Technology (1st ed.). CRC Press. 2001. https://doi.org/10.1201/9781482283662.
Cho, et al., Seq-Scope: Submicrometer-resolution spatial transcriptomics for single cell and subcellular studies. BioRxiv. 50 pages (2021).
Choi, et al., Recent advances in photo-crosslinkable hydrogels for biomedical applications. Biotechniques. 66(1):40-53 (2019).
Cortes-Llanos et al, A technology of a different sort: microraft arrays. Lab Chip. 21(17):3204-3218 (2021).
Curley et al, Fabrication of micropatterned hydrogels for neural culture systems using dynamic mask projection photolithography, J. Visualized Experiments, 48: e2636 (2011).
D'Eramo et al., Microfluidic actuators based on temperature-responsive hydrogels, Microsystems & Nanoengineering. 4:17069, pp. 1-7 (2018).
Ding et al., Single-cell RNA sequencing in breast cancer: understanding tumor heterogeneity and paving roads to individualized therapy. Cancer Communications. 40(8):329-344 (2020).
Drury et al., Hydrogels for tissue engineering: scaffold design variables and applications. Biomaterials. 24(24):4337-4351 (2003).
Eyer, et al., A microchamber array for single cell isolation and analysis of intracellular biomolecules. Lab Chip. 12(4):765-772 (2012).
Eyer, et al., Implementing Enzyme-linked immunosorbent assays on a microfluidic chip to quantify intracellular molecules in single cells. Anal. Chem. 85(6):3280-3287 (2013).
Fattahi, et al., Photodegradable hydrogels for rapid screening, isolationm and genetic characterization of bacteria with rare phenotypes. ACS, Biomacromolecules. 21(8):3140-3151 (2020).
Fattahi, Niloufar. Hydrogel interfaces for applications in microbial biotechnology. PhD Dissertation; Kansas State University. 172 Pages (2021).
Gauvin et al, Microfabrication of complex porous tissue engineering scaffolds using 3D projection stereolithography, Biomaterials. 33(15): 3824-3834 (2012).
Geckil et al, Engineering hydrogels as extracellular matrix mimics, Nanomedicine (Lond.) 5(3): 469-484 (2010).
Griffin et al, Photodegradable macromers and hydrogels for live cell encapsulation and release, J. Amer. Chem. Soc., 134: 13103-13107 (2012).
Haeberle et al., Microfluidic platforms for lab-on-a-chip applications, Lab Chip, 2007,7(9), 1094-1110.
Hahn et al, Photolithographic patterning of polyethylene glycol hydrogels, Biomaterials, 27: 2519-2524 (2006).
Hammoudi et al, Long-term spatially defined coculture within three-dimensional photopatterned hydrogels, Tissue Engineering, 16(6): 1621-1628 (2010).
Han et al, Fabrication of three-dimensional scaffolds for heterogeneous tissue engineering, Biomed. Microdevices, 12: 721-725 (2010).
Hashimshony, Tamar, et al.,CEL-Seq2: sensitive highly-multiplexed single-cell RNA-Seq. Genome Biology 17:17-77 (2016).
Heo et al, A microfluidic bioreactor based on hydrogel-entrapped E. coli: Cell viability, lysis, and intracellular enzyme reactions, Anal. Chem., 75: 22-26 (2003).
Hong et al, Cell microarray technologies for high-throughput cell-based sensors, Sensors, 17: 1293 (2017).
Huang et al, Light-addressable electrodeposition of cell-encapsulated alginate hydrogels for a cellular microarray using a digital micromirror device, Biomicrofluidics, 5: 034109 (2011).
Huang et al, Light-addressed electrodeposition of enzyme-entrapped chitosan membranes for multiplexed enzyme-based bioassays using a digital micromirror device, Sensors, 13: 10711-10724 (2013).
Ifkovits et al, Review: Photopolymerizable and degradable biomaterials for tissue engineering applications, Tissue Engineering, 13(10): 2369-2385 (2007).
Jen, et al., Single-cell chemical lysis on microfluidic chips with arrays of microwells. Sensors 2012, 12, 347-358; doi:10.3390/s120100347.
Kikuchi et al, Arraying heterotypic single cells on photoactivatable cell-culturing substrates, Langmuir, 24: 13084-13095 (2008).
Kivlehan et al, Three-dimensional hydrogel structures as optical sensor arrays, or the detection of specific DNA sequences, Anal. Biochem., 421: 1-8 (2012).
Kloxin et al, Photodegradable hydrogels for dynamic tuning of physical and chemical properties, Science, 324(5923): 59-63 (2009).
Koh, Cell microarrays based on hydrogel microstructures for the application to cell-based biosensor, Chapter 7, in Biological Microarrays: Methods and Protocols, Methods in Molecular Biology, vol. 671 (2011).
Koh et al, Fabrication of cell-containing hydrogel microstructures inside fluidic devices that can be used as cell-based biosensors. Analytical and Bioanalytical Chemistry. 385(8): 1389-1397 (2006).
Koh et al, Poly(ethylene glycol) hydrogel microstructures encapsulating living cells. Langmuir. 18: 2459-2462 (2002).
Kovac et al, Image-predicated sorting of adherent cells using photopatterned hydrogels, Adv. Healthc. Mater. 2(4): 552-556 (2013).
Lee et al, Single-cell multiomics: technologies and data analysis methods, Experimental & Molecular Medicine, 52: 1428-1442 (2020).
Levalley, et al., On-demand and tunable dual wavelength release of antibody using light-responsive hydrogels. ACS Applied Bio Materials. 3(10): 6944-6958 (2020).
Liu et al, A microfluidic photolithography for controlled encapsulation of single cells inside hydrogel microstructures. Science China Chemistry. 55(4): 494-501 (2012).
Lu et al, A digital micro-mirror device-based system for the microfabrication of complex, spatially patterned tissue engineering scaffolds, J. Biomed. Mater. Research, 77A(2): 396-405 (2006).
Lui et al, Controlled photopolymerization of hydrogel microstructures inside microchannels for bioassays. LabChip. 9(9):1301-1305 (2009).
Maruyama et al, Immobilization of individual cells by local photopolymerization on a chip. Analyst. 130(3):304-310 (2005).
Naiser et al, A versatile maskless microscope projection photolithography system and its application in light-directed fabrication of DNA microarrays, Rev. Sci. Instr., 77: 063711 (2006).
Negishi et al, High-throughput manipulation of circulating tumor cells using a multiple single-cell encapsulation system with a digital micromirror device, Anal. Chem., 90: 9734-9741 (2018).
Nguyen et al, Photopolymerizable hydrogels for tissue engineering applications, Biomaterials, 23: 4307-4314 (2002).
Nichol et al, Cell-laden microengineered gelatin methacrylate hydrogels, Biomaterials, 31(21): 5536-5544 (2010).
Nicodemus et al, Cell encapsulation in biodegradable hydrogels for tissue engineering applications, Tissue Engineering, Part B, 14(2): 149-165 (2008).
Oldenhof, et al., Imaging-assisted hydrogel formation for single cell isolation. Sci Rep 10, 6595 (2020). https://doi.org/10.1038/s41598-020-62623-6.
Panda et al, Stop-flow lithography to generate cell-laden microgel particles, LabChip, 8(7): 1056-1061 (2008).
Papavasiliou et al, Three-dimensional patterning of poly(ethylene glycol) hydrogels through surface-initiated photopolymerization, Tissue Engineering, part C, 14(2): 129-140 (2008).
PCT/US2022/011720 International Search Report and Written Opinion dated Jun. 7, 2022.
PCT/US2022/033116 International Search Report and Written Opinion dated Nov. 3, 2022.
Pollock et al, Highly multiplexed and quantitative cell-surface protein profiling using genetically barcoded antibodies, Proc. Natl. Acad. Sci., 115(11): 2836-2841 (2018).
Russell et al, Mass transfer in rapidly photopolymerized poly(ethylene glycol) hydrogels used for chemical sensing, Polymer, 42: 4893-4901 (2001).

(56) References Cited

OTHER PUBLICATIONS

Shendure, Jay. et al. Accurate Multiplex Polony Sequencing Of An Evolved Bacterial Genome. Science 309(5741):1728-1732 (2005).
Shin, et al., Photodegradable hydrogels for capture, detection, and release of live cells. Angew Chem Int Ed Engl. Jul. 28, 2014; 53(31): 8221-8224. doi:10.1002/anie.201404323.
Sia and Whitesides, Microfluidic devices fabricated in poly(dimethylsiloxane) for biological studies, Electrophoresis. 24(21):3563-3576 (2003).
Soman et al, Digital microfabrication of user-defined 3D microstructures in cell-laden hydrogels, Biotechnol. Bioeng., 110(11): 3038-3047 (2013).
Steinhilber et al, A microgel construction kit for bioorthogonal encapsulation and pH-controlled release of living cells, Angew. Chem. Int. Ed., 52: 13538-13543 (2013).
Sun et al, Image-based single-cell sorting via dual-photopolymerized microwell arrays, Anal. Chem., 86: 977-981 (2014).
Suri et al, Solid freeform fabrication of designer scaffolds of hyaluronic acid for nerve tissue engineering, Biomed. Microdevices, 13: 983-993 (2011).
Suyama et al. Photobase generators: Recent progress and application trend in polymer systems, Progress in Polymer Science, 34(2009), 194-209. (Year: 2008).
Tamura, et al., Optical cell separation from three-dimensional environment in photodegradable hydrogels for pure culture techniques. Scientific Reports, May 7, 2014; 4:4793, DOI: 10.1038/srep04793.
Tanna et al, Critical testing and parameters for consideration when manufacturing and evaluating tumor-associated antigen-specific T cells, Cytotherapy, 21: 278-288 (2019).
Tibbit et al, Hydrogels as extracellular matrix mimics for 3D cell culture, Biotechnology and Bioengineering, 103(4): 655-663 (2009).
Tsang et al. Fabrication of 3D hepatic tissues by additive photopatterning of cellular hydrogels. The FASEB Journal 21(3):790-801 (2007).
Tsang. Three-Dimensional Tissue Fabrication, Advanced drug delivery reviews 56(11):1635-1647 (2004).
Tyagarajan et al, Optimizing CAR-T cell manufacturing processes during pivotal clinical trials, Molecular Therapy: Methods & Clinical Development, 16: 136-144 (2020).
Underhill et al, Bioengineering methods for analysis of cells in vitro, Ann. Rev. Cell Devel. Biol., 28: 385-410 (2012).
Unger, et al. Monolithic microfabricated valves and pumps by multilayer soft lithography. Science. Apr. 7, 2000;288(5463):113-6.
U.S. Appl. No. 17/669,315 Office Action dated Oct. 13, 2023.
U.S. Appl. No. 17/896,742 Office Action dated Sep. 14, 2023.
U.S. Appl. No. 18/219,545 Notice of Allowance dated Jan. 31, 2024.
U.S. Appl. No. 18/219,545 Office Action dated Oct. 18, 2023.
U.S. Appl. No. 17/715,843 Notice of Allowance dated Aug. 31, 2022.
U.S. Appl. No. 17/715,843 Office Action dated Jul. 8, 2022.
U.S. Appl. No. 17/896,742 Office Action dated Mar. 13, 2023.
U.S. Appl. No. 17/896,742 Office Action dated Mar. 22, 2024.
U.S. Appl. No. 17/896,742 Office Action dated Nov. 21, 2022.
U.S. Appl. No. 18/593,787 Notice of Allowance dated Jul. 11, 2024.
Van Der Vlies, et al., On Demand release and retrieval of bacteria from microwell arrays using photodegradable hydrogel membranes. ACS Appl. Bio Mater. 2019, 2, 266-276.
Vickovic et al, Massive and parallel expression profiling using microarrayed single-cell sequencing. Nature Communications. 7: 13182 (2016).
Wang et al, Broadening cell selection criteria with micropallet arrays of adherent cells. Cytometry Part A, 71A: 866-874 (2007).
Wang et al, Micromolded arrays for separation of adherent cells, LabChip, 10(21):2917-2924 (2010).
Wang et al, Micropallet arrays with poly(ethylene glycol) walls, LabChip, 8(5):734-740 (2008).
Wang et al., Clinical manufacturing of CAR T cells: foundation of a promising therapy. Molecular Therapy—Oncolytics 3:16015 (2016).
Welch et al, Selective single cell isolation for genomics using microraft arrays, Nucleic Acids Research, 44(17): 8292-8301 (2016).
Williams et al, Variable cytocompatibility of six cell lines with photoinitiators used for polymerizing hydrogels and cell encapsulation, Biomaterials, 26: 1211-1218 (2005).
Xu et al, Development of disposable PDMS micro cell culture analog devices with photopolymerizable hydrogel encapsulating living cells, Biomed. Microdevices, 14: 409-418 (2012).
Yang et al, Rapid fabrication of hydrogel microstructures using UV-induced projection printing. Micromachines. 6:1903-1913 (2015).
Yenkin et al, Mitochondrial phenotypes distinguish pathogenic MFN2 mutations by pooled functional genomics screen. bioRxiv. https//doi.org/10.1101/2021.03.12.434746 (2021).
Yuan et al, An automated microwell platform for large-scale single cell RNA-Seq, Scientific Reports. 6:33883 (2016).
Zguris et al, A novel single-step fabrication technique to create heterogeneous poly(ethylene glycol) hydrogel microstructures containing multiple phenotypes of mammalian cells. Langmuir. 21:4168-4174 (2005).
Zhang et al, Rapid fabrication of complex 3D extracellular microenvironments by dynamic optical projection stereolithography. Advanced Materials. 24(310: 4266-4270 (2012).
Adessi, Celine. et al. Solid phase DNA amplification: characterisation of primer attachment and amplification mechanisms. Nucleic acids research 28(20):E87, 1-8 (2000).
Allen, Elizabeth S. et al. Autologous lymphapheresis for the production of chimeric antigen receptor T cells. Transfusion 57(5):1133-1141 (2017).
Anderson, Rhona. Multiplex Fluorescence in situ Hybridization (M-FISH). Methods in Molecular Biology, chapter 6, vol. 659: 83-96 (2010).
Annabi, Nasim et al., Controlling the porosity and microarchitecture of hydrogels for tissue engineering. Tissue Engineering: Part B. 16(4):371-383 (2010).
Barrett, David M. et al. Chimeric Antigen Receptor Therapy For Cancer. Annual Review of Medicine 65:333-347 (2014). Published online Nov. 20, 2013.
Bayani, Jane and Squire, Jeremy A. Fluorescence In Situ Hybridization Unit 22.4 (FISH). Current Protocols in Cell Biology, Unit 22.4, Supplement 23, pp. 22.4.1-22.4.52 (2004).
Basu, Swarna and Campagnola, Paul J., Enzymatic activity of alkaline phosphatase inside protein and polymer structures fabricated via multiphoton excitation. Biomacromolecules, American Chemical Society. 5(2):572-579 (2004).
Biasco, Luca. et al. Analyzing the Genotoxicity of Retroviral Vectors in Hematopoietic Cell Gene Therapy. Molecular Therapy Methods & Clinical Development 8:21-30 (2017).
Bose, Sayantan. et al. Scalable Microfluidics for Single-cell RNA Printing and Sequencing. Genome Biology 16(1):120, 1-16 (2015).
Bradford, Jolene A, and Gayle M. Buller. Dead Cell Stains In Flow Cytometry: A Comprehensive Analysis. Poster presented at Molecular Probes. p. 1 (2009).
Chava, Suresh. et al. Measurement of Natural Killer Cell-Mediated Cytotoxicity and Migration in the Context of Hepatic Tumor Cells. Journal of Visualized Experiments 156:e60714, 1-7 (2020).
Chen, A. et al. Vector copy number quality control testing for CAR T-cells: critical validation parameters. Cytotherapy 22(5):S142, 1-1 (2020).
Chen, AO. et al. Spatiotemporal transcriptomic atlas of mouse organogenesis using DNA nanoball-patterned arrays. bioRxiv :1-75 (2021).
Chen, Ao. et al. Spatiotemporal Transcriptomic Atlas of Mouse Organogenesis2 using DNA Nanoball Patterned Arrays. bioRxiv :1-75 (2021).
Cho, Chun-Seaok. et al. Seq-Scope: Submicrometer-resolution Spatial Transcriptomics for Single Cell and Subcellular Studies. bioRxiv :1-50 (2021).
Cho, Chun-Seok. et al. Seq-Scope: Submicrometer-resolution spatial transcriptomics for single cell and subcellular studies. bioRxiv :1-50 (2021).

(56) References Cited

OTHER PUBLICATIONS

Cornetta, Kenneth. et al. Meeting FDA Guidance recommendations for replication-competent virus and insertional oncogenesis testing. Molecular Therapy Methods & Clinical Development 28:28-39 (2022).
Cui, X F. et al. Single-sperm typing: determination of genetic distance between the G gamma-globin and parathyroid hormone loci by using the polymerase chain reaction and allele-specific oligomers. Proceedings of the National Academy of Sciences of the United States of America 86(23):9389-9393 (1989).
Deforest, Cole A. and Anseth, Kristi S. Cytocompatible Click-based Hydrogels with Dynamically-Tunable Properties Through Orthogonal Photoconjugation and Photocleavage Reactions. Nature Chemistry. 3(12):925-931 (2011).
Deleye, Lieselot. et al. Performance of four modern whole genome amplification methods for copy number variant detection in single cells. Scientific Reports 7:3422, 1-9 (2017).
Deleye, Lieselot. et al. Whole genome amplification with SurePlex results in better copy number alteration detection using sequencing data compared to the MALBAC method. Scientific Reports 5:11711, 1-13 (2015).
Desfarges, Sébastien, and Angela Ciuffi. Retroviral Integration Site Selection. Viruses 2(1):111-130 (2010).
Dittrich, Petra and Jakubowski, Norbert. Current trends in single cell analysis. Analytical and Bioanalytical Chemistry. 406(27):6957-6961 (2014).
Dury, Jeanie L. et al. Hydrogels for tissue engineering: scaffold design variables and applications. Biomaterials 24(24):4337-4351 (2003).
Edelman, Gerald M. and Gally, Joseph A. Degeneracy and complexity in biological systems. Proc Natl Acad Sci USA. 98(24):13763-13768 (2001).
EP22737222.4 Extended-European Search Report dated Dec. 16, 2024.
Fairbanks, Benjamin D. et al., A Versatile Synthetic Extracellular Matrix Mimic via Thiol-Norbornene Photopolymerization. Advanced Materials. 21(48):5005-5010 (2009).
Fairbanks, Benjamin D. et al., Photodegradable, Photoadaptable Hydrogels via Radical-Mediated Disulfide Fragmentation Reaction. Macromolecules. 44(8):2444-2450 (2011).
Fischbach, Michael A. et al. Cell-based Therapeutics: the Next Pillar of Medicine. Science Translational Medicine 5(179):179ps7, 1-6 (2013).
Fu, Xiaonan et al, Continuous polony gels for tissue mapping with high resolution and RNA capture efficiency. bioRxiv (2021.03.17. 435795).
Gao, Shipeng et al., Oriented immobilization of antibodies onto sensing platforms—A critical review. Analytica Chimica Acta. 1189:338907, pp. 1-24 (2022).
Garagorri, Nerea. et al. Keratocyte behavior in three-dimensional photopolymerizable poly(ethylene glycol) hydrogels. Acta Biomaterialia 4(5):1139-1147 (2008).
Goldring, Chris E P. et al. Assessing the safety of stem cell therapeutics. Cell Stem Cell 8(6):618-628 (2011).
Greenberg, Marc M, and John L. Gilmore. Cleavage of Oligonucleotides from Solid-Phase Supports Using o-Nitrobenzyl Photochemistry. 59(4):746-753 (1994).
Gunderson, Kevin L. et al., Decoding randomly ordered DNA arrays. Genome Research. 14(5):870-877 (2004).
Holmes, Christopher P. Model Studies for New o-Nitrobenzyl Photolabile Linkers: Substituent Effects on the Rates of Photochemical Cleavage. The Journal of Organic Chemistry 62(8):2370-2380 (1997).
Hou, Young. et al. Comparison of variations detection between whole-genome amplification methods used in single-cell resequencing. Gigascience 4:37, 1-16 (2015).
Jung, Sukwon et al., Controlled network structures of chitosan-poly(ethylene glycol) hydrogel microspheres and their impact on protein conjugation. Biochemical Engineering Journal. 135:123-132 (2018).
Kabb, Christopher P. et al., Photoreversible Covalent Hydrogels for Soft-Matter Additive Manufacturing. ACS Applied Materials and Interfaces. 10(19):16793-16801(2018).
Kahl, Jeffrey D, and Marc M. Greenberg. Solution-Phase Bioconjugate Synthesis Using Protected Oligonucleotides Containing 3'-Alkyl Carboxylic Acids. The Journal of Organic Chemistry 64(2):507-510 (1999).
Kahl, Jeffrey D. et al. High-Yielding Method for On-Column Derivatization of Protected Oligodeoxy-nucleotides and Its Application to the Convergent Synthesis of 5',3'-Bis-conjugates. Journal of Organic Chemistry 63(15):4870-4871 (1998).
Kang, Joo H. et al, Analysis of pressure-driven air bubble elimination in a microfluidic device. Lab on a Chip. 8:176-178 (2008).
Kharkar, Prathamesh M. et al., Design of Thiol- and Light-sensitive Degradable Hydrogels using Michael-type Addition Reactions. Polymer Chemistry. 6(31):5565-5574 (2015).
Kharkar, Prathamesh M. et al., Designing degradable hydrogels for orthogonal control of cell microenvironments. Chem Soc Rev. 42(17):7335-7372 (2013).
Kim, Sung Ah. et al. An Efficient and Reliable DNA Extraction Method for Preimplantation Genetic Diagnosis: a Comparison of Allele Drop Out and Amplification Rates Using Different Single Cell Lysis Methods. Fertility and Sterility 92(2):814-818 (2009).
Kim, Tae Kyung, and James H Eberwine. Mammalian cell transfection: the present and the future. Analytical and Bioanalytical Chemistry 397(8):3173-3178 (2010).
Levine, Bruce L. et al. Global Manufacturing of CAR T Cell Therapy. Molecular Therapy. Methods & Clinical Development 4:92-101 (2016).
Lichtenberg, Jessanne Y. et al., Non-Specific Adsorption Reduction Methods in Biosensing. Sensors (Basel). 19(11):2488, pp. 1-17 (2019).
Liu, Yang. et al. High-spatial-resolution multi-omics sequencing via deterministic barcoding in tissue. Cell 183(6):1665-1681 (2020).
MacKay, Ian M. et al. Real-time PCR in virology. Nucleic Acids Research 30(6):1292-1305 (2002).
Mallory, Xian F. et al. Methods for copy number aberration detection from single-cell DNA-sequencing data. Genome Biology 21:208, pp. 1-22 (2020).
Nebbioso, Angela et al., Time-resolved analysis of DNA-protein interactions in living cells by UV laser pulses. Scientific Reports. 7(1):11725, pp. 1-13 (2017).
Neumann, Alexander J. et al., Nondestructive evaluation of a new hydrolytically degradable and photo-clickable PEG hydrogel for cartilage tissue engineering. Acta Biomaterialia. 39:1-11 (2016).
Paugh, Barbara S. et al. Reference standards for accurate validation and optimization of assays that determine integrated lentiviral vector copy number in transduced cells. Scientific Reports 11:389, 1-9 (2021).
PCT/US2022/033116 International Preliminary Report on Patentability dated Dec. 21, 2023.
PCT/US2023/015806 International Search Report and Written Opinion dated Aug. 4, 2023.
PCT/US2023/015806 Invitation to Pay Additional Fees dated May 22, 2023.
PCT/US2023/017896 International Search Report and Written Opinion dated Jul. 3, 2023.
PCT/US2023/068154 International Search Report and Written Opinion dated Oct. 10, 2023.
PCT/US2023/070428 International Search Report and Written Opinion dated Nov. 6, 2023.
Picelli, Simone. et al. Tn5 Transposase and Tagmentation Procedures for Massively Scaled Sequencing Projects. Genome Research 24(12):2033-2040 (2014).
Pon, Richard T. Solid-Phase Supports for Oligonucleotide Synthesis. Methods in Molecular Biology 20:465-496 (1993).
Porter, Shaina N. et al. Lentiviral and targeted cellular barcoding reveals ongoing clonal dynamics of cell lines in vitro and in vivo. Genome Biology 15:R75, 1-14 (2014).
Quan, Jiayuan. et al. Parallel on-chip Gene Synthesis and Application to Optimization of Protein Expression. Nature biotechnology 29(5):449-452 (2011).

(56) References Cited

OTHER PUBLICATIONS

Quan, Li Na. et al. Edge stabilization in reduced-dimensional perovskites. Nature Communications 11(1):170, 1-9 (2020).
Recek, Nina. et al. Protein adsorption on various plasma-treated polyethylene terephthalate substrates. Molecules 18(10): 12441-12463 (2013).
Reimhult, Erik and, Höök, Fredrik. Design of surface modifications for nanoscale sensor applications. Sensors (Basel). 15(1):1635-1675 (2015).
Restifo, Nicholas P. et al. Adoptive Immunotherapy for Cancer: Harnessing the T Cell Response. Nature Reviews. Immunology 12(4):269-281 (2012).
Saliba Antoine-Emmanuel et al., Single-cell RNA-seq: advances and future challenges. Nucleic Acids Research. 42(14):8845-8860 (2014).
Schmid, Ingrid. et al. Sensitive method for measuring apoptosis and cell surface phenotype in human thymocytes by flow cytometry. Cytometry 15(1):12-20 (1994).
Schmidt, Manfred. et al. High-resolution Insertion-site Analysis by Linear Amplification-mediated PCR (LAM-PCR). Nature Methods 4(12):1051-1057 (2007).
Sekine, Kazuhiko. et al. Panning of Multiple Subsets of Leukocytes on Atibody-decorated Poly(ethylene) Glycol-coated Glass Slides. Journal of Immunological Methods 313(1-2):96-109 (2006).
Serien, Daniela and Sugioka, Koji. Fabrication of three-dimensional proteinaceous micro- and nano-structures by femtosecond laser cross-linking. Opto-Electronic Advances. 1(4):18000801-18000818 (2018).
Serien, Daniela et al., Femtosecond Laser Direct Write Integration of Multi-Protein Patterns and 3D Microstructures into 3D Glass Microfluidic Devices. Applied Sciences. 8(2):147, pp. 1-13 (2018).
Shifrut, Eric. et al. Genome-wide CRISPR Screens in Primary Human T Cells Reveal Key Regulators of Immune Function. Cell 175(7):1958-1971.e1-e15 (2018).
Shih, Han and Lin, Chien-Chi. Cross-linking and degradation of step-growth hydrogels formed by thiol-ene photoclick chemistry. Biomacromolecules. 13(7):2003-2012 (2012).
Singh-Gasson, Sangeet. et al. Maskless Fabrication of Light-directed Oligonucleotide Microarrays Using a Digital Micromirror Array. Nature Biotechnology 17(10):974-978 (1999).
Southern, Edwin M. et al, Parallel synthesis and analysis of large numbers of related chemical compounds: applications to oligonucleotides. Journal of Biotechnology, 35(2-3): 217-227 (1994).
Spencer, Sarah J. et al. Massively Parallel Sequencing of Single Cells by epicPCR Links Functional Genes With Phylogenetic Markers. ISME Journal 10(2):427-436 (2016).
Strategies for Attaching Oligonucleotides to Solid Supports. IDT-Integrated DNA Technologies:1-7 (2014).
Tamminen, Manu V, and Marko PJ Virta. Single Gene-based Distinction of Individual Microbial Genomes From a Mixed Population of Microbial Cells. Frontiers in Microbiology 6:195, 1-11 (2015).
Thornhill, Alan R. et al. A Comparison of Different Lysis Buffers to Assess Allele Dropout From Single Cells for Preimplantation Genetic Diagnosis. Prenatal Diagnosis 21(6):490-497 (2001).
Trilling, Anke K. Antibody orientation on biosensor surfaces: a minireview. Analyst. 138(6):1619-1627 (2013).
U.S. Appl. No. 18/593,787 Non-Final Office Action dated May 7, 2024.
Van Dam, Robert Michael. Solvent-resistant elastomeric microfluidic devices and applications. Doctoral Thesis, California Institute of Technology, Pasadena, California, 334 pages (2005).
Vaninsberghe, Michael. et al. Highly multiplexed single-cell quantitative PCR. PLoS One 13(1):e0191601, 1-18 (2018).
Venkatesan, Hariharan, and Marc M. Greenberg. Improved Utility of Photolabile Solid Phase Synthesis Supports for the Synthesis of Oligonucleotides Containing 3'-Hydroxyl Termini. The Journal of Organic Chemistry 61(2):525-529 (1996).
Verma, Sandeep, and Fritz Eckstein. Modified Oligonucleotides: Synthesis and Strategy for Users. Annual Review of Biochemistry 67(1):99-134 (1998).
Vistain, Luke F. and Tay, Savas. Single-Cell Proteomics. Trends in Biochemical Scciences. 46(8):661-672 (2021).
Volozonoka, Ludmila. et al. Whole Genome Amplification in Preimplantation Genetic Testing in the Era of Massively Parallel Sequencing. International Journal of Molecular Sciences 23(9):4819, 1-24 (2022).
Wahlgren, Marie and Arnebrant, Thomas et al, "Protein adsorption to solid surfaces," TIBTECH, 9: 201-208 (1991).
Wang, Xiuyan, and Isabelle Riviere. Clinical Manufacturing of CAR T cells: Foundation of a Promising Therapy. Molecular Therapy Oncolytics 3:16015, 1-7 (2016).
Wang, Xuefeng. et al. DNA copy number profiling using single-cell sequencing. Briefings in Bioinformatics 19(5):731-736 (2018).
Wang, Yong and Navin, Nicholas E. Advances and Applications of Single-Cell Sequencing Technologies. 58(4):598-609 (2015).
Winther, Jakob R. and Thorpe, Colin. Quantification of thiols and disulfides. Biochimica et Biophysica Acta (BBA). 1840(2):838-846 (2014).
Yu, Zhilong. et al. Microfluidic Whole Genome Amplification Device for Single Cell Sequencing. Analytical Chemistry 86(19):9386-9390 (2014).
Zhang, Lin. et al. Whole Genome Amplification From a Single Cell: Implications for Genetic Analysis. Proceedings of the National Academy of Sciences of the United States of America 89(13):5847-5851 (1992).
Zhu, He. et al. A Miniature Cytometry Platform for Capture and Characterization of T-lymphocytes from Human Blood. Analytica Chimica Acta 608(2):186-196 (2008). Online published Dec. 28, 2007.
Zhu, Y Y. et al. Reverse Transcriptase Template Switching: a SMART Approach for full-length cDNA library Construction. BioTechniques 30(4):892-897 (2001).
EP22821163.7 Extended European search report dated Mar. 21, 2025.
Hou, Ping et al. Photo-cross-linked biodegradable hydrogels based on n-arm-poly(ethylene glycol), poly(-caprolactone) and/or methacrylic acid for controlled drug release. Journal of biomaterials applications 32(4):511-523 (2017).
PCT/US2024/059913 International Search Report and Written Opinion dated Apr. 7, 2025.

\* cited by examiner

Hydrogel Generation using a Physical Masks 1660   1670

Surface Proteins

RNA Transcripts

DEVICES AND METHODS FOR ANALYZING BIOLOGICAL SAMPLES

CROSS REFERENCE

This application is a continuation of U.S. patent application Ser. No. 18/593,787, filed Mar. 1, 2024, which is a continuation of U.S. patent application Ser. No. 18/219,545, filed Jul. 7, 2023, now U.S. Pat. No. 12,030,047, issued Jul. 9, 2024, which is a continuation of International Application No. PCT/US2022/011720, filed Jan. 7, 2022, which claims the benefit of U.S. Provisional Application No. 63/135,463, filed Jan. 8, 2021, and U.S. Provisional Application No. 63/253,500, filed Oct. 7, 2021, each of which are incorporated herein by reference in entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BACKGROUND

In the field of cellular biology, single-cell analysis can include the study of genomics, transcriptomics, proteomics, metabolomics, and cell-cell interactions at the single-cell level. Due to the heterogeneity seen in both eukaryotic and prokaryotic cell populations, analyzing a single cell can make it possible to discover mechanisms not seen when studying a bulk population of cells. In single-cell analysis, changes in single cells can be tracked or observed at the level of genes, proteins, or other cellular components. For example, in cancer, where cells may be mutating, it can be of interest to see how cancers change at the genetic level. These patterns of somatic mutations and copy number aberrations can be observed using single-cell sequencing.

SUMMARY

Recognized herein is a need for compartmentalizing components of a biological sample to perform one or more assays on an individual component within a compartment. The one or more assays may be performed with or without the need for additional processing of the individual component (e.g., without the need for nucleotide amplification steps), while retaining spatial information of the individual components. Compartments may be generated or deconstructed on demand to localize (that is, to constrain to a compartment) or release targeted components of the biological sample.

Provided herein is a method comprising: providing a fluidic device comprising an analyte and one or more polymer precursors; identifying a discrete area within the fluidic device; and selectively supplying a unit of energy generated from the energy source to the fluidic device to generate a polymer matrix from said one or more polymer precursors within the fluidic device, wherein the polymer matrix is within the discrete area or adjacent to the discrete area. In some embodiments, the fluidic device comprises a flow channel. In some embodiments, the fluidic device comprises an open configuration, for example, as shown by the embodiment of FIG. 20. In some embodiments, the fluidic device contains one or more discrete locations wherein the one or more discrete locations are not in fluidic communication with another discrete location. In some embodiments, the one or more discrete locations are one or more wells on a surface of plate. In some embodiments, when discrete locations are defined by wells or cavities or containers in or on a surface, the one or more discrete locations are open at the top. That is, in some embodiments, the one or more discrete locations comprise an analyte or biological component. In some embodiments, a unit of energy is an amount of energy, such as light energy, effective to cause the synthesis of chambers in a channel. A value of a unit of energy for a given embodiment may vary widely depending on, but not limited to, such factors as the nature of the spatial energy modulating element, the size of a channel, the size and geometry of the desired chambers, the nature of the polymer precursors, and the like.

In some embodiments, the fluidic device further comprises a spatial energy modulating element. In some embodiments, the fluidic device comprises a surface having a capture probe immobilized thereto, wherein the capture probe couples to the analyte to immobilize the analyte to the surface. In some embodiments, the polymer matrix is generated adjacent to or surrounding the analyte to immobilize the analyte. In some embodiments, the polymer matrix forms a hydrogel. In some embodiments, the capture probe comprises one or more functional groups capable of interacting with the analyte. In some embodiments, the one or more functional groups comprise a complimentary DNA sequence to target DNA or RNA.

In some embodiments, the energy source is in optical communication with said fluidic device. In some embodiments, the spatial energy modulating element is a light generating device, such as a digital micromirror device. In some embodiments, the light generating device generates light at 350 nm to 800 nm. In some embodiments, the light generating device generates light at 350 nm to 600 nm. In some embodiments, the light generating device generates light at 350 nm to 450 nm. In some embodiments, the light generating device generates UV light. In some embodiments, selectively supplying a unit of energy generated from the energy source to the fluidic device to generate a polymer matrix within the fluidic device is performed using a spatial energy modulating element that is a spatial light modulator (SLM). In some embodiments, the SLM is a digital micromirror device (DMD). In some embodiments, the SLM is a laser beam steered using a galvanometer. In some embodiments, the SLM is liquid-crystal based. Light energy from a spatial light modulator or spatial energy modulating element may be used to photo-crosslink polymer precursors to form polymer matrix walls that make up chambers formed in a channel.

In some embodiments, the area of the discrete area is less than the area of the fluidic device. In some embodiments, the analyte is captured within the discrete area. In some embodiments, the size and shape of the discrete area is adjustable according to the analyte size, the analyte shape, or other properties of the analyte. In some embodiments, an algorithm is used to determine the shape and size of the discrete area. In some embodiments, the algorithm is a supervised, a self-supervised, or an unsupervised learning algorithm. In some embodiments, the discrete area is identified optically. In some embodiments, the discrete area is identified using a detector configured to detect the location of the analyte within from an image from light collected from the fluidic device. In some embodiments, the detector configured to detect the location of the analyte within the fluidic device is a microscope objective for imaging the fluidic device. In some embodiments, an algorithm is used to determine where the analyte is located based on the imaging. In some embodiments, the imaging is bright-field imaging, phase-contrast imaging, or fluorescence imaging, or any combination thereof. In some embodiments, the algorithm is a supervised, a self-supervised, or an unsupervised learning algorithm. In some embodiments, the objective is coupled to an energy source to emit energy to the discrete area in the fluidic device.

In some embodiments, the method further comprises introducing one or more reagents to the polymer matrix that react with the analyte. In some embodiments, the one or more reagents flow through a membrane. In some embodiments, the membrane is semi-permeable. In some embodiments, the membrane comprises pores. In some embodiments, the pores are less than 10 um. In some embodiments, the one or more reagents comprise one or more of the following: an enzyme, a drug molecule, oligonucleotide, primer, or any combination thereof. In some embodiments, the one or more reagents is a lysis reagent, for example, for lysing cells that are selectively to be removed from the channel of the fluidic device. In some embodiments, the one or more reagents is a nucleic acid denaturation reagent. In some embodiments, the one or more reagents degrades the polymer matrix.

In some embodiments, the analyte is a cell component. In some embodiments, the analyte is a small molecule composed of nucleic acids, amino acids, intracellular proteins, surface proteins, secreted proteins, exosomes, metabolites or lipids, or any combination thereof. In some embodiments, the analyte is captured by capture probes within the polymer matrix. In some embodiments, the analyte is captured by capture probes on the surface of the polymer matrix.

In some embodiments, the analyte is released from the cell upon interaction with a reagent. In some embodiments, the reagent is an oxidative or a reducing agent. In some embodiments, the reagent is an organic or inorganic molecule. In some embodiments, the organic or inorganic molecule is a pharmaceutical compound or detergent. In some embodiments, the reagent is a protein. In some embodiments, the reagent is a DNA aptamer. In some embodiments, the reagent is a bead carrying biomolecules. In some embodiments, the reagent is a biological species. In some embodiments, the biological species is a virus or cell.

In some embodiments, the analyte is released from the cell upon exposure to an energy source. In some embodiments, the energy source is UV light for lysing cells. In some embodiments, the energy source is visible light for lysing cells. In some embodiments, the UV light is used to activate a photoactivated detergent and lyse the cell. In some embodiments, the visible light is used to activate a photo-activated detergent and lyse the cell.

In some embodiments, the method further comprises identifying the analyte or a component thereof. In some embodiments, the analyte is a nucleic acid, amino acid, intracellular protein, surface protein, secreted protein, exosome, metabolite or lipid, or any combination thereof. In some embodiments, the analyte is a nucleic acid molecule, and the identifying comprises sequencing the nucleic acid molecule or a derivative thereof.

In some embodiments, the method further comprises measuring a quality of the analyte or a component thereof. In some embodiments, the quality is the shape or size of the analyte or component thereof. In some embodiments, the method further comprises performing one or more functional assays to analyze the cell or component thereof to assess cell viability, cell morphology, cell secretions, cell responses, intercellular interactions, or any combination thereof. In some embodiments, the one or more functional assays is a colorimetric assay or fluorescent assay. In some embodiments, one or more functional assays are performed using bright-field phase contrast or fluorescent imaging of the analyte.

In some embodiments, the method further comprises performing one or more omics assays to characterize and quantify the cell or component thereof. In some embodiments, one or more omics assays is a proteomic, transcriptomic, genomic, or epigenomic assay, or any combination thereof. In some embodiments, the one or more omics assays is a multi-omic assay.

Another aspect of the present disclosure provides method for processing an analyte, comprising: providing a fluidic device comprising the analyte and one or more polymer precursors; and configuring a digital micromirror device to direct a unit of energy generated from the energy source to a discrete area of the fluidic device to generate a polymer matrix from said one or more polymer precursors within the fluidic device, wherein the polymer matrix comprises or encapsulates the analyte.

In some embodiments, the fluidic device comprises a flow channel (sometimes referred to herein as a "channel"). In some embodiments, the fluidic device comprises an open configuration. In some embodiments, the fluidic device contains one or more discrete locations wherein the one or more discrete locations are not in fluidic communication with another discrete location. In some embodiments, the one or more discrete locations are one or more well plates. In some embodiments, the one or more discrete locations are open at the top. In some embodiments, the one or more discrete locations comprise the analyte.

In some embodiments, the discrete area is adjacent to or surrounding the analyte. In some embodiments, the discrete area is adjustable according to the analyte size, the analyte shape, or other properties of the analyte. In some embodiments, the discrete area is identified optically. In some embodiments, a detector is configured to detect the location of said analyte within the fluidic device. In some embodiments, the detector configured to detect the location of said analyte within said fluidic device is a microscopic objective for imaging the fluidic device via an image of the fluidic channel. In some embodiments, an algorithm is used to determine where the analytes or biological components are located based on the imaging. In some embodiments, the imaging is bright-field imaging, phase-contrast imaging, or fluorescence imaging, or any combination thereof. In some embodiments, algorithm is a supervised, a self-supervised, or an unsupervised learning algorithm. In some embodiments, the objective is coupled to the energy source in optical communication with the fluidic device. In some embodiments, based on information extracted by an algorithm from an image of the fluidic channel, the digital micromirror device to direct the unit of energy to the fluidic device.

In some embodiments, the method further comprises introducing one or more reagents to the polymer matrix that react with the analyte. In some embodiments, the one or more reagents flow through a membrane. In some embodiments, the membrane is semi-permeable. In some embodiments, the membrane comprises pores. In some embodiments, the pores are less than 10 um. In some embodiments, the one or more reagents is an enzyme, oligonucleotide, primer, or any combination thereof. In some embodiments, the one or more reagents is a lysis reagent. In some embodiments, the one or more reagents is a nucleic acid denaturation reagent. In some embodiments, the one or more reagents degrades the polymer matrix.

In some embodiments, the analyte is a component of a cell. In some embodiments, the cell component is a small molecule composed of nucleic acids, amino acids, intracellular proteins, surface proteins, secreted proteins, exosomes, metabolites or lipids, or any combination thereof. In some embodiments, the analyte is captured by capture probes within the polymer matrix. In some embodiments, the analyte is captured by capture probes on the surface of the polymer matrix.

In some embodiments, the analyte is released from the cell upon interaction with a reagent. In some embodiments, the reagent is an oxidative or a reducing agent. In some embodiments, the reagent is an organic or inorganic molecule. In some embodiments, the organic or inorganic molecule is a pharmaceutical compound or detergent. In some embodiments, the reagent is a protein. In some embodiments, the reagent is a DNA aptamer. In some embodiments, the reagent is a bead carrying biomolecules. In some embodiments, the reagent is a biological species. In some embodiments, the biological species is a virus or cell.

In some embodiments, the analyte is released from the cell upon exposure to an energy source. In some embodiments, the energy source is UV light for lysing cells. In some embodiments, the energy source is visible light for lysing cells. In some embodiments, the UV light is used to activate a photoactivated detergent and lyse the cell. In some embodiments, the visible light is used to activate a photoactivated detergent and lyse the cell.

In some embodiments, the method further comprises identifying the analyte or a derivative thereof. In some embodiments, the analyte is a nucleic acid molecule, and the identifying comprises sequencing the nucleic acid molecule or a derivative thereof. In some embodiments, the method further comprises measuring a quality of the analyte. In some embodiments, the quality is the shape or size of the analyte.

In some embodiments, the method further comprises performing one or more functional assays to analyze the analyte to assess cell viability, cell morphology, cell secretions, cell responses, intercellular interactions, or any combination thereof. In some embodiments, the one or more functional assays is a colorimetric assay or fluorescent assay. In some embodiments, the one or more functional assays is performed using bright-field phase contrast or fluorescent imaging of the analyte.

In some embodiments, the method further comprises performing one or more omics assays to characterize and quantify the analyte or a component thereof. In some embodiments, the one or more omics assays is a proteomic, transcriptomic, genomic, or epigenomic assay, or any combination thereof. In some embodiments, the one or more omics assays is a multi-omic assay.

Another aspect of the present disclosure provides a method for processing an analyte, comprising: providing a fluidic device comprising the analyte and one or more polymer precursors; and using the one or more polymer precursors to generate a polymer matrix from said one or more polymer precursors within the fluidic device, wherein the polymer matrix comprises the analyte, and wherein the generation of the polymer matrix is performed in absence of a physical photomask.

In some embodiments, the fluidic device comprises a flow channel. In some embodiments, the fluidic device comprises an open configuration. In some embodiments, the fluidic device contains one or more discrete locations wherein the one or more discrete locations is not in fluidic communication with another discrete location. In some embodiments, the one or more discrete locations are one or more well plates. In some embodiments, the one or more discrete locations are open at the top. In some embodiments, the one or more discrete locations comprise the analyte.

In some embodiments, the fluidic device further comprises one or more monomers. In some embodiments, the fluidic device further comprises a spatial energy modulating element. In some embodiments, the fluidic device comprises a surface having a capture probe immobilized thereto, wherein the capture probe couples to the analyte to immobilize the analyte to the surface.

In some embodiments, the polymer matrix is generated adjacent to or surrounding the analyte to immobilize the analyte. In some embodiments, the polymer matrix forms a hydrogel. In some embodiments, the capture probe comprises one or more functional groups capable of interacting with the analyte. In some embodiments, the one or more functional groups comprise a complimentary DNA sequence to target DNA or RNA.

In some embodiments, the generation of a polymer matrix within said fluidic device comprises exposing the one or more polymer precursors to an energy source. In some embodiments, the energy source is a light generating device. In some embodiments, the light generating device generates light at 350 nm to 800 nm. In some embodiments, the light generating device generates light at 350 nm to 600 nm. In some embodiments, the light generating device generates light at 350 nm to 450 nm. In some embodiments, the light generating device generates UV light. In some embodiments, the generation of a polymer matrix within said fluidic device is performed using a spatial light modulator (SLM). In some embodiments, the SLM is a digital micromirror device (DMD). In some embodiments, the SLM is a laser beam steered using a galvanometer. In some embodiments, the SLM is liquid-crystal based.

In some embodiments, the polymer matrix is generated in a discrete area of the fluidic device. In some embodiments, the discrete area is adjacent to or surrounding the analyte. In some embodiments, the area of the discrete area is less than the area of the fluidic device. In some embodiments, the analyte is captured within the discrete area. In some embodiments, the size and shape of the discrete area is adjustable according to the analyte size, the analyte shape, or other properties of the analyte. In some embodiments, an algorithm is used to determine the shape and size of the discrete area. In some embodiments, the algorithm is a supervised, a self-supervised, or an unsupervised learning algorithm.

In some embodiments, the discrete area is optically identified. In some embodiments, a detector is configured to detect the location of said analyte within said fluidic device. In some embodiments, the detector configured to detect the location of the analyte within the fluidic device is a microscope objective for imaging the fluidic device. In some embodiments, an algorithm is used to determine where the analyte is located based on the imaging. In some embodiments, the imaging is bright-field imaging, phase-contrast imaging, or fluorescence imaging, or any combination thereof. In some embodiments, the algorithm is a supervised, a self-supervised, or an unsupervised learning algorithm. In some embodiments, the objective is coupled to an energy source to emit energy to the discrete area in the fluidic device.

In some embodiments, the method further comprises introducing one or more reagents to the polymer matrix that react with the analyte. In some embodiments, the one or more reagents flow through a membrane. In some embodiments, the membrane is semi-permeable. In some embodiments, the membrane comprises pores. In some embodiments, the pores are less than 10 um. In some embodiments, the one or more reagents is an enzyme, a drug molecule, oligonucleotide, primer, or any combination thereof. In some embodiments, the one or more reagents is a lysis reagent. In some embodiments, the one or more reagents is a nucleic acid denaturation reagent. In some embodiments, the one or more reagents degrades the polymer matrix.

In some embodiments, the analyte is a component of a cell. In some embodiments, the analyte is a small molecule composed of nucleic acids, amino acids, intracellular proteins, surface proteins, secreted proteins, exosomes, metabolites or lipids, or any combination thereof.

In some embodiments, the analyte is captured by capture probes within the polymer matrix. In some embodiments, the analyte is captured by capture probes on the surface of the polymer matrix.

In some embodiments, the analyte is released from the cell upon interaction with a reagent. In some embodiments, the reagent is an oxidative or a reducing agent. In some embodiments, the reagent is an organic or inorganic molecule. In some embodiments, the organic or inorganic molecule is a pharmaceutical compound or detergent. In some embodiments, the reagent is a protein. In some embodiments, the reagent is a DNA aptamer. In some embodiments, the reagent is a bead carrying biomolecules. In some embodiments, the reagent is a biological species. In some embodiments, the biological species is a virus or cell.

In some embodiments, the analyte is released from the cell upon exposure to an energy source. In some embodiments, the energy source is UV light for lysing cells. In some embodiments, the energy source is visible light for lysing cells. In some embodiments, the UV light is used to activate a photoactivated detergent and lyse the cell. In some embodiments, the visible light is used to activate a photoactivated detergent and lyse the cell.

In some embodiments, the method further comprises identifying the analyte or a derivative thereof. In some embodiments, the analyte is a nucleic acid molecule, and the identifying comprises sequencing the nucleic acid molecule or a derivative thereof. In some embodiments, the method further comprises measuring a quality of the analyte. In some embodiments, the quality is the shape or size of the analyte.

In some embodiments, the method further comprises performing one or more functional assays to analyze the analyte to assess cell viability, cell morphology, cell secretions, cell responses, intercellular interactions, or any combination thereof. In some embodiments, the one or more functional assays is a colorimetric assay or fluorescent assay. In some embodiments, the one or more functional assays is performed using bright-field phase contrast or fluorescent imaging of the analyte.

In some embodiments, the method further comprises performing one or more omics assays to characterize and quantify the analyte or a component thereof. In some embodiments, the one or more omics assays is a proteomic, transcriptomic, genomic, or epigenomic assay, or any combination thereof. In some embodiments, the one or more omics assays is a multi-omic assay.

Another aspect of the present disclosure provides a system comprising a fluidic device containing one or more biological components and one or more polymer precursors. The system may further comprise at least one energy source in communication with the fluidic device. In some embodiments, the at least one energy source supplies energy to the fluidic device to cause the one or more polymer precursors to form at least one polymer matrix on or adjacent to the biological component.

In some embodiments, the fluidic device comprises a channel disposed therethrough. In some embodiments, a first surface is disposed along a portion of the channel, and a second surface is disposed opposite of the first surface. In some embodiments, the fluidic device comprises a chamber disposed therein. In some embodiments, a first surface is disposed along a portion of the chamber, and a second surface is disposed opposite of the first surface. In some embodiments, the first surface is a lower surface. In some embodiments, the second surface is an upper surface. In some embodiments, the fluidic device further comprises one or more capture elements immobilizing at least one of the one or more biological components at a location adjacent to the first surface forming an immobilized biological component. In some embodiments, the first surface is disposed adjacent to the energy source. In some embodiments, the energy source is a light source. In some embodiments, the energy source is an array of electrodes. In some embodiments, the energy source supplies electrochemical energy to the one or more polymer precursors to form an array of polymer matrices. In some embodiments, at least two of the one or more polymer precursors are coupled to the first surface forming a pattern on the first surface.

In some embodiments, the at least one polymer matrix is formed on or adjacent to the pattern. In some embodiments, the at least one polymer matrix is coupled to the first surface. In some embodiments, the at least one polymer matrix extends from the first surface to the second surface such that the at least one polymer matrix surrounds at least a portion of the immobilized biological component.

In some embodiments, the at least one energy source is in at least one of optical communication, electrochemical communication, electromagnetic communication, thermal communication, or microwave communication with the fluidic device. In some embodiments, the at least one energy source comprises a light generating device, a heat generating device, an electrochemical generating device, an electrode, or a microwave device. In some embodiments, the system further comprises a photolithographic device or a digital micromirror device (DMD) configured to control a spatial distribution of the energy from the energy source.

In some embodiments, the one or more capture elements comprise a physical trap, a geometric trap, a well, an electrochemical trap, a chemical affinity trap, one or more magnetic particles, an electrophoretic trap, a dielectrophoretic trap, or a combination thereof. In some embodiments, the chemical affinity trap comprises streptavidin, an antibody, or a combination thereof. In some embodiments, the physical trap comprises a polymer matrix. In some embodiments, the polymer matrix comprises a hydrogel. In some embodiments, the electrochemical trap comprises a gold electrode, a platinum electrode, an indium tin oxide (ITO) electrode, or other suitable electrochemical trap. In some embodiments, the one or more capture elements are disposed in a pattern on the first surface. In some embodiments, the one or more capture elements comprises a well. In some embodiments, the well is from 1 μm (micrometer) to 50 μm in diameter. In some embodiments, the well is from 0.1 μm to 100 μm in depth.

In some embodiments, the one or more biological components is a plurality of biological components. In some embodiments, the plurality of biological components is coupled to the one or more capture elements. In some embodiments, the fluidic device is a microfluidic device or a nanofluidic device. In some embodiments, the fluidic device is used for nucleic acid sequencing.

In some embodiments, the nucleic acid sequencing comprises next-generation sequencing, short-read sequencing, nanopore sequencing, sequencing by synthesis, sequencing by in-situ hybridization, or an optical readout.

In some embodiments, the one or more biological components comprise a cell, a cell lysate, a nucleic acid, a microbiome, a protein, a mixture of cells, a spatially-linked biological component, or a metabolite. In some embodiments, the mixture of cells comprises a first cell type and a second cell type. In some embodiments, the first cell type is different than the second cell type. In some embodiments, the cell is an animal cell (e.g., a human cell), a plant cell, a fungal cell, or a bacterial cell. In some embodiments, the one or more biological components comprise a tumor spheroid or a spatially linked biological sample.

In some embodiments, the nucleic acid is DNA of 100 base pairs or greater or RNA of 50 bases or greater. In some embodiments, the cell lysate comprises DNA from 50 bp (base pairs) to 100 Gbp (giga base pairs) or RNA from 50 bp to 100 kbp (kilo base pairs). In some embodiments, the at least one polymer matrix comprises a hydrogel. In some embodiments, the fluidic device further comprises one or more polymer precursors. In some embodiments, the one or more polymer precursors comprise hydrogel precursors. In some embodiments, the at least one polymer matrix inhibits passage of the immobilized biological component. In some embodiments, the at least one polymer matrix forms a polymer matrix wall extending from the first surface to the second surface to form a chamber within the channel. For example, such chamber may comprise a cylinder shell or a polygon shell, comprising an inner space, or interior and a polymer matrix wall. In some embodiments, such chambers have annular-like cross-sections. As used herein, the term "annular-like cross-section" means a cross-section topologically equivalent to an annulus. In some embodiments, the inner space, or interior, of a chamber has an inner diameter from 1 μm to 500 μm and a volume in the range of from 1 picoliter to 200 nanoliters, or from 100 picoliters to 100 nanoliters, or from 100 picoliters to 10 nanoliters. In some embodiments, the polymer matrix wall has a thickness of at least 1 μm (micrometer). In some embodiments, a polymer matrix wall having an annular-like cross-section has an aspect ratio (i.e., height/width) of 1 or less. In some embodiments, aspect ratio and polymer matrix wall thickness are selected to maximize chamber stability against forces, such as reagent flow through the channel, washings, and the like. In some embodiments, the at least one polymer matrix wall is a hydrogel wall. In some embodiments, the at least one polymer matrix is degradable. In some embodiments, the degradation of the at least one polymer matrix is "on demand."

In some embodiments, on demand degradation may be implemented using polymer precursors that permit photo-crosslinking and photo-degradation, for example, using different wavelengths for crosslinking and for degradation. For example, Eosin Y may be used for radical polymerization at defined regions using 500 nm wavelength, after which illumination at 380 nm can be used to cleave the cross linker. In other embodiments, photo-caged hydrogel cleaving reagents may be included in the formation of polymer matrix walls. For example, acid labile crosslinkers (such as esters, or the like) can be used to create the hydrogel and then UV light can be used to generate local acidic conditions which, in turn, degrades the hydrogel.

In some embodiments, the at least one polymer matrix is degradable by at least one of: (i) contacting the at least one polymer matrix with a cleaving reagent; (ii) heating the at least one polymer matrix to at least 90° C.; or (iii) exposing the at least one polymer matrix to a wavelength of light that cleaves a photo-cleavable crosslinker that crosslinks the polymer of the at least one polymer matrix. In some embodiments, the at least one polymer matrix comprises a hydrogel. In some embodiments, the cleaving reagent degrades the hydrogel. In some embodiments, the cleaving reagent comprises a reducing agent, an oxidative agent, an enzyme, a pH based cleaving reagent, or a combination thereof. In some embodiments, the cleaving reagent comprises dithiothreitol (DTT), tris(2-carboxyethyl)phosphine (TCEP), tris(3-hydroxy propyl)phosphine (THP), or a combination thereof.

In some embodiments, the at least one polymer matrix allows passage of a reagent. In some embodiments, the at least one polymer matrix comprises pores. In some embodiments, an average size of the pores is modulated using a chemical reagent, by applying heat, applying electricity, applying light, or a combination thereof. In some embodiments, the reagent comprises at least one of enzymes, chemicals, oligonucleotides, or primers having a size of less than 50 base pairs.

In some embodiments, the reagent comprises lysozyme, proteinase K, random hexamers, polymerase, transposase, ligase, catalyzing enzyme, deoxynucleotide triphosphates, buffers, cell culture media, or divalent cations. In some embodiments, the at least one polymer matrix comprises pores that are sized to allow diffusion of a reagent through the at least one polymer matrix but are too small to allow DNA or RNA for analysis to traverse the pores. In some embodiments, DNA or RNA retained have lengths that are sequencable using conventional sequencing-by-synthesis techniques. For example, such DNA or RNA comprise at least 50 nucleotides, or in some embodiments, at least 100 nucleotides. In some embodiments, the at least one polymer matrix comprises a hydrogel. In some embodiments, the hydrogel comprises polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly (lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetraacrylate, or combinations or mixtures thereof. In some embodiments, the hydrogel comprises an enzymatically degradable hydrogel, PEG-thiol/PEG-acrylate, acrylamide/N,N'-bis(acryloyl)cystamine (BACy), or PEG/PPO. In some embodiments, the following precursors and crosslinker may be used to form chambers with degradable polymer matrix (hydrogel) walls. Polymer precursors may be formed by using any hydrogel precursor and crosslinkers of Table 1A (columns 1 and 3, respectively). The resulting polymer matrices may be degraded with the indicated degradation agents in Table 1A (column 4).

TABLE 1A

| Precursors | Hydrogels | Crosslinkers | Degradation Agents |
|---|---|---|---|
| Acrylamide | Poly-acrylamide | Bis-acryloyl cystamine (structure 1) | DTT/TCEP/THP |
| PEG-based acryloyl | PEG | Bis(2-methacryloly)oxyethyl disulfide (structure 2) | DTT/TCEP/THP |

TABLE 1A-continued

| Precursors | Hydrogels | Crosslinkers | Degradation Agents |
|---|---|---|---|
| Dextran-based acryloyl | Dextran | N,N'-(1,2-Dihydroxyl-ethylene)bis-acrylamide structure (3) | NaIO4 |
| Polysaccharide-base acryloyl | Poly-saccharide | Structure 4 | NaOH, ethanolamine DTT/TCEP/THP |
| Gelatin-base acryloyl | Gelatin | Structure 5 | NaOH, ethanolamine, nucleophilic bases |
| | | Structure 6 | NaOH, alkali, organic bases |
| | | Structure 7 | Acid |

TABLE 1B

| Structure Number | Structure |
|---|---|
| 1 | 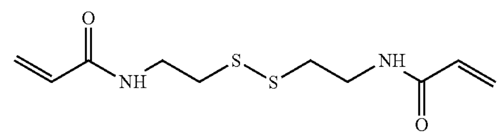 [SMILES: C=CC(=O)NCCSSCCNC(=O)C=C] |
| 2 | 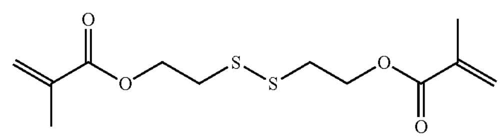 [SMILES: C=C(C)C(=O)OCCSSCCOC(=O)C(=C)C] |
| 3 | 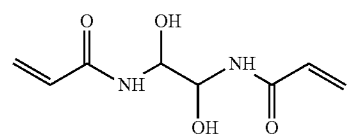 |
| 4 | 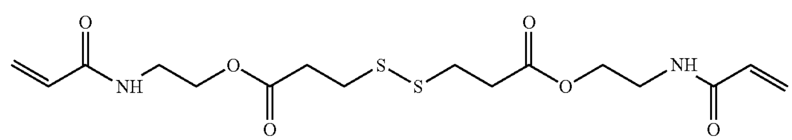 [SMILES: C=CC(=O)NCCOC(=O)CCSSCCC(=O)OCCNC(=O)C=C] |
| 5 | 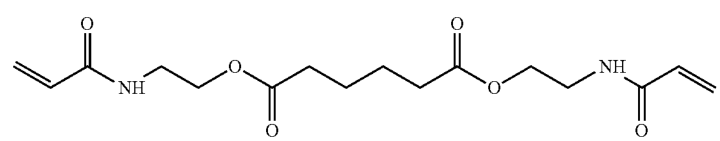 [SMILES: C=CC(=O)NCCOC(=O)CCCCC(=O)OCCNC(=O)C=C] |
| 6 | 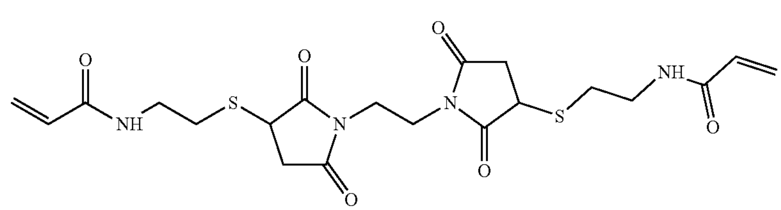 [SMILES: C=CC(=O)NCCSC1CC(=O)N(CCN2C(=O)CC(SCCNC(=O)C=C)C2=O)C1=O] |
| 7 | 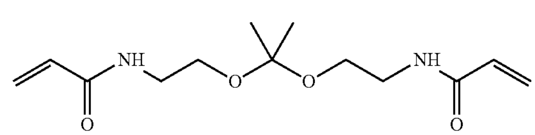 [SMILES: C=CC(=O)NCCOC(C)(C)OCCNC(=O)C=C] |

In some embodiments, the first surface, the second surface, or both comprise one or more barcodes. In some embodiments, the one or more barcodes comprise an identifier to identify a source of the one or more biological components. In some embodiments, the source comprises a specimen from which the one or more biological components are collected. In some embodiments, the source comprises a physiological or an anatomical source from which the one or more biological components are collected. In some embodiments, the anatomical source comprises an organ of a subject. In some embodiments, the subject is a human. In some embodiments, the one or more barcodes are configured to bind the one or more biological components, or a molecule made by the one or more biological components.

In some embodiments, the first surface, the second surface, or both comprise one or more compounds configured to bind the one or more biological components. In some embodiments, the first surface or the second surface is functionalized with a surface polymer. In some embodiments, the surface polymer is functionalized with an oligonucleotide, an antibody, a cytokine, a chemokine, a protein, an antibody derivative, an antibody fragment, a carbohydrate, a toxin, an aptamer, or any combination thereof. In some embodiments, a surface of the polymer matrix is functionalized with an oligonucleotide, an antibody, a cytokine, a chemokine, a protein, an antibody derivative, an antibody fragment, a carbohydrate, a toxin, an aptamer, or any combination thereof. In some embodiments, the surface polymer comprises polyethylene glycol (PEG), a silane polymer, pyridinecarboxaldehyde (PCA), an acrylamide, an agarose, or a combination thereof.

In some embodiments, the system further comprises a detector for identifying the one or more of the biological components, the one or more barcodes, or a combination thereof. In some embodiments, the detector comprises a camera (fluorescent camera).

In some embodiments, the system further comprises a stage that holds the fluidic device. In some embodiments, the system further comprises a sequencing device for obtaining sequencing data. In some embodiments, the sequencing data is generated using next-generation sequencing, short-read sequencing, nanopore sequencing, sequencing by synthesis, sequencing by in-situ hybridization, or an optical readout.

In some embodiments, the system further comprises a spatial energy modulating element to selectively supply the energy to the fluidic device. In some embodiments, the spatial energy modulating element is generated using the detector identifying the position of the at least one biological component. In some embodiments, the spatial energy modulating element comprises a physical photomask, a virtual photomask, a physical electrode distribution pattern, or a virtual electrode distribution pattern. In some embodiments, the spatial energy modulating element comprises a photolithographic mask or a digital micromirror device (DMD) mask.

Another aspect of the present disclosure provides a method of analyzing a biological component. The method may comprise (a) introducing one or more biological components into a fluidic device; (b) disposing a first portion of the one or more biological components adjacent a first surface of the fluidic device; and (c) forming one or more polymer matrices adjacent a first portion of the first surface to localize at least one of the one or more biological components to the first portion.

In some embodiments, the method further comprises: (d) agitating the one or more biological components within the fluidic device; (e) disposing a second portion of the one or more biological components adjacent the first surface of the fluidic device; and (f) forming one or more polymer matrices adjacent a second portion of the first surface to immobilize at least one of the one or more biological component of the second portion. The step of agitating in this and other embodiments may prevent or disrupt aggregation of biological components, such as, biological cells. Agitating may also induce a more uniform distribution of biological components on a first surface within a channel.

In some embodiments, the method further comprises identifying a position of at least one of the one or more biological components such that at least one energy source supplies energy to the fluidic device to form the one or more polymer matrices on or adjacent the identified position.

Another aspect of the present disclosure provides a method of analyzing a biological component. The method may comprise: (a) introducing the biological component into a fluidic device; (b) coupling the biological component to one or more capture elements disposed on a first surface or second surface of the fluidic device to yield a coupled biological component; and (c) forming a polymer matrix on or adjacent to the coupled biological component.

In some embodiments, the method further comprises introducing one or more polymer precursors into the fluidic device. In some embodiments, forming the polymer matrix comprises supplying energy to the fluidic device to form the polymer matrix.

In some embodiments, the energy is selectively supplied to one or more portions of the fluidic device. In some embodiments, the method further comprises a spatial energy modulating element to selectively supply the energy to the fluidic device. In some embodiments, the spatial energy modulating element comprises a physical photomask, a virtual photomask, a physical electrode distribution pattern, or a virtual electrode distribution pattern.

In some embodiments, the spatial energy modulating element comprises a photolithographic mask or a digital micromirror device (DMD) mask. In some embodiments, the energy is supplied via a light energy source, a heat energy source, an electrochemical energy source, or an electromagnetic energy source.

In some embodiments, the polymer matrix is coupled to the first surface. In some embodiments, the energy forms the polymer matrix around a portion of the coupled biological component. In some embodiments, at least a portion of the biological component is encapsulated by the polymer matrix. In some embodiments, an entirety of the biological component is encapsulated by the polymer matrix.

In some embodiments, the method further comprises coupling a first biological component to a first capture element to form a first analysis chamber and coupling a second biological component to a second capture element to form a second analysis chamber. In some embodiments, the first analysis chamber is adjacent to the second analysis chamber. In some embodiments, the first analysis chamber is disposed from 5 micrometer (µm) to 1,000 µm away from the second analysis chamber.

In some embodiments, the method further comprises analyzing the first biological component in the first analysis chamber and analyzing the second biological component in the second analysis chamber. In some embodiments, the method further comprises actuating a first reaction in the first biological component and actuating a second reaction in the second biological component. In some embodiments, the first reaction and the second reaction are different. In some embodiments, the method further comprises actuating a third reaction in the first biological component and actuating a fourth reaction in the second biological component. In some embodiments, the third reaction and the fourth reaction are different.

In some embodiments, the method further comprises obtaining a genome, transcriptome, proteome, epigenome, methylome, secretome, or metabolome of the coupled biological component.

In some embodiments, the proteome comprises secreted proteins, surface proteins, or a combination thereof. In some embodiments, the transcriptome is a substantially full-length transcriptome. In some embodiments, the transcriptome is a full-length transcriptome. In some embodiments, the method further comprises sequencing at least one nucleic acid of the biological component. In some embodiments, the sequencing does not comprise amplification of a sequencing library. In some embodiments, the nucleic acid library from the biological component is sequenced within a same chamber. In some embodiments, the method further comprises coupling a barcode to the biological component or a molecule produced by the biological component.

In some embodiments, the method further comprises exposing the biological component or the coupled biological component to an analyte. In some embodiments, the biological component comprises one or more microbes. In some embodiments, the analyte comprises an antimicrobial agent or a microbial growth promoting agent. In some embodiments, the method further comprises screening the one or more microbes for susceptibility to the antimicrobial agent. In some embodiments, the analyte comprises a pharmaceutical agent.

In some embodiments, the method further comprises screening an effect of the pharmaceutical agent on the biological component. In some embodiments, the method further comprises screening the biological component for production of a target molecule.

In some embodiments, the target molecule comprises at least one of an antibody, a cytokine, a chemokine, a protein, an antibody derivative, an antibody fragment, a carbohydrate, a toxin, or an aptamer.

In some embodiments, the method further comprises forming the polymer matrix around the biological component such that the biological component is disposed within a structure formed by the polymer matrix.

In some embodiments, the method further comprises analyzing a local parameter in the first analysis chamber or the second analysis chamber. In some embodiments, a level of the local parameter in the first analysis chamber is different from a level of the local parameter in the second analysis chamber. In some embodiments, the local parameter comprises a pH, an oxygen concentration, or a CO2 concentration.

In some embodiments, the one or more capture elements comprise a polymer matrix. In some embodiments, the polymer matrix comprises a hydrogel.

Another aspect of the present disclosure provides a method of obtaining a transcriptome of a biological component. The method may comprise (a) forming a polymer matrix on or adjacent to the biological component to form an analysis chamber; and (b) performing one or more reactions in the analysis chamber to obtain the transcriptome of the biological component. In some embodiments, the biological component remains in or substantially in the analysis chamber during performance of the one or more reactions.

In some embodiments, the method further comprises coupling the biological component to a capture element disposed in a fluidic device to yield a coupled biological component. In some embodiments, the method further comprises providing energy from an energy source to the fluidic device to form the polymer matrix. In some embodiments, the energy is provided selectively using a spatial energy modulating element. In some embodiments, the spatial energy modulating element is generated based on a location of the biological component. In some embodiments, the spatial energy modulating element comprises a physical photomask, a virtual photomask, a physical electrode distribution pattern, a virtual electrode distribution pattern, a photolithographic mask, or a digital micromirror device (DMD) mask.

In some embodiments, the biological component comprises RNA. In some embodiments, the RNA is from 50 bases to 100 kb (kilobase bases). In some embodiments, the polymer matrix comprises pores that are sized to allow diffusion of a reagent through the polymer matrix but are too small to allow the RNA to traverse the pores. In some embodiments, the one or more reactions comprise RNA sequencing.

Another aspect of the present disclosure provides a method of analyzing two or more biological components. The method may comprise (a) introducing a first biological component and a second biological component into a fluidic device; (b) forming a polymer matrix on or adjacent to the first biological component to form a first analysis chamber and forming a polymer matrix on or adjacent to the second biological component to form a second analysis chamber; and (c) analyzing one or more features of the first biological component and the second biological component. In some embodiments, the first analysis chamber is adjacent to the second analysis chamber in the fluidic device. In some embodiments, the one or more features comprise a first feature and a second feature. In some embodiments, (c) comprises analyzing the first feature and the second feature of the first biological component in the first analysis chamber.

In some embodiments, the first biological component remains in the first analysis chamber between analysis of each of the first feature and the second feature. In some embodiments, the one or more features comprises a response to an analyte, a response to a pharmaceutical agent, a response to an antimicrobial agent, production of a target compound, production of a target molecule, production of a nucleic acid, or production of a protein. In some embodiments, the first biological component is in biological communication with the second biological component. In some embodiments, the biological communication generates a biological response in the first biological component or in the second biological component. In some embodiments, the biological communication comprises a molecule comprising a protein, a nucleic acid, a cytokine, a chemokine, or a combination thereof, generated by the first biological component or by the second biological component.

Another aspect of the present disclosure provides a method for identifying a nucleic acid molecule. The method may comprise providing a polymer matrix comprising the nucleic acid molecule, and detecting the nucleic acid molecule in absence of nucleic acid amplification.

In some embodiments, the nucleic acid molecule is a deoxyribonucleic acid (DNA) molecule.

In some embodiments, the polymer matrix forms a chamber localizing the nucleic acid. In some embodiments, the chamber is formed on demand. In some embodiments, the polymer matrix is degraded on demand. In some embodiments, the DNA is 100 base pairs or greater. In some embodiments, the nucleic acid is a ribonucleic acid molecule (RNA). In some embodiments, the RNA is 50 nucleotides or greater. In some embodiments, the method further comprises generating a nucleic acid library from the biological component within the chamber. In some embodiments, the nucleic acid library is sequenced within the chamber.

Another aspect of the present disclosure provides method for processing a biological component. The method may comprise determining a genome sequence, a transcriptome, a proteome, or an epigenome in absence of nucleic acid amplification. In some embodiments, the processing is performed in a single microfluidic device. In some embodiments, the cell is at least partially within a polymer matrix. In some embodiments, the polymer matrix is degraded on demand. In some embodiments, the method further comprises determining methylation in the cell.

Another aspect of the present disclosure provides a method comprising identifying a plurality of nucleic acid molecules of a plurality of cells without barcoding individual nucleic acid molecules of the plurality of nucleic acid molecules. In some embodiments, extracting the plurality of nucleic acid molecules and identifying are performed in a single microfluidic device.

In some embodiments, the identifying comprises sequencing. In some embodiments, the method further comprises forming a polymer matrix on or adjacent to individual cells of the plurality of cells such that the individual cells are separated from one another. In some embodiments, the method further comprises extracting the individual nucleic acid molecules the individual cells. In some embodiments, the sequencing comprises sequencing the individual nucleic acid molecules within the polymer matrix. In some embodiments, the sequencing comprises next-generation sequencing, short-read sequencing, nanopore sequencing, sequencing by synthesis, sequencing by in-situ hybridization, or an optical readout.

Another aspect of the present disclosure provides a method comprising (a) providing a plurality of nucleic acid molecules within a plurality of matrices; and (b) sequencing the plurality of nucleic acid molecules while the plurality of nucleic acid molecules is within the plurality of matrices. In some embodiments, individual nucleic acid molecules of the plurality of nucleic acid molecules are from different cells. In some embodiments, the plurality of matrices is disposed in a fluidic device. In some embodiments, the plurality of matrices comprises a plurality of cells. In some embodiments, the plurality of cells comprises the plurality of nucleic acid molecules. In some embodiments, the sequencing comprises next-generation sequencing, short-read sequencing, nanopore sequencing, sequencing by synthesis, sequencing by in-situ hybridization, or an optical readout.

Another aspect of the present disclosure provides a method of analyzing a biological component. The method may comprise (a) introducing one or more biological components into a fluidic device; (b) disposing a first portion of the one or more biological components adjacent a first surface of the fluidic device; and (c) forming one or more polymer matrices adjacent a first portion of the first surface to localize at least one of the one or more biological component to the first portion. In some embodiments, the method further comprises: (d) agitating the one or more biological components within the fluidic device; (e) disposing a second portion of the one or more biological components adjacent the first surface of the fluidic device; and (f) forming one or more polymer matrices adjacent a second portion of the first surface to immobilize at least one of the one or more biological component of the second portion. In some embodiments, the method further comprises identifying a position of at least one of the one or more biological components such that at least one energy source supplies energy to the fluidic device to form the one or more polymer matrices on or adjacent the identified position.

Another aspect of the present disclosure provides a system comprising a fluidic device. The fluidic device may comprise a flow channel, an analysis channel disposed adjacent to the flow channel, a layer disposed between the flow channel and the analysis channel, and at least one energy source in communication with the fluidic device. In some embodiments, at least one flow inhibition element is disposed within the flow channel to inhibit flow of a biological component. In some embodiments, the layer comprises at least one sealable aperture disposed adjacent the at least one flow inhibition element. In some embodiments, the at least one sealable aperture is configured to allow passage of the biological component. In some embodiments, the at least one energy source is configured to form a polymer matrix within the analysis channel.

In some embodiments, a portion of the flow channel is substantially parallel with a portion of the analysis channel. In some embodiments, the at least one sealable aperture is configured to transition from a sealed state to an open state. In some embodiments, passage of the biological component through the at least one sealable aperture is inhibited in the sealed state. In some embodiments, passage of the biological component through the at least one sealable aperture is inhibited in the sealed state. In some embodiments, when the at least one sealable aperture is in the sealed state, the at least one sealable aperture is sealed with at least one of an agarose gel, a temperature-soluble polymer, an N-isopropylacrylamide (NIPAAm) polymer, a wax compound, or an alginate.

In some embodiments, the flow channel comprises a surface disposed opposite of a flow channel surface of the layer. In some embodiments, at least one of the at least one inhibition elements extends from the surface toward the flow channel surface such that flow of the biological component in the flow channel is inhibited by the at least one inhibition element. In some embodiments, the analysis channel comprises a surface disposed opposite of the analysis channel surface of the layer. In some embodiments, the flow channel is removably couplable to the analysis channel. In some embodiments, the surface of the analysis channel comprises one or more barcodes. In some embodiments, the barcode comprises an oligonucleotide.

In some embodiments, the polymer matrix is coupled to at least one of the surface of the analysis channel or the analysis channel surface of the layer. In some embodiments, the polymer matrix extends from the surface of the analysis channel to the analysis channel surface of the layer such that the polymer matrix surrounds at least a portion of the biological component.

In some embodiments, the at least one energy source is in at least one of optical communication, electrochemical communication, electromagnetic. communication, thermal communication, or microwave communication with the fluidic device. In some embodiments, the at least one energy source. comprises a light generating device, a heat generating device, an electrochemical generating device, an electrode, or a microwave device.

In some embodiments, the biological component comprises a plurality of biological components.

In some embodiments, the fluidic device is a microfluidic device or a nanofluidic device. In some embodiments, the fluidic device comprises a sequencing flow cell. In some embodiments, the fluidic device is used for nucleic acid sequencing. In some embodiments, the biological component comprises a cell, a nucleic acid, a microbiome, a protein, a combination of cells, a spatially-linked biological component, or a metabolite. In some embodiments, the cell is an animal cell (e.g., a human cell), a plant cell, a fungal cell, a bacterial cell, a tumor spheroid, or a combination thereof. In some embodiments, the nucleic acid is DNA of 100 base pairs or greater or RNA of 50 bases or greater.

In some embodiments, the polymer matrix comprises a hydrogel. In some embodiments, the fluidic device further comprises one or more polymer precursors. In some embodiments, the one or more polymer precursors comprise hydrogel precursors. In some embodiments, the polymer matrix comprises a polymer matrix wall having a width of at least 1 µm. In some embodiments, the polymer matrix inhibits passage of the biological component. In some embodiments, the polymer matrix wall is a hydrogel wall. In some embodiments, the polymer matrix is degradable. In some embodiments, the degradation of the polymer matrix is "on demand." In some embodiments, the polymer matrix is degradable by at least one of (i) contacting the polymer matrix with a cleaving reagent; (ii) heating the polymer matrix to at least 90° C.; or (iii) exposing the polymer matrix to a wavelength of light that cleaves a photo-cleavable crosslinker that crosslinks the polymer of the polymer matrix.

In some embodiments, the sealable aperture is transitioned to the open state by at least one of: (i) contacting the sealable aperture with a cleaving reagent; (ii) heating the sealable aperture to at least 90° C.; or (iii) exposing the sealable aperture to a wavelength of light that cleaves a photo-cleavable crosslinker that crosslinks the polymer of the sealable aperture. In some embodiments, the polymer matrix comprises a hydrogel. In some embodiments, the cleaving reagent is configured to degrade the polymer matrix. In some embodiments, the cleaving reagent comprises a reducing agent, an oxidative agent, an enzyme, a pH based cleaving reagent, or a combination thereof. In some embodiments, the cleaving reagent comprises dithiothreitol (DTT), tris(2-carboxyethyl)phosphine (TCEP), tris(3-hydroxy propyl)phosphine (THP), or a combination thereof.

In some embodiments, the polymer matrix allows passage of a reagent. In some embodiments, the polymer matrix comprises pores. In some embodiments, a size of the pores are controlled by changing a composition of the one or more polymer precursors, the at least one energy source, or a combination thereof.

In some embodiments, the reagent comprises at least one of enzymes, chemicals, oligonucleotides, or primers having a size of less than 50 base pairs. In some embodiments, the reagent comprises lysozyme, proteinase K, random hexamers, polymerase, transposase, ligase, catalyzing enzyme, deoxynucleotide triphosphates, buffers, cell culture media, or divalent cations.

In some embodiments, the polymer matrix comprises pores that are sized to allow diffusion of a reagent through the matrix but are too small to allow DNA or RNA to traverse the pores. In some embodiments, the polymer matrix comprises a hydrogel. In some embodiments, the hydrogel comprises polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly (lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetraacrylate, or combinations or mixtures thereof. In some embodiments, the hydrogel comprises an enzymatically degradable hydrogel, PEG-thiol/PEG-acrylate, acrylamide/N,N'-bis(acryloyl)cystamine (BACy), or PEG/PPO.

In some embodiments, the surface comprises one or more barcodes. In some embodiments, the surface of the analysis channel comprises one or more compounds configured to bind the biological component. In some embodiments, the surface of the analysis channel is functionalized with a surface polymer. In some embodiments, the surface polymer is functionalized with an oligonucleotide, an antibody, a cytokine, a chemokine, a protein, an antibody derivative, an antibody fragment, a carbohydrate, a toxin, an aptamer, or any combination thereof. In some embodiments, a surface of the polymer matrix is functionalized with an oligonucleotide, an antibody, a cytokine, a chemokine, a protein, an antibody derivative, an antibody fragment, a carbohydrate, a toxin, an aptamer, or any combination thereof. In some embodiments, the surface polymer comprises polyethylene glycol (PEG), a silane polymer, pyridinecarboxaldehyde (PCA), an acrylamide, an agarose, or a combination thereof.

In some embodiments, the system further comprises a detector for identifying the one or more of the biological components, the one or more barcodes, or a combination thereof. In some embodiments, the detector comprises a camera. In some embodiments, the system further comprises a stage that holds the fluidic device. In some embodiments, the system further comprises a sequencing device for obtaining sequencing data.

In some embodiments, the system further comprises a spatial energy modulating element to selectively supply the energy to the fluidic device. In some embodiments, the spatial energy modulating element comprises a physical photomask, a virtual photomask, a physical electrode distribution pattern, a virtual electrode distribution pattern. In some embodiments, the spatial energy modulating element comprises a photolithographic mask or a digital micromirror device (DMD) mask.

Another aspect of the present disclosure provides a method of analyzing a biological component. The method may comprise (a) introducing the biological component into a flow channel of a fluidic device; (b) inhibiting flow of the biological component adjacent to an inhibition element; (c) disposing the biological component from the flow channel to an analysis channel of the fluidic device; and (d) forming a polymer matrix on or adjacent to the biological component in the analysis channel either before or after the disposition of the biological component in the analysis channel. In some embodiments, a sealable aperture is disposed adjacent to the inhibition element.

In some embodiments, prior to the disposing in (c), the sealable aperture is degraded using at least one of (i) contacting the sealable aperture with a cleaving reagent; (ii) heating the sealable aperture to at least 90° C.; or (iii) exposing the sealable aperture to a wavelength of light that cleaves a photo-cleavable crosslinker that crosslinks the polymer of the sealable aperture. In some embodiments, the method further comprises introducing one or more polymer precursors into the fluidic device. In some embodiments, forming the polymer matrix comprises supplying energy to the fluidic device to form the polymer matrix. In some embodiments, the energy is selectively supplied to one or more portions of the fluidic device. In some embodiments, the method further comprises activating a spatial energy modulating element to selectively supply the energy to the fluidic device. In some embodiments, the spatial energy modulating element comprises a physical photomask, a virtual photomask, a physical electrode distribution pattern, or a virtual electrode distribution pattern. In some embodiments, the spatial energy modulating element comprises a photolithographic mask or a digital micromirror device (DMD) mask. In some embodiments, the energy is supplied via light energy source, a heat energy source, an electrochemical energy source, or an electromagnetic energy source.

In some embodiments, the polymer matrix is coupled to a surface of the analysis channel. In some embodiments, the energy forms the polymer matrix around a portion of the coupled biological component. In some embodiments, at least a portion of the biological component is encapsulated by the polymer matrix. In some embodiments, an entirety of the biological component is encapsulated by the polymer matrix.

In some embodiments, the method further comprises encapsulating a first biological component to form a first analysis chamber and encapsulating a second biological component to form a second analysis chamber. In some embodiments, the first analysis chamber is adjacent to the second analysis chamber. In some embodiments, the first analysis chamber is disposed from 5 micrometer (µm) to 1,000 µm away from the second analysis chamber.

In some embodiments, the method further comprises analyzing the first biological component in the first analysis chamber and analyzing the second biological component in the second analysis chamber. In some embodiments, the method further comprises actuating a first reaction in the first biological component and actuating a second reaction in the second biological component. In some embodiments, the first reaction and the second reaction are different. In some embodiments, the method further comprises actuating a third reaction in the first biological component and actuating a fourth reaction in the second biological component. In some embodiments, the third reaction and the fourth reaction are different.

In some embodiments, the method further comprises obtaining a genome, transcriptome, proteome, epigenome, methylome, secretome, or metabolome of the biological component. In some embodiments, the transcriptome is a substantially full-length transcriptome.

In some embodiments, the transcriptome is a full-length transcriptome. In some embodiments, the method further comprises sequencing the biological component. In some embodiments, the sequencing does not comprise amplification of a sequencing library. In some embodiments, the method further comprises a barcode configured to be coupled to the biological component or a molecule produced by the biological component.

In some embodiments, the method further comprises exposing the biological component or the first biological component to an analyte. In some embodiments, the biological component comprises one or more microbes. In some embodiments, the analyte comprises an antimicrobial agent, a microbial growth promoting chemical, or a combination thereof. In some embodiments, the method further comprises screening the one or more microbes for susceptibility to the antimicrobial agent. In some embodiments, the analyte comprises a pharmaceutical agent.

In some embodiments, the method further comprises screening an effect of the pharmaceutical agent on the biological component. In some embodiments, the method further comprises screening the biological component for production of a target molecule. In some embodiments, the target molecule comprises at least one of an antibody, a cytokine, a chemokine, a protein, an antibody derivative, an antibody fragment, a carbohydrate, a toxin, or an aptamer.

In some embodiments, the method further comprises forming the polymer matrix around the biological component such that the biological component is disposed within a structure formed by the polymer matrix. In some embodiments, the method further comprises analyzing a local parameter in the first analysis chamber or the second analysis chamber. In some embodiments, a level of the local parameter in the first analysis chamber is different from a level of the local parameter in the second analysis chamber. In some embodiments, the local parameter comprise a pH, an oxygen concentration, or a CO2 concentration.

Another aspect of the present disclosure provides a non-transitory computer readable medium comprising machine executable code that, upon execution by one or more computer processors, implements any of the methods above or elsewhere herein.

In some embodiments, the invention provides a method of analyzing one or more biological components, such as mammalian cells, of a biological sample comprising the following steps: (a) providing a fluidic device having (i) a channel with an inlet and an outlet, the channel being bounded by a first wall having a first surface and a second wall having a second surface wherein the first and second walls are disposed opposite one another across the channel, (ii) a spatial energy modulating element disposed adjacent to the first wall, the spatial energy modulating element being capable of projecting energy across the channel with predetermined beam characteristics; (b) loading the channel with a reaction mixture comprising a biological sample and one or more polymer precursors; (c) synthesizing one or more chambers in the channel around each of one or more biological components by projecting energy across the channel such that the projected energy cross-links the one or more polymer precursors to form polymer matrix walls of the chambers. In some embodiments, the channel is planar in shape with width and breadth being large with respect to its height. The cross-section of the channel perpendicular to the direction of reagent flow is typically rectangular. Reaction mixtures or other reagents, e.g. wash solutions, and the like, are loaded into the channel through an inlet and are removed through an outlet. In some embodiments, such reagents or mixtures may be pumped through the inlet and into the channel, for example, using a syringe pump. In some embodiments, an outlet may be a vent port for air from the channel to escape whenever a reagent is loaded into the channel by way of the inlet, thereby displacing air.

In some embodiments, the invention provides a method of analyzing one or more biological components, such as mammalian cells, of a biological sample comprising the following steps: (a) providing a fluidic device having (i) a channel, the channel being bounded by a first wall having a first surface, (ii) a spatial energy modulating element disposed adjacent to the first wall, the spatial energy modulating element being capable of projecting energy across the first wall into the channel with predetermined beam characteristics; (b) loading the channel with a reaction mixture comprising a biological sample and one or more polymer precursors; (c) synthesizing one or more chambers in the channel around each of one or more biological components by projecting energy into the channel such that the projected energy cross-links the one or more polymer precursors to form polymer matrix walls of the chambers. This embodiment is sometimes referred to herein as an "open configuration" of the system of the invention. In some open configuration embodiments, the chambers comprise wells or containers which are open at the top. In some embodiments, the top of a well or container is opposite a first surface.

In some embodiments, the fluidic device of the method further comprises a detector disposed adjacent to the second wall or opposite the first wall from the spatial energy modulating element in open configuration embodiments. The detector is positioned so that it is capable of detecting optical signals from one or more biological components, such as mammalian cells, distributed over the first surface in chambers. In some embodiments, the first and second walls each comprise optically transmissive material, for example, so that a spatial energy modulating element may project light energy to the interior of the channel, and so that a detector may detect optical signals, such as fluorescent emissions or reflected light from biological components. In some embodiments, the projected energy from the spatial energy modulating element is a light energy from a light beam. In some embodiments, the light beam projected by the spatial energy modulating element may have a complex cross-section that permits (in various embodiments) the simultaneous synthesis of a plurality of chambers. Optically transmissive materials include, but are not limited to, glass, quartz, plastic, and like materials.

In some embodiments, the step of synthesizing chambers includes positioning the chambers so that they encapsulate the one or more biological components based on the optical signals detected by the detector. That is, in some embodiments, the detector is operationally associated with the spatial energy modulating element to selectively project one or more light beams to locations where detected optical signals indicate the presence of biological components of interest. In such embodiments, the detector and spatial energy modulating element are operationally associated so that the spatial energy modulating element is configured to generate an energy beam having predetermined beam characteristics. For example, one such characteristic may be a beam cross-section which results in the biological components of interest being encapsulated by chambers. In such operational association, optical signals detected by the detector may include, but is not limited to, morphology of biological components, for example, cell morphology; motility of biological components, such as cells; interaction of one cell type with another cell type, such as binding of one cell type to another cell type; a presence, absence or quantity of a label on the biological component, or the like.

In some embodiments, when chambers are formed or synthesized the polymer matrix walls of the chambers extend from the first surface to the second surface to form chambers each having an interior. In other embodiments, a fluidic device may not have a second wall with a second surface, which is referred to herein as an "open configuration." In such embodiments, chambers form open cylinder or well shapes on the first surface. The height and thickness of the well walls are determined in part by the intensity and duration of photo-illumination by the spatial energy modulating element. In some embodiments, predetermined beam characteristics comprise a beam having an annular-like cross-section. In other embodiments, predetermined beam characteristics comprise a beam having a cross-section comprising a plurality of annular-like shapes, which may be isolated and noncontiguous, or which may include contiguous annular-like shapes. In other embodiments, predetermined beam characteristics comprise a beam that generates a plurality of chambers wherein a portion of the chambers share polymer matrix walls with one or more other chambers of the plurality, such as shown in FIG. 25B.

In some embodiments, the step of loading may further include a step of agitating reaction mixture, for example, by vibrating, shaking or agitating the channel, to reduce aggregation of the biological components. Such agitation may be for a few minutes, e.g. 1-30 minutes, to an hour or more, e.g. 1-2 hours.

In some embodiments, the first or second surface, usually the first surface, includes one or more capture elements for specifically capturing one or more predetermined biological components of said biological sample, for example, selected cells, such as lymphocytes, or the like. In some embodiments, the step of loading may include incubating the reaction mixture containing such predetermined biological components under conditions to permit the one or more capture elements to capture the one or more predetermined biological components. Such incubation may be for a few minutes to an hour or more. In some embodiments, such incubation time may be in the range of from 1 minute to 10 hours, or from 10 minutes to 2 hours, or from 30 minutes to 2 hours.

In some embodiments, the method of the invention includes removing the reaction mixture from the channel after the step of synthesizing the chambers is completed. Such removing may include washing the channel with a buffer solution.

In some embodiments, the method of the invention, after chambers are formed, includes a step of loading said channel analytical assay reagents for determining one of more characteristics of said biological components encapsulated in said chambers, wherein the analytical assay reagents are capable of passing through said polymer matrix walls and are capable of generating one or more optical signals indicative of the one or more characteristics. A wide variety of analytical assays may be performed, as indicated else where in the present application, including RNA or DNA identification and/or sequencing, protein identification and/or quantification, omics assays, or the like.

In some embodiments, the polymer matrix walls of chambers are degradable by treating the chambers with a degradation agent. In such embodiments, the method of the invention may include the further steps of (a) identifying one or more of said chambers having said biological components with selected characteristics based on said one or more optical signals generated from operation of the analytical assay reagents; (b) loading the channel with a second reaction mixture comprising second polymer precursors, wherein the second polymer precursors are capable of forming second polymer matrix walls which are nondegradable for at least one degradation agent; and (c) synthesizing second chambers encapsulating the identified chambers. In some such embodiments, the original chambers having degradable polymer matrix wall may be degraded by treatment with a degradation agent which leaves the second chambers intact, which permits the biological components of interest to be isolated.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Introduction

Figure 1:
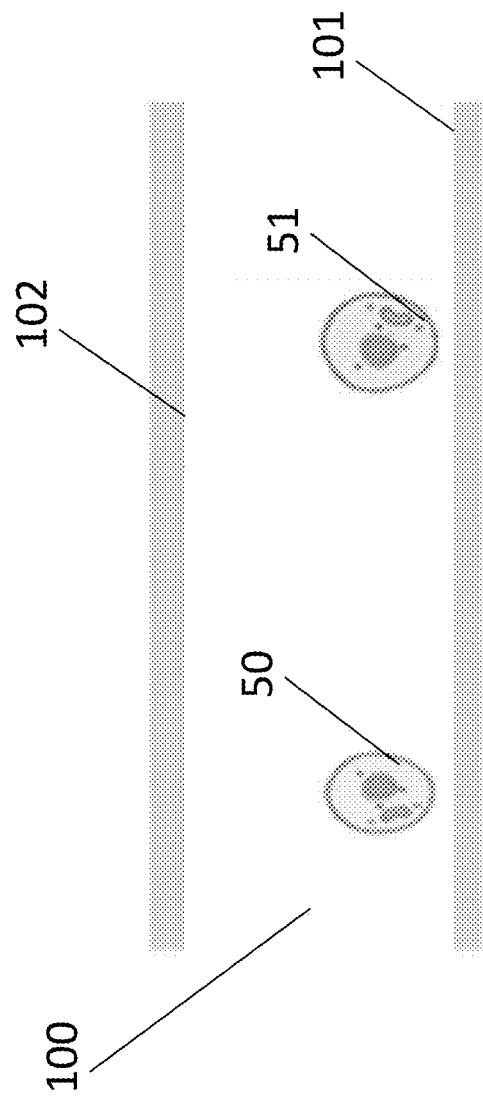
FIG. 1 shows a schematic illustration of a portion of a channel disposed in a fluidic device, according to some embodiments.

Analyzing biological samples on a level of a cell's physical properties, proteome, transcriptome, genome, epigenome, methylome, secretome, or metabolome can be performed on single cells or on a population of cells. For example, genetic material from a cell can be analyzed separately from, or in combination with, genetic materials from other cells. While analyzing components of a sample individually may generate data with higher resolution and less noise or cross-contamination, this approach can be costly and time consuming. On the other hand, analyzing a sample or a plurality of samples in bulk can be cost and time efficient but may generate undesired, or less desired, output (e.g., due to heterogeneity). For example, a particular datum may not be trackable to a source in the sample. A spatial association of the sample components may also be lost. For example, two components of a sample may be adjacent to one another in their biologically relevant state but after pooling a plurality of samples or components of a sample, the spatial information between the two components may be lost.

To avoid generating heterogenous samples, individual components of the sample may be compartmentalized. This can allow individual components of a sample to be processed simultaneously, or substantially simultaneously, while retaining spatial information intact and reducing processing steps. Additionally, by preventing cross-contamination and loss of material during extraneous sample processing, the generated data may be of higher quality (e.g., the data may have a higher signal to noise ratio as appropriate). Some methods may preserve spatial information by barcoding individual or groups of compartments in a sample. These methods may combine the barcoded components and may not perform multiple assays on the same component within a compartment or analysis chamber. Some of these methods may require nucleotide amplification steps that can introduce biases in the generated data.

In order to compartmentalize individual components of a biological sample, a polymer matrix (e.g., a hydrogel matrix) can be formed adjacent to or around at least of portion of an individual component in a fluidic device. The hydrogel matrix may be selectively generated to surround a component after the system detects the component or hydrogel matrices can be generated according to a predefined pattern in a fluidic device. The hydrogel matrix may allow reagents and smaller entities to pass while retaining the individual component of the biological sample in place. Because one or more individual components can be localized within a fluidic device (e.g., encapsulated) and the localized components be exposed to one or more reagents and/or washing solutions during and/or in between analyses, multiple assays can be performed within the compartments (e.g., simultaneously, substantially simultaneously, serially, etc.).

Different assays may be performed in different locations of the fluidic device, for example, to test effects of different treatment conditions. Additionally, because components are not generally mixed and combined, low concentrations of components (e.g., due to dilution) can be prevented. For example, when analyzing genomic material, an amplification step can be avoided due to the preservation of the genetic material in each compartment. By having two or more components within a compartment, interactions between components can be studied as well. The polymer matrix can be degradable "on demand" allowing for controlled localization and release mechanisms. The solutions provided herein can retain spatial information of the components and generate data on a cellular, proteomic, transcriptomic, or genomic level. Since spatial information is retained, the data can be associated (e.g., linked) with phenotypic data. Further, the solutions provided herein can retain spatial information of the components and link data (e.g., phenotypic data) on a cellular, proteomic, transcriptomic, or genomic level.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least" precedes the first numerical value in a series of two or more numerical values, the term "at least" applies to each of the numerical values in that series of numerical values. For example, at least 1, 2, or 3 is equivalent to at least 1, at least 2, or at least 3.

Whenever the term "less than" precedes the first numerical value in a series of two or more numerical values, the term "less than" applies to each of the numerical values in that series of numerical values. For example, less than 3, 2, or 1 is equivalent to less than 3, less than 2, or less than 1.

The terms "coupled to," "connected to," and "in communication with," as used herein, generally refer to any form of interaction between two or more entities, including mechanical, electrical, magnetic, electromagnetic, fluid, biological, and thermal interaction. Two components may be coupled to each other even though they are not in direct contact with each other.

The terms "polypeptide" and "peptide," as used interchangeably herein, generally refer to a polymer of amino acids in which an amino acid may be linked to another amino acid by a peptide bond. In some examples, a polypeptide is a protein. The amino acid may be a naturally occurring amino acid or a non-naturally occurring amino acid (e.g., an amino acid analogue). The polypeptide can be linear or branched. The polypeptide can include modified amino acids. The polypeptide may be interrupted by non-amino acids. A polypeptide can occur as a single chain or an associated chain. The polypeptide may include a plurality of amino acids. The polypeptide may have a secondary and tertiary structure (e.g., the polypeptide may be a protein). In some examples, the polypeptide can comprise at least 2, 3, 4, 5, 6, 7, 8, 9, 10, 20, 30, 40, 50, 100, 1,000, 10,000, or more amino acids. The polypeptide may be a fragment of a larger polymer. In some examples, the polypeptide can be a fragment of a larger polypeptide, such as a fragment of a protein.

The term "amino acid," as used herein, generally refers to a naturally occurring or non-naturally occurring amino acid (e.g., an amino acid analogue). The non-naturally occurring amino acid may be an engineered or synthesized amino acid.

The term "sample," as used herein, generally refers to a chemical or biological sample containing a biological component. The biological component may comprise a cell, a nucleic acid, a microbiome, a protein, a combination of cells, a metabolite, a combination thereof, or any other suitable component of a biological sample. For example, a sample can be a biological sample including one or more cells. For another example, a sample can be a biological sample including one or more polypeptides. The biological sample can be obtained (e.g., extracted or isolated) from or include blood (e.g., whole blood), plasma, serum, urine, saliva, mucosal excretions, sputum, stool, and tears. The biological sample can be a fluid or tissue sample (e.g., skin sample). In some instances, the sample may be derived from a homogenized tissue sample (e.g., brain homogenate, liver homogenate, or kidney homogenate). In certain embodiments, the sample may include a specific type of cell (e.g., a neuronal cell, muscle cell, liver cell, or kidney cell). The sample may comprise or be acquired from a diseased cell or tissue (e.g., a tumor cell or a necrotic cell), In some embodiments, the sample may include or may be from a disease-associated inclusion (e.g., a plaque, a biofilm, a tumor, or a non-cancerous growth). In certain embodiments, the sample may include or may be obtained from a cell-free bodily fluid, such as whole blood, saliva, or urine. In various embodiments, the sample can include circulating tumor cells. In some cases, the sample may include or may be an environmental sample (e.g., soil, waste, or ambient air), industrial sample (e.g., samples from any industrial processes), or a food sample (e.g., dairy product, vegetable product, or meat product). The sample may be processed prior to loading into a microfluidic device. For example, the sample may be processed to purify a certain cell type or polypeptide and/or to include reagents.

As used herein, the term "polymer matrix" generally refers to a phase material (e.g., continuous phase material) that comprises at least one polymer. In some embodiments, the polymer matrix refers to the at least one polymer as well as the interstitial space not occupied by the polymer. A polymer matrix may be composed of one or more types of polymers. A polymer matrix may include linear, branched, and crosslinked polymer units. A polymer matrix may also contain non-polymeric species intercalated within its interstitial spaces not occupied by polymer chains. The intercalated species may be solid, liquid, or gaseous species. For example, the term "polymer matrix" may encompass desiccated hydrogels, hydrated hydrogels, and hydrogels containing glass fibers. A polymer matrix may comprise a polymer precursor, which generally refers to one or more molecules that upon activation can trigger or initiate a polymeric reaction.

A polymer precursor can be activated by electrochemical energy, photochemical energy, a photon, magnetic energy, or any other suitable energy. As used herein, the term "polymer precursor" includes monomers (that are polymerized to produce a polymer matrix) and crosslinking compounds, which may include photo-initiators, other compounds necessary or useful for generating polymer matrices, and the like.

As used herein, the term "physical photomask" generally refers to a physical structure having a plurality of apertures or holes through which light may be projected. Physical photomasks can be used to create hydrogel matrices as described herein by causing the polymer precursor solution to polymerize and forming three-dimensional structures that correspond to the pattern on the photomask. A physical photomask can be patterned with a specific layout or geometric pattern. A physical photomask may be adhered to the upper surface of a flow cell.

In some embodiments, as used herein, the term "local parameter" means a value of a parameter (such as, pH) in or immediately adjacent to a chamber formed by polymer matrix walls.

As used herein, the term "on demand" means an operation may be directed to individual, discrete, selected locations (e.g. a spatial location of polymer precursor solution; or a selected polymer matrix chamber). Such selection may be based on manual observation of optical signals or data collected by a detector, or such selection may be based on a computer algorithm operating on optical signals or data collected by a detector. Manual observation of optical signals or data collected by a detector can include either real-time detection or detection at a time period prior to modulating a unit of energy to polymerize polymer precursors or degrading a chamber. For example, a subset of chambers (all formed with photo-degradable polymer matrix walls) may be pre-selected for releasing and removing their contents based on position information and the values of optical signals from an analytical assay carried out in the chambers. The pre-selected chambers may be photo-degraded by selectively projecting a light beam of appropriate wavelength characteristics (for example, with the spatial energy modulating element) to degrade the polymer matrix walls of the pre-selected chambers. In another example, a plurality of chambers may be observed in real-time (e.g. via fluorescent microscopy) for detection of an analyte of interest and one or more chambers of the plurality of chambers is selected, in real-time, upon detection of the analyte of interest, for degradation.

As used herein, the terms "microfluidic" and "nanofluidic" in reference to devices are used interchangeably herein, each means an integrated system for capturing, moving, mixing, dispensing or analyzing small volumes of fluid, including samples (which, in turn, may contain or comprise cellular or molecular analytes of interest), reagents, dilutants, buffers, or the like. Generally, reference to "microfluidics" and "nanofluidics" denotes different scales in the size of devices and volumes of fluids handled. In some embodiments, features of a microfluidic device have cross-sectional dimensions of less than a few hundred square micrometers and have passages, or channels, with capillary dimensions, for example, having maximal cross-sectional dimensions of from about 500 µm to about 0.1 µm. In some embodiments, microfluidics devices have volume capacities in the range of from 1 µL to a few nL, e.g. 10-100 nL. Dimensions of corresponding features, or structures, in nanofluidics devices are typically from 1 to 3 orders of magnitude less than those for microfluidics devices. One skilled in the art would know from the circumstances of a particular application which dimensionality would be pertinent. In some embodiments, microfluidic or nanofluidic devices have one or more chambers, ports, and channels that are interconnected and in fluid communication and that are designed for carrying out one or more analytical reactions or processes, either alone or in cooperation with an appliance or instrument that provides support functions, such as sample introduction, fluid and/or reagent driving means, such as positive or negative pressure, acoustical energy, or the like, temperature control, detection systems, data collection and/or integration systems, and the like. In some embodiments, microfluidics and nanofluidics devices may further include valves, pumps, filters and specialized functional coatings on interior walls, e.g. to prevent adsorption of sample components or reactants, facilitate reagent movement by electroosmosis, or the like. Such devices may be fabricated as an integrated device in a solid substrate, which may be glass, plastic, or other solid polymeric materials, and may have a planar format for ease of detecting and monitoring sample and reagent movement, especially via optical or electrochemical methods. In some embodiments, such devices are disposable after a single use. The fabrication and operation of microfluidics and nanofluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437; Cao, "Nanostructures & Nanomaterials: Synthesis, Properties & Applications," (Imperial College Press, London, 2004); Haeberle et al, LabChip, 7: 1094-1110 (2007); Cheng et al, Biochip Technology (CRC Press, 2001); and the like.

As used herein, the term "analyte" generally refers to a discrete biological or chemical entity to be measured, detected, and/or distinguished using the methods and systems described herein. In some embodiments, an analyte may be a biological component as described herein.

Systems for Analysis of Biological Components

The present disclosure provides systems for compartmentalizing or isolating one or more biological components. The system can include a fluidic device containing or including one or more biological components. The fluidic device may contain or include one or more polymer precursors. In some cases, the fluidic device can comprise a first surface configured to couple or receive at least one of the one or more biological components to form a coupled biological component. The systems may also include at least one energy source, wherein the energy source is in communication with the fluidic device. In some embodiments, the energy source may be in optical communication with the fluidic device. In various embodiments, the at least one energy source may form a polymer matrix on or adjacent to at least a portion of the one or more biological components.

In some cases, a sample may be introduced of provided to the system. In certain cases, the sample may comprise one or more biological components. The system may be used to separate one or more biological components from one another. In various cases, the biological components may be physically separated. In some cases, the biological components may be in fluidic communication with one another. In certain cases, the biological components may be in chemical communication with one another. The system may be used for single-cell analysis. In some embodiments, the system may be used for single-cell analysis on a genome level. For example, the system may be used for genome sequencing. For another example, the system may be used for deoxyribonucleic acid (DNA) sequencing. The system may be used for DNA sequencing of cell-free DNA, whole genome sequencing, whole exome sequencing, targeted sequencing, or 16S sequencing. The system may be used for studying DNA tags attached to biomolecules of interest. The biomolecules may comprise proteins, metabolites, etc. In some cases, the DNA may be a nuclear DNA or a mitochondrial DNA. The system may be used for single-cell or bulk analysis on a transcriptome level. For example, the system may be used for ribonucleic acid (RNA) sequencing. For example, the system may be used for 3' or 5' gene expression analysis, immune repertoire study of a cell, or full-length mRNA analysis. In some embodiments, the system may be used for single-cell analysis on a proteome level. The system may be used for functional assay(s) of a biological component. The system may be used for studying surface proteins, secreted proteins, or metabolites of a biological component. In some cases, the system may be used to measure a quality of a biological component. In some cases, the measured quality may be the size or shape of a biological component. In some cases, the system may be used to study epigenomics, DNA methylation, or chromatin accessibility in a biological component. The system may be used for other suitable assays, experiments, and processes.

In certain embodiments, the system may be used for single-cell analysis on an indirect cell-cell interaction level. For example, an effect of one or more molecules produced from a first cell on a second cell can be analyzed using the system as provided herein. In various embodiments, the system may be used for analyzing direct cell-cell interactions. For example, two or more cells (e.g., a first cell and a second cell) can be in physical contact and the effect or effects of the first cell on the second cell, or vice versa, can be analyzed using the system as disclosed herein. In some embodiments, the system may be used for drug response analysis in a biological component. In certain embodiments, the system may be used for analyzing a biological component's response to various physiological conditions (e.g., various media, temperature, mechanical stimuli, etc.).

In some cases, the sample comprises a biological sample. The biological sample may comprise a biological component. In some embodiments, the biological sample may comprise 1, 2, 3, 4, 5, 6, 7, 8, 9, 10, 15, 20, 30, 40, 50, 100, 200, 300, 400, 500, 600, 700, 1,000, 10,000, 105, $10^6$, $10^7$, $10^8$, $10^9$, $10^{10}$, $10^{20}$, or more biological components. The biological sample may include any number of biological components between any of the two numbers mentioned herein. In some embodiments, the biological sample may comprise more than $10^{20}$ biological components. The biological component may comprise a cell. In some embodiments, the cell may comprise a eukaryotic cell, a prokaryotic cell, a fungal cell, a protozoan, an algal cell, a plant cell, an animal cell (e.g., a human cell), or any other suitable cell.

The biological component may comprise a cell, a virus, a bacterium, a nucleic acid (e.g., DNA, or RNA), a protein, or a combination thereof. The combination may comprise a DNA-protein complex, an RNA-protein complex, or a combination thereof. In certain embodiments, a nucleic acid may comprise DNA. The DNA may be at least 10 base pair (bp) long. In some embodiments, the DNA is at least 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp long, or longer than 800 bp.

Polymer precursors may be formed by using any hydrogel precursor and crosslinkers of Table 1A (columns 1 and 3, respectively). The resulting polymer matrices may be degraded with the indicated degradation agents in Table 1A (column 4).

TABLE 1A

| Precursors | Hydrogels | Crosslinkers | Degradation Agents |
|---|---|---|---|
| Acrylamide | Poly-acrylamide | Bis-acryloyl cystamine (structure 1) | DTT/TCEP/THP |
| PEG-based acryloyl | PEG | Bis(2-methacryloly)oxyethyl disulfide (structure 2) | DTT/TCEP/THP |
| Dextran-based acryloyl | Dextran | N,N'-(1,2-Dihydroxyl-ethylene)bis-acrylamide structure (3) | NaIO4 |
| Polysaccharide-base acryloyl | Poly-saccharide | Structure 4 | NaOH, ethanolamine DTT/TCEP/THP |
| Gelatin-base acryloyl | Gelatin | Structure 5 | NaOH, ethanolamine, nucleophilic bases |
| | | Structure 6 | NaOH, alkali, organic bases |
| | | Structure 7 | Acid |

TABLE 1B

| Structure Number | Structure |
|---|---|
| 1 | ![structure 1: N,N'-bis(acryloyl) cystamine - CH2=CH-C(O)-NH-CH2CH2-S-S-CH2CH2-NH-C(O)-CH=CH2] |
| 2 | ![structure 2: bis(2-methacryloyloxyethyl) disulfide] |
| 3 | ![structure 3: N,N'-(1,2-dihydroxyethylene)bisacrylamide - CH2=CH-C(O)-NH-CH(OH)-CH(OH)-NH-C(O)-CH=CH2] |

TABLE 1B-continued

| Structure Number | Structure |
|---|---|
| 4 | [structure: acrylamide-NH-CH2CH2-O-C(O)-CH2CH2-S-S-CH2CH2-C(O)-O-CH2CH2-NH-acrylamide] |
| 5 | [structure: acrylamide-NH-CH2CH2-O-C(O)-(CH2)3-C(O)-O-CH2CH2-NH-acrylamide] |
| 6 | [structure: acrylamide-NH-CH2CH2-S-(maleimide)-N-CH2CH2-N-(maleimide)-S-CH2CH2-NH-acrylamide] |
| 7 | [structure: acrylamide-NH-CH2CH2-O-C(CH3)2-O-CH2CH2-NH-acrylamide] |

In certain embodiments, one or more polymer precursors may be added to or included with the biological sample. One or more biological samples and one or more polymer precursors may be introduced into the system (e.g., into the fluidic device of the system). The one or more biological samples and the one or more polymer precursors may be introduced into the fluidic device in any order (e.g., in parallel, sequentially, etc.). For example, the biological sample(s) may be introduced prior to the polymer precursor(s), the polymer precursor(s) may be introduced prior to the biological sample(s), the biological sample(s) and polymer precursor(s) may be introduced simultaneously (or substantially simultaneously), or in any other suitable manner or order. In some embodiments, a polymer precursor may include one or more hydrogel precursors. The one or more polymer precursors may be stored and/or introduced separately into the system. In some cases, the one or more polymer precursors may be mixed with the one or more biological components prior to introduction into the system. In various cases, the one or more polymer precursors may be mixed with the one or more biological components after introduction into the system.

The system may comprise a fluidic device. In some embodiments, the fluidic device may include one or more polymer precursors. In other words, one or more polymer precursors may be disposed within at least a portion of the fluidic device (e.g., within at least a portion of a channel of the fluidic device). In some embodiments, the fluidic device may comprise one or more channels or chambers. In some embodiments, the fluidic device may include at least 1, 2, 3, 4, 5, 6, 7, 8, 9, 10, 15, 20, 30, 40, 50, 100, 200, 300, 400, 500, 600, 700, 1,000, 10,000 channels or chambers, or any number of channels or chambers between any of the two numbers mentioned herein. In some embodiments, the fluidic device comprises more than 10,000 channels or chambers. As described herein, the fluidic device may include one or more channels. The fluidic device may also, or alternatively, include one or more chambers. The terms channel and chamber may be used interchangeably in the disclosure herein unless indicated otherwise. For example, a channel or a chamber of the fluidic device may comprise a first surface, a second surface, or more surfaces.

A channel or chamber of a fluidic device (also sometimes referred to as a "flow chamber," or "reaction chamber," as opposed to a chamber that is formed from polymer matrix walls within a channel) may receive or be configured to receive a biological sample. FIG. 1 shows a schematic illustration of a portion of a channel 100 that may be disposed in at least a portion of a fluidic device of a system as provided herein. The fluidic device may comprise a channel 100. The channel 100 may comprise a first surface 101. Further, the channel 100 may comprise a second surface 102. In some embodiments, the first surface 101 and the second surface 102 are disposed, placed, or positioned opposite of one another (e.g., as depicted in FIG. 1). In some embodiments, the first surface and second surface are substantially parallel, so that the perpendicular distance between them is substantially the same throughout the channel, for example, where chambers are formed. In some embodiments, the perpendicular distance between a first surface and a second surface depends in part and the nature and size of the biological components to be analyzed. In some embodiments, such as, those adapted to analyzing mammalian cells, the perpendicular distance between a first surface and a second surface may be in the range of from 10 µm to 500 µm, or in the range of from 50 µm to 250 µm. In some embodiments, the perpendicular distance between a first surface and a second surface may be in the range of from twice the average size of the biological component to be analyzed to five times the average size of the biological component to be analyzed. In some embodiments, the perpendicular distance between a first surface and a second surface may be in the range of from twice the average size of the largest biological component in the biological sample to five times the average size of the largest biological component in the biological sample. In some embodiments, the first surface 101 may be a lower surface. In certain embodiments, the second surface 102 may be an upper surface. The terms "lower" and "upper" are not intended to be limiting and are used herein for convenience when referring to the figures. The channel 100 may receive a biological sample comprising one or more biological components 50, 51. The channel 100 may receive one or more polymer precursors. As illustrated in FIG. 1, the biological components 50, 51 may include cells. However, as discussed herein, the biological components may include tissues, proteins, nucleic acids, etc. In some embodiments, the first surface 101, the second surface 102, or both surfaces may couple or receive, or be configured to couple or receive, at least one of the one or more biological components 50, 51. In some cases, the first surface 101 may couple or receive, or be configured to couple or receive, a biological component (e.g., biological components 50, 51). In certain cases, the second surface 102 may couple or receive, or be configured to couple or receive, a biological component (e.g., biological components 50, 51).

In certain cases, a channel may have a rectangular, circular, semi-circular, oval cross-section, or other suitably shaped cross-section. Accordingly, the channel may have a single, internal surface. In some cases, a channel may have a triangular, square, rectangular, polygonal, or other cross-section. Accordingly, the channel may have three or more internal surfaces. One or more of the internal surfaces may be couple or receive, or be configured to couple or receive, the one or more biological components.

In some cases, the first surface 101, the second surface 102, or both surfaces 101, 102 may be functionalized, for example, with a coating (e.g., a surface coating). In some embodiments, the surface coating may be a surface polymer. Some non-limiting examples of surface coatings may include a capture reagent (e.g., pyridinecarboxaldehyde (PCA)), a functional group to capture one or more moieties (e.g., a chemical moiety), an acrylamide, an agarose, a biotin, a streptavidin, a strep-tag II, a linker, a functional group comprising an aldehyde, a phosphate, a silicate, an ester, an acid, an amide, an alkyne, an azide, an aldehyde dithiolane, or a combination thereof. In various embodiments, the surface coating may include a functional group to capture one or more moieties. For example, the acrylamide, the agarose, etc. may include such a functional group. In certain embodiments, the surface polymer may comprise polyethylene glycol (PEG), a thiol, an alkene, an alkyne, an azide, or combinations thereof. In various embodiments, the surface polymer may comprise a silane polymer. In some embodiments, the surface polymer may be functionalized with at least one of an oligonucleotide, an antibody, a cytokine, a chemokine, a protein, an antibody derivative, an antibody fragment, a carbohydrate, a toxin, or an aptamer.

In some cases, the first surface 101, the second surface 102, or both surfaces 101, 102 may comprise one or more barcodes (e.g., nucleic acid barcodes). In some embodiments, the first surface 101, the second surface 102, or both surfaces 101, 102 may comprise 1, 2, 3, 4, 5, 6, 7, 8, 9, 10, 15, 20, 30, 40, 50, 100, 200, 300, 400, 500, 600, 700, 1,000, 10,000, 50,000, 100,000, 250,000, 500,000, 1,000,000, 2,000,000, 5,000,000, 10,000,000, 15,000,000 barcodes, or any number of barcodes between any of the two numbers mentioned herein. The barcodes may cover an area of about 500 nm$^2$ to about 500 μm$^2$. In some embodiments, the first surface 101, the second surface 102, or both surfaces 101, 102 may comprise at most about 10,000,000 total number of barcodes. The barcodes may be different from one another (e.g., each barcode may be unique). In certain embodiments, a first portion or subset of the barcodes may be different from a second portion or subset of the barcodes. There may be 2, 3, 4, 5, 10, 15, 20, 25, 50, 75, 100, 1,000, 10,000 portions or subsets of the barcodes, or any number of portions or subsets of the barcodes between any of the two numbers mentioned herein. In some cases, a barcode (or a portion/subset of barcodes) may be associated with the location of the barcode on a surface (location coordinates (e.g., x-, y-coordinates) on a surface of a channel). A barcode may be attached to or coupled to the captured biological component. In some embodiments, the barcode may be a unique identifier that distinguishes a biological component from other biological components (e.g., that identifies a first biological component versus a second biological component). In some embodiments, a barcode may comprise a nucleic acid sequence (e.g., common sequence) to capture a biological component, or used in amplification. In some embodiments, a barcode may comprise a unique identifier comprising a unique nucleic acid sequence (e.g., DNA sequence, RNA sequence, etc.), protein tag, antibody, or an aptamer. In some embodiments the barcode may comprise a fluorescent molecule. In some embodiments, a location of the captured biological component may be associated with the unique identifier to, for example, retain spatial information of a biological component.

In some embodiments, the fluidic device may be a flow cell. For example, the fluidic device may be used for sequencing (e.g., DNA or RNA sequencing). In some embodiments, the fluidic device may be a microfluidic device. In certain embodiments, the fluidic device may be a nanofluidic device.

The system disclosed herein may comprise one or more energy sources. The energy source may be in communication with the fluidic device. In some embodiments, the energy source may be in optical communication with the fluidic device. In some cases, the energy source can be used to form one or more polymer matrices in the fluidic device (e.g., on or adjacent to a surface of a channel or chamber of the fluidic device). In some embodiments, the energy source may comprise a light generating device, a heat generating device, an electrochemical reaction generating device, an electrode, or a microwave device. A polymer matrix may be formed in a channel of the fluidic device. The energy source may direct or transfer energy to a predetermined position in the fluidic device. The energy may cause or activate the one or more polymer precursors to form a polymer matrix (e.g., to polymerize) in the predetermined position.

In some embodiments, the polymer matrix may comprise a hydrogel. In some embodiments, the hydrogel may be porous enough, or have pores of a suitable size, to allow movement or transfer of a reagent (e.g., an enzyme, a chemical compound, a small molecule, an antibody, etc.) through the polymer matrix, while the hydrogel may not allow movement or transfer of the biological component (e.g., DNA, RNA, a protein, a cell, etc.) through the polymer matrix. In some embodiments, the pores may have a diameter from 5 nm to 100 nm. In some embodiments, the pores may have a diameter from 5 nm to 10 nm, 10 nm to 20 nm, 20 nm to 30 nm, 30 nm to 40 nm, 50 nm to 60 nm, 60 nm to 70 nm, 70 nm to 80 nm, 80 nm to 90 nm, 90 nm to 100 nm. In some embodiments, the pores may have a diameter larger than 100 nm. In some embodiments, the pores may have a diameter smaller than 5 nm. The reagent may comprise an enzyme or a primer having a size of less than 50 base pairs (bp). A primer may comprise a single-stranded DNA (ssDNA). In some embodiments, a primer may have a size from 5 bp to 50 bp. In some embodiments, a primer may have a size from 5 bp to 10 bp, 10 bp to 20 bp, from 20 bp to 30 bp, 30 bp to 40 bp, or 40 bp to 50 bp. In some embodiments, a primer may have a size of more than 50 bp. In certain cases, a primer may have a size of less than 5 bp. A reagent may comprise a lysozyme, a proteinase K, hexamers (e.g., random hexamers), a polymerase, a transposase, a ligase, a catalyzing enzyme, a deoxyribonuclease, a deoxyribonuclease inhibitor, a ribonuclease, a ribonuclease inhibitor, DNA oligos, deoxynucleotide triphosphates, buffers, detergents, salts, divalent cations, or any other suitable reagent.

In some embodiments, the one or more reagents flow through a membrane. In some embodiments, the membrane is semi-permeable. In some embodiments, the membrane comprises pores. In some embodiments, the pores are less than 1 micrometer wide. In some embodiments, the width of the pores is about 0.5 micrometers to about 15 micrometers. In some embodiments, the width of the pores is about 0.5 micrometers to about 1 micrometer, about 0.5 micrometers to about 5 micrometers, about 0.5 micrometers to about 10 micrometers, about 0.5 micrometers to about 15 micrometers, about 1 micrometer to about 5 micrometers, about 1 micrometer to about 10 micrometers, about 1 micrometer to about 15 micrometers, about 5 micrometers to about 10 micrometers, about 5 micrometers to about 15 micrometers, or about 10 micrometers to about 15 micrometers. In some embodiments, the width of the pores is about 0.5 micrometers, about 1 micrometer, about 5 micrometers, about 10 micrometers, or about 15 micrometers. In some embodiments, the width of the pores is at least about 0.5 micrometers, about 1 micrometer, about 5 micrometers, or about 10 micrometers. In some embodiments, the width of the pores is at most about 1 micrometer, about 5 micrometers, about 10 micrometers, or about 15 micrometers. In some embodiments, the one or more reagents is an enzyme, a drug molecule, oligonucleotide, primer, or any combination thereof. In some embodiments, the one or more reagents is a lysis reagent. In some embodiments, the one or more reagents is a nucleic acid denaturation reagent. In some embodiments, the one or more reagents degrades the polymer matrix.

Figure 22:
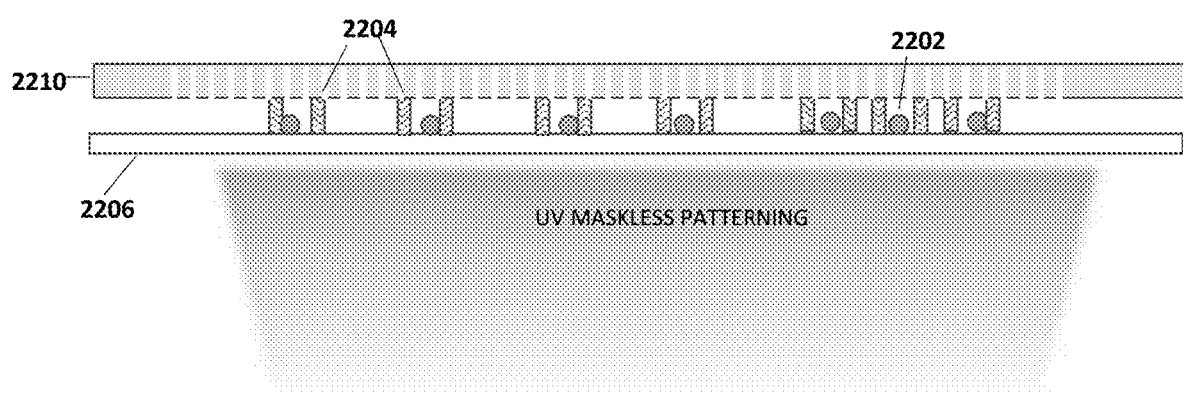
FIG. 22 shows a fluidic device with a porous membrane on top of the polymer matrices, according to some embodiments.
Figure 23:
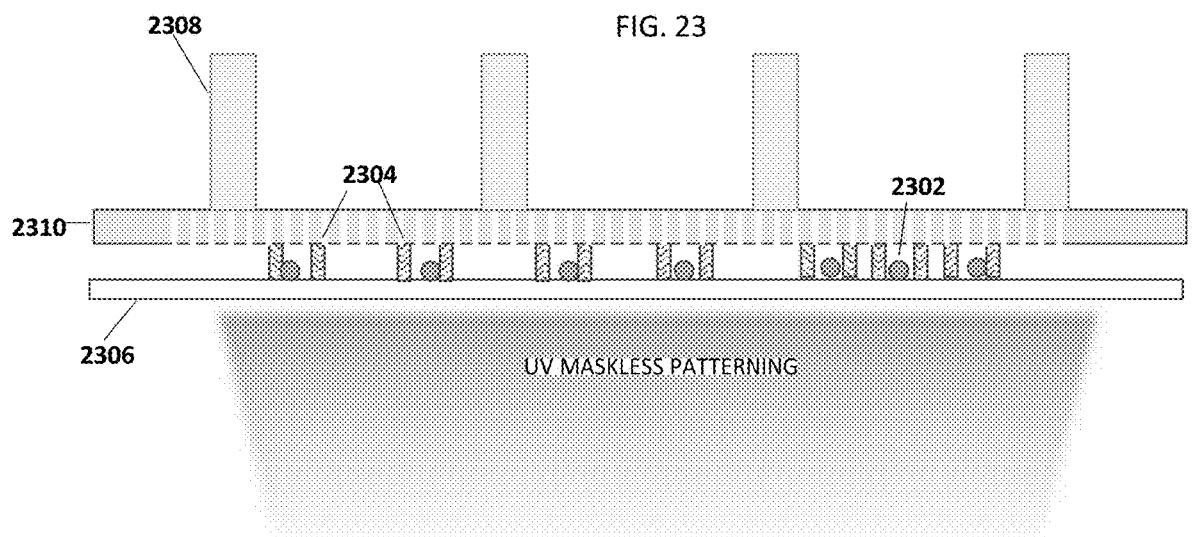
FIG. 23 shows a well plate with hydrogel traps inside the wells and a porous membrane on top of the polymer matrices, according to some embodiments.

FIG. 22 shows a fluidic device with a porous membrane 2210 on top. The biological components 2202 are encapsulated and/or localized on the surface of a fluidic device 2206 using polymer matrices 2204. Reagents that fit through the pores in the membrane 2210 can enter the polymer matrices and react with the biological component 2202. In some embodiments, as shown in FIG. 23, the polymer matrices 2304 and biological components 2302 are seeded on a well plate 2306, and a porous membrane 2310 sits on top of the polymer matrices 2304. Reagents that fit through the pores in the membrane 2310 can enter the polymer matrices and react with the biological component 2302. Due to the walls of the well 2308, there may be no fluidic communication between different wells, so different reagents can be used in each individual well.

Figure 2A:
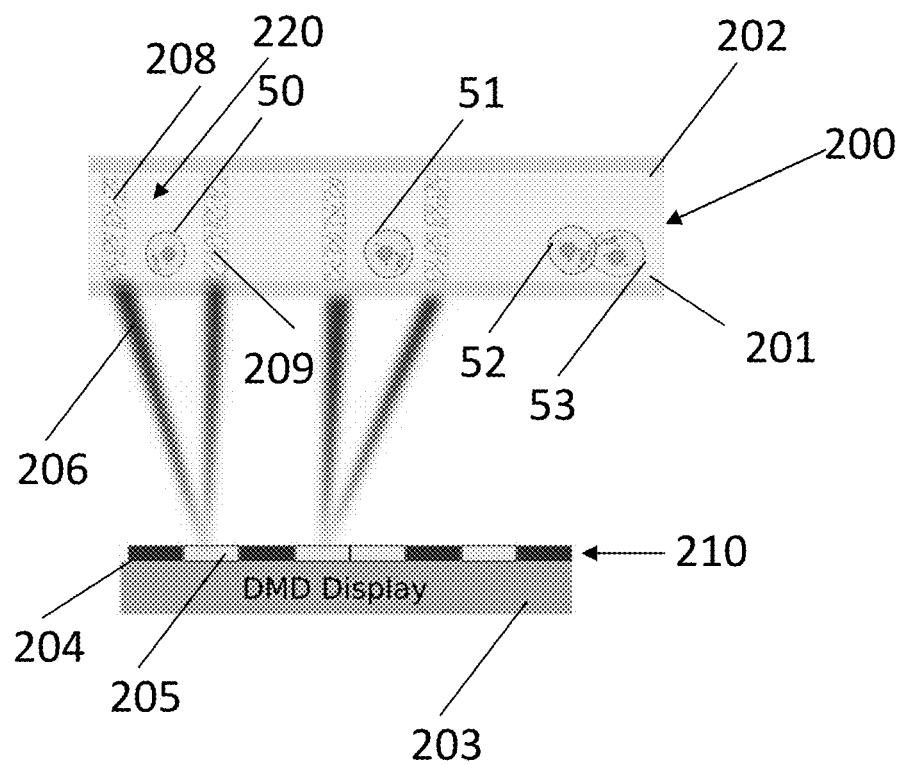
FIG. 2A shows a portion of a system as provided herein including an energy source, according to some embodiments.

FIG. 2A shows a portion of a system as provided herein including an energy source 203. The embodiment of FIG. 2A may include components that resemble components of FIG. 1 in some respects. For example, the embodiment of FIG. 2A includes a channel 200 that may resemble the channel 100 of FIG. 1. It will be appreciated that the illustrated embodiments may have analogous features. Accordingly, like features are designated with like reference numerals, with the leading digits incremented to "2." Relevant disclosure set forth above regarding similarly identified features thus may not be repeated hereafter. Moreover, specific features of the system provided herein, and related components shown in FIG. 2A may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system and related components of FIG. 2A. Any suitable combination of the features, and variations of the same, described with respect to the system and components illustrated in FIG. 1, can be employed with the system and components of FIG. 2A, and vice versa. This pattern of disclosure applies equally to further embodiments depicted in subsequent figures and described hereafter.

With continued reference to FIG. 2A, the channel 200 of the system may include a first surface 201 and a second surface 202. In some embodiments, the energy source 203 may comprise one or more energy emitting portions (e.g., an energy emitting portion 205). In some embodiments, the energy source 203 may comprise one or more non-emitting portions (e.g., a non-emitting portion 204). The non-emitting portion 204 may not emit, or be configured to emit, energy. In some embodiments, the emitting portion 205 can emit energy in the form of electromagnetic waves (e.g., microwaves, light, heat, etc.) to at least a portion of the fluidic device. In certain embodiments, the emitting portion 205 can emit energy to the fluidic device. In some embodiments, the fluidic channel may be coupled to on a movable stage. In other embodiments, light may be projected to or onto at least a portion of the fluidic channel to generate one or more polymer matrices. The light may be directed to various parts of the fluidic channel. In some embodiments, the emitting portion 205 may be coupled to an objective (e.g., a microscope objective or lens), where the objective may be moved to different portions of the fluidic device. The objective may provide a shape (e.g., virtual or physical mask) to allow light to form a pattern on the fluidic device, in order to form a polymer matrix similar or complementary to the pattern. In various embodiments, the one or more polymer precursors in the fluidic device or mixed with the biological sample can absorb emitted energy 206. In some embodiments, the emitted energy 206 can form, or be sufficient to form, a polymer matrix from the one or more polymer precursors. For example, a portion of the one or more polymer precursors within the channel 200 of the fluidic device may be activated by the emitted energy and a polymerization reaction may be initiated to form a polymer matrix.

In some embodiments, the energy source may emit energy to a larger portion of the fluidic channel or almost the entire surface of the fluidic channel. A physical mask may be used to block the energy emitted to one or more portions of the fluidic channel. The energy source (e.g., light source) may be coupled to the fluidic device via an objective (e.g., a microscope objective or lens). The energy source may be directed to a portion of the fluidic channel (e.g., via a movable objective). In some cases, the light source, the objective, and/or the fluidic channel are movable to allow emission of energy to the fluidic channel so as to generate a pattern on at least a portion of a surface of the fluidic device. The polymer matrix may be formed similarly or complementary to the pattern of energy emission.

A polymer precursor may comprise an activating molecule that can absorb the emitted energy 206 to initiate polymerization of the one or more polymer precursors in the fluidic device. Non-limiting examples of the activating molecule may include a photocatalyst, a photoactivator, a photoacid generator, or a photobase generator. In some embodiments, a first polymer matrix 208 and/or a second polymer matrix 209 can be formed on or adjacent to a biological component 50. In certain embodiments, the first polymer matrix 208 and the second polymer matrix 209 can form an analysis chamber or compartment 220 that separates (e.g., physically separates) the biological component 50 from other biological components (e.g., biological components 51, 52, or 53) in the fluidic device. Stated another way, the polymer matrix may compartmentalize the channel (e.g., channel 200). In various embodiments, the polymer matrix may partially surround a biological component. For example, a polymer structure surrounding a biological component may form a closed structure (e.g., a hollow cylinder-shaped polymeric structure) or a partially open structure (e.g., a crescent-shaped polymeric structure). In some embodiments, two or more polymer matrices may be formed adjacent to a biological component forming a compartment separating the biological component from other biological components. In certain embodiments, the polymer matrix may comprise or form a wall (e.g., a polymer matrix wall).

In various embodiments, the polymer matrix comprises a hydrogel. In some embodiments, the polymer matrix wall may be a hydrogel wall. In some embodiments, a hydrogel or hydrogel wall may comprise polyethylene glycol (PEG)-thiol, PEG-acrylate, acrylamide, N,N'-bis(acryloyl)cystamine (BAC), PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, dextran-acrylamide, hyaluronan, pectin, carrageenan, gelatin, chitosan, cellulose, collagen, bisacrylamide, diacrylate, diallylamine, triallylamine, divinyl sulfone, diethylene glycol diallyl ether, ethylene glycol diacrylate, polymethyleneglycol diacrylate, poly(ethyleneglycol) diacrylate, trimethylopropoane trimethacrylate, ethoxylated trimethylol triacrylate, ethoxylated pentaerythritol tetraacrylate, or combinations or mixtures thereof. A hydrogel or hydrogel wall may comprise a degradable cross-linker (e.g., N,N'-Bis(acryloyl) cystamine, chitosan, poly(ε-caprolactone) diacrylate, polylactide diacrylate, polylactide dimethacrylate, poly(lactide-co-glycolide, poly-caprolactone molecules, or other suitable degradable cross-linkers).

In some embodiments, the surface of the polymer matrix or hydrogel may be functionalized by coupling a functional group to the polymer matrix or hydrogel. Some non-limiting examples of functional group may include a capture reagent (e.g., pyridinecarboxaldehyde (PCA)), an acrylamide, an agarose, a biotin, a streptavidin, a strep-tag II, a linker, a functional group comprising an aldehyde, a phosphate, a silicate, an ester, an acid, an amide, an aldehyde dithiolane, PEG, a thiol, an alkene, an alkyne, an azide, or a combination thereof. In some cases, the functionalized polymer matrix may be used to capture biomolecules inside a polymer matrix compartment formed adjacent to (e.g., around or on) the biological component. The biomolecule may be produced by the biological component (e.g., secretome from a cell). The functionalized surface of the polymer matrix inside the compartment may be used to capture reagents or molecules from outside the compartment. The functionalized surface may increase surface area covered by a reagent, a molecular sensor, or any molecule of interest (e.g., an antibody).

In some embodiments, the compartment surrounding a biological component may comprise a polygon base. In various embodiments, the compartment surrounding a biological component may comprise a circular or oval base (see, e.g., the compartment 220 or the compartment 222 in FIG. 2C). In certain embodiments, the polymer matrix wall of the compartment may have a thickness (e.g., a width) from 1 μm to 250 μm. The polymer matrix wall may have a thickness from 1 μm to 250 μm. The polymer matrix wall or compartment may have a thickness from 1 μm to 5 μm, 1 μm to 10 μm, 1 μm to 20 μm, 1 μm to 30 μm, 1 μm to 40 μm, 1 μm to 50 μm, 1 μm to 100 μm, 1 μm to 150 μm, 1 μm to 250 μm, 5 μm to 10 μm, 5 μm to 20 μm, 5 μm to 30 μm, 5 μm to 40 μm, 5 μm to 50 μm, 5 μm to 100 μm, 5 μm to 150 μm, 5 μm to 250 μm, 10 μm to 20 μm, 10 μm to 30 μm, 10 μm to 40 μm, 10 μm to 50 μm, 10 μm to 100 μm, 10 μm to 150 μm, 10 μm to 250 μm, 20 μm to 30 μm, 20 μm to 40 μm, 20 μm to 50 μm, 20 μm to 100 μm, 20 μm to 150 μm, 20 μm to 250 μm, 30 μm to 40 μm, 30 μm to 50 μm, 30 μm to 100 μm, 30 μm to 150 μm, 30 μm to 250 μm, 40 μm to 50 μm, 40 μm to 100 μm, 40 μm to 150 m, 40 μm to 250 μm, 50 μm to 100 m, 50 μm to 150 m, 50 μm to 250 m, 100 μm to 150 μm, 100 μm to 250 μm, or 150 μm to 250 μm. The polymer matrix wall or compartment may have a thickness of about 1 μm, about 5 μm, about 10 μm, about 20 μm, about 30 μm, about 40 μm, about 50 μm, about 100 μm, about 150 μm, or about 250 μm. The polymer matrix wall or compartment may have a thickness of at least 1 μm, 5 μm, 10 μm, 20 μm, 30 μm, 40 μm, 50 μm, 100 μm, 150 μm, 250 μm, or more. The polymer matrix wall or compartment may have a thickness of at most 5 μm, 10 μm, 20 μm, 30 μm, 40 μm, 50 μm, 100 μm, 150 μm, or 250 μm. The polymer matrix wall or compartment may have a thickness of less than 1 μm.

Figure 2B:
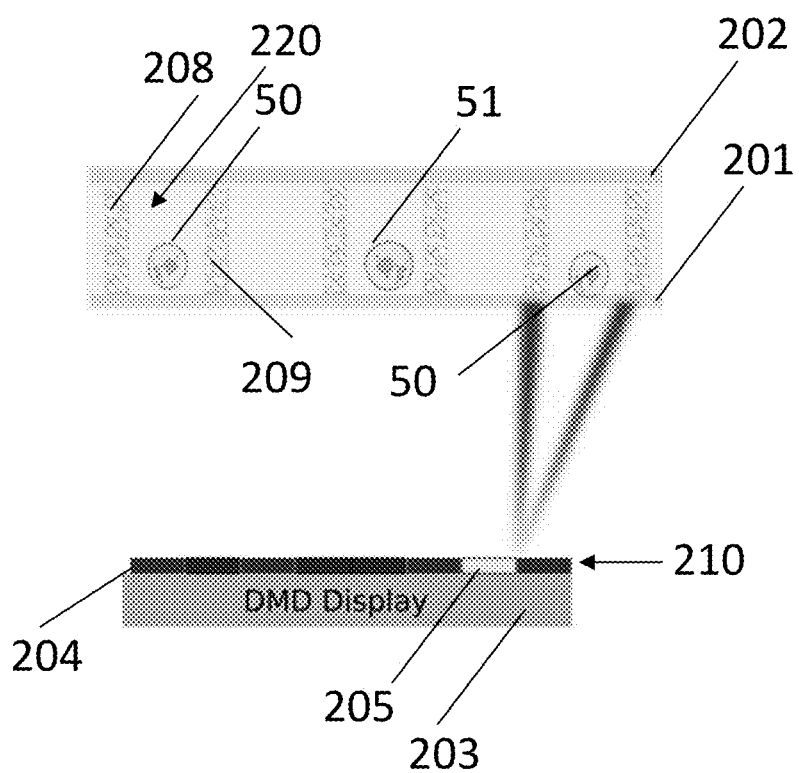
FIG. 2B shows a polymer matrix being formed around a biological component in a portion of a system as provided herein, according to some embodiments.
Figure 2C:
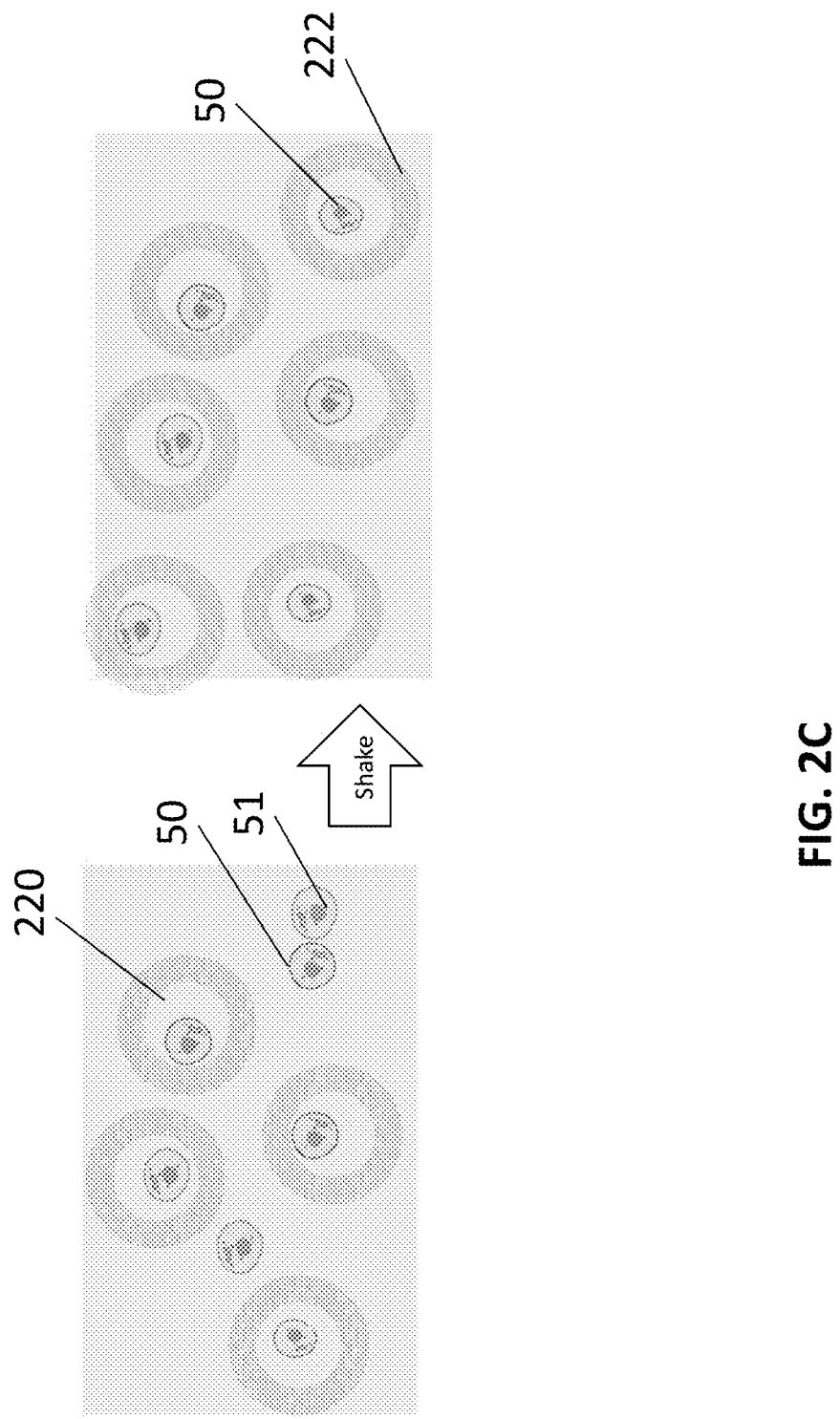
FIG. 2C shows a method of forming a polymer matrix around a biological component in a system as provided herein, according to some embodiments.

With continued reference to FIG. 2A, the polymer matrix 208, 209, or at least a portion of the polymer matrix 208, 209, may be coupled to the first surface 201, the second surface 202, or both surfaces 201, 202. In certain embodiments, the polymer matrix, or at least a portion of the polymer matrix, may be coupled to a third surface, a fourth surface, a fifth surface, etc. as appropriate. In various embodiments, the polymer matrix 208, 209 may extend from the first surface 201 to the second surface 202 (e.g., through at least a portion of a lumen of the channel 200 or a cavity of a chamber) such that the polymer matrix surrounds, or substantially surrounds, the biological component 50. In some embodiments, two or more biological components (e.g., biological components 50, 51 of FIG. 2C) that are in close physical proximity may be separated (e.g., by agitating or shaking the fluidic device). The fluidic device may be agitated or shaken by physical movement, use of a sonic pulse, changing a flow in the channel, or any other suitable method of agitation. A polymer matrix may then be formed that surrounds (or partially surrounds) the biological components that are separated. FIG. 2B shows polymer matrices 208, 209 formed surrounding the biological component 50 after being separated from the biological component 51. FIG. 2C shows a process, according to various embodiments, of separating the two biological components 50, 51, which are in close proximity. That is, by agitating or shaking the fluidic device the biological components 50, 51 can be separated. In some embodiments, separation of the biological components is achieved through fluidic pressure, flow pulsation, dielectrophoresis, optothermal flow, or some combination thereof. In some cases, separation of the biological components is achieved through acoustic vibration. FIG. 2C also shows a polymer matrix being formed to generate a compartment 222 surrounding the biological component 50 after the separation of the biological components 50, 51.

With continued reference to FIG. 2A, in some cases, the energy source 203 can, or be configured to, form or produce one or more emitting portions 205 and one or more non-emitting portions 204. The systems disclosed herein may further include a spatial energy modulating element to direct energy from the energy source to one or more targeted portions of the fluidic device. For example, the spatial energy modulating element may be configured to selectively direct the energy from the energy source to form a polymer matrix in a discrete area of the fluidic device. In some embodiments, the discrete area is chosen based on the location of a biological component. In some embodiments, the area of the discrete area is less than the area of the fluidic device. In some embodiments, a biological component is captured within the discrete area. In some embodiments, the size and shape of the discrete area is adjustable according to the size, shape, or other properties of the biological component. In some embodiments, an algorithm is used to determine the shape and size of the discrete area. In some embodiments, the algorithm is a supervised, a self-supervised, or an unsupervised learning algorithm. The spatial energy modulating element may be configured to selectively direct the energy by, for example, inhibiting or preventing energy from being directed to one or more portions other than the one or more targeted portions of the fluidic device. In some embodiments, the spatial energy modulating element may comprise a physical mask. In some cases, the spatial energy modulating element may comprise a virtual mask. In some cases, the spatial energy modulating element may be a spatial light modulator (SLM). In some embodiments, the SLM is a digital micromirror device (DMD). In some embodiments, the SLM is a laser beam steered using a galvanometer. In some embodiments, the SLM is liquid-crystal based.

Figure 24A:
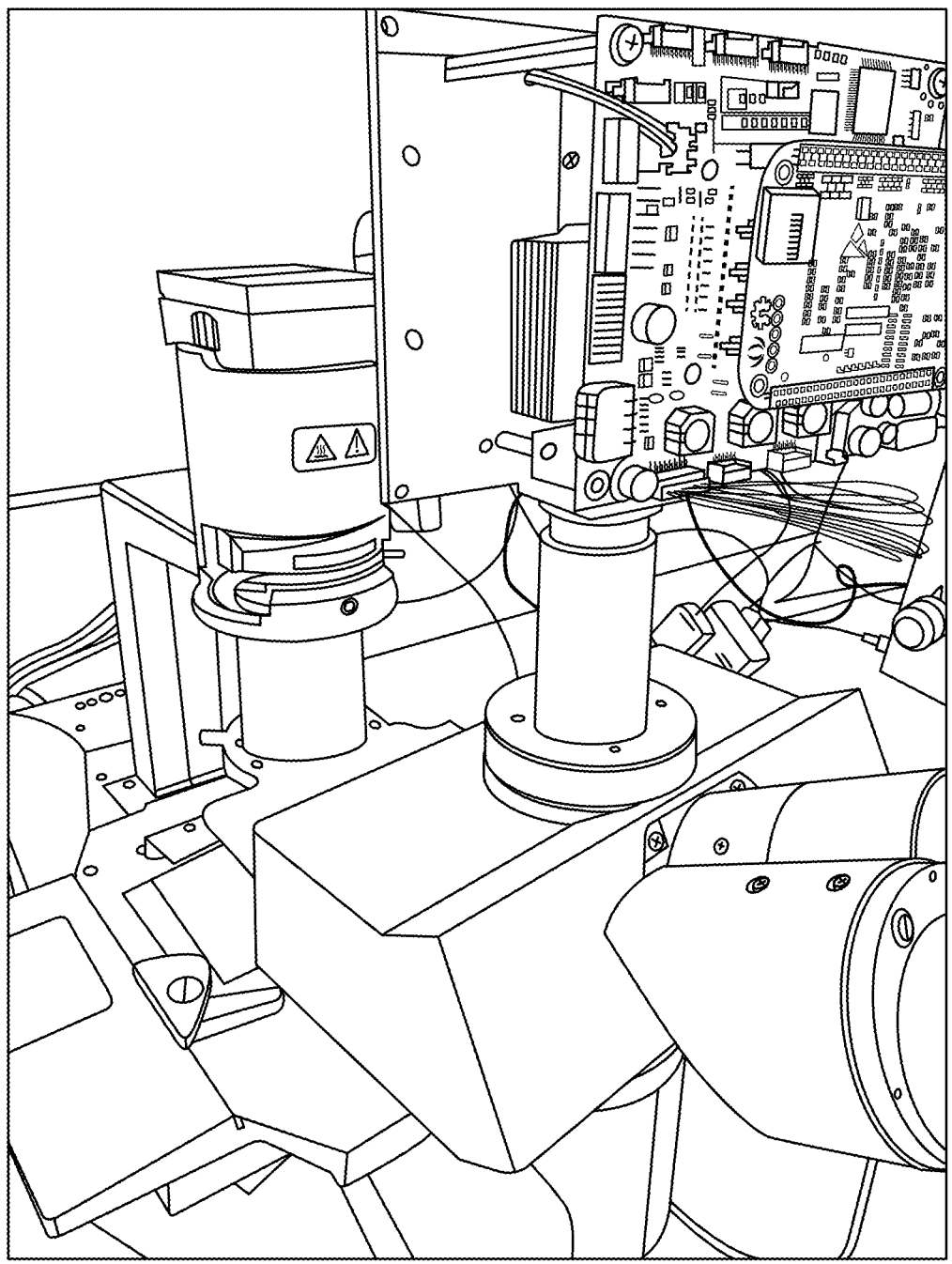
FIG. 24A shows a microscope equipped with a DMD and integrated UV illumination LED, according to some embodiments.
Figure 24B:
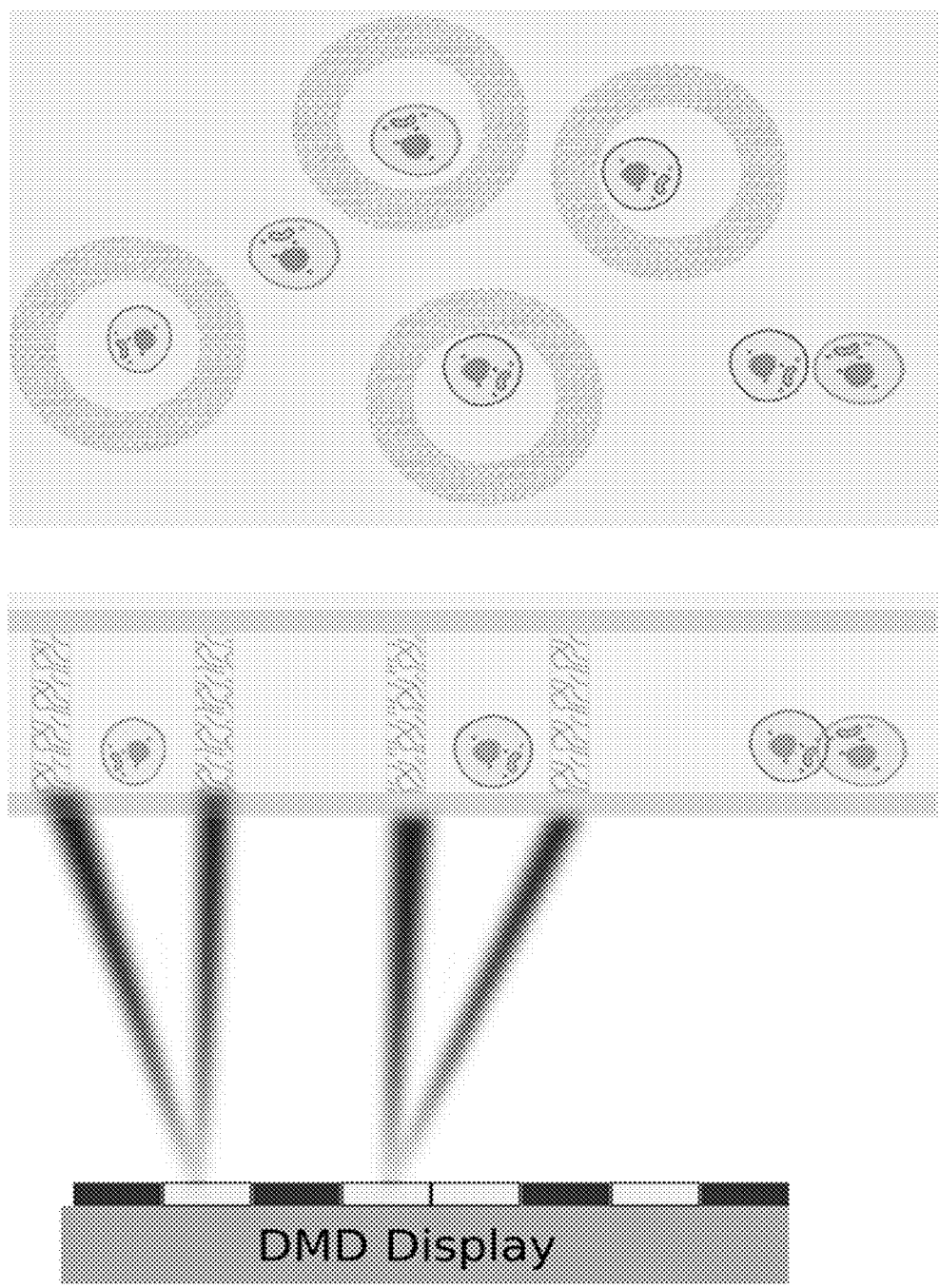
FIG. 24B shows a schematic illustration of a DMD projecting a virtual mask image onto a fluidic channel filled with polymer precursor to generate a polymer matrix, according to some embodiments.
Figure 24C:
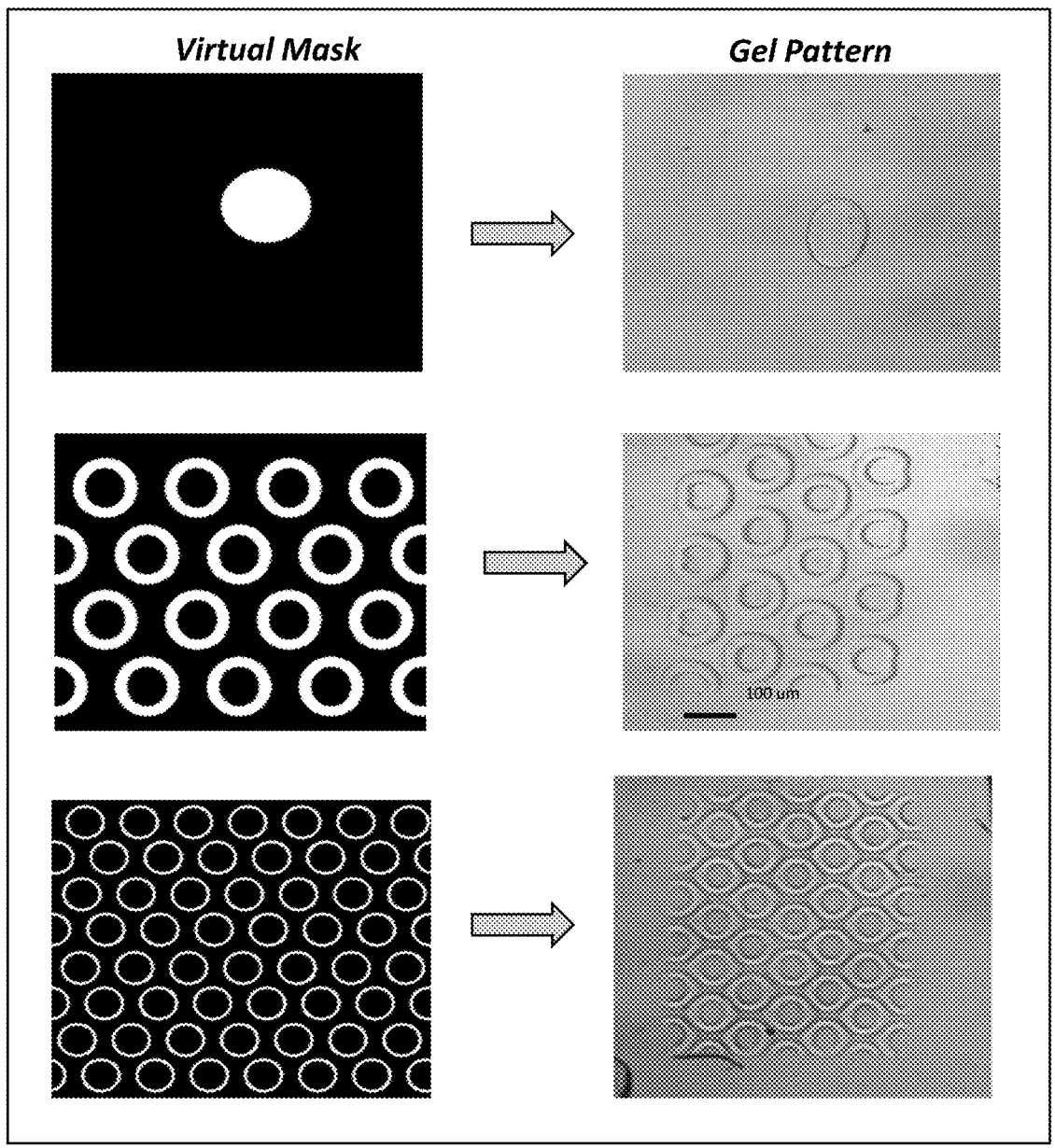
FIG. 24C shows various virtual mask images that were projected using a DMD and the corresponding polymer matrices generated inside a fluidic device, according to some embodiments.

FIG. 24A shows a microscope equipped with a DMD and integrated UV illumination LED, according to some embodiments. FIG. 24B shows the DMD setup projecting a virtual mask image onto the channel filled with polymer precursor to generate a polymer matrix, according to some embodiments. FIG. 24C shows various virtual mask images that were projected using the DMD and the corresponding hydrogel structures generated inside the fluidic device.

In certain cases, the spatial energy modulating element may be configured to control one or more electrodes that can selectively provide energy to the one or more targeted portions of the fluidic device. The electrode concept may also be used to provide spatially modulated energy to form the hydrogel structure. In some implementations, one or more electrodes can be arranged at pre-determined locations in the fluidic channel, thus allowing formation of the hydrogel in those locations. In alternative implementations, the electrodes can be in the form of an array. The elements of the array can be turned on or off on demand to create the desired spatial pattern of energy to form the desired shape of the hydrogels. For example, one or more electrodes (e.g., an array of electrodes) may be disposed within one or more portions of the fluidic device. For another example, one or more electrodes (e.g., an array of electrodes) may be in communication (e.g., electrical communication) with one or more portions of the fluidic device.

In some embodiments, the energy source is a light generating device. In some embodiments, the light generating device generates light at about 350 nanometers to about 800 nanometers. In some embodiments, the light generating device generates light at about 350 nanometers to about 400 nanometers, about 350 nanometers to about 450 nanometers, about 350 nanometers to about 600 nanometers, about 350 nanometers to about 800 nanometers, about 400 nanometers to about 450 nanometers, about 400 nanometers to about 600 nanometers, about 400 nanometers to about 800 nanometers, about 450 nanometers to about 600 nanometers, about 450 nanometers to about 800 nanometers, or about 600 nanometers to about 800 nanometers. In some embodiments, the light generating device generates light at about 350 nanometers, about 400 nanometers, about 450 nanometers, about 600 nanometers, or about 800 nanometers. In some embodiments, the light generating device generates light at least about 350 nanometers, about 400 nanometers, about 450 nanometers, or about 600 nanometers. In some embodiments, the light generating device generates light at most about 400 nanometers, about 450 nanometers, about 600 nanometers, or about 800 nanometers. In some embodiments, the light generating device generates UV light.

In some embodiments, a mask may prevent, or be configured to prevent, one or more portions of the energy emitting surface 210 of the energy source 203 from emitting energy (e.g., non-emitting portions 204). In some embodiments, the mask may be a virtual mask (e.g., a computer code or a digital system). In certain embodiments, the mask can prevent the energy from being emitted to a location where a biological component is present. This may allow or permit forming a polymer matrix adjacent to, on, or encapsulating the biological component (e.g., to retain a cell, proteins, DNA molecules, RNA molecules, or other target molecules at a location on the fluidic channel). In other embodiments, the mask may facilitate the polymerization such that the polymer matrix is on the biological component. In various embodiments, the mask may be a physical mask (e.g., an opaque material, a thermal shield, or an electromagnetic shield). In some embodiments, the mask (e.g., a virtual mask or a physical mask) can be generated using, or in combination with, a detector that detects or identifies a location of a biological component. In some embodiments, the detector comprises a camera. In some embodiments, the detector comprises a light detector, conductivity detector, an ultrasound detector, an ultrasonic sensor, a piezoelectric sensor, a combination thereof, or another suitable detecting device.

In some embodiments, the first surface 201 or the second surface 202 may comprise a detector that detects, or is configured to detect, one or more locations of one or more biological components in the fluidic device (e.g., in the channel 200). In certain embodiments, the energy source 203 can comprise, be coupled to, or be in communication with a detector that detects, or is configured to detect, a location of a biological component in the fluidic device. In some embodiments, the detector may be a microscope objective for imaging the fluidic device. In various embodiments, a mask may be generated using an image obtained from at least a portion of the fluidic device. The mask may allow or permit the energy source 203 to emitting energy in or toward one or more locations or positions where one or more biological components are present on or adjacent the first surface 201. The mask may inhibit or prevent the energy source 203 from emitting energy in or toward one or more locations or positions where one or more biological components are present on or adjacent the first surface 201. In some embodiments, the image may be obtained from a camera (e.g., a digital camera, fluorescent imaging camera, etc.). In some embodiments, the imaging is bright-field imaging, phase-contrast imaging, or fluorescence imaging, or any combination thereof. In some embodiments, the camera may be coupled to, connected to, or in communication with the energy source 203. For example, the camera (not shown) may be in electrical communication with the energy source 203. In some embodiments, the energy source 203 may comprise the camera. In various embodiments, the energy source 203 may comprise a microscope (e.g., a fluorescence microscope, a confocal microscope, lens-free imaging system, a transmission electron microscopy (TEM), a scanning electron microscope (SEM), etc.). The microscope may be used to detect one or more positions of one or more biological components (e.g., in combination with the detector).

In some embodiments, an algorithm is used to determine where a biological component or analyte is located based on the imaging. In some embodiments, the algorithm is a supervised, a self-supervised, or an unsupervised learning algorithm. In some embodiments, the objective is coupled to an energy source to emit energy to the predetermined portion in the fluidic channel.

Figure 9A:
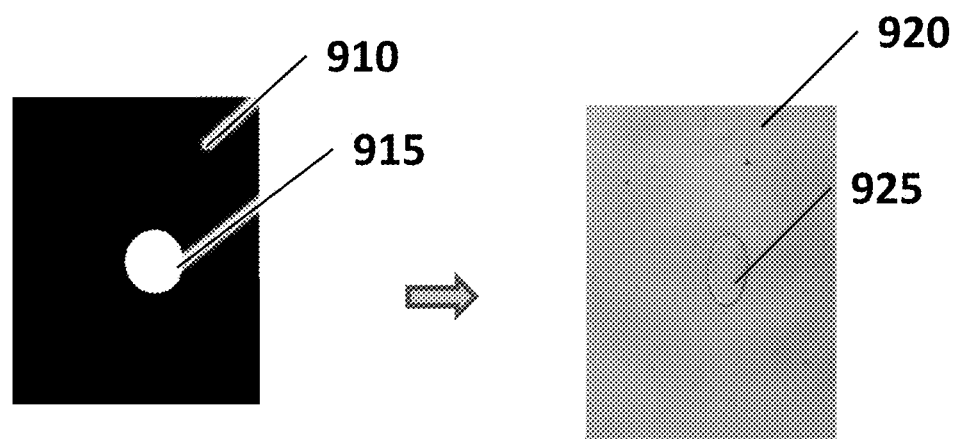
FIG. 9A shows a portion of a spatial energy modulating element and a cylindrical polymer matrix, according to some embodiments.
Figure 9B:
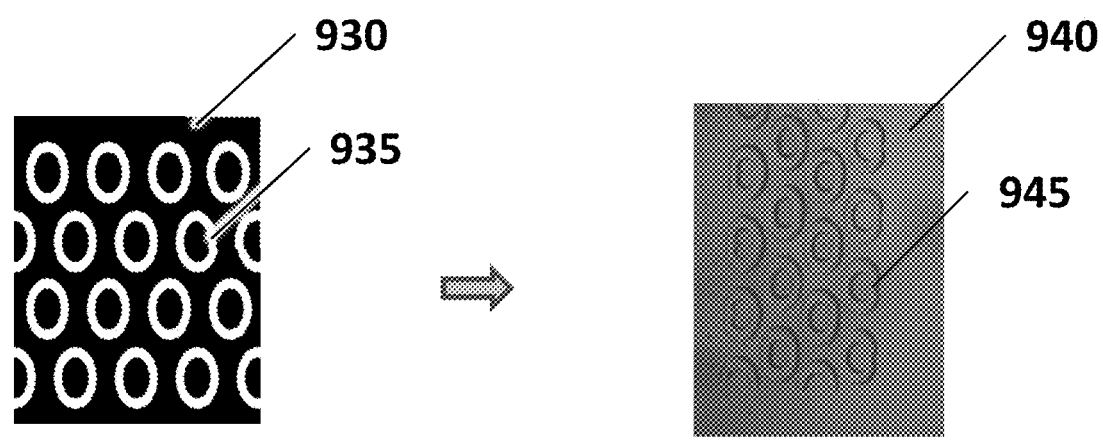
FIG. 9B shows a portion of a spatial energy modulating element and polymer matrices in the shape of hollow cylinders, according to some embodiments.

FIG. 9A shows an example of a mask comprising an energy masking region 910 and an energy transparent region 915. Energy from an energy source may be blocked by the energy masking region 910 to prevent the energy to form any polymer matrix in a portion of the fluidic device (e.g., portion 920). Energy transparent region 915 may allow the energy to communicate with the fluidic device to form a polymer matrix 925. FIG. 9B shows another example of a mask, where the energy transparent region 935 is in shape of a hollow cylinder (e.g., donut). Energy being masked by a masking region 930 may prevent energy communication with a portion of the fluidic device (e.g., a portion 940). The energy transparent region 935 may deliver energy to the fluidic device to form a polymer matrix 945. The polymer matrix 945 may be in shape of a hollow cylinder.

Figure 10:
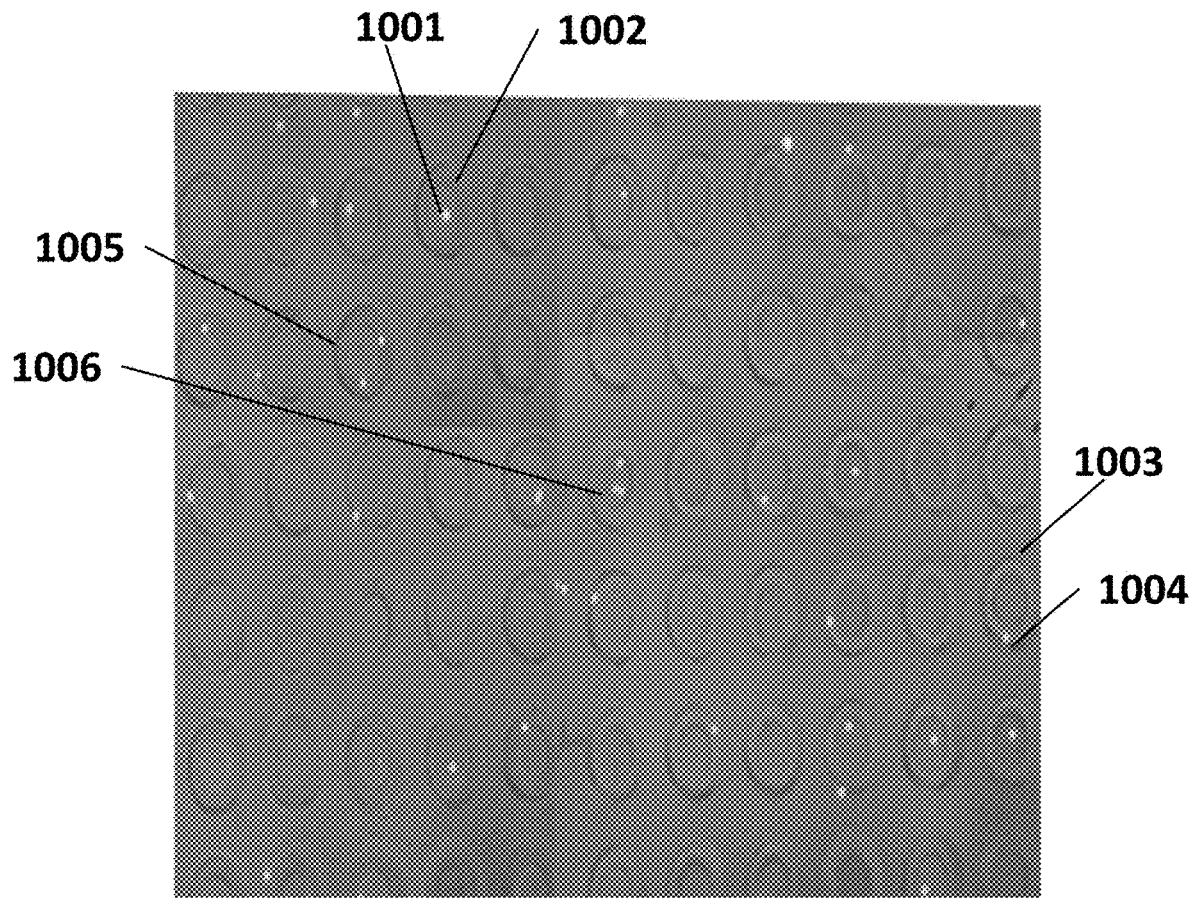
FIG. 10 shows a micrograph of polymer matrix compartments encapsulating one or more biological components, according to some embodiments.

FIG. 10 shows an example of biological components (i.e., indicated as white spots) encapsulated and/or localized using polymer matrices. In some cases, a biological component 1001 may be localized within a hollow region of a polymer matrix compartment 1002. In some other cases, a polymer matrix 1003 may be formed on a biological component 1004. In some alternative cases, a polymer matrix 1005 may localize more than one biological component. A biological compartment polymer matrix 1006 may encapsulate one or more biological components.

Figure 20:
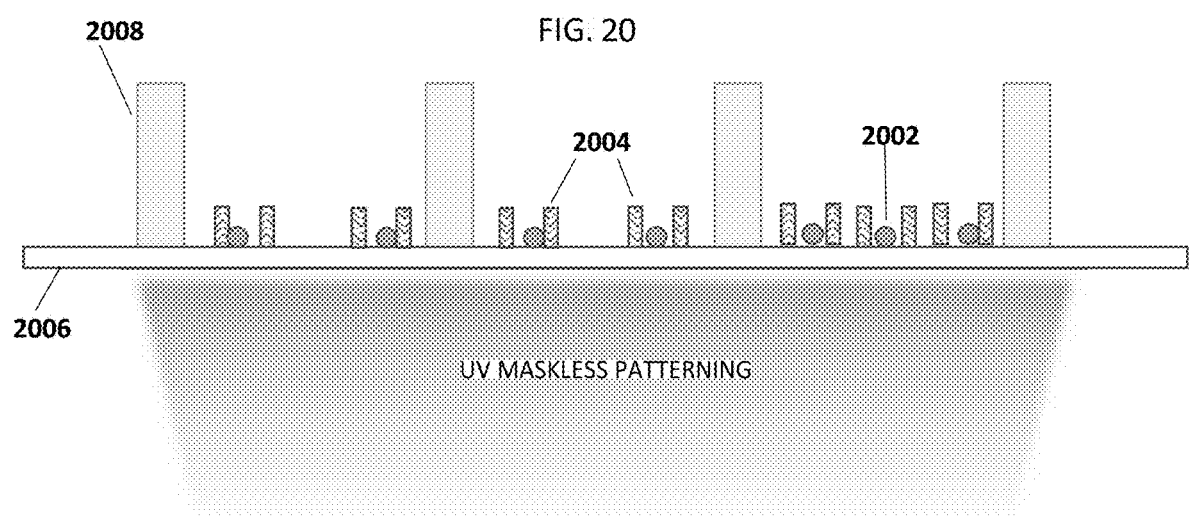
FIG. 20 shows polymer matrices inside a well plate format, according to some embodiments.

In some embodiments, the fluidic device contains one or more discrete locations wherein the one or more discrete locations are not in fluidic communication with another discrete location. In some embodiments, the one or more discrete locations comprise the analyte. In some embodiments, the one or more discrete locations are one or more well plates. FIG. 20 shows an example of biological components 2002 encapsulated and/or localized on a well plate using polymer matrices 2004. In some embodiments, the polymer matrices 2004 and biological components 2002 are seeded on a well plate 2006. In some embodiments, the biological components are introduced to the fluidic device along with polymer precursors. The polymer matrices may be formed by UV photopatterning in absence of a physical photomask. Walls 2008 may separate individual wells. The well plate could have any number of wells. For example, the well plate could have 6, 12, 24, 48, or 96 wells. In some embodiments, each well has a diameter of about 1 millimeter to about 100 millimeters. In some embodiments, each well has a diameter of about 1 millimeter to about 2 millimeters, about 1 millimeter to about 5 millimeters, about 1 millimeter to about 10 millimeters, about 1 millimeter to about 20 millimeters, about 1 millimeter to about 50 millimeters, about 1 millimeter to about 100 millimeters, about 2 millimeters to about 5 millimeters, about 2 millimeters to about 10 millimeters, about 2 millimeters to about 20 millimeters, about 2 millimeters to about 50 millimeters, about 2 millimeters to about 100 millimeters, about 5 millimeters to about 10 millimeters, about 5 millimeters to about 20 millimeters, about 5 millimeters to about 50 millimeters, about 5 millimeters to about 100 millimeters, about 10 millimeters to about 20 millimeters, about 10 millimeters to about 50 millimeters, about 10 millimeters to about 100 millimeters, about 20 millimeters to about 50 millimeters, about 20 millimeters to about 100 millimeters, or about 50 millimeters to about 100 millimeters. In some embodiments, each well has a diameter of about 1 millimeter, about 2 millimeters, about 5 millimeters, about 10 millimeters, about 20 millimeters, about 50 millimeters, or about 100 millimeters. In some embodiments, each well has a diameter of at least about 1 millimeter, about 2 millimeters, about 5 millimeters, about 10 millimeters, about 20 millimeters, or about 50 millimeters. In some embodiments, each well has a diameter of at most about 2 millimeters, about 5 millimeters, about 10 millimeters, about 20 millimeters, about 50 millimeters, or about 100 millimeters.

One well may not be in fluidic communication with another well. The walls of each well 2008 may prevent fluid from traveling between the wells. In some cases, one or more assays may be conducted or performed on the biological component in a well. Different assays may be conducted or performed in different wells. For example, 6 different assays may be performed on biological components seeded on a 6-well plate.

Figure 21:
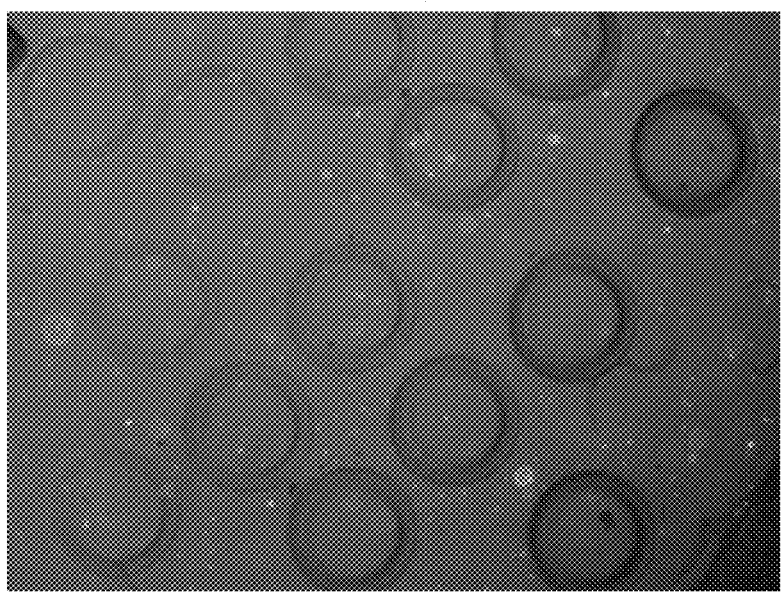
FIG. 21 shows polymer matrices inside 10 mm size wells, according to some embodiments.

In some embodiments, the one or more discrete locations are open at the top. FIG. 21 shows gel microwell structures inside 10-millimeter size wells. The structures are open at the top, according to some embodiments. Fluorescent beads that are loaded into the fluidic device may also enter the wells, confirming that the wells are open at the top.

Figure 3:
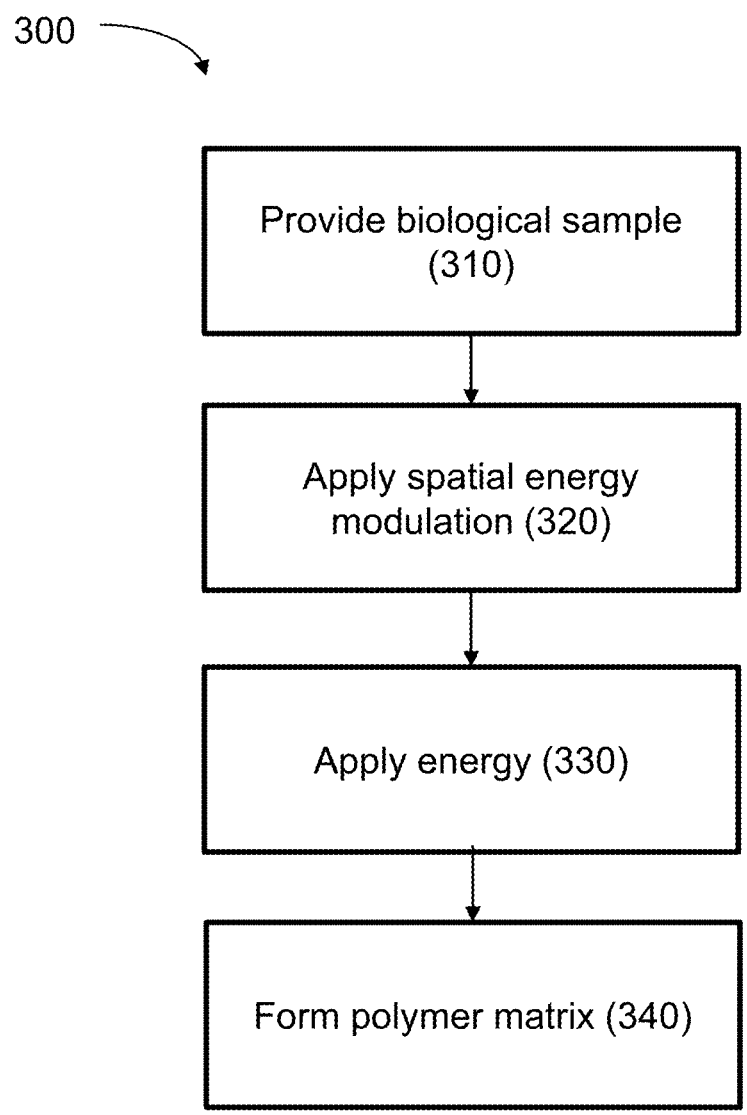
FIG. 3 is a flow chart depicting an embodiment of forming a polymer matrix.

FIG. 3 is a flow chart of forming a polymer matrix on or adjacent to one or more biological components, according to some embodiments of the present disclosure. The process 300 may be performed manually or automatically (e.g., by an appropriately programmed computer system). In step 310, a biological sample may be deposited, introduced, or provided into at least a portion of the fluidic device. In some embodiments, a mask may then be formed or generated to render one or more portions of the energy source directed towards a biological component non-emitting (step 320). In step 330, the energy source may apply or provide energy to at least a portion of the fluidic device. In some embodiments, the energy source can activate or initiate polymer precursors such that the polymer precursors form a polymer matrix (e.g., via energy provided by the energy source). In some embodiments, an imaging of the fluidic device can be performed subsequent to step 310 and prior to step 320 to determine or identify a location of the biological components to generate a mask. In some embodiments, the mask is a virtual mask. In some embodiments, the polymer matrix may form a compartment that partially or completely surrounds a biological component.

In certain cases, the energy source may be manipulated such that the polymer matrix is formed in different steps. For example, the energy source may initiate a plurality of polymer precursors such that the polymer precursors form an open compartment (e.g., a crescent shape or half-cylinder polymer matrix). The open compartment may operate to capture and/or contain a biological component (e.g., a cell), or a portion of a sample, to a portion of the fluidic device. The orientation of the energy source or the fluidic device may be adjusted, and an additional portion of polymer matrix may be formed. This additional portion may be used to form one or more compartments in conjunction with the pre-formed half-cylinder polymer matrix. In other embodiments polymer matrix compartments can be formed in at least 2, 3, 4, 5, or more matrix-forming steps.

Figure 11A:
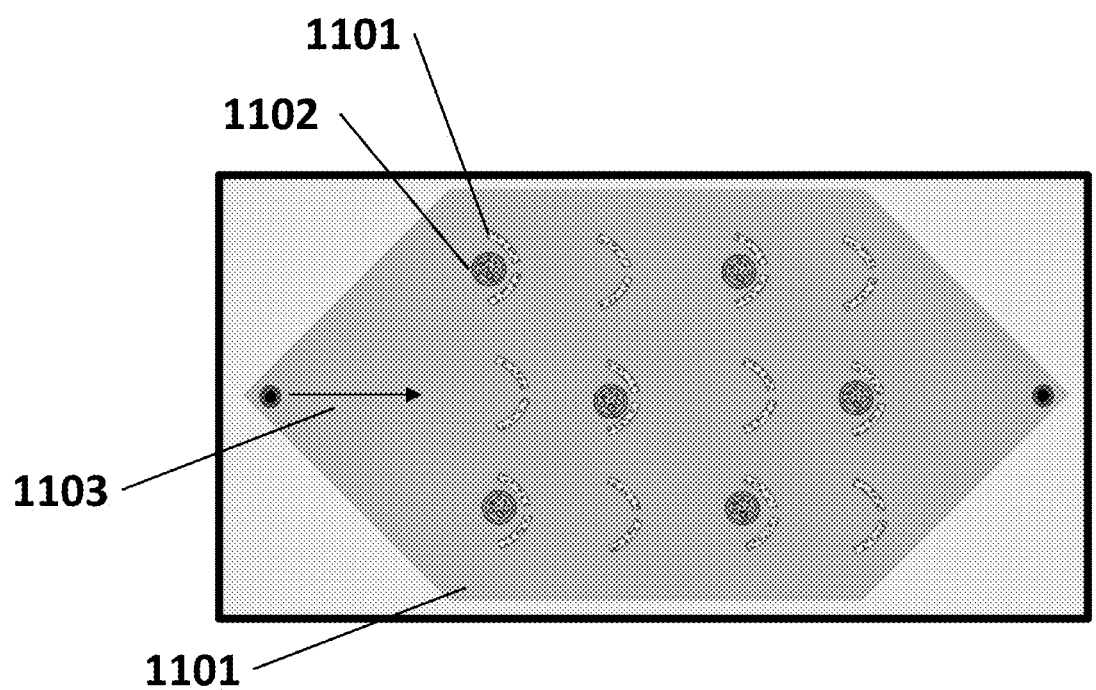
FIG. 11A illustrates open compartments formed in a multi-step polymer matrix formation process, according to some embodiments.
Figure 11B:
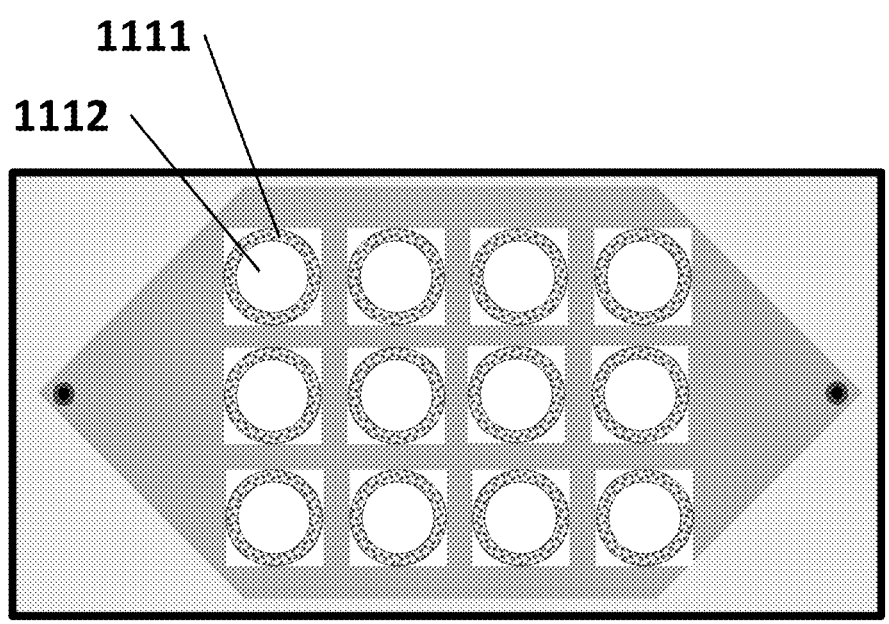
FIG. 11B illustrates closed compartments formed in a multi-step polymer matrix formation process, according to some embodiments.

FIG. 11A and FIG. 11B show an example of multi-step polymer matrix compartment generation. FIG. 11A shows a first step of the multi-step generation, where open compartments (e.g., an open compartment 1101 made from a polymer matrix) may be generated to capture and/or contain a biological component (e.g., a biological component 1102). A sample comprising the biological component 1102 may have a flow direction 1103 within the fluidic device (e.g., a portion of a fluidic device 1100). The open compartment 1101 may be formed by generating a polymer matrix using an energy source and an energy modulation unit as described herein. The open compartment may intersect a portion of the direction of the flow 1103 of the sample in the fluidic device. The polymer matrix open compartment 1101 may be oblique or perpendicular to the direction of the flow 1103 of the sample in the fluidic device. FIG. 11B shows a second step of the multi-step generation, where the open compartments (e.g., open compartment 1101) are sealed off or closed by forming polymer matrix adjacent, around, or on the biological component (e.g., biological component 1112). In some cases, in the second step a biological component may be completely or substantially completely encapsulated by the polymer matrix (e.g., to form a closed compartment 1111). In some cases, the polymer matrix that may form adjacent, around, or on the biological component localizes the biological component to a location on the fluidic device 1100. Genomic and/or proteomic material may be extracted from the localized biological component. The polymer matrix may further localize the extracted materials. The fluidic device may then provide a surface where the extracted material can be sequenced. In some embodiments, the extracted materials may be eluted and transferred to another device or surface for sequencing. In other embodiments, the sequencing may be performed through short-read sequencing, nanopore sequencing, sequencing by synthesis, sequencing by in-situ hybridization, any optical readout using a microscope, or any other suitable method of sequencing.

One or more surfaces of the fluidic device may comprise an optical (e.g., fluorescence), mechanical, electrical, or biochemical sensing element or sensor. The sensing element may comprise a fluorescent tag, an enzyme, a primer, an oligonucleotide, or a sensor molecule (e.g., a biochemical sensor molecule). The sensing element may be used to detect and/or measure a pH, an oxygen concentration, a $CO_2$ concentration, or any other suitable variable. The sensing element may detect and/or measure a parameter locally. For example, the sensing element may detect and/or measure a pH, an oxygen concentration, or a $CO_2$ concentration within a compartment (e.g., a polymer matrix shell cylinder) surrounding the biological component.

Systems with Capture Elements

The present disclosure also provides systems including one or more capture elements for immobilizing and/or compartmentalizing one or more biological components. The system can include a fluidic device. The fluidic device can include or contain one or more biological components. Further, the fluidic device can include or contain one or more polymer precursors. In some embodiments, the fluidic device can include a first surface (e.g., in a channel and/or chamber of the fluidic device). The fluidic device can include one or more capture elements. The capture elements can immobilize, or be configured to immobilize, at least one of the one or more biological components at a location on or adjacent to the first surface (or any suitable surface). Immobilization or coupling of a biological component to a capture element can form an immobilized biological component. The system may further include at least one energy source in communication with the fluidic device. In certain embodiments, the at least one energy source can provide or supply energy, or be configured to provide or supply energy, to at least a portion of the fluidic device. Accordingly, the energy source can activate or cause the one or more polymer precursors (e.g., disposed in the fluidic device) to form at least one polymer matrix on or adjacent to an immobilized biological component. In various embodiments, the fluidic device may further include a platform or a stage to hold the fluidic device. In some embodiments, the system may also include a sequencing device (e.g., a next-generation sequencing device) to obtain sequencing data. The polymer matrix formed in the fluidic device may be used to capture and localize a biological component. Genomic and/or proteomic material may be extracted using the fluidic device. The fluidic device may then provide a surface where the extracted material can be sequenced. In some embodiments, the extracted materials may be eluted and transferred to another device or surface for sequencing. In other embodiments, the sequencing may be performed through short-read sequencing, nanopore sequencing, sequencing by synthesis, sequencing by in-situ hybridization, or any optical readout using a microscope.

In order to immobilize a biological component, a fluidic device may comprise one or more capture sites. A capture site may include a capture element. In some embodiments, the one or more capture elements or sites may comprise or be disposed in a pattern. A fluidic device may comprise 1, 2, 3, 4, 5, 6, 7, 8, 9, 10, 15, 20, 30, 40, 50, 100, 200, 300, 400, 500, 600, 700, 1,000, 10,000, $10^5$, $10^6$, $10^7$, $10^8$, $10^9$, $10^{10}$, $10^{20}$ capture elements, or any number of capture elements between any of the two numbers mentioned herein. In some embodiments, the fluidic device may comprise more than $10^{20}$ capture elements.

Figure 4A:
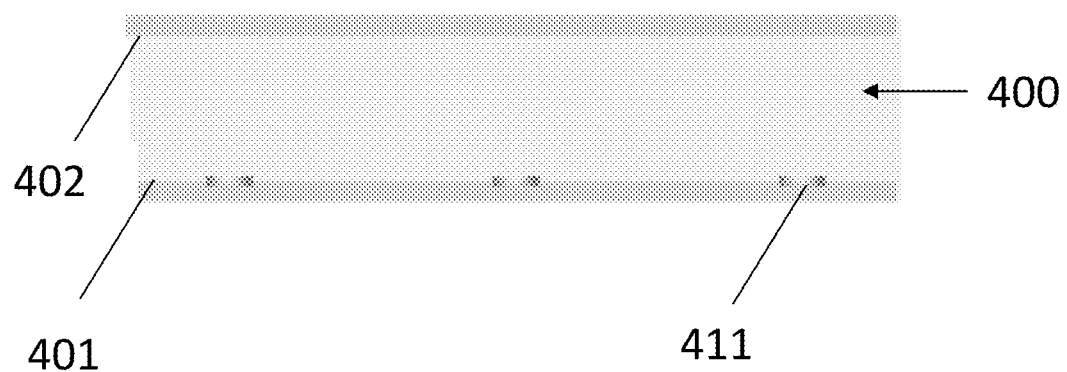
FIG. 4A shows a portion of a channel including capture elements in a fluidic device, according to some embodiments.
Figure 4B:
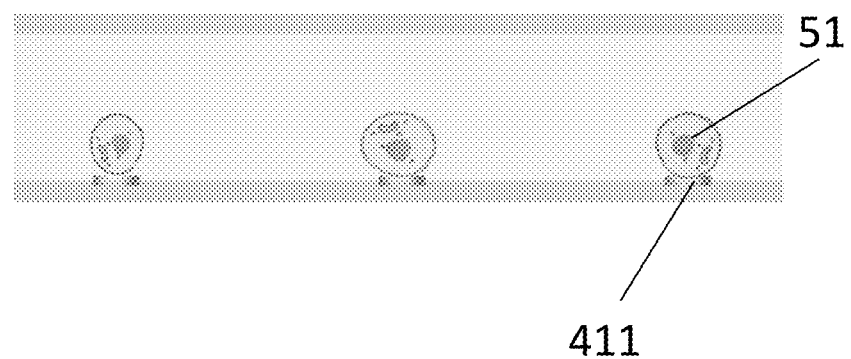
FIG. 4B illustrates biological components coupled to capture elements on a surface of a portion of a channel in a fluidic device, according to some embodiments.

The fluidic device may comprise a channel. The fluidic device may comprise a chamber. FIG. 4A shows an example of at least a portion of a channel 400 in a fluid device. One or more capture elements 411 may be disposed or positioned on a first surface 401 of the fluidic device. In some cases, a second surface 402 may comprise one or more capture elements. The capture elements may be disposed on both surfaces or any other suitable surface. A capture element may comprise or be at least partially formed by a functional group. Some non-limiting examples of functional groups include a capture reagent (e.g., pyridinecarboxaldehyde (PCA)), a biotin, a streptavidin, a strep-tag II, a linker, or a functional group that can react with a molecule (e.g., an aldehyde, a phosphate, a silicate, an ester, an acid, an amide, an alkyne, an azide, or an aldehyde dithiolane). The functional group may couple specifically to an N-terminus or a C-terminus of a peptide. The functional group may couple specifically to an amino acid side chain. The functional group may couple to a side chain of an amino acid (e.g., the acid of a glutamate or aspartate, the thiol of a cysteine, the amine of a lysine, or the amide of a glutamine or asparagine). The functional group may couple specifically to a reactive group on a particular species, such as a membrane-bound molecule on a cell (e.g., a glycoprotein of a eukaryotic cell or a pilus on a plasma of a prokaryote). In some examples, the capture elements can comprise fibronectin. In another example, the capture elements can comprise RGD peptides. In some cases, capture elements may comprise antibodies. In some examples, the functional motif can be reversibly coupled and cleaved (e.g., by using an enzyme). FIG. 4B illustrates an example of a biological component 51 in contact with or coupled to a capture element 411. In some cases, a repelling surface coating (e.g., PEG) may be used to prevent the polymer matrix form covering or trapping a biological component.

In various instances, the capture element may comprise a physical trap, a hydrodynamic trap, a geometric trap, a well, an electrochemical trap (e.g., trapping charge molecules), streptavidin, an antibody, an aptamer, affinity binding (e.g., a peptide that may bind to a surface protein of a cell), one or more magnetic material (e.g., magnetic disk, magnetic array, or magnetic particles), a dielectrophoretic trap (e.g., electrode array), or a combination thereof. The trap may comprise a polymer matrix or hydrogel. The polymer matrix or hydrogel trap may be constructed or deconstructed on demand using an energy source and/or degradation similar to the polymer matrix compartments mentioned herein. For example, a capture element may comprise a well. The well may be from 1 µm to 50 µm in diameter. In some embodiments, the well may be from 1 µm to 20 µm, 20 µm to 30 µm, 30 µm to 40 µm, or 40 µm to 50 µm in diameter. The well may be more than 50 µm in diameter. The well may be less than 1 µm in diameter. In some embodiments, the well may be from 0.1 µm to 100 µm in depth. In certain embodiments, the well may be more than 100 µm in depth. The well may be less than 0.1 µm in depth. The depth of the well may be from 0.1 µm to 0.5 µm, 0.1 µm to 1 µm, 0.1 µm to 5 µm, 0.1 µm to 10 µm, 0.1 µm to 20 µm, 0.1 µm to 30 µm, 0.1 µm to 50 µm, 0.1 µm to 100 µm, 0.5 µm to 1 µm, 0.5 µm to 5 µm, 0.5 µm to 10 m, 0.5 µm to 20 m, 0.5 µm to 30 m, 0.5 µm to 50 µm, 0.5 µm to 100 µm, 1 µm to 5 µm, 1 µm to 10 µm, 1 µm to 20 µm, 1 µm to 30 µm, 1 µm to 50 µm, 1 µm to 100 µm, 5 µm to 10 µm, 5 µm to 20 µm, 5 µm to 30 µm, 5 µm to 50 µm, 5 µm to 100 µm, 10 µm to 20 µm, 10 µm to 30 µm, 10 µm to 50 µm, 10 µm to 100 µm, 20 µm to 30 µm, 20 µm to 50 µm, 20 µm to 100 µm, 30 µm to 50 µm, 30 µm to 100 µm, or 50 µm to 100 µm. The depth of the well may be about 0.1 µm, about 0.5 µm, about 1 µm, about 5 µm, about 10 µm, about 20 µm, about 30 µm, about 50 µm, or about 100 µm. The depth of the well may be at least 0.1 µm, 0.5 µm, 1 µm, 5 µm, 10 µm, 20 µm, 30 µm, or 50 µm. The depth of the well may be at most 0.5 µm, 1 µm, 5 µm, 10 µm, 20 µm, 30 µm, 50 µm, or 100 µm.

Figure 12A:
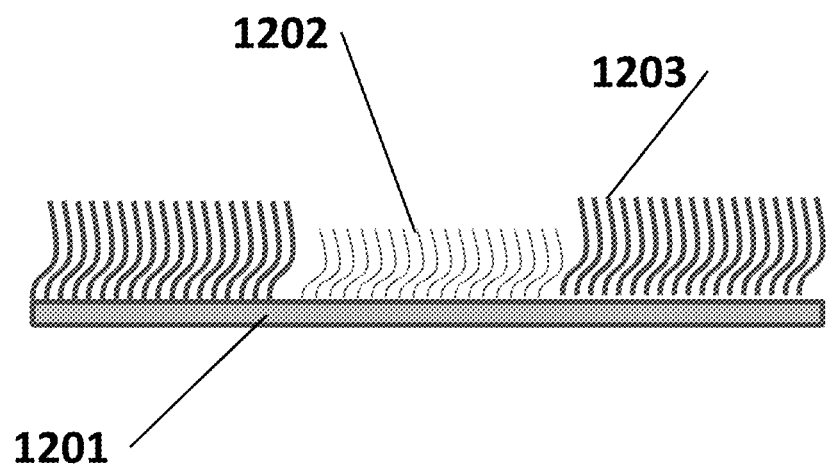
FIG. 12A is a schematic illustration of a portion of a surface of a fluidic device coated with repelling elements, according to some embodiments.
Figure 12B:
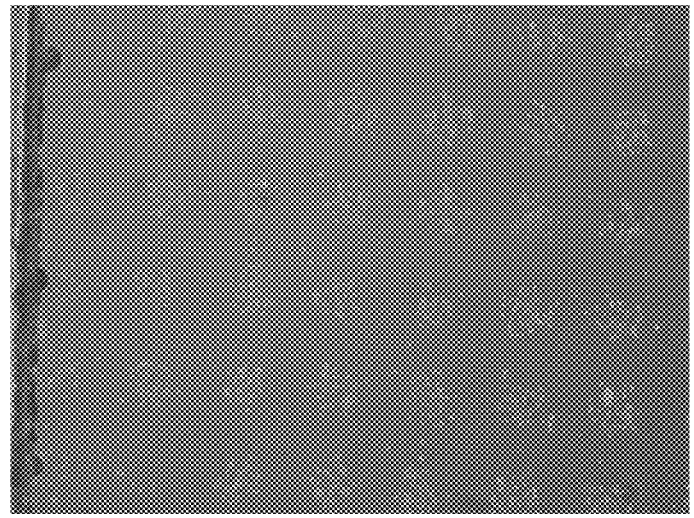
FIG. 12B shows a micrograph of biological components captured on a surface using repelling elements, according to some embodiments.
Figure 12C:
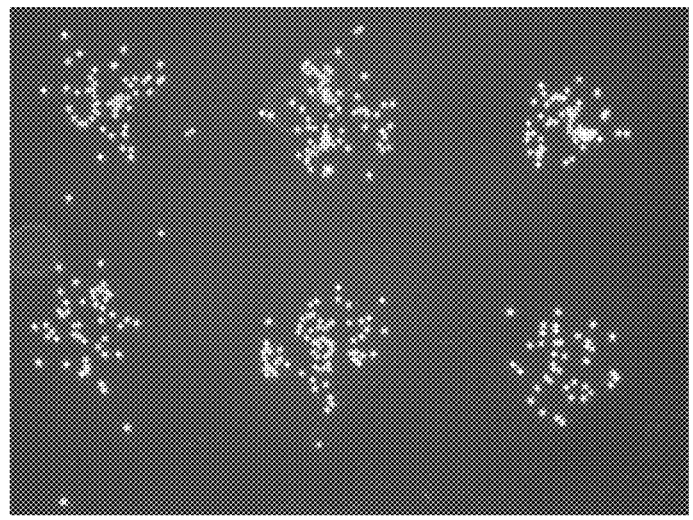
FIG. 12C shows a higher magnification micrograph of biological components captured on a surface using repelling elements, according to some embodiments.

In some embodiments, the fluidic device may comprise a repelling surface coating that may be used to prevent capturing of a biological component at predefined locations. FIG. 12A illustrates a portion of a surface 1201 of a fluidic device, where the surface 1201 may comprise a capturing site 1202 and a repelling site 1203. The surface 1201 may be functionalized using a surface coating (e.g., PEG) to generate the repelling site 1203. The repelling site 1203 may prevent biological components from binding to the surface 1201 at the location of the repelling site 1203 and drive the biological component to the capture site 1202. In some cases, the surface 1201 may only comprise the repelling sites without a capturing site. The repelling site may initially localize the biological components. A polymer matrix may be formed by directing an energy source to the repelling sites to form compartments adjacent to the biological components that may be located in between the repelling sites. FIG. 12B shows an example of biological components contained in predefined locations in the fluidic device. FIG. 12C shows a higher magnification example of biological components contained in predefined locations in the fluidic device.

An energy source may be used to form a polymer matrix on, around, or adjacent to at least a portion of a captured biological component. In some embodiments, a mask may be used to allow or permit the energy source to direct energy toward a location or position of a captured biological component. In certain embodiments, a mask may be used to inhibit or prevent the energy source from directing energy toward a location or position of a captured biological component. The mask may be configured to direct the energy to predetermined or selected locations to form a polymer matrix surrounding or at least partially surrounding the one or more biological components. The mask may be generated based at least in part on a pattern of the capture sites (e.g., the pattern of the capture sites/elements on a surface of a fluidic device). In some embodiments, the mask may be configured to prevent energy from being directed to a location surrounding a capture site or element which has not captured or coupled a biological component. In certain cases, to analyze a single cell, the mask may be configured to prevent the energy from being emitted adjacent to a location of a capture element which has captured or coupled two or more biological components. In some embodiments, the mask may be configured to allow or permit energy to be emitted adjacent to a location of a capture element which has captured two or more biological components, for example, to allow analysis of cell-cell interactions. In certain embodiments, the mask may be a photolithographic mask or another suitable mask, as described herein. In some embodiments, the system may further comprise a detector, for example, to detect a location of a biological component, as described herein. The mask may be generated based at least in part on the detected location of a biological component. Additionally, the mask may selectively direct or supply energy from the energy source to the fluidic device, as described herein.

Figure 4C:
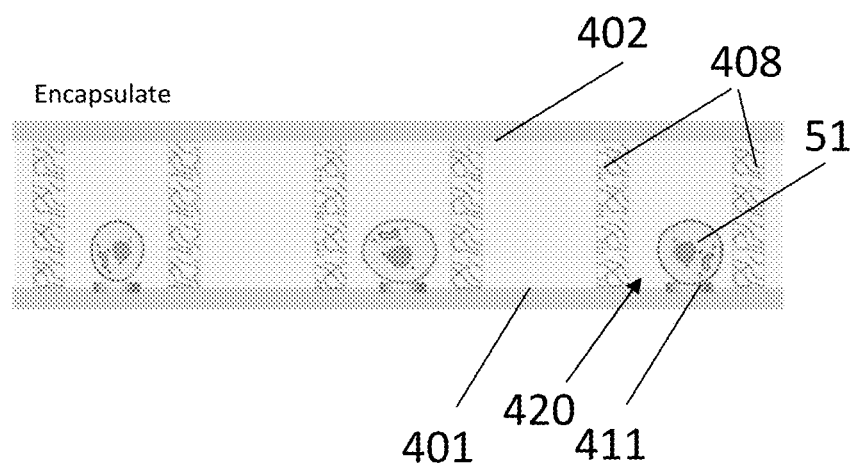
FIG. 4C illustrates polymer matrices disposed around biological components in a portion of a channel of a fluidic device, according to some embodiments.

FIG. 4C illustrates an example of a method of forming polymer matrices adjacent to (e.g., surrounding) biological components. A polymer matrix 408 may be formed adjacent to a capture element 411. The polymer matrix 408 may be configured to hold a biological component 51 in place or within an analysis chamber or compartment 420. The compartment 420 may be formed, at least in part, by the polymer matrix 408, the first surface 401, and the second surface 402 forming a chamber or at least partially sealed-off space within the fluidic device (e.g., around the biological component 51). In some embodiments, the polymer matrix 408 may form the compartment 420 surrounding the biological component 51. The compartment 420 may hold the biological component 51 in place. The polymer matrix 408 and/or the compartment 420 may inhibit or prevent a compound associated with the biological component 51 from leaving the compartment. In some embodiments, the compound associated with the biological component may comprise a nucleic acid (e.g., DNA or RNA), a protein, a metabolite, an enzyme, an antibody, combinations thereof, or any other suitable compound or material. In some embodiments, the surface of the polymer matrix or hydrogel may be functionalized by coupling a functional group to the polymer matrix or hydrogel. The functionalized surface of the polymer matrix inside the compartment may be coupled to a capturing element (e.g., an antibody) to capture a molecule secreted by the biological component (e.g., secreted protein). The capturing element or the captured molecule may then be read out by a sensing molecule or by a labeling method, for example, by fluorescent labeling. In some embodiments, a polymer matrix may be configured to allow passage of one or more compounds associated with a biological component. In some embodiments, a polymer matrix may be configured to allow passage of a reagent. The reagent may comprise, for example, one or more enzymes, chemicals, oligonucleotides (e.g., one or more primers having a size of less than 50 base pairs), lysozymes, proteinase K, random hexamers, polymerases, transposases, ligases, catalyzing enzymes, deoxynucleotide triphosphates, buffers, cell culture media, divalent cations, combinations thereof, or any other suitable reagent.

The pore size in the polymer matrix may be modulated using a chemical reagent, or by applying heat, electricity, light, or another suitable stimulus. In other words, the polymer matrix may comprise tunable properties (e.g., the pore size) In some cases, the polymer matrix may comprise a thermoresponsive or temperature-responsive polymer. A thermoresponsive polymer (e.g., poly(N-isopropylacrylamide) (NIPAAM)) may phase separate from a solution upon heating or upon cooling (e.g., polymer showing lower critical solution temperature (LCST) or upper critical solution temperature (UCST). The polymer matrix may comprise polymer which may collapse at high temperature in order to, for example, control the pore size of the hydrogel or polymer matrix. Non-limiting examples of thermoresponsive polymers that may be used to form hydrogel/polymer matrix with tunable properties may include Poly(N-vinyl caprolactam), Poly(N-ethyl oxazoline), Poly(methyl vinyl ether), Poly(acrylic acid-co-acrylamide), or a combination thereof. A change in temperature may close or open a pore in the polymer matrix to allow a reagent, a nucleic acid molecule, a protein, or any biomolecule or molecule smaller than the pore size to be released from the polymer matrix compartment. In some cases, the released molecule may be a molecule of interest. The released molecule may be collected for analysis. The pore size may be decreased after releasing the molecule(s) to localize the biological component and other molecules within the polymer matrix. In some cases, the remaining localized molecules may be a molecule (s) of interest. For example, the pore size may be adjusted to allow a protein tag (e.g., shorter DNA oligomers) to be released from the polymer matrix compartment and the fluidic chambers. The protein tag may then be collected while the mRNA remain localized within the polymer matrix compartment for further analysis.

The polymer matrix may have a pore size of about 5 nanometers (nm) to about 100 nm. The polymer matrix may have a pore size of about 5 nm to about 10 nm, about 5 nm to about 20 nm, about 5 nm to about 30 nm, about 5 nm to about 40 nm, about 5 nm to about 50 nm, about 5 nm to about 60 nm, about 5 nm to about 70 nm, about 5 nm to about 80 nm, about 5 nm to about 90 nm, about 5 nm to about 100 nm, about 5 nm to about 110 nm, about 10 nm to about 20 nm, about 10 nm to about 30 nm, about 10 nm to about 40 nm, about 10 nm to about 50 nm, about 10 nm to about 60 nm, about 10 nm to about 70 nm, about 10 nm to about 80 nm, about 10 nm to about 90 nm, about 10 nm to about 100 nm, about 10 nm to about 110 nm, about 20 nm to about 30 nm, about 20 nm to about 40 nm, about 20 nm to about 50 nm, about 20 nm to about 60 nm, about 20 nm to about 70 nm, about 20 nm to about 80 nm, about 20 nm to about 90 nm, about 20 nm to about 100 nm, about 20 nm to about 110 nm, about 30 nm to about 40 nm, about 30 nm to about 50 nm, about 30 nm to about 60 nm, about 30 nm to about 70 nm, about 30 nm to about 80 nm, about 30 nm to about 90 nm, about 30 nm to about 100 nm, about 30 nm to about 110 nm, about 40 nm to about 50 nm, about 40 nm to about 60 nm, about 40 nm to about 70 nm, about 40 nm to about 80 nm, about 40 nm to about 90 nm, about 40 nm to about 100 nm, about 40 nm to about 110 nm, about 50 nm to about 60 nm, about 50 nm to about 70 nm, about 50 nm to about 80 nm, about 50 nm to about 90 nm, about 50 nm to about 100 nm, about 50 nm to about 110 nm, about 60 nm to about 70 nm, about 60 nm to about 80 nm, about 60 nm to about 90 nm, about 60 nm to about 100 nm, about 60 nm to about 110 nm, about 70 nm to about 80 nm, about 70 nm to about 90 nm, about 70 nm to about 100 nm, about 70 nm to about 110 nm, about 80 nm to about 90 nm, about 80 nm to about 100 nm, about 80 nm to about 110 nm, about 90 nm to about 100 nm, about 90 nm to about 110 nm, or about 100 nm to about 110 nm. The polymer matrix may have a pore size of about 5 nm, about 10 nm, about 20 nm, about 30 nm, about 40 nm, about 50 nm, about 60 nm, about 70 nm, about 80 nm, about 90 nm, about 100 nm, or about 110 nm. The polymer matrix may have a pore size of at least about 5 nm, about 10 nm, about 20 nm, about 30 nm, about 40 nm, about 50 nm, about 60 nm, about 70 nm, about 80 nm, about 90 nm, about 100 nm, or less. The polymer matrix may have a pore size of at most about 10 nm, about 20 nm, about 30 nm, about 40 nm, about 50 nm, about 60 nm, about 70 nm, about 80 nm, about 90 nm, about 100 nm, about 110 nm, or more.

A polymer matrix may be degradable. In some embodiments, the degradable polymer matrix may be depolymerized (e.g., into polymer precursors). At least a portion of the polymer precursors from a degraded polymer matrix may be used again to form another polymer matrix. An energy source as provided herein may be used to depolymerize a polymer matrix. In some embodiments, by depolymerizing a polymer matrix, a compartment surrounding a biological component may be deconstructed (e.g., to release the biological component). In some embodiments, releasing the biological component may also include releasing a biological component from a captured element. That is, the biological component may be detached or uncoupled from the capture element. In some embodiments, a capture element, or a portion of a capture element, may be cleaved using a chemical compound (e.g., an agarase, a dextranase, a metalloproteinase, or other enzyme) or by providing energy to the capture site or capture element using the energy source (e.g., light mediated degradation). In some cases, the capture element may be cleaved using hydrolysis, ester hydrolysis, enzymatic hydrolysis, reversible click reactions, or photolytic cleaving. In some cases, the capture element may be uncoupled from a surface or a biological component by applying physical force (e.g., sonication, agitating the fluidic device, etc.). In some cases, a capture element may comprise agarose which may be degraded or cleaved using an agarase. In some cases, a capture element may comprise dextran which may be degraded or cleaved using dextranase. In some cases, a capture element may comprise a metalloproteinase (MMP) degradable peptide. In certain cases, the biological component may be decoupled from a capture element using a chemical method (e.g., using a digesting enzyme to cleave a bond) or a physical method (e.g., using an energy source to provide heat, microwave, electromagnetic waves, electromagnetic field, sonic waves, etc.).

In some embodiments, a polymer matrix may be contacted with a cleavage mix to degrade or depolymerize the polymer matrix. In some embodiments, the cleavage mix may comprise dithiothreitol (DTT), β-mercaptoethanol, glutathione, tris(2-carboxyethyl)phosphine (TCEP), tris(3-hydroxy propyl)phosphine (THP), or a combination thereof. In some embodiments, heat may be directed to a polymer matrix to degrade or depolymerize the polymer matrix. In some embodiments, the polymer matrix may be heated to at least 90° C. In some embodiments, the polymer matrix may be heated to from 80° C. to 100° C., 90° C. to 110° C., 110° C. to 120° C., 120° C. to 180° C., or 180° C. to 250° C. A wavelength of light appropriate to cleave a photocleavable crosslinker that crosslinks a polymer matrix may be directed to a polymer matrix to degrade or depolymerize the polymer matrix. In some embodiments, the fluidic device may comprise a photoactive compound (e.g., a photoacid generator or a photobase generator) that can degrade or depolymerize the polymer matrix upon exposure to light energy (e.g., a wavelength of light).

The polymer matrix may comprise a hydrogel. In some embodiments, the polymer matrix may form a wall, where the polymer matrix wall may be coupled to a first surface and/or the second surface. In some embodiments, the wall may be a hydrogel wall. The polymer matrix wall or the hydrogel wall may have a thickness from 1 µm to 250 µm. The polymer matrix wall or hydrogel wall may have a thickness from 1 µm to 5 µm, 1 µm to 10 µm, 1 µm to 20 µm, 1 µm to 30 µm, 1 µm to 40 µm, 1 µm to 50 µm, 1 µm to 100 µm, 1 µm to 150 µm, 1 µm to 250 Pin, 5 µm to 10 µm, 5 µm to 20 µm, 5 µm to 30 µm, 5 µm to 40 µm, 5 µm to 50 µm, 5 µm to 100 µm, 5 µm to 150 µm, 5 µm to 250 µm, 10 µm to 20 µm, 10 µm to 30 µm, 10 µm to 40 µm, 10 µm to 50 µm, 10 µm to 100 µm, 10 µm to 150 µm, 10 µm to 250 µm, 20 µm to 30 µm, 20 µm to 40 µm, 20 µm to 50 µm, 20 µm to 100 µm, 20 µm to 150 µm, 20 µm to 250 µm, 30 µm to 40 µm, 30 µm to 50 µm, 30 µm to 100 µm, 30 µm to 150 µm, 30 µm to 250 µm, 40 µm to 50 µm, 40 µm to 100 µm, 40 µm to 150 µm, 40 µm to 250 µm, 50 µm to 100 µm, 50 µm to 150 µm, 50 µm to 250 µm, 100 µm to 150 µm, 100 µm to 250 µm, or 150 µm to 250 µm. The polymer matrix wall or hydrogel wall may have a thickness of about 1 µm, about 5 µm, about 10 µm, about 20 µm, about 30 µm, about 40 µm, about 50 µm, about 100 µm, about 150 µm, or about 250 µm. The polymer matrix wall or hydrogel wall may have a thickness of at least 1 µm, 5 µm, 10 µm, 20 µm, 30 µm, 40 µm, 50 µm, 100 µm, 150 µm, 250 µm, or more. The polymer matrix wall or hydrogel wall may have a thickness of at most 5 µm, 10 µm, 20 µm, 30 µm, 40 µm, 50 µm, 100 µm, 150 µm, or 250 µm. The polymer matrix wall or hydrogel wall may have a thickness of less than 1 µm.

In some embodiments, a hydrogel may comprise polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, ethoxylated pentaerythritol tetraacrylate, or combinations or mixtures thereof. In some embodiments, the hydrogel may comprise PEG-thiol/ PEG-acrylate, acrylamide/N,N'-bis(acryloyl)cystamine (BACy), or PEG/PPO. For example, a PEG molecule may comprise a multi-arm PEG derivative with thiol groups at each terminal of the arms connected to one pentaerythritol core. A reactive free thiol, SH, sulfhydryl, or mercapto group may selectively react with the microfluidic surface (e.g., a maleimide or a transition metal surface) including gold, silver, etc. PEG-SH can be air oxidized to form S—S disulfide (disulfide) bonds, which can be reversed with reducing agents to form reversible PEGylation or PEG hydrogel.

As discussed, the polymer matrix (e.g., hydrogel) may be porous enough to allow passage of a reagent (e.g., an enzyme, a reagent, a small molecule, an antibody), while preventing passage of the captured biological component (e.g., DNA, RNA, a protein, cells, etc.) or a compound associated with the biological component (e.g., DNA, RNA, an antibody, a secreted compound from a cell, etc.). In some embodiments, a reagent may comprise an enzyme, or a primer having a size of less than 50 base pairs (bp). A primer may have a size from 5 pb to 50 bp. In some embodiments, a primer may have a size from 5 pb to 10 bp, 10 bp to 20 bp, 20 bp to 30 bp, 30 bp to 40 bp, or 40 bp to 50 bp. In certain embodiments, a primer may have a size of more than 50 bp. In various embodiments, a primer may have a size of less than 5 bp.

In certain embodiments, a first surface, a second surface, or both surfaces of a channel in the fluidic device may be functionalized, as described herein. A surface (e.g., a first surface, a second surface, a third surface, etc.) of the fluidic device may comprise a compound configured to bind to a biological component (e.g., a captured biological component). In some embodiments, a surface (e.g., the first surface, the second surface, the third surface, etc.) of the fluidic device may comprise one or more barcodes. One or more surfaces may comprise oligos to from DNA clusters for sequencing. In some cases, one or more surfaces may comprise one or more nanopore readers for direct DNA and/or RNA readout. One or more surfaces may comprise nanowells to capture single RNA molecules and/or single DNA molecules or to contain a DNA/RNA library. In some alternative cases, one or more surfaces may comprise patterned hydrophobic/hydrophilic features for selective deposition of DNA nanoballs. Nanoballs may be generated by circularization and amplification of DNA libraries from DNA/RNA molecules.

One or more surfaces of the fluidic device may comprise an optical (e.g., fluorescence), mechanical, electrical, or biochemical sensing element or sensor. The sensing element may comprise a fluorescent tag, an enzyme, a primer, an oligonucleotide, or a sensor molecule (e.g., a biochemical sensor molecule). The sensing element may be used to detect and/or measure a pH, an oxygen concentration, a $CO_2$ concentration, or any other suitable variable. The sensing element may detect and/or measure a parameter locally. For example, the sensing element may detect and/or measure a pH, an oxygen concentration, or a $CO_2$ concentration within a compartment (e.g., a polymer matrix shell cylinder) surrounding or encapsulating the biological component.

Multi-Tiered Systems

Also provided herein are systems for analyzing a biological component comprising at least a flow channel (e.g., a first or upper layer) and an analysis channel (e.g., a second or lower layer). The system may comprise a fluidic device including a flow channel, an analysis channel, and a layer or wall disposed between the flow channel and the analysis channel. The system may include at least one energy source in communication with the fluidic device, as described herein. The analysis channel may be disposed adjacent to the flow channel, where at least one flow inhibition element may be disposed within the flow channel to inhibit or stop flow of the biological component in the flow channel. The layer disposed between the flow channel and the analysis channel may comprise at least one sealable aperture disposed at or adjacent to the at least one flow inhibition element. One or more biological components may be stopped or trapped adjacent to the sealable aperture. The at least one sealable aperture may be configured to allow passage of the one or more biological components. For example, the sealable aperture may be configured to allow passage of the one or more biological components from the flow channel to the analysis channel. The at least one energy source may be in communication with the analysis channel. Furthermore, the at least one energy source may form, or be configured to form, a polymer matrix within the analysis channel.

As described herein, in some embodiments, the fluidic device may comprise a microfluidic device or a nanofluidic device. In certain embodiments, the fluidic device may be used for nucleic acid sequencing. In some cases, the fluidic device may comprise a nucleic acid sequencing flow cell. In other cases, sequencing may comprise short-read sequencing, nanopore sequencing, sequencing by synthesis, sequencing by in-situ hybridization, sequencing through collection of any optical readouts, or any other suitable method of sequencing. As described herein, the biological component may comprise a cell, a cell lysate, a nucleic acid, a microbiome, a protein, a mixture of cells, a spatially-linked biological component, a metabolite, a combination thereof, or any other suitable biological component. In some cases, the mixture of cells may comprise two or more different cell types. For example, the mixture of cells may comprise a first cell type and a second cell type. In some cases, the mixture of cells may comprise 2, 3, 4, 5, 6, 7, 8, 9, 10, or more cell types. A cell may be a mammalian cell (e.g., a human cell), a fungal cell, a bacterial cell, a tumor spheroid, a combination thereof, or any other suitable cell. In some cases, the biological component may comprise a tumor spheroid or a spatially-linked biological component (or sample).

In some cases, the nucleic acid may comprise at least 100 bases or base pairs. In certain embodiments, a nucleic acid comprises a DNA or an RNA. The DNA may be at least 100 bp long. In some embodiments, the DNA may include at least 50 bp, 100 bp, 200 bp, 300 bp, 400 bp, 500 bp, 600 bp, 700 bp, 800 bp, 900 bp, 1,000 bp, 10 kilo base pairs (kbp), 100 kbp, 1 mega base pair (Mbp), 100 Mbp, 1 giga base pair (Gbp), 10 Gbp, 100 Gbp, or more base pairs. The biological component may comprise a DNA molecule that comprises any number of base pairs in between the mentioned numbers herein. For example, the DNA may comprise from 50 bp to 1,000 bp, 300 bp to 10 kbp, or 1,000 bp to 10 Gbp. The RNA may be dsRNA. The dsRNA may comprise at least 50 bp, 100 bp, 200 bp, 300 bp, 400 bp, 500 bp, 600 bp, 700 bp, 800 bp, 900 bp, 1,000 bp, 10 kbp, or 100 kbp. The biological component may comprise a dsRNA molecule that includes any number of base pairs in between the mentioned numbers herein. For example, the dsRNA may comprise from 50 bp to 1,000 bp, 300 bp to 10 kbp, or 1,000 bp to 100 kbp. The RNA may be ssRNA. The ssRNA may comprise at least 50 nucleotides to 100,000 nt. The ssRNA may comprise from 50 nt to 100 nt, 50 nt to 1,000 nt, 50 nt to 10,000 nt, 50 nt to 100,000 nt, 100 nt to 1,000 nt, 100 nt to 10,000 nt, 100 nt to 100,000 nt, 1,000 nt to 10,000 nt, 1,000 nt to 100,000 nt, or 10,000 nt to 100,000 nt. In some cases, the ssRNA may be less than 50 nucleotides long. The ssRNA may be more than 100,000 nucleotides long.

In some embodiments, the flow channel or a portion thereof may be parallel, or substantially parallel, with the analysis channel or at least a portion thereof. In some embodiments, the flow channel may be removably couplable to the analysis channel. For example, a user may remove the flow channel from the analysis channel. Accordingly, a portion of the fluidic device comprising the analysis channel may be used to conduct various analyses or experiments. With the portion of the fluidic device comprising the flow channel removed, the portion of the fluidic device comprising the analysis channel may be more accessible, e.g., to detectors, cameras, or other devices for analyzing the biological components within the analysis channel.

In some cases, the analysis channel may include polymer matrix structures for capturing or trapping a biological component or a molecule or compound produced by the biological component (e.g., prior to introduction of the biological components into the fluidic device). For example, a user may obtain an analysis channel that includes polymer matrix structures. That is, the user may not form the polymer matrix structures. In various cases, the analysis channel may be configured to include polymer matrix structures for capturing or trapping a biological component or a molecule or compound produced by the biological component. For example, in such embodiments, subsequent to introduction of the biological components into the fluidic device and the analysis channel, one or more polymer matrix structures may be formed in the analysis channel. The analysis channel may be configured for a screening process, a library preparation, or another suitable process. In some embodiments, the screening process may be for drug screening, antibiotic screening, culture conditions screening, or CRISPR screening. In certain cases, a plurality of samples may be placed into a plurality of channels. The plurality of samples may be screened against a variety of conditions in other signal-containing channels.

The sealable aperture may be configured to transition from a sealed state to an open state. For example, a sealable aperture may comprise a heat sensitive polymer that can melt, for example, upon receiving heat and render the sealable aperture open. In some cases, the passage of the biological component through the sealable aperture may be inhibited in the sealed state. In certain cases, the passage of the biological component through the sealable aperture may be allowed in the open state. In some cases, the sealable aperture may be sealed with an agarose gel, a temperature-soluble polymer, an N-isopropylacrylamide (NIPAAm) polymer, a wax compound, an alginate, or any other suitable compound or material.

Figure 6A:
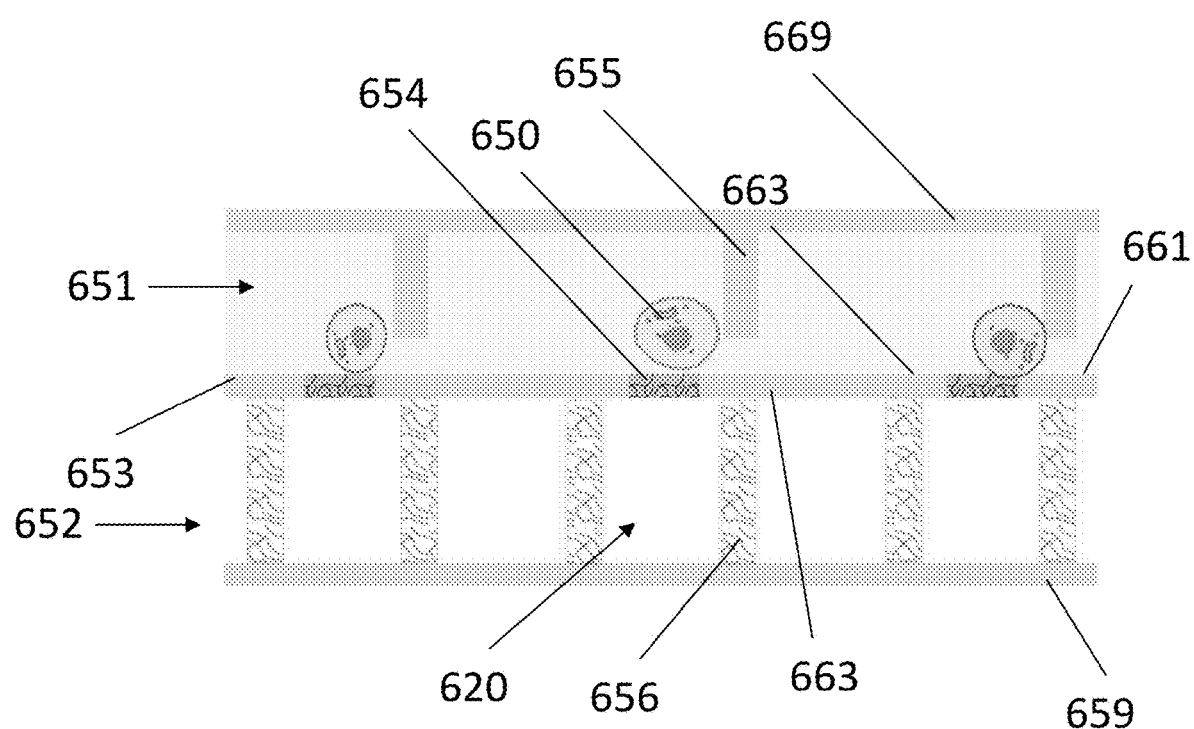
FIG. 6A shows a portion of another embodiment of a fluidic device including a sealable aperture.
Figure 6B:
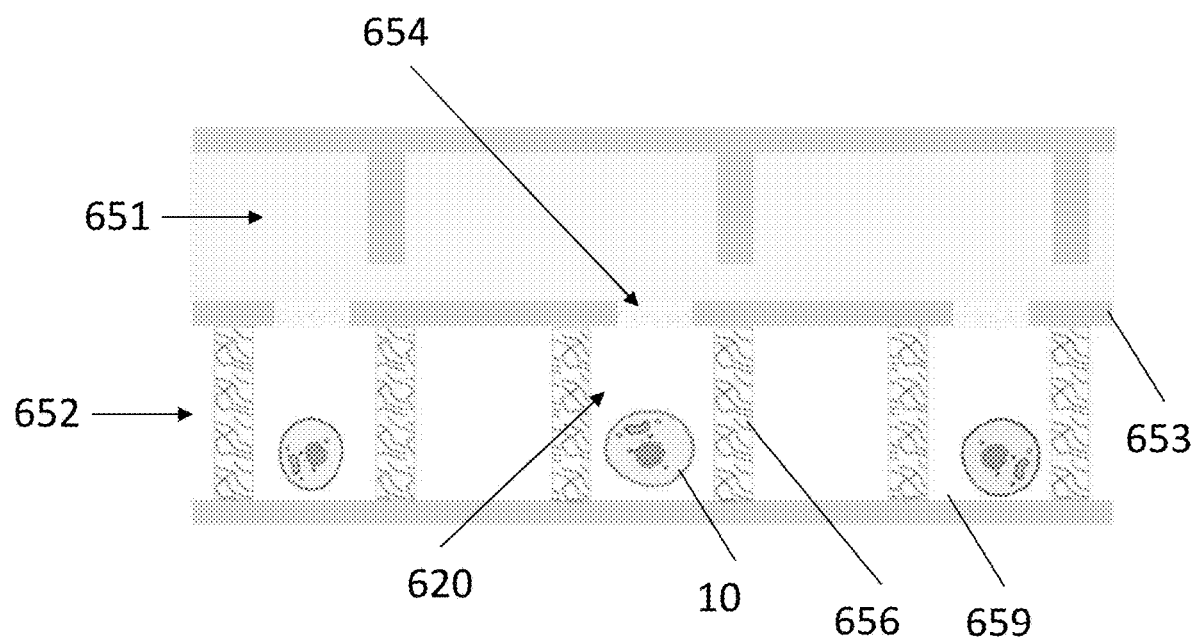
FIG. 6B shows a method of trapping biological components in a portion of a fluidic device, according to some embodiments.

FIGS. 6A and 6B show a portion of a fluidic device configured to trap a biological component 50. The fluidic device may comprise a flow channel or chamber 651, an analysis channel or chamber 652, and a layer or wall 653 disposed between at least a portion of the flow channel 651 and the analysis channel 652. The layer 653 may comprise one or more sealable apertures or openings 654. Additionally, one or more flow inhabitation elements 655 may inhibit or prevent, or be configured to inhibit or prevent, the biological component 50 from flowing along the flow channel 611. A flow inhibition element 655 may be configured to stop or trap the biological component 50 adjacent to a sealable aperture 654. As described herein, the sealable aperture 614 may be configured to transition from a sealed state (e.g., a closed state) or configuration to an open state or configuration. FIG. 6A shows an example of the sealable aperture 614 in a sealed state. FIG. 6B shows an example of the sealable aperture 654 in an open state. Upon transitioning to a sealed state to an open state, the sealable aperture 654 may allow or permit passage of the biological component 50 from at least a portion of the flow channel 651 to at least a portion of the analysis channel 652. In certain instances, the analysis channel 652 may be placed, or configured to be placed, below the flow channel 651 to allow the biological component 50 to be transferred to the analysis channel 652 from the flow channel 651 by a force provided (e.g., via gravity, high pressure pulse by pressurizing a flow in the flow channel, and generating negative pressure in the analysis channel). In some embodiments, the fluidic device may be spun or centrifuged to disposed the one or more biological components from the flow channel to the analysis channel. Reagents can be disposed or passed through at least a portion of the analysis channel 652, for example, to conduct analyses or experiments are provided herein.

As shown in FIG. 6A, the flow inhibition element 655 may be disposed within at least a portion of the flow channel 651 to inhibit or prevent flow of a biological component (e.g., biological component 50) in the flow channel 651. The flow inhibition element 655 may be configured to capture or trap the biological component 50 in at least a portion of the flow channel 651. In some cases, the flow inhibition element 655 may extend from a surface (e.g., surface 669) of the flow channel 651. In some cases, the surface 669 may be disposed opposite of a flow channel surface 661, which is adjacent to the layer 653.

In various cases, the analysis channel 652 may comprise a surface 659 disposed opposite of the analysis channel surface 663, which is adjacent to or a surface of the layer 653. The analysis channel 652 may comprise one or more polymer matrices 656. The analysis channel 652 may comprise one or more polymer precursors. For example, one or more polymer precursors may be disposed in at least a portion of the analysis channel 652. The one or more polymer matrices 656 may be formed using an energy source which provides energy to the one or more polymer precursors in the analysis channel 602. The energy source may be in optical communication, electrochemical communication, electromagnetic communication, thermal communication, or microwave communication with the fluidic device or the analysis channel 652. In some cases, the energy source may be a light generating device, a heat generating device, an electrochemical generating device, an electrode, a microwave device, or a combination thereof. The energy source may selectively provide energy to the analysis channel 652 to form polymer matrices at predefined locations. A spatial energy modulating element may be used to selectively provide energy to the analysis channel 652.

In some cases, the spatial energy modulating element may comprise a photolithographic mask, a DMD system, or other suitable mask. The one or more polymer matrices 656 may be formed before the sealable aperture 654 transitions to an open state (e.g., as shown in FIG. 6A). For example, a polymer matrix may be formed and aligned with the sealable aperture such that the biological component 650 held by the inhibition element 655 may directed (e.g., fall by gravity or by fluid pressure) into a compartment 620 when the sealable aperture 654 is rendered open. The one or more polymer matrices 656 may be formed after the sealable aperture 654 transitions to an open state (e.g., as shown in FIG. 6B). The one or more polymer matrices 656 may form an analysis chamber or compartment 620, as described herein.

Figure 7A:
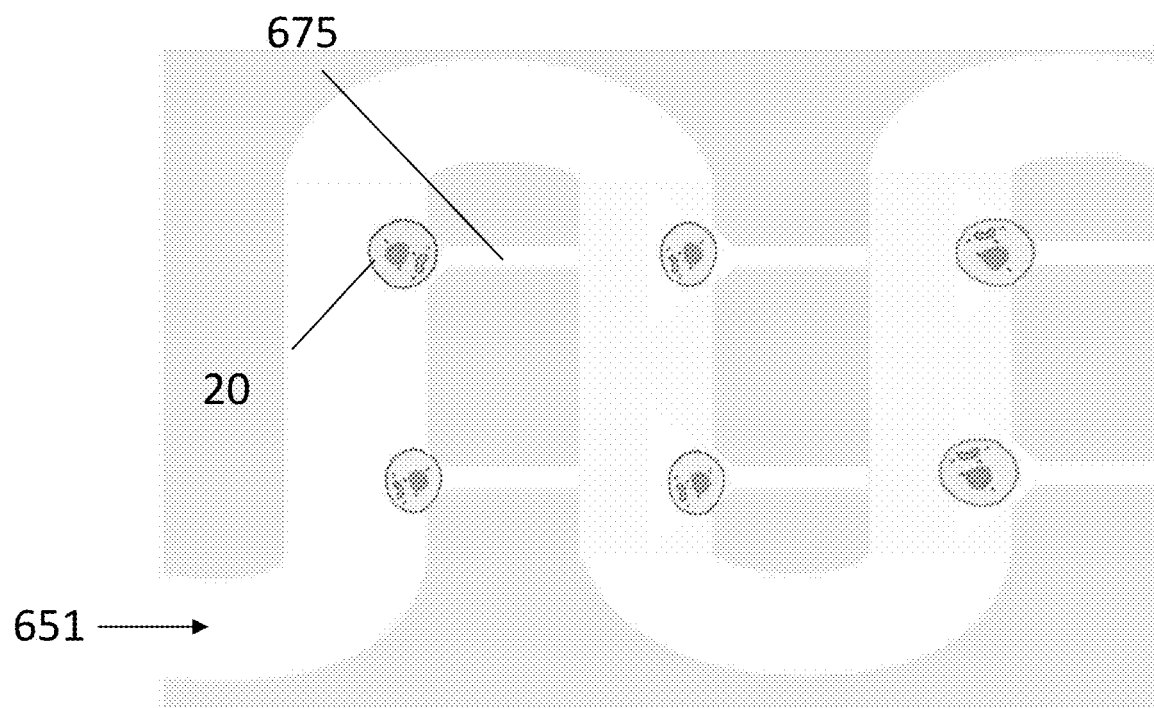
FIG. 7A shows a top view of a schematic of a portion of a fluidic device, according to some embodiments.
Figure 7B:
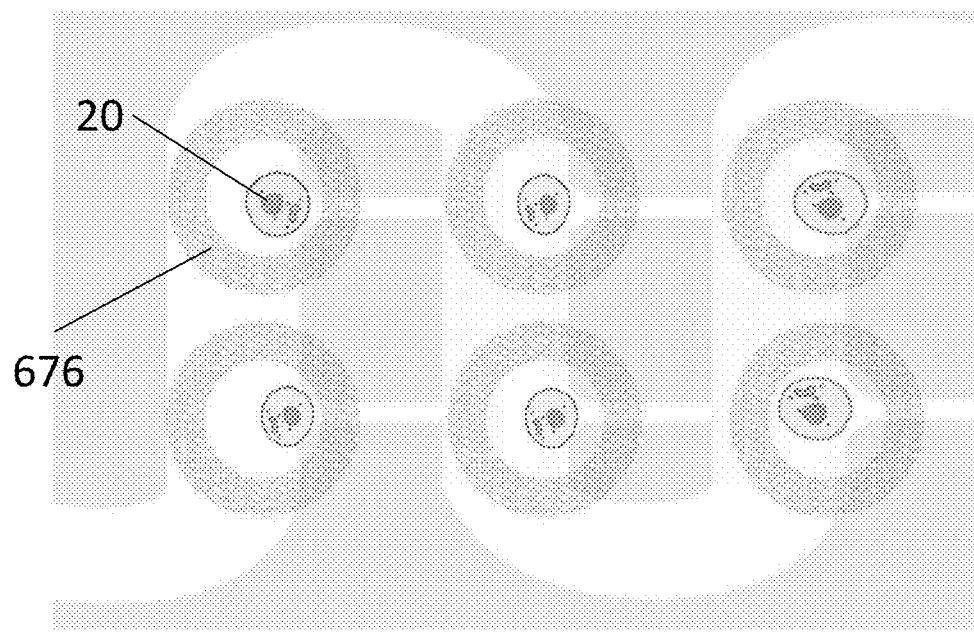
FIG. 7B shows a top view of a schematic of a portion of a fluidic device including polymer matrices, according to some embodiments.

FIGS. 7A and 7B show a top view of a fluidic device. A flow inhibition channel 675 may be configured to inhibit a biological component 20 from flowing along a flow channel 651. Flow of a fluid (e.g., a fluid including the biological component) through the flow channel 651 and the flow inhibition channel 651 may cause the biological component 20 to be trapped or stopped at an opening of the flow inhibition channel 675 as depicted in FIG. 7A. As illustrated, a dimension (e.g., a width) of the flow inhibition channel 675 may be too small or narrow to allow or permit passage of the biological component 20 through the flow inhibition channel 675. As shown in FIG. 7B, a polymer matrix 676 may be formed on or adjacent to (e.g., surrounding) the biological component 20. In some cases, the polymer matrix may surround at least a portion of the biological component. The fluidic device of FIGS. 7A and 7B may be a single-layer fluidic device. That is, the polymer matrix may be formed in the flow channel 651. As illustrated, a path of the flow channel 651 may be circuitous. For example, the flow channel 651 may include one or more curves. In some embodiments, the path of the flow channel may be straight, substantially straight, in a zig-zag pattern, or any other suitable shape.

In certain embodiments, the fluidic device of FIGS. 7A and 7B may comprise two or more layers. For example, the fluidic device may include a flow channel and an analysis channel (similar to the system shown in FIGS. 6A and 6B). Further, a sealable aperture may be disposed at or adjacent to a portion of a flow inhibition channel. In such embodiments, the biological component may be transferred into the analysis channel (e.g., disposed adjacent to or below the flow channel) through a sealable aperture, as described herein. In some cases, the analysis channel may receive two or more biological components. For example, the analysis channel may receive 2, 3, 4, 5, 6, 7, 8, 9, 10, or more biological components.

Figure 8:
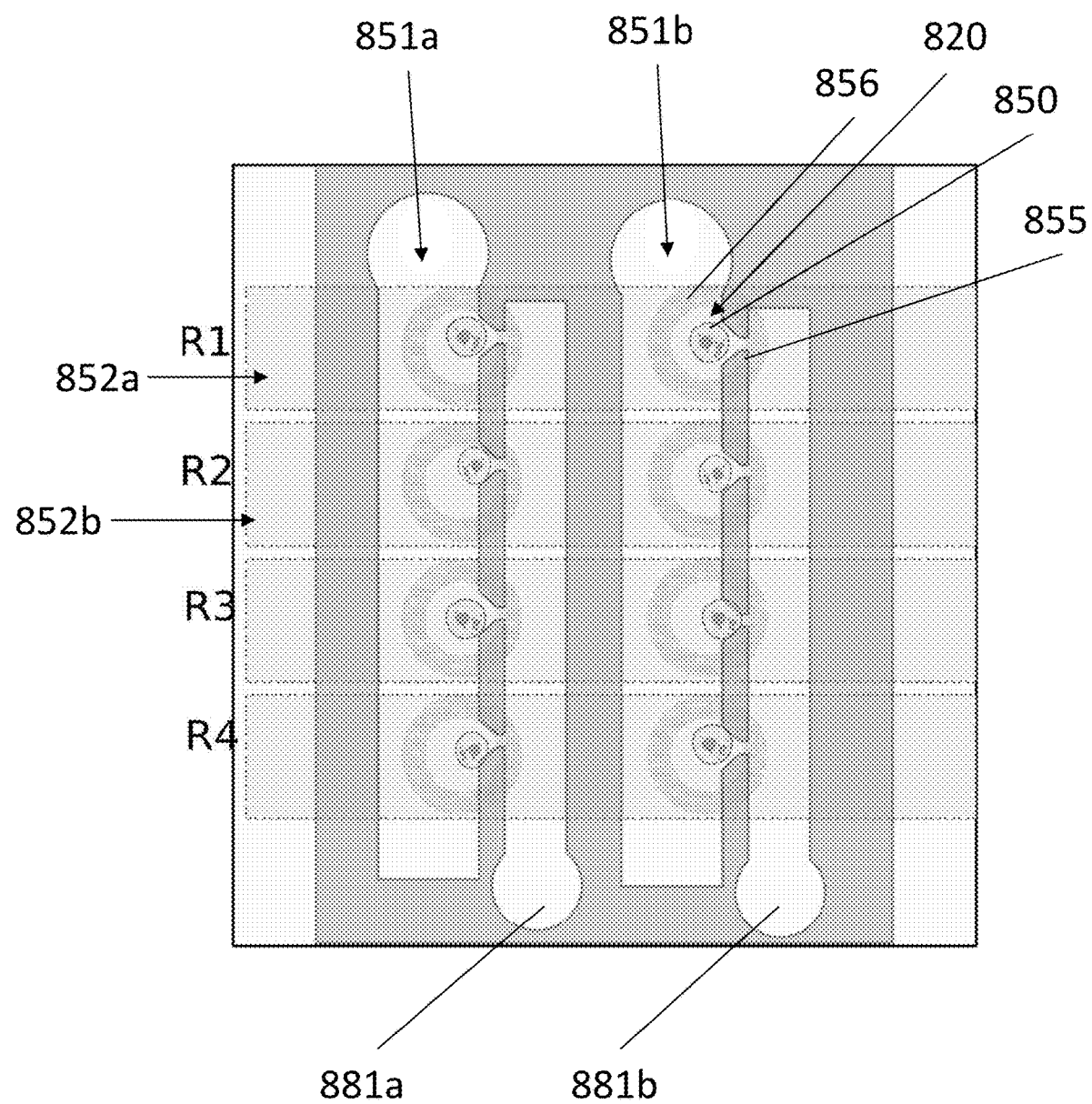
FIG. 8 shows a top view of a schematic of a portion of a fluidic device including multiple different reagents, according to some embodiments.

FIG. 8 shows an example of a fluidic device including, or configured for, a plurality of reagents and/or analytes (R1, R2, R3, and R4). The fluidic device may comprise a first flow channel 851a to receive one or more biological components from a first sample. The first flow channel 851a may allow or permit flow or passage of one or more biological components from the first sample. Further, the first flow channel 851a may allow or permit flow or passage of one or more polymer precursors. The fluidic device may comprise a second flow channel 851b to receive one or more biological components from a second sample. The second flow channel 851b may allow or permit flow or passage of one or more biological components from the second sample. Further, the second flow channel 851b may allow or permit flow or passage of one or more biological components from the second sample.

The first flow channel 851a and/or the second flow channel 851b may comprise a plurality of inhibition elements (e.g., inhibition element 855). A biological component (e.g., biological component 50) may be trapped or localized by the inhibition element 855. As described herein, the first flow channel 851a and/or the second flow channel 851b may comprise one or more sealable apertures disposed at or adjacent to the one or more inhibition elements 855 that can be opened (e.g., transitioned from a sealed state to an open state) to allow the biological component to move into a first analysis channel 852a or a second analysis channel 852b. The first and second flow channels 851a, 851b may be disposed above the first and second analysis channels 852a, 852b (e.g., in an upper layer and a lower layer similar to the fluidic device illustrated in FIGS. 6A and 6B). A polymer matrix 856 may be formed surrounding the biological component 50. The polymer matrix 856 may partially surround the biological component 50. The polymer matrix 856 may form a compartment or an analysis chamber 820 to localize the biological component 50 within at least a portion of an analysis channel (e.g., analysis channels 851a, 851b).

The first analysis channel 852a may comprise one or more reagents and/or analytes that are different from the one or more reagents and/or analytes in the second analysis channel 852b. The first analysis channel 852a may comprise one or more reagents and/or analytes that are the same as the one or more reagents and/or analytes in the second analysis channel 852b. In some cases, the fluidic device may include at least 2, 3, 4, 5, 6, 7, 8, 9, 10, 15, 25, 50, or more flow channels In certain cases, the fluidic device may include at least 2, 3, 4, 5, 6, 7, 8, 9, 10, 15, 25, 50, or more analysis channels. The fluidic device may analyze a plurality of biological components in parallel. The plurality of biological components may be exposed to one or more different reagents and/or analytes, as provided herein. Such a configuration (e.g., as shown in FIG. 8) may allow a plurality of biological components in one or more samples to be analyzed under various conditions provided by the different reagents and/or analytes. The fluidic device, shown in FIG. 8, may be used for a screening process. The screening process may be for drug screening, antibiotic screening, culture conditions screening, or CRISPR screening. The screening process may be performed in combinatorial manner. For example, a plurality of samples may be loaded in a plurality of flow channels (e.g., in parallel) which may be screened against a plurality of conditions in the plurality of analysis channels.

The first and/or the second samples may be homogenous or heterogenous. For example, the one or more biological components in the first sample may be the same or different. The first sample may be different from the second sample. In some cases, a biological component may be released from a compartment or analysis chamber 820 by selectively degrading a polymer matrix, as described herein. In other words, a polymer matrix may be degraded "on demand" (e.g., by a user or as directed by a computer). In various embodiments, the degradation may be achieved through the use of localized stimuli. In certain embodiments, the degradation may be achieved through the use of heat, light, electrochemical reactions, or some combination thereof. The released biological component may be collected using an outlet channel (e.g., outlet channel 881a or 881b).

As described in reference to the fluidic device of FIGS. 6A and 6B, a layer may be disposed between the flow channels 851a, 851b and the analysis channels 852a, 852b. The analysis channel surface adjacent to the layer (e.g., similar to surface 661 shown in FIG. 6A), the analysis channel surface opposite of the layer (e.g., similar to surface 659 shown in FIG. 6A), or both may comprise one or more barcodes, as described herein.

In some cases, the channels (e.g., channels 100, 200, 400) and/or the analysis channels (e.g., analysis channels 652, 852a, 852b) may comprise molecules in addition to, or instead of, the one or more barcodes. For example, any of the surfaces of the one or more channels and/or analysis channels may comprise an optical (e.g., fluorescence), mechanical, electrical or biochemical sensing element or sensor. The sensing element may comprise a fluorescent tag, an enzyme, a primer, an oligonucleotide, or a sensor molecule (e.g., a biochemical sensor molecule). The sensing element may be used to detect and/or measure a pH, an oxygen concentration, a $CO_2$ concentration, or any other suitable variable. The sensing element may detect and/or measure a parameter locally. For example, the sensing element may detect and/or measure a pH, an oxygen concentration, or a $CO_2$ concentration within a compartment (e.g., a polymer matrix shell cylinder) surrounding the biological component.

Figure 16A:
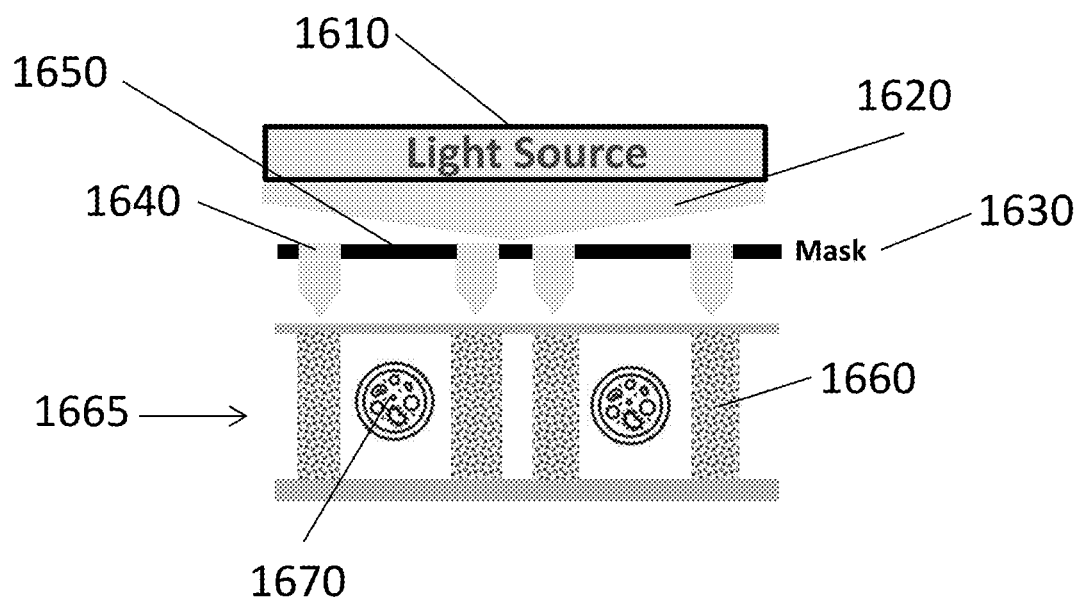
FIG. 16A illustrates an example of forming a polymer matrix using an energy modulating element, according to some embodiments.

FIG. 16A shows a portion of any of a system as provided herein including an energy source 1610 (e.g., a light source) and a spatial energy modulating element (e.g., a mask) 1630. In some embodiments, the energy source 1610 may be coupled to an objective (e.g., a microscope objective or lens). The energy source 1610 may emit energy as electromagnetic waves (e.g., microwaves, light, heat, etc.). In some embodiments, the emitted energy 1620 may form, or may be sufficient to form, a polymer matrix 1660 within at least a portion of the channel 1665. In some embodiments, the energy source 1610 is configured to emit energy towards only specific targeted portions of the channel 1665. In some embodiments, this can be achieved through the use of the spatial energy modulating element or mask 1630. For example, the non-emitting portions 1650 of the spatial energy modulating element 1630 may inhibit or prevent energy from being directed to one or more locations on the channel 1665 (e.g., a location of a biological component). The emitting portions 1640 may allow energy emitted 1620 by the energy source 1610 to contact targeted locations on the channel 1665. In some embodiments, the mask 1630 comprising the emitting portions 1640 and the non-emitting portions 1650 may comprise physical components (e.g., an opaque material, a thermal shield, an electromagnetic shield, etc.). In other embodiments, the mask 1630, the emitting portions 1640, the non-emitting portions 1650, or some combination thereof, may comprise digital components (e.g., a computer code or digital system to operate electrodes, etc.). For example, a digital or a virtual mask may render one or more electrodes, or arrays of electrodes, to produce spatially-modulated energy (e.g., light, electrical current, etc.) to form the patterned polymer matrix 1660.

With continued reference to FIG. 16A, in some cases, the polymer matrix 1660, or at least a portion of polymer matrix 1660, may surround, or substantially surround, the biological component 1670. In some embodiments, the polymer matrix 1660 may, by itself or in conjunction with the channel and other surfaces, may encapsulate the biological component 1670.

In some embodiments, any of the surfaces of the channel or analysis channel may be configured to carry a functional group, as described herein. In certain embodiments, the system may further comprise a detector for detecting (or identifying) the biological component, the one or more barcodes, or a combination thereof, as described herein. In various embodiments, the system may further comprise a platform or a stage that is configured to hold the fluidic device. In some embodiments, the system may further comprise a sequencing device. In some cases, the system may further comprise a spatial energy modulating element to selectively supply the energy to the fluidic device, as described herein.

Figure 16B:
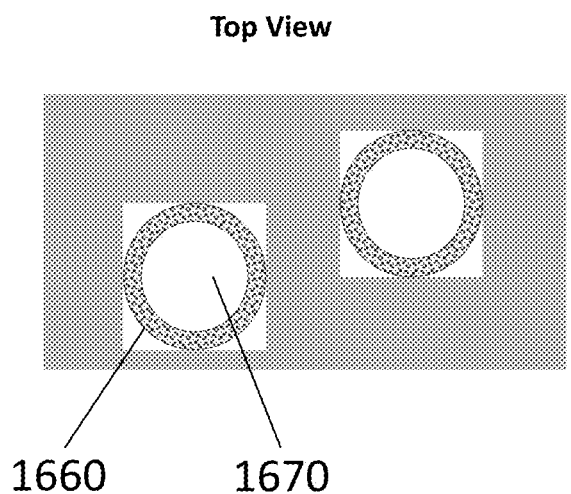
FIG. 16B illustrates a top view of an example of a polymer matrix formed using an energy modulating element, according to some embodiments.

FIG. 16B shows a top view of a channel as provided herein. Emitted energy from an energy source may be modulated spatially as described herein to form a polymer matrix 1660. In some instances, the polymer matrix 1660 may encapsulate the biological component 1670. In certain instances, the biological component may be encapsulated by the walls of the channel in and/or with a polymer matrix 1660.

Figure 17A:
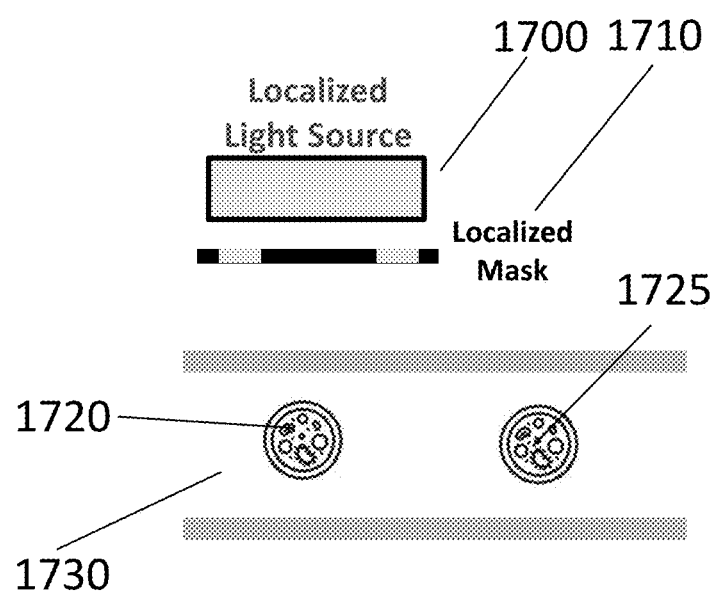
FIGS. 17A-17E illustrate exemplary steps of forming a polymer matrix using a movable energy modulating element, according to some embodiments.
Figure 17B:
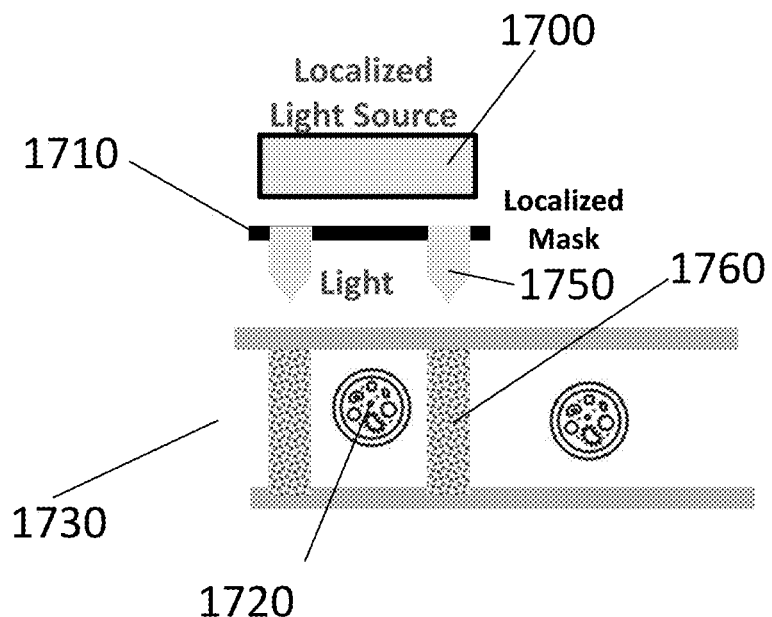

FIG. 17A-17E illustrates an example workflow of applying energy to any of the fluidic devices described herein to form a polymer matrix. FIG. 17A shows a portion of a channel 1730 of a fluidic device, a first biological component 1720, a second biological component 1725, an energy source (e.g., a light source) 1700, and an energy modulating element (e.g., a mask or localized mask) 1710. In some embodiments, the energy source 1700 may be positioned adjacent to or near the channel 1730 such that energy sufficient to trigger hydrogel polymerization may be directed from the energy source 1700 to at least a portion of the channel 1730. In some embodiments, the spatial energy modulating element 1710 may be used to selectively allow the energy from the energy source 1700 to communicate with at least a portion of the fluidic device. A biological sample or a biological component 1720, 1725 may be present within the channel 1730. FIG. 17B shows a first step of hydrogel formation at a first location (e.g., adjacent to the first biological component 1720). The energy source 1700 may emit energy 1750 sufficient to form a polymer matrix 1760 within the channel 1730 adjacent to the first biological component 1720.

Figure 17C:
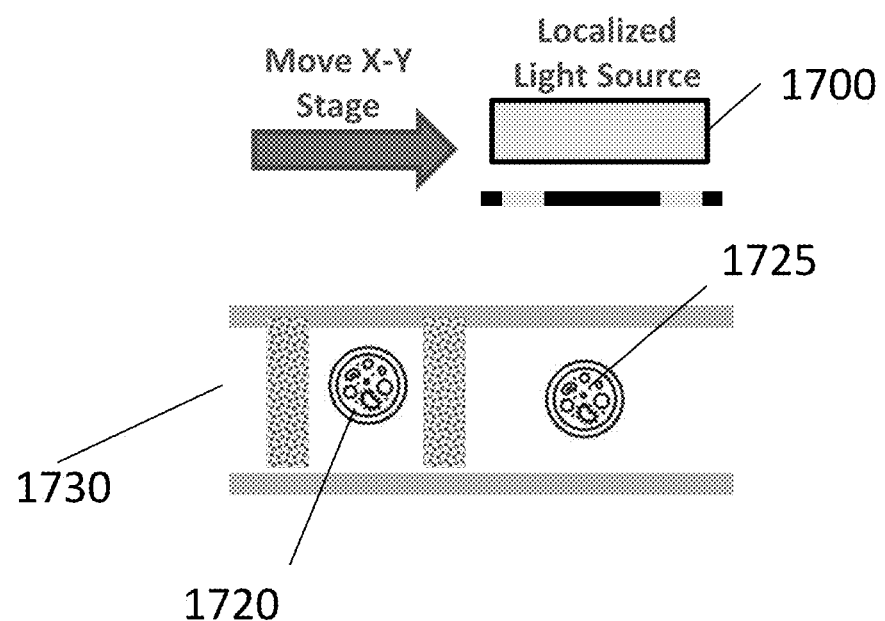

In some embodiments, the energy may be guided by or passed through a spatial energy modulating element 1710, as described herein. In some examples, a polymer matrix may form at locations in the channel corresponding to emitting portions of the spatial energy modulating element 1710. FIG. 17C shows a second step of hydrogel formation in a channel 1730 where the relative positions of the energy source 1700 and the channel 1730 may be changed. In some embodiments, the fluidic device may be placed on a movable stage. In certain embodiments, the energy source 1700 may be movable or coupled to a movable stage. In various embodiments, the mask 1710 may be movable or coupled to a movable stage. In some embodiments, some combination of the energy source 1700, the mask 1710, and the fluidic device may be configured to be movable with respect to one another. In some embodiments, the spatial energy modulating element 1710 may be a virtual spatial energy modulating element, and the position of the emitting areas may be changed digitally.

Figure 17D:
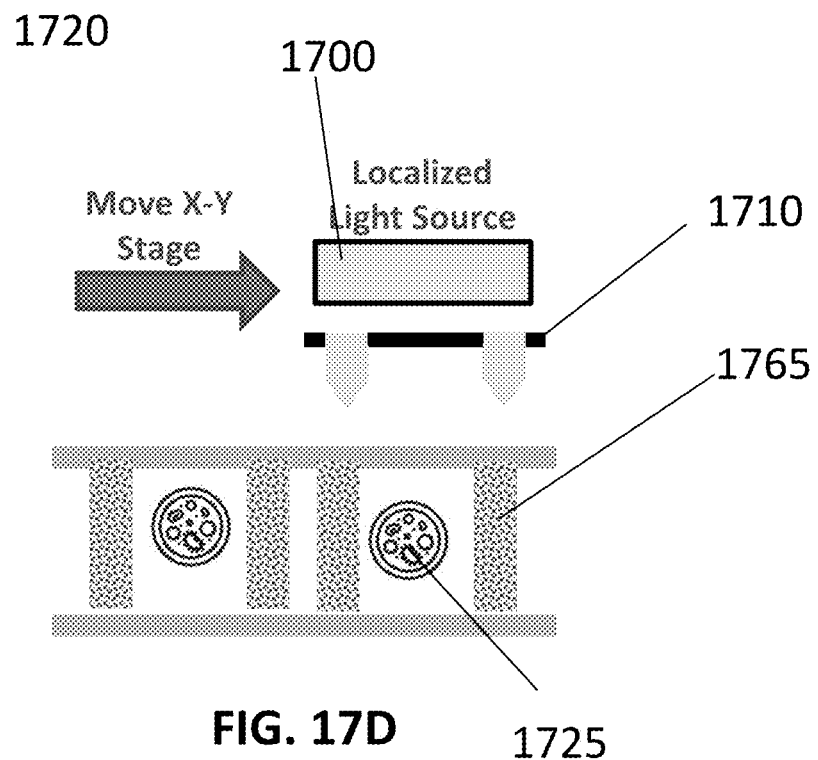
Figure 17E:
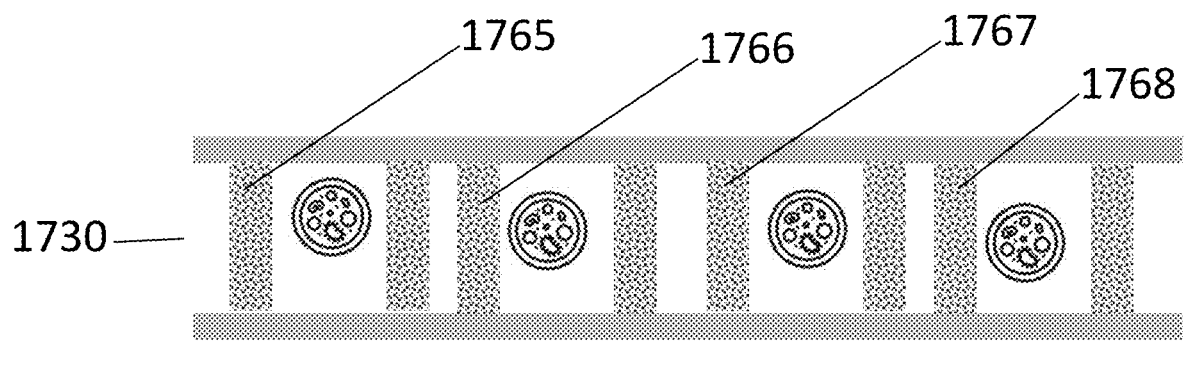

FIG. 17D shows a third step, where energy from the energy source 1700 passing through the energy modulating element (or mask) 1710 may form a polymer matrix at a second location (e.g., adjacent to a second biological component 1765). In some embodiments, the energy source 1700, the mask 1710, and the fluidic device may be moved with respect to one another to form different hydrogel patterns comprising a plurality of hydrogels matrices (e.g., hydrogel matrix 1765, 1766, 1767, and 1768) within the channel 1730 using energy from the energy source, as described herein (FIG. 17E).

Methods of Analyzing Biological Components

Also provided herein are methods for analyzing biological components. The method may comprise introducing a biological component into a fluidic device and forming a polymer matrix on or adjacent to the biological component. The method may further include coupling the biological component to one or more capture elements disposed on a surface (e.g., a first surface) of the fluidic device to yield a coupled biological component. Accordingly, a polymer matrix may be formed on or adjacent to the coupled biological component.

Figure 5:
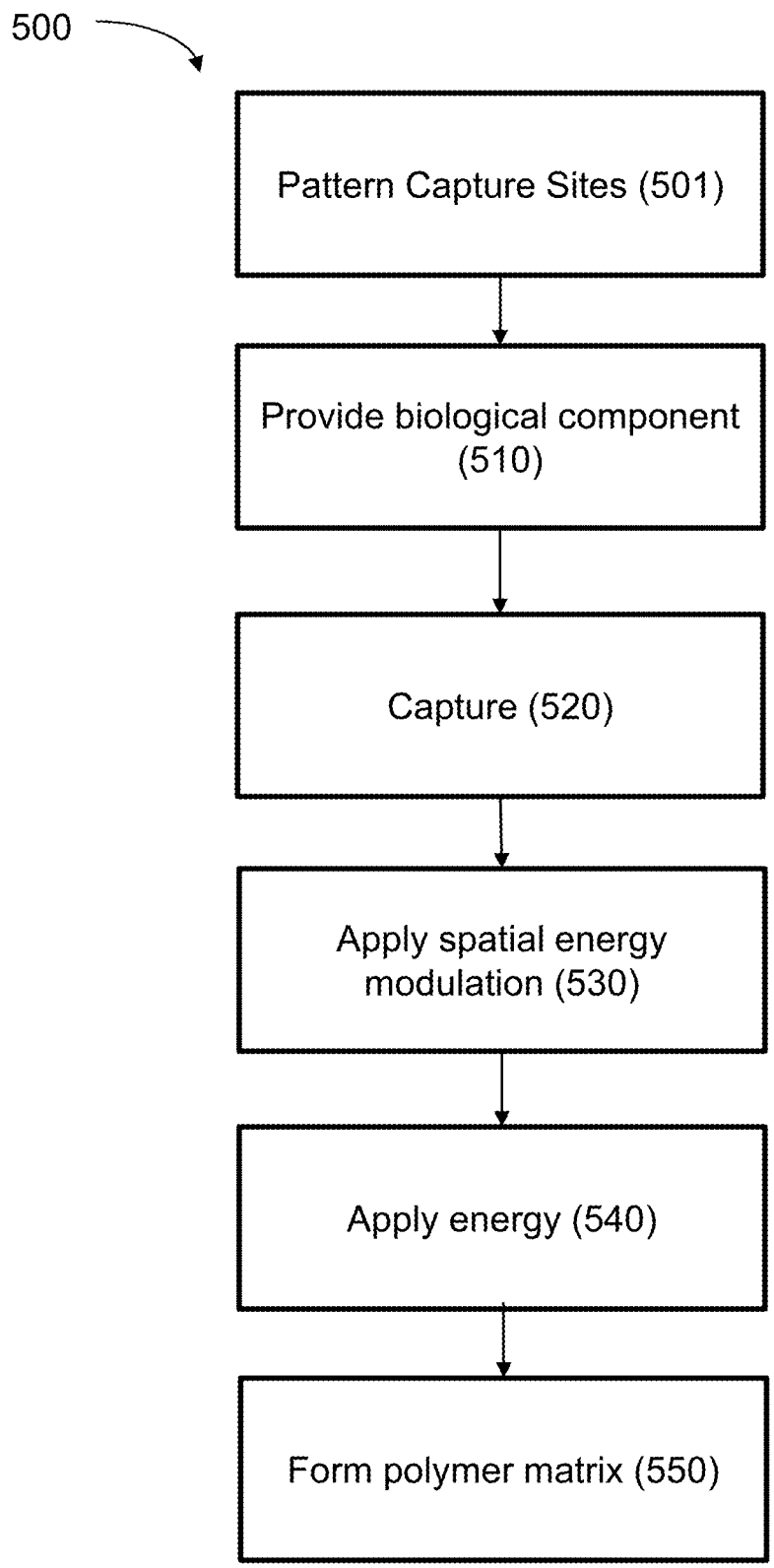
FIG. 5 is a flow chart depicting an embodiment of forming a polymer matrix around a biological component coupled to a surface.

FIG. 5 is a flow chart of an example of a method of analyzing a biological component using a system comprising a fluidic device as disclosed herein. The method 500 may comprise providing and/or introduced a biological sample 510 into the fluidic device, which may comprise, or may be suspected to comprise, a biological component. In a capturing step 520, a capture element in the fluidic device may capture and/or couple the biological component, e.g., such that the biological component is immobilized. In some cases, the immobilizing of the biological component may be performed by using a repelling surface coating to contain a biological component within a portion of the surface that may not have a repelling surface, as described herein. In some cases, the capturing step may not be used, and the biological components may be distributed over the surface randomly prior to step 530. In step 530, a spatial energy modulating element (e.g., a mask) may be applied selectively to provide energy from an energy source to the fluidic device to form one or more polymer matrices. In some embodiments, the mask may be configured to selectively supply energy adjacent to a biological component to form a polymer matrix adjacent to the biological component. In certain embodiments, the mask may be configured to selectively supply energy on a biological component to form a polymer matrix that encapsulates at least a portion of the biological component. The mask may be applied based at least in part on a location of the biological component. The method 500 may further comprise forming or generating a predefined or predetermined pattern of capture sites/elements on one or more surfaces (e.g., a first surface, a second surface, a third surface, etc.) of the fluidic device before step 510. In some cases, the predefined or predetermined pattern of capture sites/elements may be generated on the fluidic device prior to method 500. In some embodiments, each capture site may be configured to carry one or more capturing element, as described herein.

In some embodiments, a detector, as provided herein, may be used to detect a location or position of a biological component. A mask may then be generated based at least in part on the detected location or position of the biological component. In step 540, the generated mask may be used in combination with an energy source to selectively apply energy to the fluidic device and/or the biological sample introduced into the fluidic device in step 510. In certain embodiments, the mask may be a photolithographic mask or another suitable mask. In step 550, a polymer matrix may be formed by applying energy sufficient to polymerize the polymer precursors in the fluidic device and/or the biological sample introduced into the fluidic device in 510 (e.g., from the energy source). The energy may comprise electrochemical energy, electromagnetic energy, thermal energy, microwave energy, or any other suitable energy. In some embodiments, the energy may be light energy, as discussed herein.

In certain embodiments, the polymer matrix may be formed adjacent to a biological component. In some embodiments, the polymer matrix may be formed on a biological component (e.g., to encapsulate the biological component). The polymer matrix may be formed in between two biological components to prevent contact (e.g., physical contact) between the two biological components. In various embodiments, at least a portion of the biological component may be surrounded by the polymer matrix. In some embodiments, one or more biological components in the biological sample may be surrounded by a polymer matrix such that two biological components may be separated from one another by a polymer matrix (e.g., one or more polymer matrix walls). The biological component may be encapsulated by the polymer matrix. In certain embodiments, the polymer matrix may comprise a hydrogel. In various embodiments, the polymer matrix may form a compartment around the biological component (e.g., by surrounding a biological component) to form an analysis chamber.

As described elsewhere herein, one or more assays may be conducted or performed on the biological component in the analysis chamber. One or more biological components in the biological sample may be captured and an analysis chamber may be formed adjacent to and/or surrounding each of the captured biological components. The order of the steps or actions of the methods described in connection with the embodiments disclosed may be varied. Thus, any order in the drawings or detailed description is for illustrative purposes only and is not meant to imply a required order, unless otherwise specified.

In some embodiments, one or more functional assays may be conducted or performed on the biological component in the polymer matrix. In some embodiments, the functional assays will be used to assess cell viability, cell morphology, cell secretions, cell responses, intercellular interactions, or any combination thereof. In some embodiments, a colorimetric assay or fluorescent assay may be conducted or performed. In some embodiments, a functional assay is performed using bright-field phase contrast or fluorescent imaging of the analyte. In some embodiments, a cell may be lysed, and a functional assay will be performed on a component thereof. Because one or more individual components can be localized within a fluidic device (e.g., encapsulated) and the localized components be exposed to one or more reagents and/or washing solutions during and/or in between analyses, multiple assays can be performed within the compartments (e.g., simultaneously, substantially simultaneously, serially, etc.). Different assays may be performed in different locations of the fluidic device, for example, to test effects of different treatment conditions.

In some embodiments, one or more omics assays may be performed to characterize and quantify the biological component or a component thereof. The omics assay may be a proteomic, transcriptomic, genomic, or epigenomic assay, or any combination thereof. In some embodiments, the one or more omics assays is a multi-omic assay.

Also provided herein are methods for obtaining a transcriptome of a biological component. The method may comprise coupling the biological component to a capture element disposed in a fluidic device to yield a coupled biological component. The method may include forming a polymer matrix on or adjacent to the coupled biological component to form an analysis chamber. The method may further include conducting or performing one or more reactions in the analysis chamber to obtain the transcriptome of the biological component. The biological component may remain in the analysis chamber during performance of the one or more reactions. In some embodiments, the biological component may not be coupled to a capture element disposed in a fluidic device. For example, the biological component can be localized by forming a polymer matrix on or adjacent to the biological component without coupling the biological device to the capture element. The transcriptome may be captured by target capture probes on the surface. The capture probe can include a barcode which decodes the location of the biological component and differentiates the source biological component. Further biochemical processing can be performed on the captured transcriptome of the biological component in order to convert it to DNA and determine its sequence using a form of sequencing or hybridization.

The method may further comprise directing energy from an energy source to at least a portion of the fluidic device to form the polymer matrix on or adjacent to the biological component to form the compartment or analysis chamber. The energy may be directed to the fluidic device selectively to form analysis chambers at predefined locations in the fluidic device. The selective directing of the energy may be performed using a spatial energy modulating element (e.g., a mask as described herein). In some embodiments, the method may further comprise detecting a biological component using a detector. Information from the detected biological component (e.g., a location of the biological component in the fluidic device) may be used to form or generate the spatial energy modulating element. For example, the spatial energy modulating element may inhibit or prevent energy from being directed to a location adjacent to the biological component. In some embodiments, the spatial energy modulating element may selectively direct energy to a location adjacent to the biological component. In some embodiments, the spatial energy modulating element may selectively direct energy on the biological component.

In certain cases, the method may comprise directing energy from an energy source to a predetermined portion of the fluidic device to form polymer matrix structures at predetermined locations in the fluidic device or in predetermined patterns in the fluidic device. In some embodiments, a detector (e.g., to detect the locations of one or more biological components) may be used. In various embodiments, a detector may not be used. A certain number of the polymer matrix structures may be formed or generated on or adjacent to a biological component. Stated another way, there may be a sufficient number of biological components in the fluidic device such that it is not necessary to first determine the locations of the biological components before forming the polymer matrix structures.

The spatial energy modulating element may comprise a physical photomask, a virtual photomask, a physical electrode distribution pattern, a virtual electrode distribution pattern, a photolithographic mask, a DMD system, or any other suitable mask. A physical or virtual photomask may, for example, prevent energy from being directed to a portion of the fluidic device while allowing energy to be directed to another portion of the fluidic device. An electrode distribution pattern may comprise electrically activating one or more electrodes (e.g., an array of electrodes) to allow energy to be directed to a portion of the fluidic device. An electrode may be rendered "off" or incapable of producing energy in a location where a polymer matrix may not be formed. An electrode may be rendered "on" at a location where a polymer matrix may be formed.

In some cases, the biological component may comprise a cell or a transcriptome thereof. A cell may comprise a eukaryotic cell, a prokaryotic cell, a fungal cell, an algal cell, a protozoan, a plant cell, an animal cell (e.g., a human cell), or any other suitable cell. The one or more reactions performed may comprise RNA sequencing. In some embodiments, the one or more reactions performed may comprise analysis of a transcriptome (e.g., under different or varying conditions). For example, one or more reactions may be performed to analyze the effect or effects of temperature, a small molecule, a toxin, a cell-cell interaction, an infection, etc. on a transcriptome. In some embodiments, the analysis of the transcriptome may provide a gene expression profile for a cell or a combination of cells. In certain embodiments, the one or more reactions performed may comprise a hybridization-based readout of the gene expression. The transcriptome may comprise messenger RNA (mRNA), long non-coding RNA (lncRNA), mitochondrial RNA, or total RNA. In some embodiments, other types of RNA (e.g., ribosomal RNA (rRNA)) may be analyzed and or sequenced. The RNA may comprise at least 50 nucleotides (nt), 100 nt, 200 nt, 300 nt, 400 nt, 500 nt, 600 nt, 700 nt, 800 nt, 900 nt, 1,000 nt, 10,000 nt, or more nucleotides. The biological component may comprise any number of nucleotides in between any two numbers mentioned herein. The RNA may be a double-stranded RNA (dsRNA) molecule or a single-stranded RNA (ssRNA) molecule.

Also provided herein are methods for analyzing two or more biological components. The method may comprise introducing a first biological component and a second biological component into a fluidic device. The method may include forming a polymer matrix on or adjacent to the first biological component to form a first analysis chamber. The method may further include forming a polymer matrix on or adjacent to the second biological component to form a second analysis chamber. The first analysis chamber may be adjacent to the second analysis chamber. The method may further comprise, analyzing one or more features of the first biological component and/or the second biological component.

In some embodiments, one or more features of the first biological component and/or the second biological component may comprise a response to an analyte, a response to a pharmaceutical agent, a response to an antimicrobial agent, production of a target compound by a cell or a community of cells, production of a target molecule, production of a nucleic acid, production of a protein, or any other suitable response. The one or more features may comprise at least 1, 2, 3, 4, 5, 6, 7, 8, 9, 10, 15, 25, 50, 100, or more features of the first biological component. The one or more features may comprise at least 1, 2, 3, 4, 5, 6, 7, 8, 9, 10, 15, 25, 50, 100, or more features of the second biological component. In some cases, a feature of the first biological component may be compared to the same feature of the second biological component. In various embodiments, 2, 3, 4, 5, 6, 7, 8, 9, 10, 15, 25, 50, 100, or more features of the first biological component and/or the second biological component may be analyzed or monitored. In certain embodiments, a feature of the first biological component may be compared to a different feature of the second biological component. For example, a first feature in the first biological component may comprise a response to an analyte or a pharmaceutical agent causing the first biological component to generate a compound or molecule (e.g., an antibody, a protein, an enzyme, etc.). A second feature in the second biological component may then comprise a response of the second biological component to the molecule or compound generated by the first biological component.

In some cases, a first feature and a second feature in the first biological component or the second biological component may be analyzed. For example, the first feature and the second feature may be analyzed in the first biological component in a response to a compound or a molecule generated by the second biological component. This may be used to elucidate one or more interactions between the first biological component and the second biological component.

The interaction may comprise a communication (e.g., a biological communication) between the first and the second biological components. In some cases, the interaction may comprise a biochemical communication between the first and the second biological components. In some embodiments, the biological communication may comprise a molecule including a protein, a nucleic acid, a cytokine, a chemokine, a combination thereof, or any other suitable molecule. The molecule may be generated by the first biological component or by the second biological component. In some cases, more than two biological components may be localized in analysis chambers formed adjacent to one another to analyze three or more features in three or more biological components. In some embodiments, this may be used to investigate interaction(s) between three or more biological components. In various embodiments, interactions between 2, 3, 4, 5, 6, 7, 10, 15, 25, 50, 100, or more biological components may be investigated.

In some cases, the first and the second biological components may include different cell types (e.g., a first cell type and a second cell type). In certain embodiments, the first biological component and the second biological component may include similar cell types, for example, cell types with varying genotypes or phenotypes. A response (e.g., a level of a response) to an analyte or pharmaceutical compound can be compared between two different cell types. In some cases, an amount of a target compound or an amount of molecule production between two different cell types can be analyzed and/or compared. In some embodiments, the first biological component and the second biological component may remain localized within the first analysis chamber and the second analysis chamber, respectively, during the analysis of the features. Such analysis or experiments can be scaled up to assess or analyze 3, 4, 5, 6, 7, 8, 9, 10, 15, 25, 50, 100 or more biological components (e.g., in parallel).

Also provided herein are methods for identifying a nucleic acid molecule. This method may comprise the capture of a biological component. The biological component may then be encapsulated by a hydrogel, which may form an analysis chamber. In some embodiments, the nucleic acid molecule can be extracted and released within the analysis chamber. This nucleic acid may be sequenced by next-generation sequencing, sequencing may be performed through short-read sequencing, nanopore sequencing, sequencing by synthesis, sequencing by in-situ hybridization, or any optical readout using, for example, a microscope. Other suitable methods of sequencing are also within the scope of this disclosure. The method may further comprise detecting the nucleic acid molecule in an absence of nucleic acid amplification.

In some embodiments, a biological component comprising a cell may be introduced into the fluidic device. A polymer matrix may then be formed on or adjacent to the biological component to form a compartment or analysis chamber. The analysis chamber may be formed by selectively directing energy from an energy source to the fluidic device, as described herein. In some embodiments, the analysis chamber may be deconstructed by degrading the polymer matrix "on demand." Degrading the polymer matrix on demand may comprise selectively directing energy to the analysis chamber, using an enzyme to digest or depolymerize the polymer matrix, or any other suitable method for degrading a polymer matrix.

A cell may be lysed to release a biological component (e.g., DNA or RNA). In certain embodiments, a biological component is released from a cell upon interaction with a reagent. In some embodiments, the reagent is an organic or inorganic molecule. In some embodiments, the organic or inorganic molecule is a pharmaceutical compound or detergent. In some embodiments, the reagent is a protein. In some embodiments, the reagent is a DNA aptamer. In some embodiments, the reagent is a bead carrying biomolecules. In some embodiments, the reagent is a biological species. In some embodiments, the biological species is a virus or cell.

In some embodiments, a biological component is released from the cell upon exposure to an energy source. In some embodiments, the energy source is UV light for lysing cells. In some embodiments, the energy source is visible light for lysing cells. In some embodiments, the UV light is used to activate a photoactivated detergent and lyse the cell. In some embodiments, the visible light is used to activate a photoactivated detergent and lyse the cell.

As described herein, the polymer matrix may have a pore size or an average pore size that may not allow the nucleic acid molecules to pass or traverse through the polymer matrix. In some cases, the analysis chamber may be used for sequencing library preparation and/or nucleic acid sequencing. The sequencing can be next-generation sequencing. The sequencing can be short-read sequencing, nanopore sequencing, sequencing by synthesis, sequencing by in-situ hybridization, or an optical readout using, for example, a microscope. The one or more nucleic acid molecules in the analysis chamber may undergo nucleic acid sequencing reaction(s) comprising, for example, DNA sequencing or RNA sequencing. A nucleic acid library may be constructed or generated. The polymer matrix may allow reagents to pass through, as described herein. The reagents may comprise primers, adapters, enzymes, and other reagents used for nucleic acid sequencing reactions.

In certain embodiments, a nucleic acid may comprise a DNA molecule or an RNA molecule. The DNA may be at least 100 bp long. In some embodiments, the DNA may include at least 50 bp, 100 bp, 200 bp, 300 bp, 400 bp, 500 bp, 600 bp, 700 bp, 800 bp, 900 bp, 1,000 bp, 10 kilo base pairs (kbp), 100 kbp, 1 mega base pairs (Mbp), 100 Mbp, 1 giga base pairs (Gbp), 10 Gbp, 100 Gbp, or more base pairs. The biological component may comprise a DNA molecule that comprises any number of base pairs in between the mentioned numbers herein. For example, the DNA may comprise from 50 bp to 1,000 bp, 300 bp to 10 kbp, or 1,000 bp to 10 Gbp. The RNA may be dsRNA. The dsRNA may comprise at least 50 bp, 100 bp, 200 bp, 300 bp, 400 bp, 500 bp, 600 bp, 700 bp, 800 bp, 900 bp, 1,000 bp, 10 kbp, or 100 kbp. The biological component may comprise a dsRNA molecule that comprises any number of base pairs in between the mentioned numbers herein. For example, the dsRNA may comprise from 50 bp to 1,000 bp, 300 bp to 10 kbp, or 1,000 bp to 100 kbp. The RNA may be ssRNA. The ssRNA may comprise from 50 nt to 100,000 nt. The ssRNA may comprise from 50 nt to 100 nt, 50 nt to 1,000 nt, 50 nt to 10,000 nt, 50 nt to 100,000 nt, 100 nt to 1,000 nt, 10 nt to 100 nt, 10 nt to 1,000 nt, or 100 nt to 1,000 nt. In some cases, the ssRNA may be less than 50 nucleotides long. The ssRNA may be more than 100,000 nucleotides long.

In some embodiments, the sequencing library construction may comprise barcoding. The barcoding may be unique in each analysis chamber to associate a nucleic acid molecule to an analysis chamber or a biological component (e.g., a cell). In some embodiments, a polymerase chain reaction (PCR) may be used for the sequencing library construction. In some cases, because the nucleic acid material may be retained within an analysis chamber and may not be diluted or lost, PCR may not be used other than for the sequencing library construction. In some embodiments, the sequencing library construction may comprise adapter ligation. In some embodiments, all the steps required for sequencing a nucleic acid molecule may be performed while the biological component and/or the nucleic acids are localized in the analysis chamber. In some embodiments, library preparation comprises transposase-assisted tagmentation of the nucleic acid molecules (e.g., by using transposons to cleave and label genomic DNA).

Also provided herein are methods for processing a cell to determine a transcriptome of the cell. In some embodiments, this method does not comprise nucleic acid amplification. In other embodiments, this method may comprise nucleic acid amplification. The method may include processing the cell to determine an epigenome of the cell. In some embodiments, a biological component comprising a cell may be introduced into a fluidic device as provided herein. A polymer matrix may be formed on or adjacent to the biological component to form an analysis chamber (e.g., around the biological component or that encapsulates the biological component). The analysis chamber may at least partially or completely surround the cell. The analysis chamber may be formed by selectively directing energy from an energy source to the fluidic device, as described herein. In some embodiments, the analysis chamber may be deconstructed or removed by degrading the polymer matrix. The polymer matrix may be degraded "on demand," as provided herein.

The biological component or products thereof may be analyzed within the analysis chamber. In some cases, the biological component or products thereof may be eluted and transferred to another device for analysis. For example, nucleic acid material or protein products from a biological component (e.g., a cell, bacteria, virus, etc.) may be extracted and/or processed (e.g., tagged, barcoded, etc.) in an analysis chamber. The nucleic acid material or protein products may then be sequenced within the analysis chambers of the fluidic device described herein. In some cases, the nucleic acid material or protein products may be eluted and transferred to another device (e.g., a sequencing flow cell) to be sequenced (e.g., using a sequencing device).

The cell may comprise a mammalian cell (e.g., a human cell), a fungal cell, a bacterial cell, an algal cell, a protozoan, a plant cell, a tumor spheroid, or a combination thereof. In some embodiments, a genome, transcriptome, proteome, epigenome, methylome, secretome, or metabolome of the cell may be extracted, for example, by lysing the cell. In some cases, one or more proteins produced and/or released by the cell can be analyzed without lysing the cell. In some cases, the genome, transcriptome, proteome, epigenome, methylome, secretome, and/or metabolome of the cell can be studied, analyzed, and/or sequenced (as appropriate) while the cell and/or the genome, transcriptome, proteome, epigenome, methylome, secretome, or metabolome of the cell may remain within the analysis chamber, or may remain substantially within the analysis chamber. In some embodiments, the nucleic acid in the cell may remain within the analysis chamber. Accordingly, nucleic acid amplification may be avoided or obviated. In some cases, one or more cells may be processed within an analysis chamber to identify and study a genome, transcriptome, proteome, epigenome, methylome, secretome, and/or metabolome in the one or more cells.

A first surface and/or a second surface of the fluidic device (similar to the surfaces 101, 102 of FIG. 1) may comprise detecting elements. The detecting elements may comprise one or more reagents or biochemical sensors. In some cases, the reagents to study the genome, transcriptome, proteome, epigenome, methylome, secretome, and/or metabolome of the cell may be introduced into the fluidic device. The polymer matrix may comprise pores allowing the reagents to pass through, but the pores may not allow nucleic acids or proteins (e.g., of the cell) to cross the polymer matrix.

Also provided herein are methods for identifying a plurality of nucleic acid molecules of a plurality of cells without barcoding individual nucleic acid molecules of the plurality of nucleic acid molecules. The method may comprise sequencing the plurality of nucleic acid molecules. In some embodiments, a plurality of biological components may be introduced into the fluidic device. A polymer matrix may be formed on or adjacent to a biological component from the plurality of biological components to form an analysis chamber that at least partially or completely surrounds or encapsulates the biological component. The analysis chamber may be formed by selectively directing energy from an energy source to the fluidic device, as described herein. In some embodiments, the analysis chamber may be deconstructed by degrading the polymer matrix "on demand," as described herein. The plurality of nucleic acid molecules of the biological component (e.g., a cell, a bacteria, a virus, etc.) may be extracted in the analysis chamber formed surrounding the biological component. The nucleic acid molecules may then be sequenced within the analysis chamber. A readout of the sequencing may be performed within the analysis chamber. Therefore, a need for a barcode to associate a nucleic acid molecule and the biological component may be avoided.

The plurality of nucleic acid molecules may be extracted from the plurality of cells. In some cases, a nucleic acid molecule of a cell may be extracted from the cell by lysing the cell within the analysis chamber (e.g., the compartment or chamber surrounding the cell). The analysis chamber may contain and/or localize the nucleic acid from the cell within the analysis chamber. Therefore, the plurality of nucleic acid molecules from the plurality of cells may be localized in individual and/or separate analysis chambers. In some embodiments, the sequencing process (e.g., nucleic acid library construction, sequencing, etc.) may be performed on the plurality of nucleic acid molecules that may be isolated or localized in separate analysis chambers. Barcoding to distinguish between a cell generating a nucleic acid molecule in the plurality of the nucleic acid molecules may therefore be avoided or obviated.

Computer Systems

Figure 15:
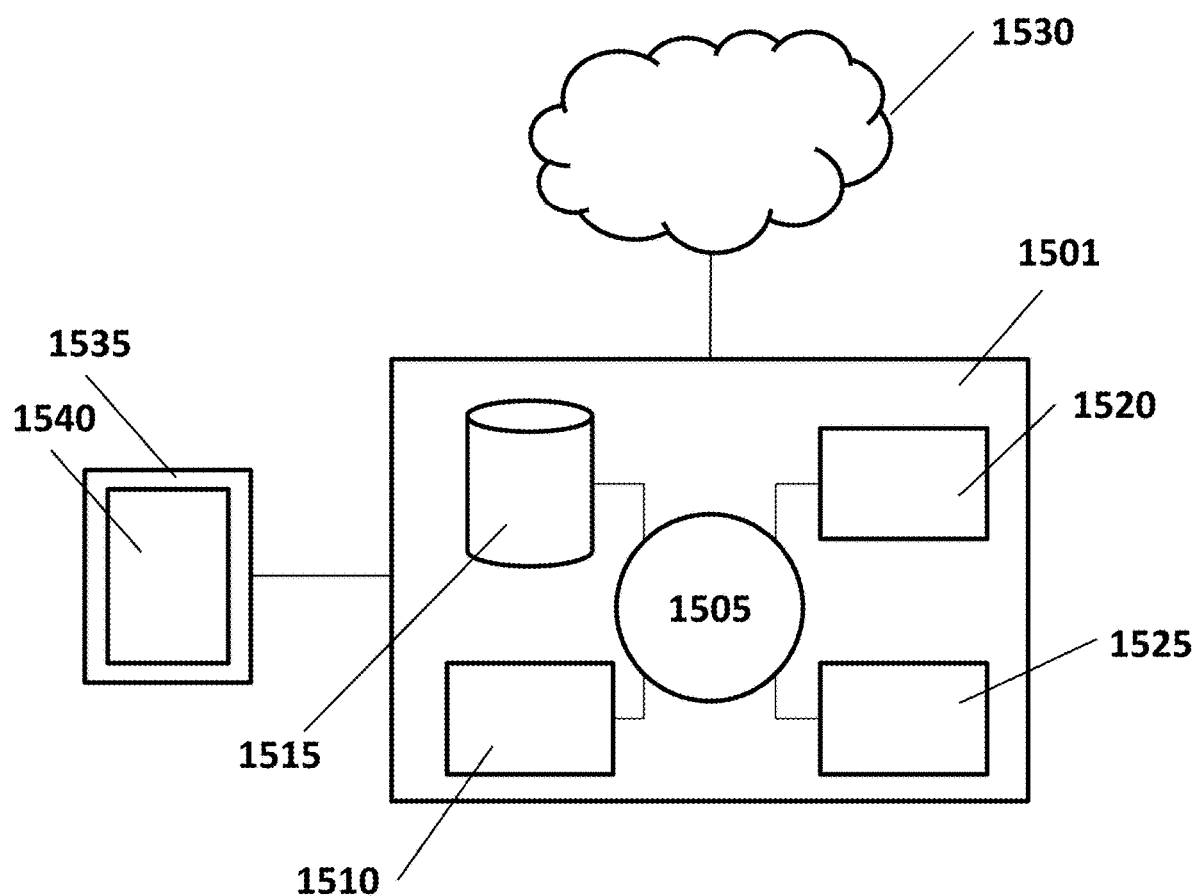
FIG. 15 shows a computer system that is programmed or otherwise configured to implement methods provided herein.

The present disclosure provides computer systems that are programmed to implement methods of the disclosure. FIG. 15 shows a computer system 1501 that may be programmed or otherwise configured to perform methods described herein. The computer system 1501 can regulate various aspects of the present disclosure, such as, for example, identifying a biological component, detecting a barcode, generating a spatial modulating element (e.g., a mask), providing energy from an energy source, or detecting or measuring a local parameter using a sensor. The detector may be a camera (e.g., a fluorescent camera), such as a charged coupled device (CCD) camera capable of collecting optical signals and position information from a plurality of sources distributed over a planar region. The computer system 1501 can be an electronic device of a user or a computer system that may be remotely located with respect to the electronic device. The electronic device can be a mobile electronic device.

The computer system 1501 includes a central processing unit (CPU, also "processor" and "computer processor" herein) 1505, which can be a single core or multi core processor, or a plurality of processors for parallel processing. The computer system 1501 also includes memory or memory location 1510 (e.g., random-access memory, read-only memory, flash memory), electronic storage unit 1515 (e.g., hard disk), communication interface 1520 (e.g., network adapter) for communicating with one or more other systems, and peripheral devices 1525, such as cache, other memory, data storage and/or electronic display adapters. The memory 1510, storage unit 1515, interface 1520 and peripheral devices 1525 are in communication with the CPU 1505 through a communication bus (solid lines), such as a motherboard. The storage unit 1515 can be a data storage unit (or data repository) for storing data. The computer system 1501 can be operatively coupled to a computer network ("network") 1530 with the aid of the communication interface 1520. The network 1530 can be the Internet, an internet and/or extranet, or an intranet and/or extranet that may be in communication with the Internet. The network 1530 in some cases may be a telecommunication and/or data network. The network 1530 can include one or more computer servers, which can enable distributed computing, such as cloud computing. The network 1530, in some cases with the aid of the computer system 1501, can implement a peer-to-peer network, which may enable devices coupled to the computer system 1501 to behave as a client or a server.

The CPU 1505 can execute a sequence of machine-readable instructions, which can be embodied in a program or software. The instructions may be stored in a memory location, such as the memory 1510. The instructions can be directed to the CPU 1505, which can subsequently program or otherwise configure the CPU 1505 to implement methods of the present disclosure. Examples of operations performed by the CPU 1505 can include fetch, decode, execute, and writeback.

The CPU 1505 can be part of a circuit, such as an integrated circuit. One or more other components of the system 1501 can be included in the circuit. In some cases, the circuit may be an application specific integrated circuit (ASIC).

The storage unit 1515 can store files, such as drivers, libraries, and saved programs. The storage unit 1515 can store user data, e.g., user preferences and user programs. The computer system 1501 in some cases can include one or more additional data storage units that are external to the computer system 1501, such as located on a remote server that may be in communication with the computer system 1501 through an intranet or the Internet.

The computer system 1501 can communicate with one or more remote computer systems through the network 1530. For instance, the computer system 1501 can communicate with a remote computer system of a user (e.g., a laptop, a personal computer, a tablet, or a mobile phone). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1501 via the network 1530.

Methods as described herein can be implemented by way of machine (e.g., computer processor) executable code stored on an electronic storage location of the computer system 1501, such as, for example, on the memory 1510 or electronic storage unit 1515. The machine executable or machine readable code can be provided in the form of software. During use, the code can be executed by the processor 1505. In some cases, the code can be retrieved from the storage unit 1515 and stored on the memory 1510 for ready access by the processor 1505. In some situations, the electronic storage unit 1515 can be precluded, and machine-executable instructions are stored on memory 1510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1501, can be embodied in programming. Various aspects of the technology may be thought of as "products" or "articles of manufacture" typically in the form of machine (or processor) executable code and/or associated data that may be carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1501 can include or be in communication with an electronic display 1535 that comprises a user interface (UI) 1540 for providing, for example, an image of a biological component, a barcode, a signal or measurement of a local parameter. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1505. The algorithm can, for example, identify a biological component, detect a barcode, generate a spatial modulating element (e.g., a mask), provide energy from an energy source, detect or measure a local parameter using a sensor, etc.

EMBODIMENTS

Embodiment 1. A system, comprising: a fluidic device containing one or more biological components and one or more polymer precursors; and at least one energy source in communication with said fluidic device, wherein said at least one energy source supplies energy to said fluidic device to cause said one or more polymer precursors to form at least one polymer matrix on or adjacent to said biological component.

Embodiment 2. The system of Embodiment 1, wherein said fluidic device comprises a channel disposed therethrough, and wherein a first surface is disposed along a portion of said channel, and a second surface is disposed opposite of said first surface.

Embodiment 3. The system of Embodiment 1 or Embodiment 2, wherein said fluidic device comprises a chamber disposed therein, wherein a first surface is disposed along a portion of said chamber, and a second surface is disposed opposite of said first surface.

Embodiment 4. The system of Embodiment 2 or Embodiment 3, wherein said first surface is a lower surface, and wherein said second surface is an upper surface.

Embodiment 5. The system of Embodiment 1, wherein said fluidic device further comprises one or more capture elements immobilizing at least one of said one or more biological components at a location adjacent to said first surface forming an immobilized biological component.

Embodiment 6. The system of Embodiment 1, wherein said first surface is disposed adjacent to said energy source, and wherein said energy source is an array of electrodes.

Embodiment 7. The system of Embodiment 6, wherein said array of electrodes supply electrochemical energy to said one or more polymer precursors to form an array of polymer matrices.

Embodiment 8. The system of Embodiment 1, wherein at least two of said one or more polymer precursors are coupled to said first surface forming a pattern on said first surface.

Embodiment 9. The system of Embodiment 8, wherein said at least one polymer matrix is formed on or adjacent to said pattern.

Embodiment 10. The system of Embodiment 5, wherein said at least one polymer matrix is coupled to said first surface.

Embodiment 11. The system of Embodiment 10, wherein said at least one polymer matrix extends from said first surface to said second surface such that said at least one polymer matrix surrounds at least a portion of said immobilized biological component.

Embodiment 12. The system of any one of Embodiments 1 to 11, wherein said at least one energy source is in at least one of optical communication, electrochemical communication, electromagnetic communication, thermal communication, or microwave communication with said fluidic device.

Embodiment 13. The system of any one of Embodiments 1 to 11, wherein said at least one energy source comprises a light generating device, a heat generating device, an electrochemical generating device, an electrode, or a microwave device.

Embodiment 14. The system of any one of Embodiments 1 to 13, further comprising a photolithographic device or a digital micromirror device (DMD) configured to control a spatial distribution of said energy from said energy source.

Embodiment 15. The system of any one of Embodiments 5 to 14, wherein said one or more capture elements comprise a physical trap, a geometric trap, a well, an electrochemical trap, a chemical affinity trap, one or more magnetic particles, an electrophoretic trap, a dielectrophoretic trap, or a combination thereof.

Embodiment 16. The system of Embodiment 15, wherein said chemical affinity trap comprises streptavidin, an antibody, or a combination thereof.

Embodiment 17. The system of Embodiment 15, wherein the physical trap comprises a polymer matrix.

Embodiment 18. The system of Embodiment 17, wherein the polymer matrix comprises a hydrogel.

Embodiment 19. The system of Embodiment 15, wherein said electrochemical trap comprises a gold electrode, a platinum electrode, or an indium tin oxide (ITO) electrode.

Embodiment 20. The system of any one of Embodiments 5 to 19, wherein said one or more capture elements are disposed in a pattern on said first surface or said second surface.

Embodiment 21. The system of any one of Embodiments 5 to 20, wherein said one or more capture elements comprises a well, wherein said well is from 1 µm (micrometer) to 50 µm in diameter, and wherein said well is from 0.1 µm to 100 µm in depth.

Embodiment 22. The system of any one of Embodiments 5 to 21, wherein said one or more biological components is a plurality of biological components, and wherein said plurality of biological components is coupled to said one or more capture elements.

Embodiment 23. The system of any one of Embodiments 1 to 22, wherein said fluidic device is a microfluidic device or a nanofluidic device.

Embodiment 24. The system of any one of Embodiments 1 to 22, wherein said fluidic device is used for nucleic acid sequencing.

Embodiment 25. The system of Embodiment 24, wherein said nucleic acid sequencing comprises next-generation sequencing, short-read sequencing, nanopore sequencing, sequencing by synthesis, sequencing by in-situ hybridization, or an optical readout.

Embodiment 26. The system of any one of Embodiments 1 to 25, wherein said one or more biological components comprise a cell, a cell lysate, a nucleic acid, a microbiome, a protein, a mixture of cells, a spatially-linked biological component, or a metabolite.

Embodiment 27. The system of Embodiment 26, wherein said mixture of cells comprises a first cell type and a second cell type, and wherein said first cell type is different than said second cell type.

Embodiment 28. The system of Embodiment 26, wherein said cell is an animal cell, a plant cell, a fungal cell, or a bacterial cell.

Embodiment 29. The system of Embodiment 28, wherein said animal cell is a human cell.

Embodiment 30. The system of any one of Embodiments 1 to 28, wherein said one or more biological components comprise a tumor spheroid or a spatially linked biological sample.

Embodiment 31. The system of any one of Embodiments 26 to 30, wherein said nucleic acid is DNA of 100 base pairs or greater or RNA of 50 bases or greater.

Embodiment 32. The system of any one of Embodiments 26 to 31, wherein said cell lysate comprises DNA from 50 bp (base pairs) to 100 Gbp (giga base pairs) or RNA from 50 bp to 100 kbp (kilo base pairs).

Embodiment 33. The system of any one of Embodiments 1 to 32, wherein said at least one polymer matrix comprises a hydrogel.

Embodiment 34. The system of any one of Embodiments 1 to 33, wherein said fluidic device further comprises one or more polymer precursors.

Embodiment 35. The system of Embodiment 34, wherein said one or more polymer precursors comprise hydrogel precursors.

Embodiment 36. The system of any one of Embodiments 5 to 35, wherein said at least one polymer matrix inhibits passage of said immobilized biological component.

Embodiment 37. The system of any one of Embodiments 1 to 36, wherein said at least one polymer matrix forms a cylinder shell or a polygon shell comprising an inner space and a polymer matrix wall.

Embodiment 38. The system of Embodiment 37, wherein said inner space has an inner diameter from 1 µm to 500 µm.

Embodiment 39. The system of Embodiment 37 or Embodiment 38, wherein said polymer matrix wall has a thickness of at least 1 µm (micrometer).

Embodiment 40. The system of Embodiment 39, wherein said at least one polymer matrix wall is a hydrogel wall.

Embodiment 41. The system of any one of Embodiments 1 to 40, wherein said at least one polymer matrix is degradable.

Embodiment 42. The system of Embodiment 41, wherein said degradation of said at least one polymer matrix is "on demand."

Embodiment 43. The system of Embodiment 41 or Embodiment 42, wherein said at least one polymer matrix is degradable by at least one of: (i) contacting said at least one polymer matrix with a cleaving reagent; (ii) heating said at least one polymer matrix to at least 90° C.; or (iii) exposing said at least one polymer matrix to a wavelength of light that cleaves a photo-cleavable crosslinker that crosslinks said polymer of said at least one polymer matrix.

Embodiment 44. The system of Embodiment 43, wherein said at least one polymer matrix comprises a hydrogel, and wherein said cleaving reagent degrades said hydrogel.

Embodiment 45. The system of Embodiment 43, wherein said cleaving reagent comprises a reducing agent, an oxidative agent, an enzyme, a pH based cleaving reagent, or a combination thereof.

Embodiment 46. The system of Embodiment 43, wherein said cleaving reagent comprises dithiothreitol (DTT), tris(2-carboxyethyl)phosphine (TCEP), tris(3-hydroxy propyl) phosphine (THP), or a combination thereof.

Embodiment 47. The system of any one of Embodiments 1 to 46, wherein said at least one polymer matrix allows passage of a reagent.

Embodiment 48. The system of any one of Embodiments 1 to 47, wherein said at least one polymer matrix comprises pores, wherein an average size of said pores is modulated using a chemical reagent, by applying heat, applying electricity, applying light, or a combination thereof.

Embodiment 49. The system of Embodiment 47 or Embodiment 48, wherein said reagent comprises at least one of enzymes, chemicals, oligonucleotides, or primers having a size of less than 50 base pairs.

Embodiment 50. The system of any one of Embodiments 47 to 49, wherein said reagent comprises lysozyme, proteinase K, random hexamers, polymerase, transposase, ligase, catalyzing enzyme, deoxynucleotide triphosphates, buffers, cell culture media, or divalent cations.

Embodiment 51. The system of any one of Embodiments 1 to 50, wherein said at least one polymer matrix comprises pores that are sized to allow diffusion of a reagent through said at least one polymer matrix but are too small to allow DNA or RNA to traverse said pores.

Embodiment 52. The system of any one of Embodiments 1 to 51, wherein said at least one polymer matrix comprises a hydrogel, and wherein said hydrogel comprises polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetraacrylate, or combinations or mixtures thereof.

Embodiment 53. The system of Embodiment 52, wherein said hydrogel comprises an enzymatically degradable hydrogel, PEG-thiol/PEG-acrylate, acrylamide/N,N'-bis(acryloyl)cystamine (BACy), or PEG/PPO.

Embodiment 54. The system of any one of Embodiments 5 to 53, wherein said first surface, said second surface, or both comprise one or more barcodes.

Embodiment 55. The system of Embodiment 54, wherein said one or more barcodes comprise an identifier to identify a source of said one or more biological components.

Embodiment 56. The system of Embodiment 55, wherein said one or more barcodes comprise an oligonucleotide.

Embodiment 57. The system of Embodiment 55, wherein said source comprises a specimen from which said one or more biological components are collected.

Embodiment 58. The system of Embodiment 55, wherein said source comprises a physiological or an anatomical source from which said one or more biological components are collected.

Embodiment 59. The system of Embodiment 58, wherein said anatomical source comprises an organ of a subject.

Embodiment 60. The system of Embodiment 59, wherein said subject is a human.

Embodiment 61. The system of any one of Embodiments 54 to 60, wherein said one or more barcodes are configured to bind said one or more biological components or a molecule made by said one or more biological components.

Embodiment 62. The system of any one of Embodiments 5 to 61, wherein said first surface, said second surface, or both comprise one or more compounds configured to bind said one or more biological components.

Embodiment 63. The system of any one of Embodiments 5 to 62, wherein said first surface, said second surface, or both is functionalized with a surface polymer.

Embodiment 64. The system of Embodiment 63, wherein said surface polymer is functionalized with an oligonucleotide.

Embodiment 65. The system of Embodiment 63, wherein said surface polymer is functionalized with an antibody, a cytokine, a chemokine, a protein, an antibody derivative, an antibody fragment, a carbohydrate, a toxin, an aptamer, or any combination thereof.

Embodiment 66. The system of any one of Embodiments 1 to 65, wherein said polymer matrix is functionalized with an oligonucleotide, an antibody, a cytokine, a chemokine, a protein, an antibody derivative, an antibody fragment, a carbohydrate, a toxin, an aptamer, or any combination thereof.

Embodiment 67. The system of Embodiment 63, wherein said surface polymer comprises polyethylene glycol (PEG), a silane polymer, pyridinecarboxaldehyde (PCA), an acrylamide, an agarose, or a combination thereof.

Embodiment 68. The system of any one of Embodiments 1 to 67, further comprising a detector for identifying said one or more of said biological components, said one or more barcodes, or a combination thereof.

Embodiment 69. The system of Embodiment 68, wherein said detector comprises a camera (fluorescent camera).

Embodiment 70. The system of any one of Embodiments 1 to 69, further comprising a stage that holds said fluidic device.

Embodiment 71. The system of any one of Embodiments 1 to 70, further comprising a sequencing device for obtaining sequencing data.

Embodiment 72. The system of Embodiment 71, wherein said sequencing data is generated using next-generation sequencing, short-read sequencing, nanopore sequencing, sequencing by synthesis, sequencing by in-situ hybridization, or an optical readout.

Embodiment 73. The system of any one of Embodiments 1 to 72, further comprising a spatial energy modulating element to selectively supply said energy to said fluidic device.

Embodiment 74. The system of Embodiment 73, wherein said spatial energy modulating element is generated using said detector identifying said position of said at least one biological component.

Embodiment 75. The system of Embodiment 73 or Embodiment 74, wherein said spatial energy modulating element comprises a physical photomask, a virtual photomask, a physical electrode distribution pattern, or a virtual electrode distribution pattern.

Embodiment 76. The system of Embodiment 73 or Embodiment 74, wherein said spatial energy modulating element comprises a photolithographic mask or a digital micromirror device (DMD) mask.

Embodiment 77. A method of analyzing a biological component, said method comprising: (a) introducing one or more biological components into a fluidic device; (b) disposing a first portion of said one or more biological components adjacent a first surface or a second surface of said fluidic device; and (c) forming one or more polymer matrices adjacent a first portion of said first surface or said second surface to localize at least one of said one or more biological components to said first portion.

Embodiment 78. The method of Embodiment 77, further comprising: (a) agitating said one or more biological components within said fluidic device; (b) disposing a second portion of said one or more biological components adjacent said first surface or said second surface of said fluidic device; and (c) forming one or more polymer matrices adjacent a second portion of said first surface or said second surface to immobilize at least one of said one or more biological component of said second portion.

Embodiment 79. The method of Embodiment 77 or Embodiment 78, further comprising identifying a position of at least one of said one or more biological components such that at least one energy source supplies energy to said fluidic device to form said one or more polymer matrices on or adjacent said identified position.

Embodiment 80. A method of analyzing a biological component, comprising: (a) introducing said biological component into a fluidic device; (b) coupling said biological component to one or more capture elements disposed on a first surface or a second surface of said fluidic device to yield a coupled biological component; and (c) forming a polymer matrix on or adjacent to said coupled biological component.

Embodiment 81. The method of Embodiment 80, further comprising introducing one or more polymer precursors into said fluidic device.

Embodiment 82. The method of Embodiment 80 or Embodiment 81, wherein forming said polymer matrix comprises supplying energy to said fluidic device to form said polymer matrix.

Embodiment 83. The method of Embodiment 82, wherein said energy is selectively supplied to one or more portions of said fluidic device.

Embodiment 84. The method of any one of Embodiments 80 to 83, further comprising a spatial energy modulating element to selectively supply said energy to said fluidic device.

Embodiment 85. The method of Embodiment 84, wherein said spatial energy modulating element comprises a physical photomask, a virtual photomask, a physical electrode distribution pattern, or a virtual electrode distribution pattern.

Embodiment 86. The method of Embodiment 84, wherein said spatial energy modulating element comprises a photolithographic mask or a digital micromirror device (DMD) mask.

Embodiment 87. The method of any one of Embodiments 82 to 86, wherein said energy is supplied via a light energy source, a heat energy source, an electrochemical energy source, or an electromagnetic energy source.

Embodiment 88. The method of any one of Embodiments 82 to 87, wherein said polymer matrix is coupled to said first surface or said second surface.

Embodiment 89. The method of any one of Embodiments 82 to 88, wherein said energy forms said polymer matrix around a portion of said coupled biological component.

Embodiment 90. The method of any one of Embodiments 80 to 89, wherein at least a portion of said biological component is encapsulated by said polymer matrix.

Embodiment 91. The method of Embodiment 90, wherein an entirety of said biological component is encapsulated by said polymer matrix.

Embodiment 92. The method of any one of Embodiments 80 to 91, further comprising coupling a first biological component to a first capture element to form a first analysis chamber and coupling a second biological component to a second capture element to form a second analysis chamber.

Embodiment 93. The method of Embodiment 92, wherein said first analysis chamber is adjacent to said second analysis chamber.

Embodiment 94. The method of Embodiment 92 or Embodiment 93, wherein said first analysis chamber is disposed from 5 micrometer (µm) to 1,000 µm away from said second analysis chamber.

Embodiment 95. The method of any one of Embodiments 92 to 94, further comprising analyzing said first biological component in said first analysis chamber and analyzing said second biological component in said second analysis chamber.

Embodiment 96. The method of any one of Embodiments 92 to 95, further comprising actuating a first reaction in said first biological component and actuating a second reaction in said second biological component.

Embodiment 97. The method of Embodiment 96, wherein said first reaction and said second reaction are different.

Embodiment 98. The method of any one of Embodiments 92 to 97, further comprising actuating a third reaction in said first biological component and actuating a fourth reaction in said second biological component.

Embodiment 99. The method of Embodiment 98, wherein said third reaction and said fourth reaction are different.

Embodiment 100. The method of any one of Embodiments 80 to 99, further comprising obtaining a genome, transcriptome, proteome, epigenome, methylome, secretome, or metabolome of said coupled biological component.

Embodiment 101. The method of Embodiment 100, wherein the proteome comprises secreted proteins, surface proteins, or a combination thereof.

Embodiment 102. The method of Embodiment 100, wherein said transcriptome is a substantially full-length transcriptome.

Embodiment 103. The method of Embodiment 100, wherein said transcriptome is a full-length transcriptome.

Embodiment 104. The method of any one of Embodiments 80 to 103, further comprising sequencing at least one nucleic acid of said biological component.

Embodiment 105. The method of Embodiment 104, wherein said sequencing does not comprise amplification of a sequencing library.

Embodiment 106. The method of Embodiment 105, wherein said nucleic acid library from said biological component is sequenced within a same chamber.

Embodiment 107. The method of any one of Embodiments 80 to 105, further comprising coupling a barcode to said biological component or a molecule produced by said biological component.

Embodiment 108. The method of any one of Embodiments 80 to 107, further comprising exposing said biological component or said coupled biological component to an analyte.

Embodiment 109. The method of Embodiment 108, wherein said biological component comprises one or more microbes, and wherein said analyte comprises an antimicrobial agent or a microbial growth promoting agent.

Embodiment 110. The method of Embodiment 109, further comprising screening said one or more microbes for susceptibility to said antimicrobial agent.

Embodiment 111. The method of Embodiment 108, wherein said analyte comprises a pharmaceutical agent.

Embodiment 112. The method of Embodiment 111, further comprising screening an effect of said pharmaceutical agent on said biological component.

Embodiment 113. The method of any one of Embodiments 80 to 108, wherein said method further comprises screening said biological component for production of a target molecule.

Embodiment 114. The method of Embodiment 113, wherein said target molecule comprises at least one of an antibody, a cytokine, a chemokine, a protein, an antibody derivative, an antibody fragment, a carbohydrate, a toxin, or an aptamer.

Embodiment 115. The method of any one of Embodiments 80 to 114, further comprising forming said polymer matrix around said biological component such that said biological component is disposed within a structure formed by said polymer matrix.

Embodiment 116. The method of any one of Embodiments 80 to 115, further comprising analyzing a local parameter in said first analysis chamber or said second analysis chamber, wherein a level of said local parameter in said first analysis chamber is different from a level of said local parameter in said second analysis chamber.

Embodiment 117. The method of Embodiment 116, wherein said local parameter comprise a pH, an oxygen concentration, or a $CO_2$ concentration.

Embodiment 118. The method of any one of Embodiments 80 to 117, wherein said one or more capture elements comprise a polymer matrix.

Embodiment 119. The method of Embodiment 118, wherein the polymer matrix comprises a hydrogel.

Embodiment 120. A method of obtaining a transcriptome of a biological component, said method comprising: (a) forming a polymer matrix on or adjacent to said biological component to form an analysis chamber; and (b) performing one or more reactions in said analysis chamber to obtain said transcriptome of said biological component, wherein said biological component remains in said analysis chamber during performance of said one or more reactions.

Embodiment 121. The method of Embodiment 120, further comprising coupling said biological component to a capture element disposed in a fluidic device to yield a coupled biological component.

Embodiment 122. The method of Embodiment 120 or Embodiment 121, further comprising providing energy from an energy source to said fluidic device to form said polymer matrix.

Embodiment 123. The method of Embodiment 122, wherein said energy is provided selectively using a spatial energy modulating element.

Embodiment 124. The method of Embodiment 123, wherein said spatial energy modulating element is generated based on a location of said biological component.

Embodiment 125. The method of Embodiment 123 or Embodiment 124, wherein said spatial energy modulating element comprises a physical photomask, a virtual photomask, a physical electrode distribution pattern, a virtual electrode distribution pattern, a photolithographic mask, or a digital micromirror device (DMD) mask.

Embodiment 126. The method of any one of Embodiments 120 to 125, wherein said biological component comprises RNA.

Embodiment 127. The method of any one of Embodiments 120 to 126, wherein said RNA is from 50 bases to 100 kb (kilobase bases).

Embodiment 128. The method of any one of Embodiments 120 to 127, wherein said polymer matrix comprises pores that are sized to allow diffusion of a reagent through said polymer matrix but are too small to allow said RNA to traverse said pores.

Embodiment 129. The method of any one of Embodiments 120 to 128, wherein said one or more reactions comprise RNA sequencing.

Embodiment 130. A method of analyzing two or more biological components, said method comprising: (a) introducing a first biological component and a second biological component into a fluidic device; (b) forming a polymer matrix on or adjacent to said first biological component to form a first analysis chamber and forming a polymer matrix on or adjacent to said second biological component to form a second analysis chamber, wherein said first analysis chamber is adjacent to said second analysis chamber in said fluidic device; and (c) analyzing one or more features of said first biological component and said second biological component.

Embodiment 131. The method of Embodiment 130, wherein said one or more features comprise a first feature and a second feature, and wherein (c) comprises analyzing said first feature and said second feature of said first biological component in said first analysis chamber.

Embodiment 132. The method of Embodiment 130 or Embodiment 131, wherein said first biological component remains in said first analysis chamber between analysis of each of said first feature and said second feature.

Embodiment 133. The method of any one of Embodiments 130 to 132, wherein said one or more features comprises a response to an analyte, a response to a pharmaceutical agent, a response to an antimicrobial agent, production of a target compound, production of a target molecule, production of a nucleic acid, or production of a protein.

Embodiment 134. The method of any one of Embodiments 130 to 133, wherein said first biological component is in biological communication with said second biological component.

Embodiment 135. The method of Embodiment 134, wherein said biological communication generates a biological response in said first biological component or in said second biological component.

Embodiment 136. The method of Embodiment 134, wherein said biological communication comprises a molecule comprising a protein, a nucleic acid, a cytokine, a chemokine, or a combination thereof, generated by said first biological component or by said second biological component.

Embodiment 137. A method for identifying a nucleic acid molecule, comprising: providing a polymer matrix comprising said nucleic acid molecule, and detecting said nucleic acid molecule in absence of nucleic acid amplification.

Embodiment 138. The method of Embodiment 137, wherein said nucleic acid molecule is a deoxyribonucleic acid (DNA) molecule.

Embodiment 139. The method of Embodiment 137 or Embodiment 138, wherein said polymer matrix forms a chamber localizing said nucleic acid.

Embodiment 140. The method any of any one of Embodiments 137 to 139, wherein said chamber is formed on demand.

Embodiment 141. The method of any one of Embodiments 137 to 140, wherein said polymer matrix is degraded on demand.

Embodiment 142. The method of any one of Embodiments 138 to 141, wherein said DNA is 100 base pairs or greater.

Embodiment 143. The method of Embodiment 137, wherein said nucleic acid is a ribonucleic acid molecule (RNA).

Embodiment 144. The method of Embodiment 143, wherein said RNA is 50 nucleotides or greater.

Embodiment 145. The method of any one of Embodiments 137 to 144, further comprising generating a nucleic acid library from said biological component within said chamber.

Embodiment 146. The method of Embodiment 145, wherein said nucleic acid library is sequenced within said chamber.

Embodiment 147. A method for processing a biological component, comprising determining a genome sequence, a transcriptome, a proteome, or an epigenome in absence of nucleic acid amplification, wherein said processing is performed in a single microfluidic device.

Embodiment 148. The method of Embodiment 147, wherein said cell is at least partially within a polymer matrix.

Embodiment 149. The method of Embodiment 147 or Embodiment 148, wherein said polymer matrix is degraded on demand.

Embodiment 150. The method of any one of Embodiments 147 to 149, further comprising determining methylation in said cell.

Embodiment 151. A method comprising identifying a plurality of nucleic acid molecules of a plurality of cells without barcoding individual nucleic acid molecules of said plurality of nucleic acid molecules, wherein extracting said plurality of nucleic acid molecules and identifying are performed in a single microfluidic device.

Embodiment 152. The method of Embodiment 151, wherein said identifying comprises sequencing.

Embodiment 153. The method of Embodiment 151 or 152, further comprising forming a polymer matrix on or adjacent to individual cells of said plurality of cells such that said individual cells are separated from one another.

Embodiment 154. The method of Embodiment 153, further comprising extracting said individual nucleic acid molecules said individual cells.

Embodiment 155. The method of Embodiment 154, wherein said sequencing comprises sequencing said individual nucleic acid molecules within said polymer matrix.

Embodiment 156. The method of Embodiment 152, wherein said sequencing comprises next-generation sequencing, short-read sequencing, nanopore sequencing, sequencing by synthesis, sequencing by in-situ hybridization, or an optical readout.

Embodiment 157. A method comprising: (a) providing a plurality of nucleic acid molecules within a plurality of matrices, wherein individual nucleic acid molecules of said plurality of nucleic acid molecules are from different cells; and (b) sequencing said plurality of nucleic acid molecules while said plurality of nucleic acid molecules is within said plurality of matrices.

Embodiment 158. The method of Embodiment 157, wherein said plurality of matrices is disposed in a fluidic device.

Embodiment 159. The method of Embodiment 157 or Embodiment 158, wherein said plurality of matrices comprises a plurality of cells, and wherein said plurality of cells comprises said plurality of nucleic acid molecules.

Embodiment 160. The method of Embodiment 157, wherein said sequencing comprises next-generation sequencing, short-read sequencing, nanopore sequencing, sequencing by synthesis, sequencing by in-situ hybridization, or an optical readout.

Embodiment 161. A method of analyzing a biological component, said method comprising: (a) introducing one or more biological components into a fluidic device; (b) disposing a first portion of said one or more biological components adjacent a first surface or a second surface of said fluidic device; and (c) forming one or more polymer matrices adjacent a first portion of said first surface to localize at least one of said one or more biological component to said first portion.

Embodiment 162. The method of Embodiment 161, further comprising: (a) agitating said one or more biological components within said fluidic device; (b) disposing a second portion of said one or more biological components adjacent said first surface of said fluidic device; and (c) forming one or more polymer matrices adjacent a second portion of said first surface to immobilize at least one of said one or more biological component of said second portion.

Embodiment 163. The method of Embodiment 161 or Embodiment 162, further comprising identifying a position of at least one of said one or more biological components such that at least one energy source supplies energy to said fluidic device to form said one or more polymer matrices on or adjacent said identified position.

Embodiment 164. A system comprising: a fluidic device comprising: a flow channel; an analysis channel disposed adjacent to said flow channel, wherein at least one flow inhibition element is disposed within said flow channel to inhibit flow of a biological component; and a layer disposed between said flow channel and said analysis channel, wherein said layer comprises at least one sealable aperture disposed adjacent said at least one flow inhibition element, and wherein said at least one sealable aperture is configured to allow passage of said biological component; and at least one energy source in communication with said fluidic device, wherein said at least one energy source is configured to form a polymer matrix within said analysis channel.

Embodiment 165. The system of Embodiment 164, wherein a portion of said flow channel is substantially parallel with a portion of said analysis channel.

Embodiment 166. The system of Embodiment 164 or Embodiment 165, wherein said at least one sealable aperture is configured to transition from a sealed state to an open state.

Embodiment 167. The system of Embodiment 166, wherein passage of said biological component through said at least one sealable aperture is inhibited in said sealed state, and wherein passage of said biological component through said at least one sealable aperture is inhibited in said sealed state.

Embodiment 168. The system of Embodiment 166 or Embodiment 167, wherein, when said at least one sealable aperture is in said sealed state, said at least one sealable aperture is sealed with at least one of an agarose gel, a temperature-soluble polymer, an N-isopropylacrylamide (NIPAAm) polymer, a wax compound, or an alginate.

Embodiment 169. The system of any one of Embodiments 164 to 168, wherein said flow channel comprises a surface disposed opposite of a flow channel surface of said layer, and wherein at least one of said at least one inhibition elements extends from said surface toward said flow channel surface such that flow of said biological component in said flow channel is inhibited by said at least one inhibition element.

Embodiment 170. The system of any one of Embodiments 164 to 169, wherein said analysis channel comprises a surface disposed opposite of said analysis channel surface of said layer.

Embodiment 171. The system of any one of Embodiments 164 to 170, wherein said flow channel is removably couplable to said analysis channel.

Embodiment 172. The system of any one of Embodiments 164 to 171, wherein said surface of said analysis channel comprises one or more barcodes.

Embodiment 173. The system of Embodiment 172, wherein the said one or more barcodes comprise an oligonucleotide.

Embodiment 174. The system of any one of Embodiments 169 to 173, wherein said polymer matrix is coupled to at least one of said surface of said analysis channel or said analysis channel surface of said layer.

Embodiment 175. The system of any one of Embodiments 169 to 174, wherein said polymer matrix extends from said surface of said analysis channel to said analysis channel surface of said layer such that said polymer matrix surrounds at least a portion of said biological component.

Embodiment 176. The system of any one of Embodiments 164 to 175, wherein said at least one energy source is in at least one of optical communication, electrochemical communication, electromagnetic. communication, thermal communication, or microwave communication with said fluidic device.

Embodiment 177. The system of any one of Embodiments 164 to 176, wherein said at least one energy source. comprises a light generating device, a heat generating device, an electrochemical generating device, an electrode, or a microwave device.

Embodiment 178. The system of any one of Embodiments 164 to 177, wherein said biological component comprises a plurality of biological components.

Embodiment 179. The system of any one of Embodiments 164 to 178, wherein said fluidic device is a microfluidic device or a nanofluidic device.

Embodiment 180. The system of any one of Embodiments 164 to 179, wherein said fluidic device comprises a sequencing flow cell.

Embodiment 181. The system of any one of Embodiments 164 to 180, wherein said fluidic device is used for nucleic acid sequencing.

Embodiment 182. The system of any one of Embodiments 164 to 181, wherein said biological component comprises a cell, a nucleic acid, a microbiome, a protein, a combination of cells, a spatially-linked biological component, or a metabolite.

Embodiment 183. The system of Embodiment 182, wherein said cell is an animal cell, a plant cell, a fungal cell, a bacterial cell, a tumor spheroid, or a combination thereof.

Embodiment 184. The system of Embodiment 183, wherein said animal cell is a human cell.

Embodiment 185. The system of Embodiment 182, wherein said nucleic acid is DNA of 100 base pairs or greater or RNA of 50 bases or greater.

Embodiment 186. The system of any one of Embodiments 164 to 185, wherein said polymer matrix comprises a hydrogel.

Embodiment 187. The system of any one of Embodiments 164 to 186, wherein said fluidic device further comprises one or more polymer precursors.

Embodiment 188. The system of Embodiment 187, wherein said one or more polymer precursors comprise hydrogel precursors.

Embodiment 189. The system of any one of Embodiments 164 to 188, wherein said polymer matrix comprises a polymer matrix wall having a width of at least 1 μm.

Embodiment 190. The system of any one of Embodiments 164 to 189, wherein said polymer matrix inhibits passage of said biological component.

Embodiment 191. The system of Embodiment 189 or Embodiment 190, wherein said polymer matrix wall is a hydrogel wall.

Embodiment 192. The system of any one of Embodiments 164 to 191, wherein said polymer matrix is degradable.

Embodiment 193. The system of Embodiment 192, wherein degradation of said polymer matrix is "on demand."

Embodiment 194. The system of Embodiment 192 or Embodiment 193, wherein said polymer matrix is degradable by at least one of: (i) contacting said polymer matrix with a cleaving reagent; (ii) heating said polymer matrix to at least 90° C.; or (iii) exposing said polymer matrix to a wavelength of light that cleaves a photo-cleavable crosslinker that crosslinks said polymer of said polymer matrix.

Embodiment 195. The system of any one of Embodiments 166 to Embodiment 194, wherein said sealable aperture is transitioned to said open state by at least one of: (i) contacting said sealable aperture with a cleaving reagent; (ii) heating said sealable aperture to at least 90° C.; or (iii) exposing said sealable aperture to a wavelength of light that cleaves a photo-cleavable crosslinker that crosslinks said polymer of said sealable aperture.

Embodiment 196. The system of Embodiment 194, wherein said polymer matrix comprises a hydrogel, and wherein said cleaving reagent is configured to degrade said polymer matrix.

Embodiment 197. The system of Embodiment 196, wherein said cleaving reagent comprises a reducing agent, an oxidative agent, an enzyme, a pH based cleaving reagent, or a combination thereof.

Embodiment 198. The system of Embodiment 196, wherein said cleaving reagent comprises dithiothreitol (DTT), tris(2-carboxyethyl)phosphine (TCEP), tris(3-hydroxy propyl)phosphine (THP), or a combination thereof.

Embodiment 199. The system of any one of Embodiments 164 to 198, wherein said polymer matrix allows passage of a reagent.

Embodiment 200. The system of any one of Embodiments 164 to 199, wherein said polymer matrix comprises pores, wherein a size of said pores are controlled by changing a composition of said one or more polymer precursors, said at least one energy source, or a combination thereof.

Embodiment 201. The system of Embodiment 199, wherein said reagent comprises at least one of enzymes, chemicals, oligonucleotides, or primers having a size of less than 50 base pairs.

Embodiment 202. The system of any one of Embodiments 199 to 201, wherein said reagent comprises lysozyme, proteinase K, random hexamers, polymerase, transposase, ligase, catalyzing enzyme, deoxynucleotide triphosphates, buffers, cell culture media, or divalent cations.

Embodiment 203. The system of any one of Embodiments 164 to 202, wherein said polymer matrix comprises pores that are sized to allow diffusion of a reagent through said matrix but are too small to allow DNA or RNA to traverse said pores.

Embodiment 204. The system of any one of Embodiments 164 to 203, wherein said polymer matrix comprises a hydrogel, and wherein said hydrogel comprises polyethylene glycol (PEG)-thiol, PEG-acrylate, acrylamide, N,N'-bis (acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetraacrylate, or combinations or mixtures thereof.

Embodiment 205. The system of Embodiment 204, wherein said hydrogel comprises an enzymatically degradable hydrogel, PEG-thiol/PEG-acrylate, acrylamide/N,N'-bis(acryloyl)cystamine (BACy), or PEG/PPO.

Embodiment 206. The system of any one of Embodiments 169 to 205, wherein said surface comprises one or more barcodes.

Embodiment 207. The system of Embodiment 206, wherein said one or more barcodes comprise an oligonucleotide.

Embodiment 208. The system of any one of Embodiments 169 to 207, wherein said surface of said analysis channel comprises one or more compounds configured to bind said biological component.

Embodiment 209. The system of any one of Embodiments 169 to 208, wherein said surface of said analysis channel is functionalized with a surface polymer.

Embodiment 210. The system of Embodiment 209, wherein said surface polymer is functionalized with an oligonucleotide.

Embodiment 211. The system of Embodiment 209, wherein said surface polymer is functionalized with an antibody, a cytokine, a chemokine, a protein, an antibody derivative, an antibody fragment, a carbohydrate, a toxin, an aptamer, or any combination thereof.

Embodiment 212. The system of any one of Embodiments 169 to 209, wherein a surface of said polymer matrix is functionalized with an oligonucleotide, an antibody, a cytokine, a chemokine, a protein, an antibody derivative, an antibody fragment, a carbohydrate, a toxin, an aptamer, or any combination thereof.

Embodiment 213. The system of Embodiment 209, wherein said surface polymer comprises polyethylene glycol (PEG), a silane polymer, pyridinecarboxaldehyde (PCA), an acrylamide, an agarose, or a combination thereof.

Embodiment 214. The system of any one of Embodiments 206 to 213, further comprising a detector for identifying said one or more of said biological components, said one or more barcodes, or a combination thereof.

Embodiment 215. The system of Embodiment 214, wherein said detector comprises a camera.

Embodiment 216. The system of any one of Embodiments 164 to 215, further comprising a stage that holds said fluidic device.

Embodiment 217. The system of any one of Embodiments 164 to 216, further comprising a sequencing device for obtaining sequencing data.

Embodiment 218. The system of any one of Embodiments 164 to 217, further comprising a spatial energy modulating element to selectively supply said energy to said fluidic device.

Embodiment 219. The system of Embodiment 218, wherein said spatial energy modulating element comprises a physical photomask, a virtual photomask, a physical electrode distribution pattern, a virtual electrode distribution pattern.

Embodiment 220. The system of Embodiment 218, wherein said spatial energy modulating element comprises a photolithographic mask or a digital micromirror device (DMD) mask.

Embodiment 221. A method of analyzing a biological component, said method comprising: (a) introducing said biological component into a flow channel of a fluidic device; (b) inhibiting flow of said biological component adjacent to an inhibition element, wherein a sealable aperture is disposed adjacent to said inhibition element; (c) disposing said biological component from said flow channel to an analysis channel of said fluidic device; and (d) forming a polymer matrix on or adjacent to said biological component in said analysis channel.

Embodiment 222. The method of Embodiment 221, wherein prior to said disposing in (c), said sealable aperture is degraded using at least one of: (i) contacting said sealable aperture with a cleaving reagent; (ii) heating said sealable aperture to at least 90° C.; or (iii) exposing said sealable aperture to a wavelength of light that cleaves a photocleavable crosslinker that crosslinks said polymer of said sealable aperture.

Embodiment 223. The method of Embodiment 221 or Embodiment 222, further comprising introducing one or more polymer precursors into said fluidic device.

Embodiment 224. The method of any one of Embodiments 221 to 223, wherein forming said polymer matrix comprises supplying energy to said fluidic device to form said polymer matrix.

Embodiment 225. The method of Embodiment 224, wherein said energy is selectively supplied to one or more portions of said fluidic device.

Embodiment 226. The method of any one of Embodiments 221 to 225, further comprising activating a spatial energy modulating element to selectively supply said energy to said fluidic device.

Embodiment 227. The method of Embodiment 226, wherein said spatial energy modulating element comprises a physical photomask, a virtual photomask, a physical electrode distribution pattern, or a virtual electrode distribution pattern.

Embodiment 228. The method of Embodiment 226, wherein said spatial energy modulating element comprises a photolithographic mask or a digital micromirror device (DMD) mask.

Embodiment 229. The method of any one of Embodiments 224 to 228, wherein said energy is supplied via light energy source, a heat energy source, an electrochemical energy source, or an electromagnetic energy source.

Embodiment 230. The method of any one of Embodiments 224 to 229, wherein said polymer matrix is coupled to a surface of said analysis channel.

Embodiment 231. The method of any one of Embodiments 224 to 229, wherein said energy forms said polymer matrix around a portion of said coupled biological component.

Embodiment 232. The method of any one of Embodiments 221 to 231, wherein at least a portion of said biological component is encapsulated by said polymer matrix.

Embodiment 233. The method of Embodiment 232, wherein an entirety of said biological component is encapsulated by said polymer matrix.

Embodiment 234. The method of any one of Embodiments 221 to 233, further comprising encapsulating a first biological component to form a first analysis chamber and encapsulating a second biological component to form a second analysis chamber.

Embodiment 235. The method of Embodiment 234, wherein said first analysis chamber is adjacent to said second analysis chamber.

Embodiment 236. The method of Embodiment 234 or Embodiment 235, wherein said first analysis chamber is disposed from 5 micrometer (μm) to 1,000 μm away from said second analysis chamber.

Embodiment 237. The method of any one of Embodiments 234 to 236, further comprising analyzing said first biological component in said first analysis chamber and analyzing said second biological component in said second analysis chamber.

Embodiment 238. The method of any one of Embodiments 234 to 237, further comprising actuating a first reaction in said first biological component and actuating a second reaction in said second biological component.

Embodiment 239. The method of Embodiment 238, wherein said first reaction and said second reaction are different.

Embodiment 240. The method of any one of Embodiments 234 to 239, further comprising actuating a third reaction in said first biological component and actuating a fourth reaction in said second biological component.

Embodiment 241. The method of Embodiment 240, wherein said third reaction and said fourth reaction are different.

Embodiment 242. The method of any one of Embodiments 221 to 241, further comprising obtaining a genome, transcriptome, proteome, epigenome, methylome, secretome, or metabolome of said biological component.

Embodiment 243. The method of Embodiment 242, wherein said transcriptome is a substantially full-length transcriptome.

Embodiment 244. The method of Embodiment 242, wherein said transcriptome is a full-length transcriptome.

Embodiment 245. The method of any one of Embodiments 221 to 244, further comprising sequencing said biological component.

Embodiment 246. The method of Embodiment 245, wherein said sequencing does not comprise amplification of a sequencing library.

Embodiment 247. The method of any one of Embodiments 221 to 246, further comprising a barcode configured to be coupled to said biological component or a molecule produced by said biological component.

Embodiment 248. The method of any one of Embodiments 221 to 247, further comprising exposing said biological component or said first biological component to an analyte.

Embodiment 249. The method of Embodiment 248, wherein said biological component comprises one or more microbes, and wherein said analyte comprises an antimicrobial agent, a microbial growth promoting chemical, or a combination thereof.

Embodiment 250. The method of Embodiment 249, further comprising screening said one or more microbes for susceptibility to said antimicrobial agent.

Embodiment 251. The method of Embodiment 248, wherein said analyte comprises a pharmaceutical agent.

Embodiment 252. The method of Embodiment 251, further comprising screening an effect of said pharmaceutical agent on said biological component.

Embodiment 253. The method of any one of Embodiments 221 to 248, wherein said method further comprises screening said biological component for production of a target molecule.

Embodiment 254. The method of Embodiment 253, wherein said target molecule comprises at least one of an antibody, a cytokine, a chemokine, a protein, an antibody derivative, an antibody fragment, a carbohydrate, a toxin, or an aptamer.

Embodiment 255. The method of any one of Embodiments 221 to 254, further comprising forming said polymer matrix around said biological component such that said biological component is disposed within a structure formed by said polymer matrix.

Embodiment 256. The method of any one of Embodiments 221 to 255, further comprising analyzing a local parameter in said first analysis chamber or said second analysis chamber, wherein a level of said local parameter in said first analysis chamber is different from a level of said local parameter in said second analysis chamber.

Embodiment 257. The method of Embodiment 256, wherein said local parameter comprise a pH, an oxygen concentration, or a $CO_2$ concentration.

EXAMPLES

The following illustrative examples are representative of embodiments of the devices and methods described herein and are not meant to be limiting in any way.

Example 1: mRNA 3' Gene Expression Workflow with External Sequencing

Figure 13A:
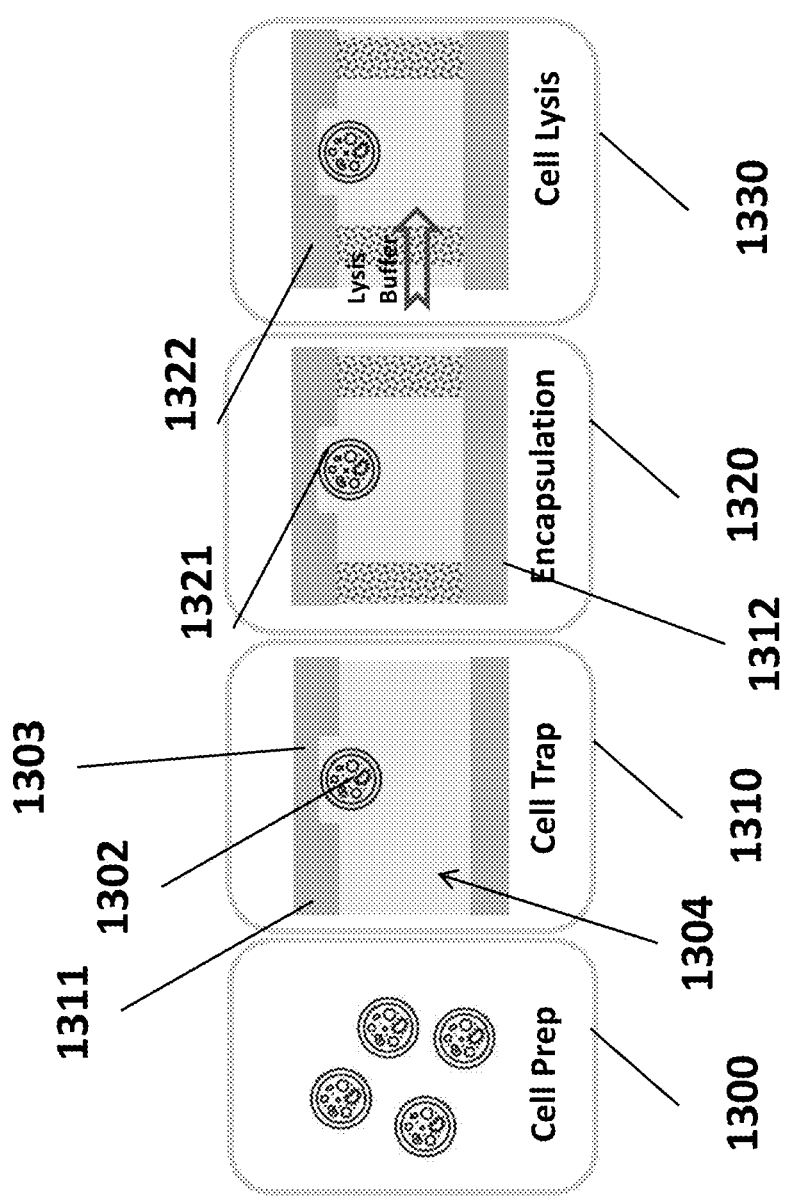
FIG. 13A is a schematic illustration of cell capturing and cell lysis steps of an exemplary mRNA 3' gene expression workflow with external sequencing.
Figure 13B:
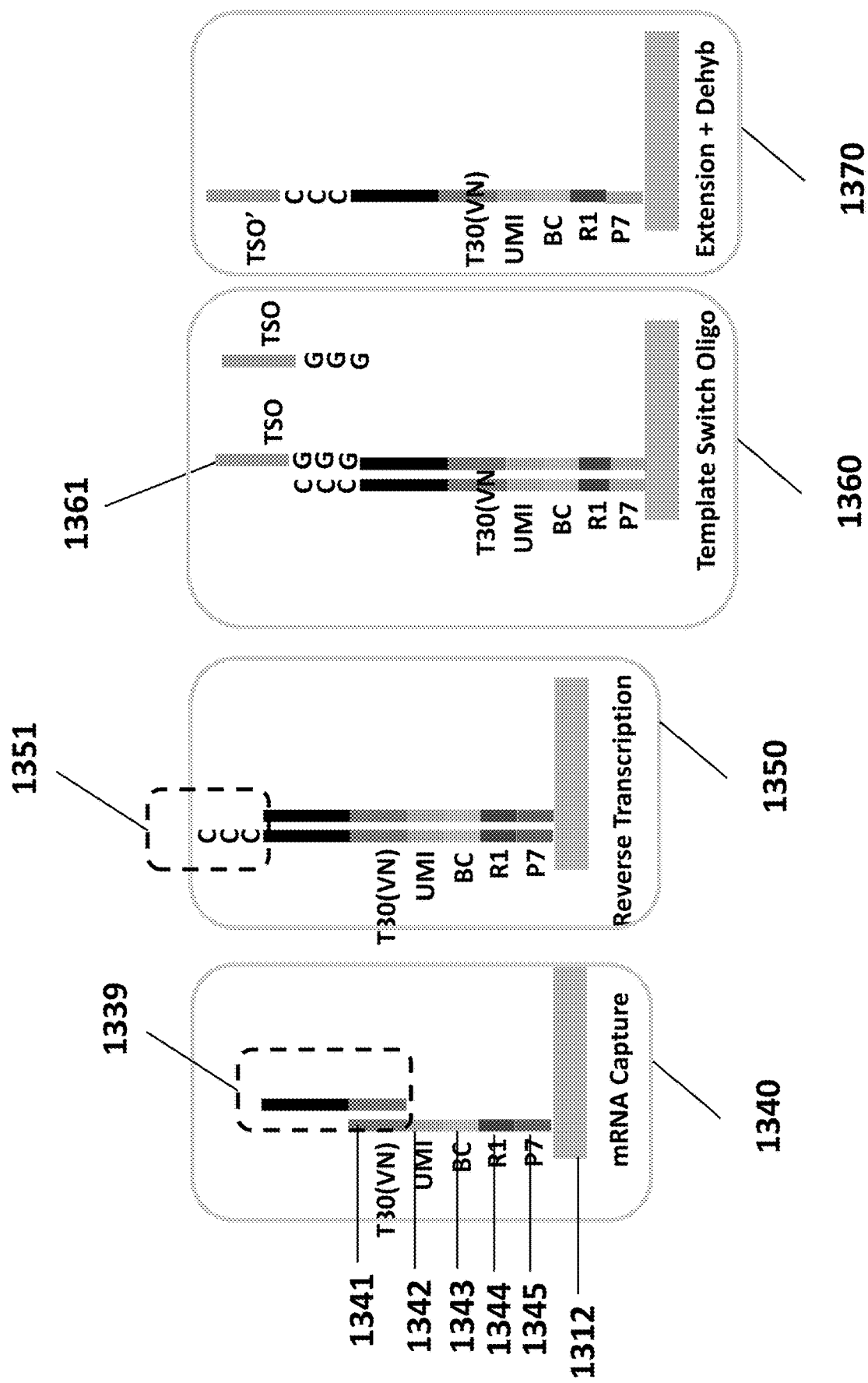
FIG. 13B is a schematic illustration of generating a cDNA library from a template mRNA in an exemplary mRNA 3' gene expression workflow with external sequencing.
Figure 13C:
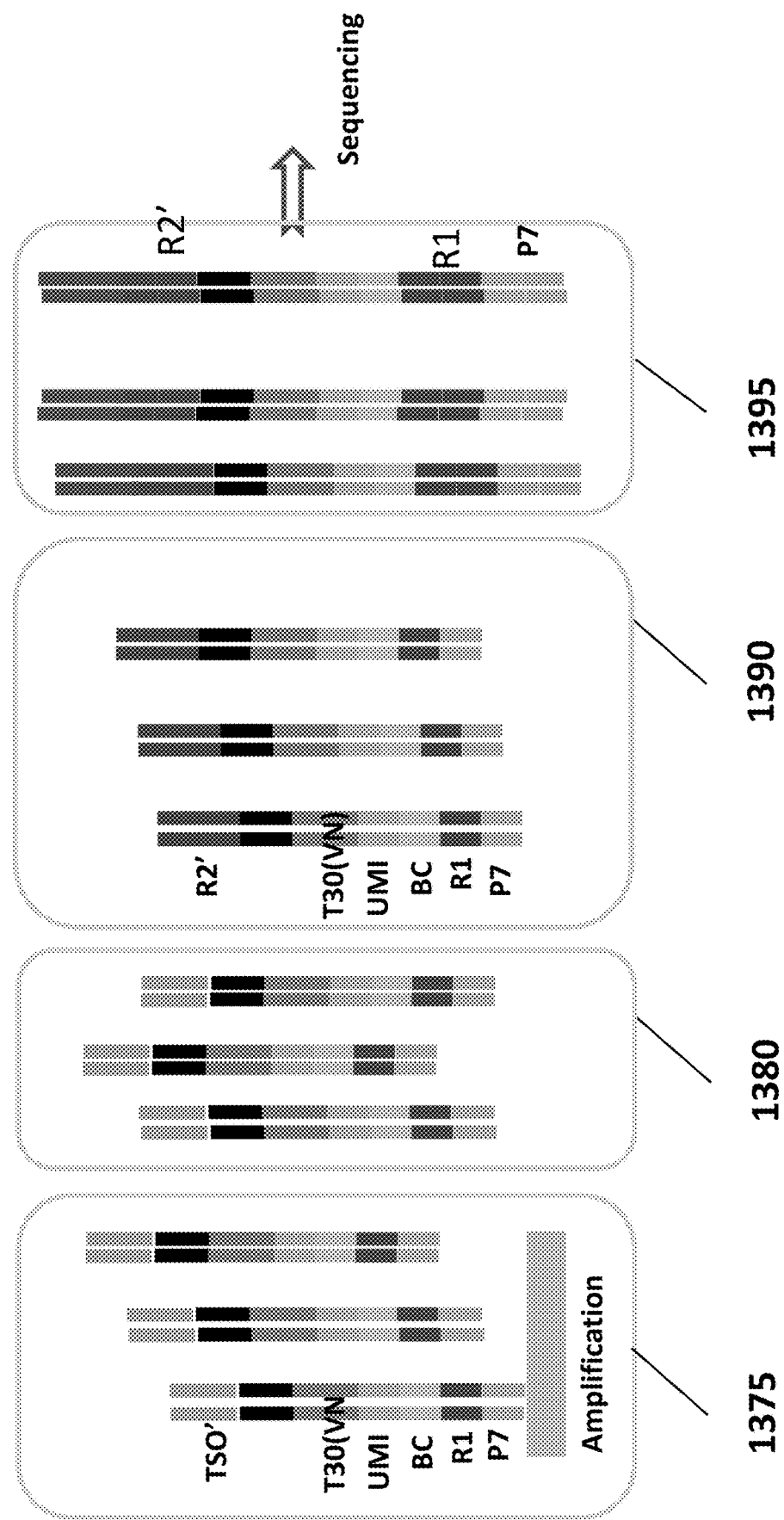
FIG. 13C is a schematic illustration of a sequence library prep in an exemplary mRNA 3' gene expression workflow with external sequencing.

This example demonstrates an mRNA 3' gene expression workflow using a fluidic device comprising a hydrogel as described herein. FIGS. 13A-13C illustrate various steps of the workflow. FIG. 13A shows the process of loading cells and processing cells to extract mRNAs. Step 1300 shows cells that are provided into the fluidic device. A cell 1302 may be trapped using a capture element or a trap 1303 as described herein, such that the cell 1302 is contained or immobilized at a location on a surface 1311 of a channel 1304 of the fluidic device (1310). The trapping can be performed on the surface 1312. Polymer matrix 1321, 1322 is generated adjacent to the cell to form a compartment to localize the cell and parts and/or products thereof (1320). Reagents flow into the channel and into the polymer matrix compartment, where the polymer matrix is porous and allows transfer of reagents. The reagents are provided to lyse the cell in order to extract genetic material from the cell (step 1330).

FIG. 13B shows an mRNA molecule 1339 that is extracted from the cell within the polymer matrix, as described herein. The mRNA 1339 is captured using a capture element that comprises various portions. In this non-limiting example, the capture element shown in step 1340 comprises an oligo 1341, a unique molecular identifier (UMI) 1342, a barcode (BC) 1343, and sequencing primers 1344, 1345. The oligo 1341 can comprise a plurality of thymine bases (e.g., 30 thymine bases) to bind to the poly-A tail of the mRNA. The UMI 1342 is used to maintain the uniqueness of the captured mRNA during the downstream amplification steps. The BC 1343 is used to associate the mRNA to the cell that it was extracted from. Furthermore, the BC could be used to associate further information about the source of the mRNA sequence such as the sample that the cell was obtained from. The sequencing primer 1344, 1345 may comprise an R1 and/or a P7 primer.

After capturing the mRNA molecule (step 1340), reverse transcription is performed to copy the mRNA into cDNA then integrate the UMI 1342, the BC 1343, and the sequencing primers 1344, 1345 into the cDNA (complementary DNA) molecule (step 1350) to generate a barcoded cDNA strand that carries information regarding, for example, the cell and/or the sample it was extracted from. In step 1360, template switch oligos (TSO) 1361 hybridize to untemplated C nucleotides 1351 added during reverse transcription in step 1350. The cDNA is then extended and denatured to form a single-strand DNA as shown in step 1370. Then the library is amplified (e.g., via PCR) (step 1375). The library produced in steps 1300 to 1375 is then eluted (step 1380) and transferred out of the fluidic device and pooled together as shown in 1390. The eluted cDNA is processed by fragmentation and adapter ligation (e.g., through tagmentation) to add sequencing adapters including specific sequences designed to interact with the sequencing platform used for sequencing as well as sample indexes (step 1395). The polymer matrix may be deconstructed after steps 1340, 1350, 1360, 1370, or 1375.

Example 2: mRNA 3' Gene Expression Workflow with Internal Sequencing

Figure 14A:
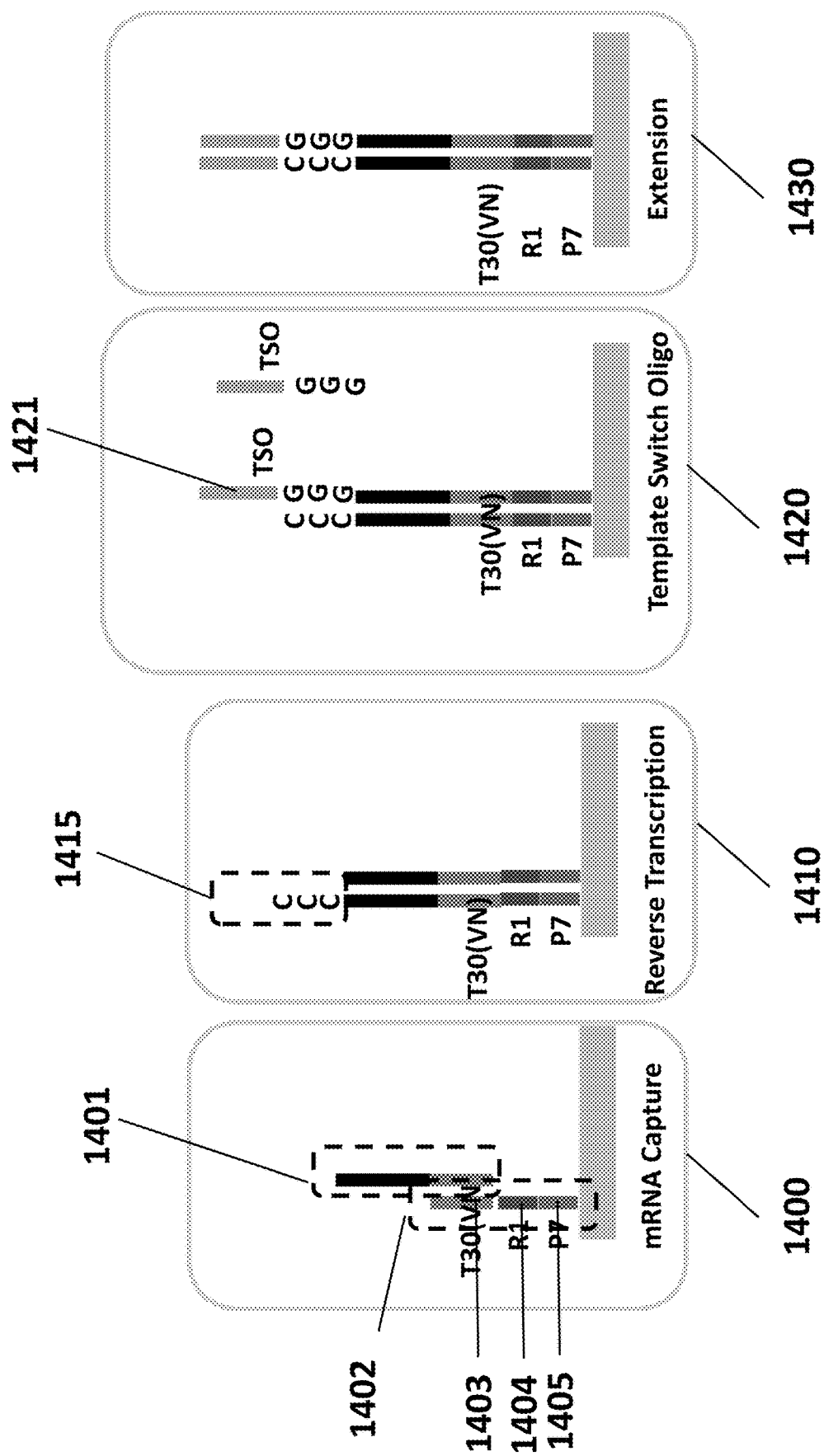
FIGS. 14A and 14B show schematic illustrations of an exemplary mRNA 3' gene expression workflow with in-situ sequencing.
Figure 14B:
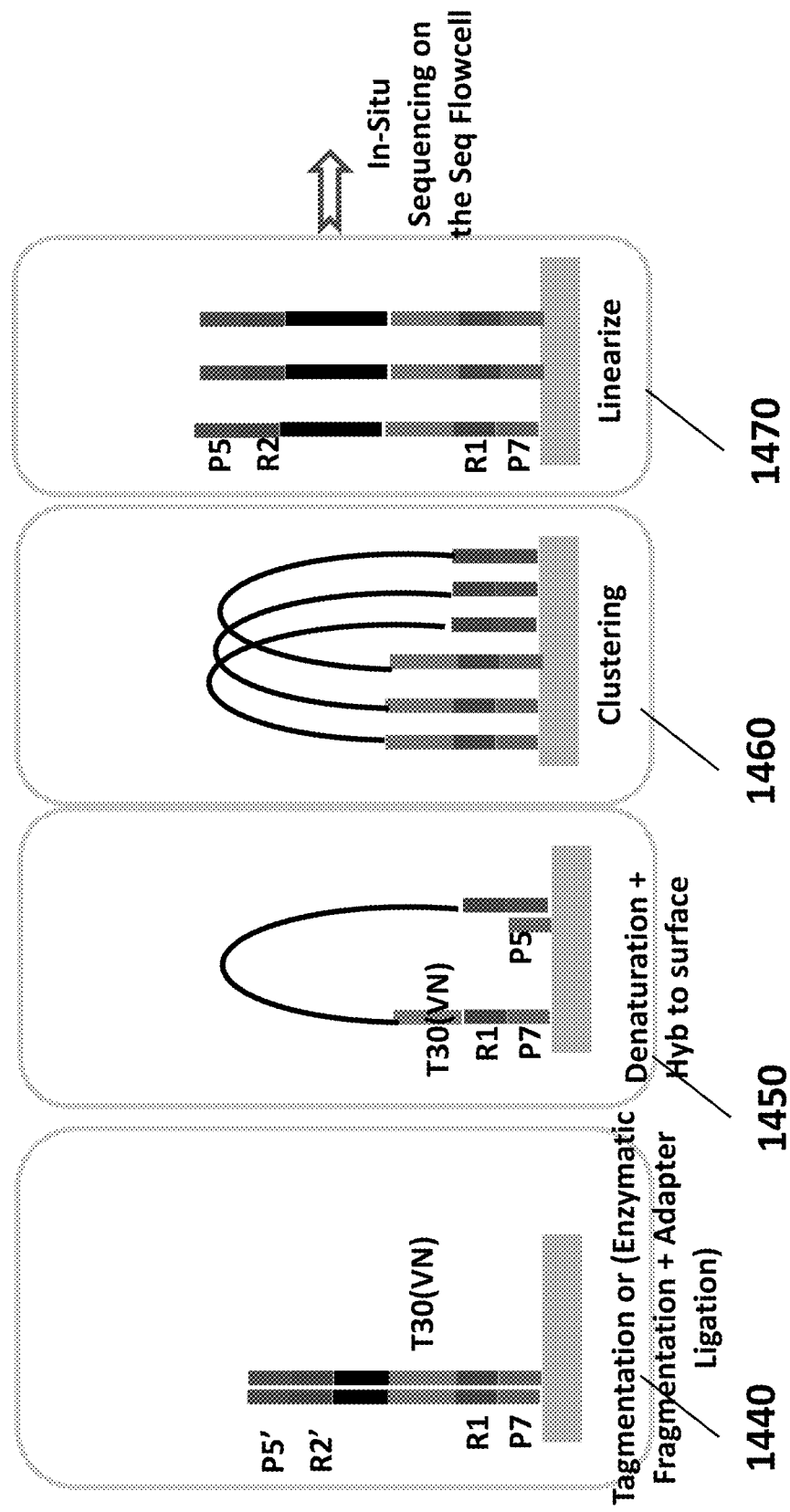

The mRNA gene expression assay can be performed using the fluidic device that is used for extracting and capturing the mRNA from a cell localized by using a polymer matrix formed as described herein. FIGS. 14A and 14B illustrate an example for the steps of preparing a library for sequencing to be performed in the fluidic device. A cell is provided into the fluidic channel, cell is localized by trapping and/or forming polymer matrix, and the mRNA is extracted by cell lysis similar to steps 1300, 1310, 1320, 1330 provided in FIG. 13A in Example 1. The mRNA 1401 extracted from the cell are then captured using a capture element 1402. In this non-limiting example, the capture element 1402 shown in step 1400 comprises an oligo 1403, and sequencing primers 1404, 1405 (e.g., R1 or P7 primers). The oligo 1403 may comprise a plurality of thymine bases 1403 (e.g., 30 thymine bases) to bind to the poly-A tail of the mRNA 1401. As shown in this example, a UMI or a barcode is not required as the sequencing is performed on the fluidic device as opposed to an external sequencing device. The spatial information (e.g., location of the polymer matrix and capturing site) associates the mRNA with the cell that generated the mRNA. In this process, the sequencing readouts share the same location and therefore are associated with the cell, which the mRNA was extracted from. After capturing the mRNA molecule (step 1400), reverse transcription is performed to copy the mRNA into cDNA (step 1410). In step 1420, template switch oligos (TSO) 1421 hybridize to untemplated C nucleotides 1415 added during reverse transcription in step 1410. The cDNA is then extended to form a double-strand DNA as shown in step 1430.

FIG. 14B illustrates the remainder of the process steps. This includes a tagmentation step or fragmentation and adapter ligation step as shown in step 1440. Then the end tail of the cDNA is hybridized onto the appropriate surface primer (step 1450). The hybridization is followed by clustering (surface amplification) the cDNA molecules (step 1460). The clustered cDNA molecules are linearized to generate single stranded molecules (step 1470). Sequencing is then performed in situ inside the fluidic device. This process does not require an amplification step, as the linearized cDNA molecules are not eluted off the surface of the fluidic device to be sent to another device for sequencing thus reducing DNA molecule losses. The association of the cDNA molecules with the location of the cell on the surface of the fluidic device may eliminate the use of any barcoding or UMI for tracking the source of the sequencing products/ read outs. In this example, the sequencing can be short-read sequencing, nanopore sequencing, sequencing by synthesis, sequencing by hybridization, or sequencing through collection of any optical readouts.

Example 3: Whole Genome Workflow

Figure 18:
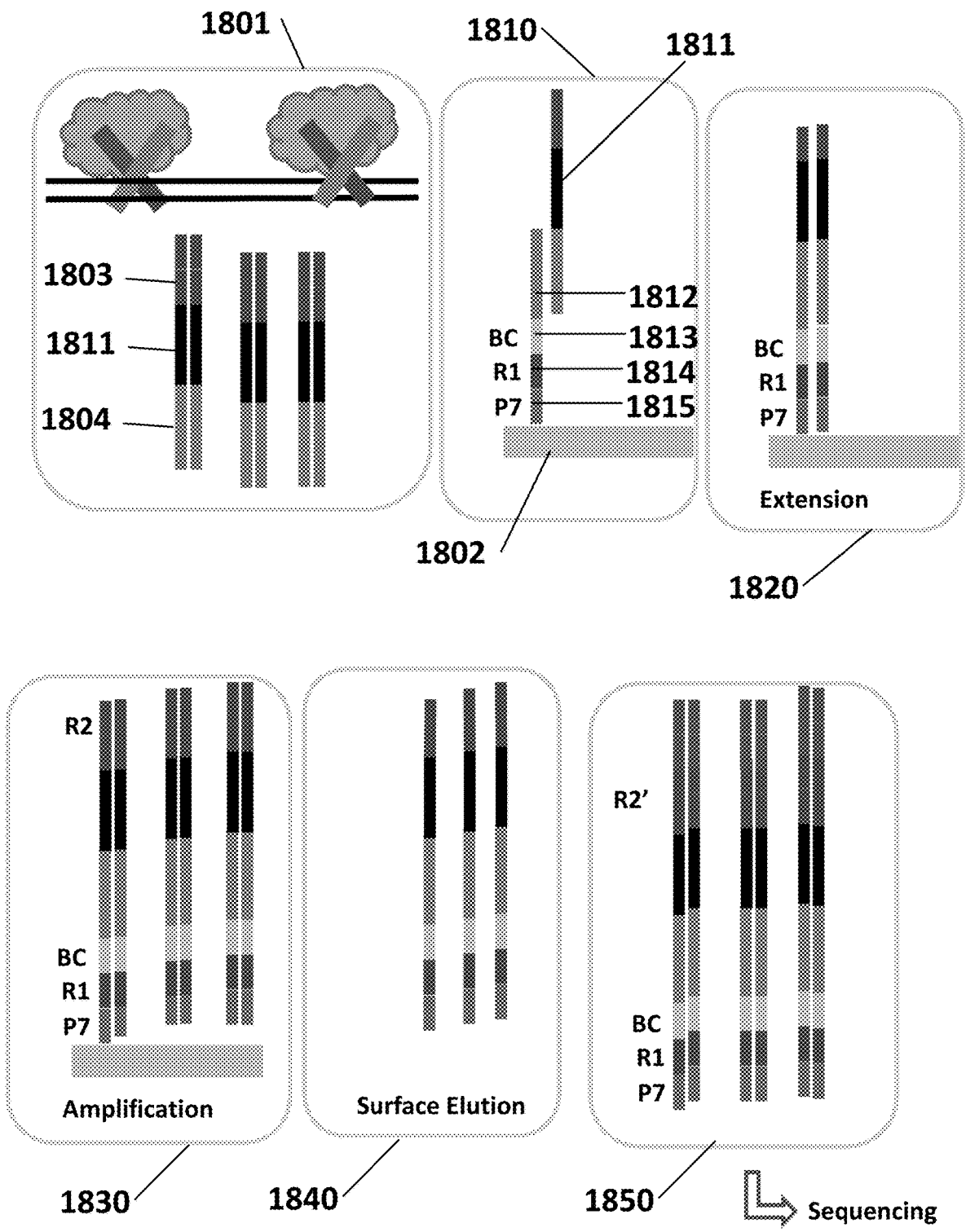
FIG. 18 shows a schematic of a whole-genome workflow, according to some embodiments.

FIG. 18 schematically illustrates a whole genome workflow followed by external sequencing. A biological component (e.g., a cell) is provided into a fluidic channel as described here, the whole genome material (e.g., DNA) is extracted by capturing and lysing a biological component using polymer matrix compartments similar to steps: 1300, 1310, 1320, and 1330 provided in FIG. 13A as discussed in Example 1. DNA may be extracted from a biological as shown in step 1801 of FIG. 18. In step 1801 a double-stranded DNA library may be generated. Step 1801 may comprise tagmentation, and/or enzymatic fragmentation and adapter ligation. In step 1801, DNA extracted from the biological component may be fragmented into fragments of predefined sizes 1811. Step 1801 may further comprise inserting one or more adapters 1803/1804 (e.g., a sequencing primer R2) to one or both ends of the DNA fragments. A denatured DNA fragment 1811 carrying one or more adapter sequences may then be captured on a surface 1802 of the fluidic channel using a capture element (step 1810). The capture element may comprise barcoding region 1813, sequencing primers 1814, 1815 (e.g., R1/R2 or P5/P7 primers), and capturing sequences 1812. The captured DNA may then be tagged, extended (step 1820) and amplified (e.g., via PCR) (step 1830). The barcode region 1813 of the capture element may ensure that the genomic material of a biological component may be uniquely tagged and later identified using, for example, sequencing. An amplified DNA prepared in step 1830 may then be eluted from the surface and transferred out of the fluidic device in step 1840. Additional primers or sample indexes may be added to the eluted molecules to prepare a sequencing library (step 1850). The eluted genomic material may then be sequenced using a device different than or separate from the fluidic device described herein. In some cases, the genomic material may be sequenced in and/or using the fluidic device described herein, where steps of elution of the genomic material and barcoding may be eliminated. The hydrogel can be dissolved after any of the steps 1810, 1820, or 1830.

Example 4: Multi-Omics Workflow

Figure 19:
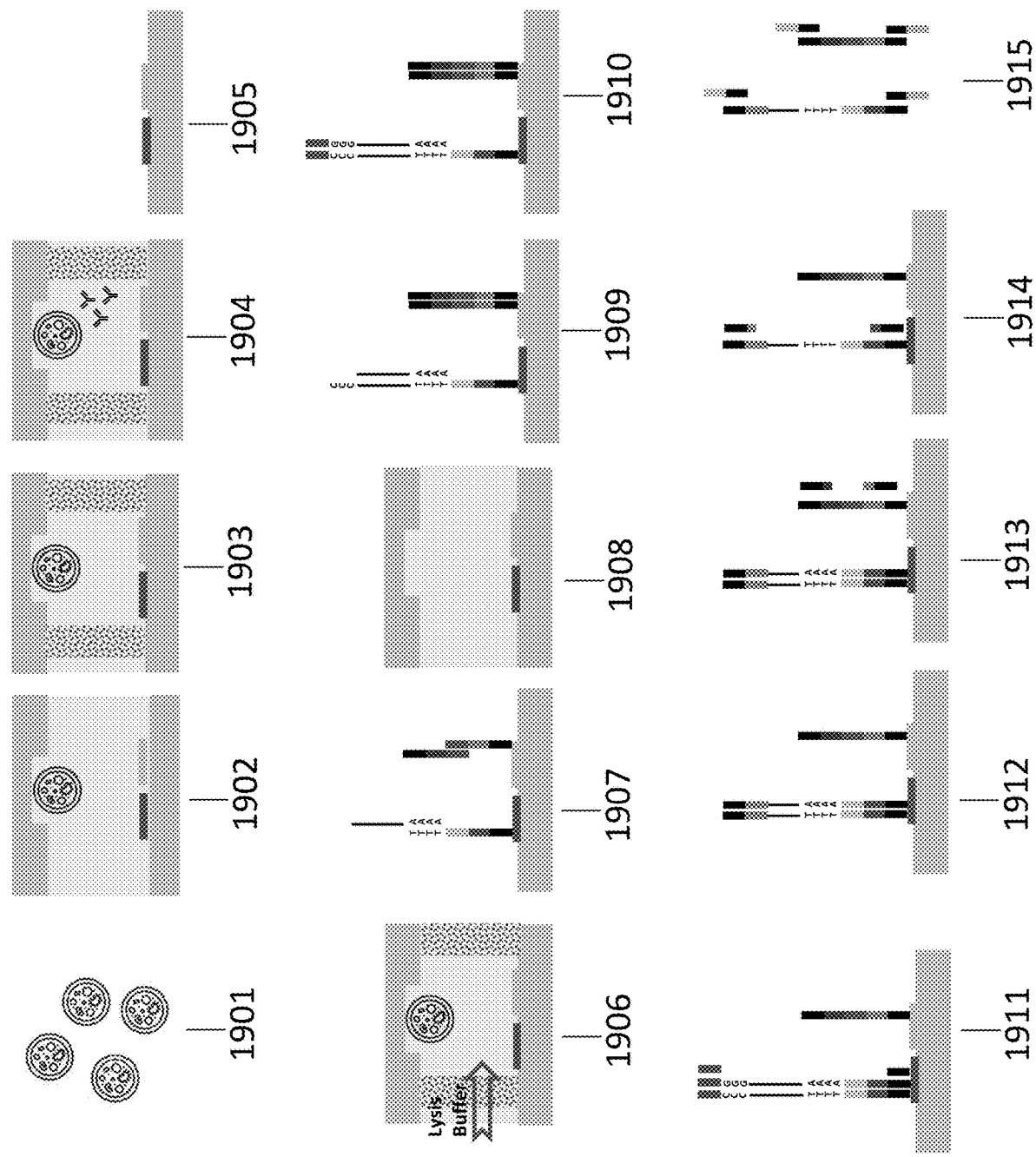
FIG. 19 shows a schematic of a multi-omics workflow, according to some embodiments.

FIG. 19 illustrates an example of a workflow for multi-omic analysis of a sample comprising a biological component. In some cases, the biological component may comprise a cell. The cell may be an animal cell (e.g., a human cell), a plant cell, a fungal cell, a bacterial cell, or any other type of cell capable of producing proteins. In step 1901, biological components can be collected to be introduced into or provided to a fluidic device. In some embodiments, a capture step 1902 may use capture elements, as described herein, to capture and/or couple a biological component to a surface of a channel disposed within the fluidic device. Capture elements may comprise a functional group, fibronectin, RGD peptides, antibodies, or other molecules as described herein. The capture element may be capable of capturing or coupling the biological component or suspected biological component. In an encapsulation step 1903 a polymer matrix may be formed adjacent to the biological component. In some embodiments, the biological component may be encapsulated entirely by the polymer matrix (e.g., hydrogel) or a portion thereof. In another embodiment, the biological component is encapsulated by the pattern of the hydrogel, or a portion thereof, and one or more surfaces of the fluidic device or channel. The polymer matrix (e.g., hydrogel) may be porous and allows transfer of reagents.

A reagent may comprise a cell incubation solution. The reagent may be provided into the channel and into the polymer matrix compartment. The cell incubation reagent may promote the biological component to growth and/or to produce and secrete a secretome. In some embodiments, a secretome comprising antibodies produced and secreted from the biological component may be localized within the polymer matrix (step 1904). In step 1905 proteins produced by and/or secreted from the biological component may be captured and tagged. A molecular barcode (e.g., fluorescent labeled antibody) may be used for tagging the protein. In step 1906, the biological component may be lysed to release genetic material (e.g., mRNA) from within the biological component, for example, by introducing of a lysis buffer into the polymer matrix compartment. In certain embodiments, an average pore size of the polymer matrix may permit, or may be induced to permit, the flow of reagents into the polymer matrix compartment. In step 1907, the genetic material released from the biological component may be captured by capture agents on a surface of the channel. The hydrogel may then be dismantled to allow further chemical processing (step 1908). For example, the captured nucleic acids may comprise ribonucleic acids (e.g., mRNA). Reverse transcription may be performed to generate a complementary DNA (cDNA) and cDNA may be extended in step 1909. In step 1910, template switching can be performed to add additional primers to cDNA molecules. Template switching may occur prior to further denaturation and extension (step 1911). The resulting nucleic acid strands may be tagmented (step 1912). The protein tags and cDNA molecules may be amplified (steps 1913 and 1914) and then eluted from the surface of the channel either sequentially or in parallel (e.g., simultaneously). The genomic and proteomic material may then be pooled (step 1915) and further processed. Further processing may comprise nucleic acid amplification, addition of more primers, gene sequencing, and/or protein analysis processes. In some embodiments, additional primers comprising sequencing primers (e.g., P5/P7 primers) and sample index may be added to the libraries of nucleic acids generated by the method described herein before sequencing the libraries.

Example 5: Single Cell Detection Using Discrete Capture Mode

Figure 25A:
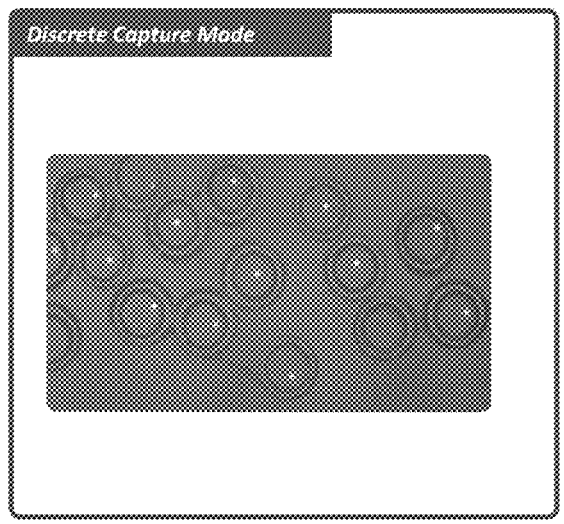
FIG. 25A shows a hydrogel structure in which individual cells are encapsulated in circular hydrogel matrices, according to some embodiments.

Jurkat cells (immortalized line of human T lymphocyte cells) can first be stained with Calcein AM dye for fluorescence imaging. The cells can be mixed with the hydrogel precursor mix containing hydrogel monomer, cross-linker and photo-initiator. The ratio of single-cell suspension and hydrogel precursor mix may be titrated until a designed cell density (e.g. ~30 cells/ul) is obtained. After loading single-cell hydrogel precursor mix to the microfluidic channel, the cells will settle down to the bottom surface of the microfluidic channel. The cells can then be imaged using a microscope. The image may be processed to identify the location of all the cells in the image. A virtual mask can be generated such that each cell is encapsulated inside a circular ring of approx. 180 um outer diameter and 30 um wall width. The virtual mask may then be projected using a DMD projector and a 10× magnification microscope objective. The UV light pattern corresponding to the virtual mask can be projected for 6 seconds and can result in the hydrogel structure shown in FIG. 25A. After patterning the hydrogel, the excess monomer and photo-initiator can be washed away with cell-compatible buffer.

Example 6: Single Cell Detection Using Contiguous Capture Mode

Figure 25B:
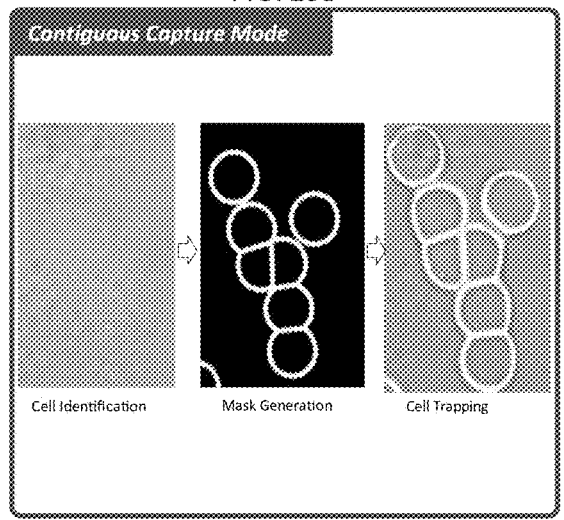
FIG. 25B shows cells identified using bright field imaging using 4× microscope objective, the resulting Voronoi mask calculated based on the location of the cells, and the hydrogel structures surrounding the cells generated using the Voronoi mask, according to some embodiments.

Jurkat cells are mixed with the hydrogel precursor mix containing hydrogel monomer, cross-linker and photo-initiator. The ratio of single-cell suspension and hydrogel precursor mix is titrated until designed cell density (e.g. ~30 cells/ul) is obtained. After loading single-cell hydrogel precursor mix to the microfluidic channel, the cells will settle down to the bottom surface of the microfluidic channel. After the cells are identified using bright field imaging, the centers of cells are identified, and a virtual mask is generated using a Voronoi algorithm that results in a non-circular shaped hydrogel matrix structure (e.g., a particular CellCage™ structure) with a single wall separating two adjacent cells that are closer than a specified distance threshold. FIG. 25B shows cells identified using bright field imaging using 4× microscope objective, the resulting Voronoi mask calculated based on the location of the cells, and the hydrogel structures surrounding the cells generated using the Voronoi mask.

Example 7: Single Cell Detection and Retention

Figure 26A:
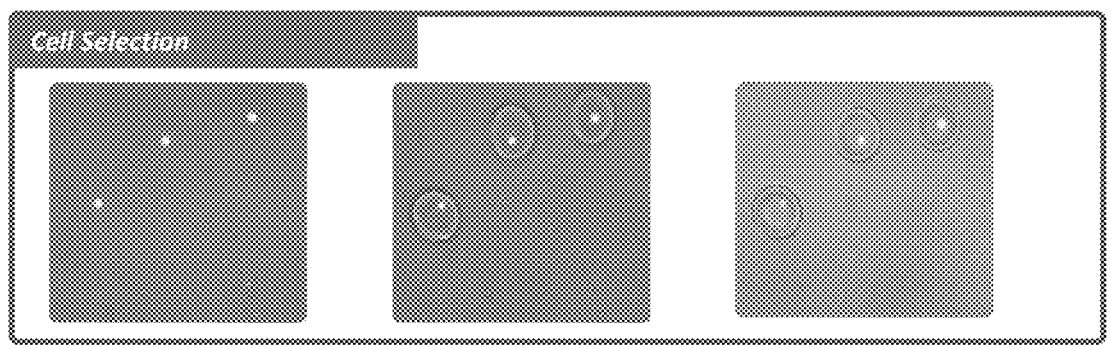
FIG. 26A illustrates selective retention of fluorescent cells in a mixture of fluorescent calcein AM stained cells and non-fluorescent cells, according to some embodiments.

FIG. 26A illustrates the selective retention of fluorescent cells in a mixture of fluorescent calcein AM stained cells and non-fluorescent cells. The mixture of mammalian cells can include Calcein AM stained and unstained cells and may be agitated gently in cell-compatible buffer to avoid cell aggregation. The single-cell suspension may be added into a hydrogel precursor mix that contains monomer, cleavable cross-linker and photo-initiator with cell-compatible buffer condition. The ratio of single-cell suspension and hydrogel precursor mix is titrated until getting designed cell density (e.g. ~30 cells/ul). Upon loading single-cell hydrogel precursor mix to the microfluidic channel, the cells settle down to the bottom surface. The cells can be imaged using brightfield and fluorescence mode, and their location is identified using image processing. A virtual mask may be generated to encapsulate only the fluorescent cells. The UV light with the specific pattern can be applied to the channel to cross-link the hydrogel within the light path. As shown in FIG. 26A, the ring-shaped hydrogel can be formed around fluorescent cells. After patterning the hydrogel, the excess monomer, photo-initiator and non-captured cells (non-fluorescent) can be washed away with cell-compatible buffer. Only fluorescent single cells are retained, and the cells will be ready for various assays and cell mRNA/DNA/protein content analysis.

Figure 26B:
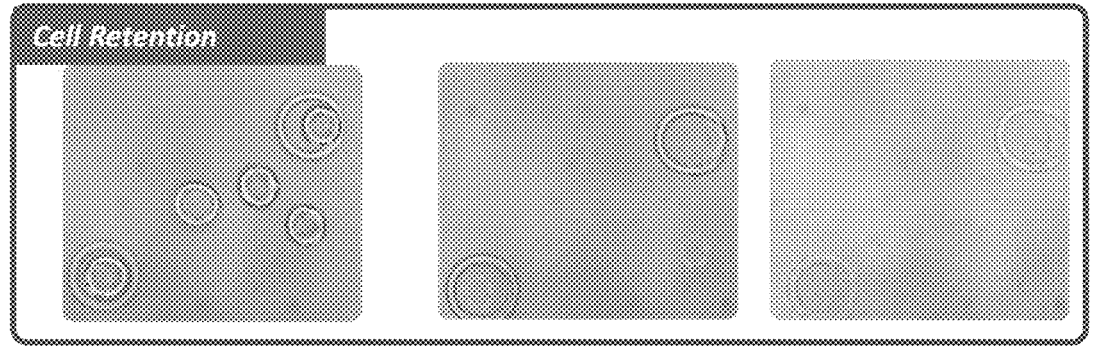
FIG. 26B illustrates selective retention of cells of interest and removal of cells that are not desired, according to some embodiments.

FIG. 26B illustrates selective retention of cells of interest and removal of cells that are not desired. Following the performance of various cell assays, the cells of interest, after a first round of encapsulation, can be retained by making a concentric ring hydrogel structure using a non-cleavable gel around the previously formed cleavable hydrogel matrix. The non-cleavable hydrogel precursor mix that contains monomer, non-cleavable cross-linker and photo-initiator may be loaded into the microfluidic channel containing hydrogel matrices. The specific pattern of UV light may be applied to form non-cleavable hydrogel rings on the selected hydrogel matrices. After washing away the non-cleavable hydrogel precursor mix, hydrogel cleaving reagents may be loaded to the microfluidic channel. This will result in the melting of the hydrogel matrix. The cells that did not get selected will not be compartmentalized and will instead be washed away. This will result in the cell retention for the cells of interest.

Example 8: Single-Cell Transcriptomic Workflow (Jurkat Cells)

Figure 27A:
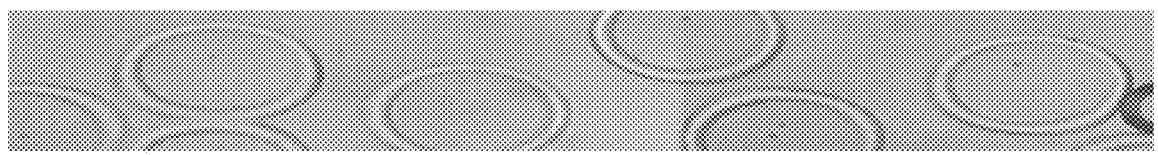
FIG. 27A shows hydrogel matrices inside a fluidic channel with a single cell inside each chamber, or CellCage™ structure, according to some embodiments.

Jurkat cells (immortalized line of human T lymphocyte cells) can be agitated gently in the cell-compatible buffer to avoid aggregation. The single-cell suspension can then be added into a hydrogel precursor mix that contains monomer, cleavable cross-linker and photo-initiator with cell-compatible buffer condition. The ratio of single-cell suspension and hydrogel precursor mix can be titrated until designed cell density is obtained. After loading single-cell hydrogel precursor mix to the microfluidic channel, the cells settle down to the bottom surface. A specific pattern of UV light may be applied to the channel to cross-link the hydrogel within the light path. As shown in FIG. 27A, a ring-shaped hydrogel matrix can be formed around each single cell. After patterning the hydrogel, the excess monomer and photo-initiator can then be washed away with cell-compatible buffer.

The top and/or bottom surface of a flow cell can be coated with an Oligo lawn consisting of poly-T mRNA capture oligos and surface amplification primers. A cell lysis buffer consisting of 200 mM Tris pH7.5, 20 mM EDTA, 2% sarcoyl, 6% Ficoll can be introduced into the channel and after lysis, the mRNA molecules released from the cell can be captured by the poly-T capture oligos on both top and bottom surface with mRNA poly-A tails hybridization. The hydrogel of the hydrogel matrix is designed to have pore size that prevents leaking of the mRNA outside the hydrogel matrix, so all of the mRNA molecules stay inside the hydrogel matrix until they are fully captured by the poly-T capture oligos. A hydrogel cleaving reagent is then loaded into the channel to dissolve the hydrogel without disturbing all mRNA molecules hybridized to the surface. The captured mRNA is converted to DNA library. A reverse transcription reagent (consisting of Maxima H+ reverse transcriptase in 1×RT buffer), template switch oligo, SUPERase-In RNase Inhibitor, and dNTPs can be loaded into the flow cell to synthesize the complementary cDNA from the mRNA molecules captured by the poly-T capture oligo anchored on the surface. The 2nd-strand cDNA is then synthesized, followed by a tagmentation reaction with a Tn5 transposase enzyme to fragment the cDNA & introduce the amplification primer to the 5'-end of the 2nd Stranded cDNA molecule. Only the anchored cDNA fragments corresponding to the 1st strand synthesized cDNA will be retained. At this step, all of the captured mRNA molecules on the surface will be converted to the cDNA library. After this, bridge amplification is performed using the surface amplification primers present on the surface in proximity to cDNA library molecules. The resulting clusters of each cDNA molecule on the surface are then sequenced using a sequencing by synthesis method to decode the sequence of single cell mRNA molecules within a compartment.

Figure 27B:
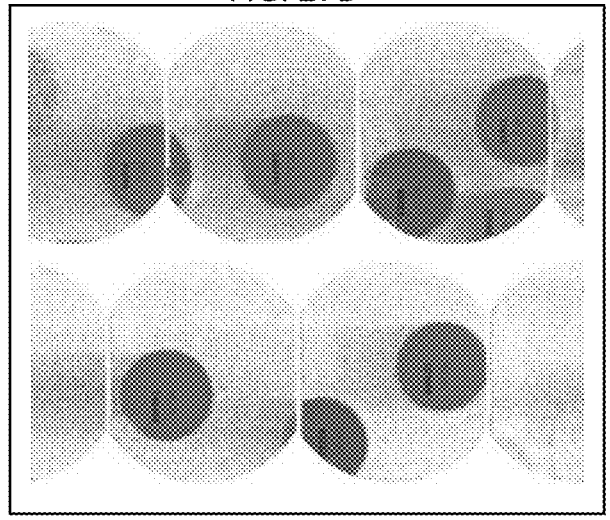
FIG. 27B is a spatial plot showing location of all the DNA clusters with sequences aligning to mRNA molecules from Jurkat cells, according to some embodiments.
Figure 27C:
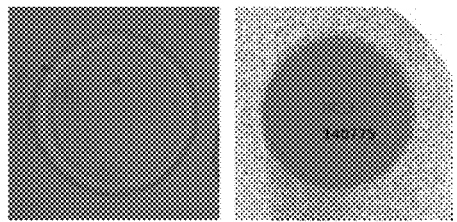
FIG. 27C shows a highlighted hydrogel matrix with a cell inside using a higher magnification image and a corresponding spatial plot of DNA sequences mapping to human mRNA, according to some embodiments.
Figure 27D:
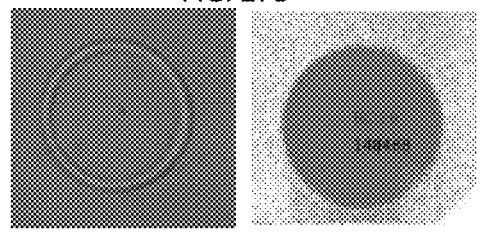
FIG. 27D shows a highlighted hydrogel matrix with a cell inside using a higher magnification image and a corresponding spatial plot of DNA sequences mapping to human mRNA, according to some embodiments.

FIG. 27A shows hydrogel matrices inside a fluidic channel with a single cell inside each hydrogel matrix. FIG. 27B is a spatial plot showing the location of DNA clusters with sequences aligning to mRNA molecules from Jurkat cells. Regions with a high density of mapped DNA clusters in the plot align with the location of hydrogel matrices, and mRNA reads within each such region corresponds to mRNA released from the single cell. The fastq files from sequencing can be mapped using STAR aligner to hg38 genome, and the x,y location of each aligned cluster within a tile is plotted to generate the spatial plot. All the DNA clusters within each hydrogel matrix is assigned a unique barcode corresponding to the identity cell that was present in it. The left panels of FIGS. 27C and 27D shows two highlighted hydrogel matrices with a cell inside each using a higher magnification image. The right panels of FIGS. 27C and 27D show the corresponding spatial plot of DNA sequences mapping to human mRNA.

Example 9: Single Cell mRNA (Jurkat and Mouse) Sequencing and Analysis

Figure 28A:
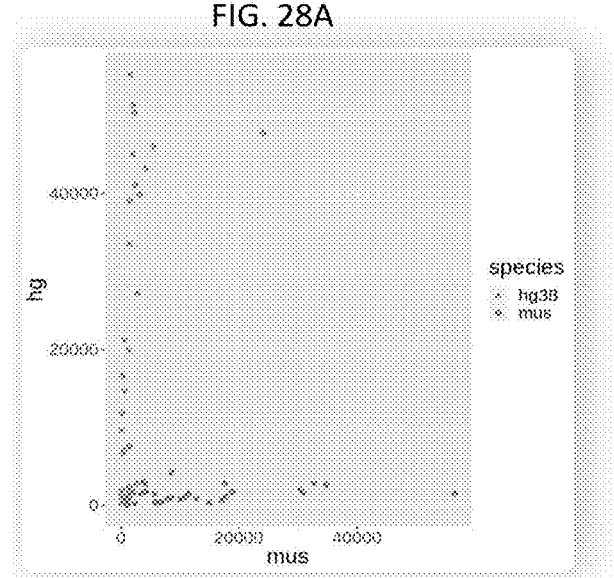
FIG. 28A is a scatterplot showing the number of reads uniquely mapping to the mouse and human genome within each hydrogel matrix, according to some embodiments.

The dataset in FIG. 28A corresponds to single cell mRNA sequencing using a mixture of human and mouse cells freshly obtained from cell cultures, according to some embodiments. Cells can be washed with 1×PBS-0.04% BSA-1% SUPERase-In. The concentration of cells can be adjusted using 1×PBS-0.04% BSA_1% SUPERase-In to have similar cell count to respect to each cell population and to have a single cell per hydrogel matrix. An equal mixture of human and mouse cells is added into the hydrogel precursor mix and encapsulated to achieve one cell per hydrogel matrix. Then, the cell can be lysed using a cell lysis buffer consisting of 200 mM Tris pH7.5.20 mM EDTA, 2% sarcoyl, and 6% Ficoll. Subsequently, after cDNA synthesis and tagmentation of the cDNA molecule, the resulting DNA library can be amplified using bridge amplification, and the DNA library can be sequenced.

Figure 28B:
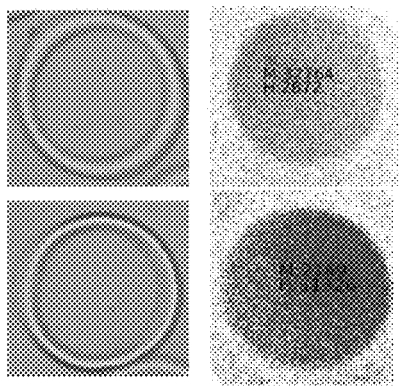
FIG. 28B shows spatial plots of DNA sequences mapping to human and mouse mRNA, according to some embodiments.

The fastq files from sequencing data can be mapped to a combined human and mouse genome and aligned using STAR aligner. The reads mapping uniquely to human or mouse genome can be extracted, and the location of the mapped reads within a tile can be plotted to obtain spatial plots of reads location. High density regions of mapped regions corresponding to hydrogel matrices are assigned a barcode. The number of reads uniquely mapping to mouse and human genome within each hydrogel matrix is calculated and plotted in the scatterplot shown in FIG. 28A. Each point in the scatterplot corresponds to a hydrogel matrix barcode and shows the number of reads mapping uniquely to human or mouse genome. The majority of reads are primarily from human or mouse genome, indicating single cell capture within each hydrogel matrix. FIG. 28B shows the corresponding spatial plots of DNA sequences mapping to human and mouse mRNA.

Example 10: Single Cell Surface Protein Workflow

Figure 29A:
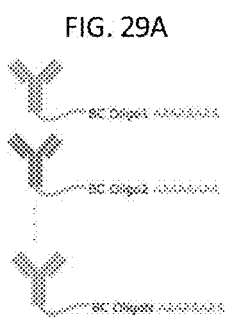
FIG. 29A shows antibody labels flanked with an oligo sequence, a barcode, and a polyA tail, according to some embodiments.

Frozen PBMC (peripheral blood mononuclear cells) cells, which can be freshly obtained or previously fixed, can be thawed gently in a waterbath at 37° C. Cells can be diluted further in RPMI medium to wash away dimethyl sulfoxide or any other solvents. Then, the PBMC can be washed and resuspended in appropriate buffer. The PBMC can first be incubated in blocking solution to reduce nonspecific binding, then the cells can be labelled with a proper antibody panel (each antibody is flanked with an oligo sequence with barcode and polyA tail, as shown in FIG. 29A) in tube. After the labelling step, cells can be washed well to get rid of excess antibodies and filtered to remove aggregations. The cell concentration is adjusted for cage array, so there is one cell per cage. Labeled cells can be added into a hydrogel precursor mix that contains monomer, cleavable cross-linker and photo-initiator with cell-compatible buffer condition. The cells can be loaded into the flowcell along with the hydrogel precursor mix and encapsulated to achieve one cell per hydrogel matrix. Cells are lysed with lysis buffer, and labelled cell surface proteins are released in the hydrogel matrix.

The top and bottom surfaces of the hydrogel matrix can have a dense lawn of poly-T mRNA capture oligos that capture the polyA tails of antibody-cell surface protein complexes. The hydrogel of the hydrogel matrix can be designed to have a pore size that prevents leaking of the antibody-labelled cell proteins outside the hydrogel matrix, so all of the labelled cell surface proteins stay inside the hydrogel matrix until they are fully captured by the surfaces. The hydrogel cleaving reagent can then be loaded to the channel to dissolve the hydrogel without disturbing labelled and captured protein molecules from the top and bottom surfaces. Then captured oligo sequence can be copied on the surface using an extension mix consisting of DNA polymerase and dNTP. After copying, the original molecules can be washed away with 0.1 N NaOH to retain a surface bound single stranded molecule. After bridge amplification using the surface amplification primers surrounding the copied molecule, a cluster of each captured oligo can be formed, and the surface is ready for sequencing to decode the content of cell surface protein.

Figure 29B:
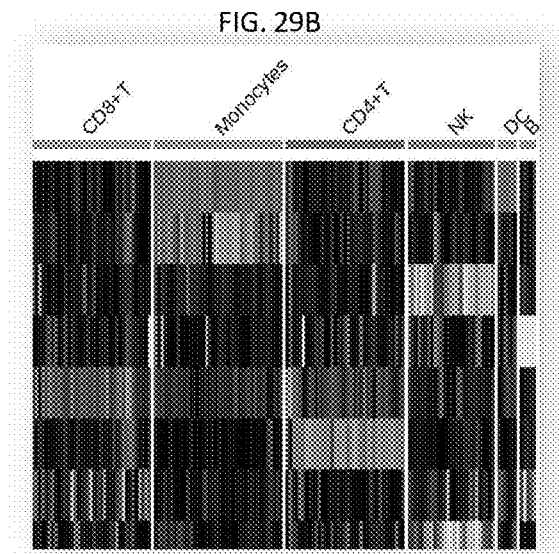
FIG. 29B shows the relative expression of various surface proteins detected after sequencing antibody barcode oligos captured after lysing cells inside a hydrogel matrix, according to some embodiments.

FIG. 29B shows the relative expression of various surface proteins detected after sequencing the antibody barcode oligos captured after lysing cells inside the hydrogel hydrogel matrix. The cells are classified into various cell types (CD8+ T cells, monocytes, CD4+ T cells, NK cells, DC cells, and B cells) based on the relative expression of these antibodies on the cell surface.

Figure 29C:
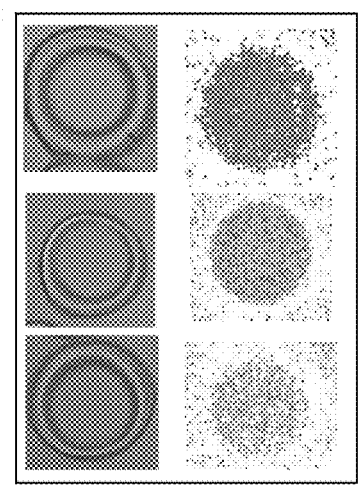
FIG. 29C shows representative cells inside cell cages and spatial plots of barcode sequence, color coded by the identity of the barcode sequence, illustrating abundance of various antibodies inside each hydrogel matrix after cell lysis, according to some embodiments.

FIG. 29C shows the representative cells inside cell cages and spatial plots of barcode sequence, color coded by the identity of the barcode sequence, illustrating abundance of various antibodies inside each hydrogel matrix after cell lysis.

Example 11: CHO Cell Secretion and mRNA Workflow

Figure 30A:
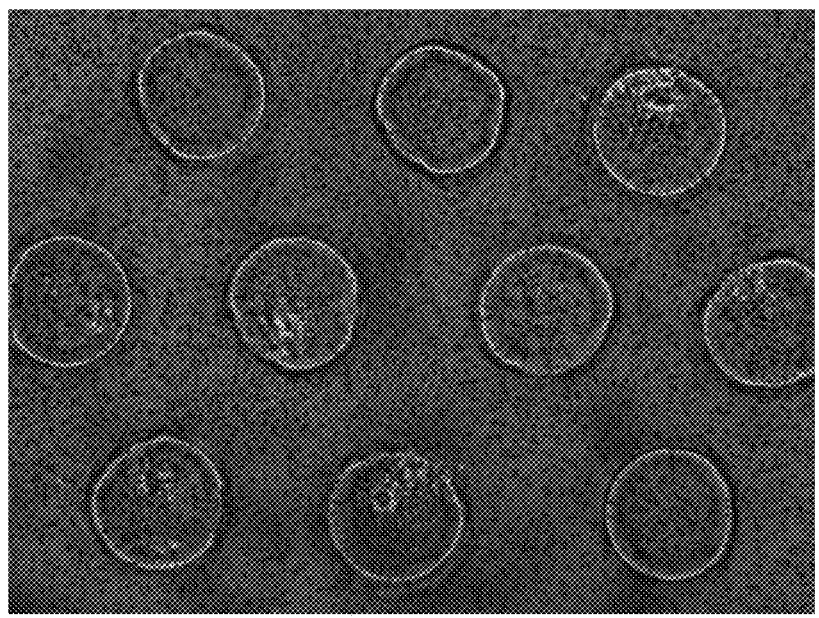
FIG. 30A shows the fluorescent signals given off from streptavidin beads that have captured IgG molecules secreted from CHO DP-12 cells, according to some embodiments.
Figure 30B:
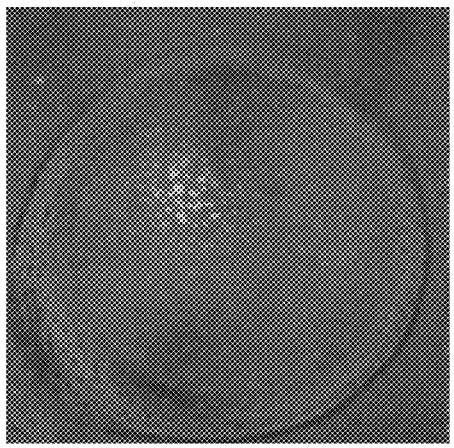
FIG. 30B shows the fluorescent signal given off from streptavidin beads that have captured IgG molecules secreted from one CHO DP-12 cell captured in a hydrogel matrix, according to some embodiments.
Figure 30C:
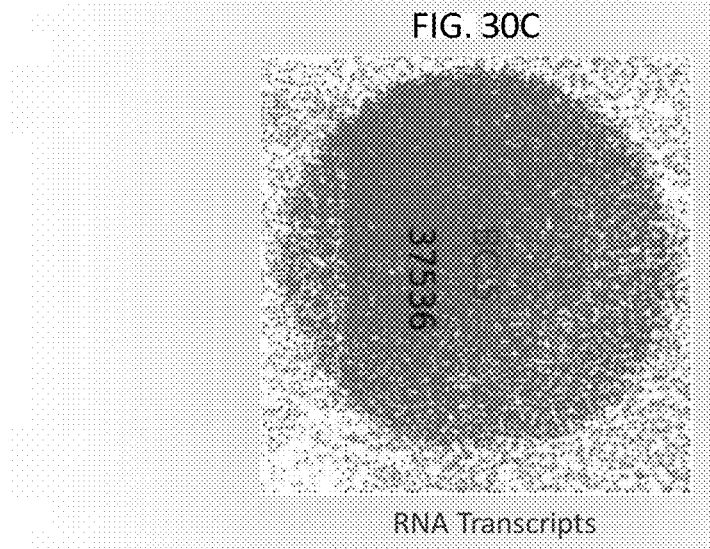
FIG. 30C shows a spatial plot of RNA sequences mapping to the CHO DP-12 cell captured in the hydrogel matrix of FIG. 30B, according to some embodiments.

The hydrogel matrix can be used for single-cell secretion protein detection since it provides an enclosed and static environment for each single cell. To analyze the IgG molecules produced and secreted from each single CHO DP-12 cell, detection beads (3 um-diameter streptavidin beads carrying the biotinylated Antibody for IgG binding) and cell capture beads (3 um-diameter streptavidin beads carrying the fibronectin molecules) can be first immobilized on the surface of the microfluidic device with amplification and poly-T mRNA capturing oligos. CHO DP-12 cells can then be loaded into the microfluidic device and immobilized by the fibronectin coated beads. Specific cell culture media for CHO DP-12 cells can then then loaded into the microfluidic device and then incubated at 37° C. for about 2-4 hours. Each CHO DP-12 cell will secrete IgG molecules, which can be collected by IgG antibodies on the 3-um streptavidin beads adjacent to the cell. After incubation, the secondary detection antibody for IgG with fluorescent dye can be loaded to the microfluidic channel. The 3-um streptavidin beads that have captured the IgG molecules secreted from the CHO DP-12 cells will light up in the fluorescent emission images, as shown in FIG. 30A. The fluorescent signal can then be used to determine the IgG secretion level for each single CHO DP-12 cell.

Following the IgG detection process, the single CHO-cell mRNA can be directly sequenced in the same hydrogel matrix. A cell lysis buffer can be introduced into the channel. After the cell is lysed, the mRNA molecules released from the cell can be captured by the poly-T capture oligos on both the top and bottom surfaces via mRNA poly-A tails hybridization. The hydrogel of the hydrogel matrix can be designed to have pore size that prevents the mRNA from leaking outside of the hydrogel matrix, so all the mRNA molecules stay inside the hydrogel matrix until they are fully captured by the poly-T capture oligos on the top and bottom surfaces. The hydrogel cleaving reagent can then be loaded into the channel to dissolve the hydrogel without disturbing all the mRNA molecules hybridized to the surface. The captured mRNA can be converted to a DNA library. A reverse transcription reagent consisting of Maxima H+ reverse transcriptase in 1× buffer can be loaded into the flow cell to synthesize the complementary cDNA from the mRNA molecules captured by the poly-T capture oligo anchored on the surface. The 2nd-strand cDNA can then be synthesized. Next, Tn-5 tagmentation can fragment the cDNA and introduce the amplification primer to the 3'-end of the 1st Stranded cDNA molecule. Only the anchored cDNA fragments (close to 3' end of the original mRNA molecule) will be retained. At this step, all of the captured mRNA molecules on the surface will be converted to the cDNA library. After this, bridge amplification can be performed using the surface amplification primers present on the surface in proximity to cDNA library molecules. The resulting clusters of each cDNA molecule on the surface can then be sequenced using a sequencing by synthesis method to decode the sequence of single cell mRNA molecules within a compartment.

Example 12: IL-2 Secretion and mRNA Workflow

IL2-secreting cells obtained from cell culture can be counted, and then the concentration can be adjusted to 1-2M cells per 1 mL in cell culture medium. 2 ul of Cell Activation Cocktail from BioLegend (without Brefeldin A) per 1 mL can be added to the cell culture, and the cell culture flask is placed in a 37° C. incubator for 3-4 hours to stimulate cells to secrete IL-2. The stimulated cells can then be washed with 1×PBS-0.04% BSA and mixed with hydrogel precursor mix to form hydrogel matrices. After cell encapsulation, cells can be washed and incubated further in a cell culture medium with Cell Activation Cocktail (2 uL of cocktail in 1 mL of cell culture medium).

An IL-2 bead-based ELISA kit can be obtained from a provider like BioLegend Inc. The bead, containing IL-2 capture antibodies, can be loaded to the microfluidic channel in PH 6.1 MES buffer to allow immobilization of the bead via surface static charges. The microfluidic channel can then be washed with 1×PBS buffer. The APTES in 1×PBS solution (0.25%) can then be loaded into the microfluidic channel to create a positively charged surface for the following cell immobilization. Stimulated Jurkat E6.1 cells in specific cell culture media containing the IL-2 stimulation chemicals for Jurkat E6.1 cells can then be loaded into the microfluidic device followed by 37° C. incubation for 4 hours. Each Jurkat E6.1 cell inside the hydrogel matrix will start to secrete IL-2 molecules, which will be collected by the IL-2 capture antibodies on the BioLegend ELISA beads adjacent to the cell. After incubation, the secondary detection antibody for IL-2 labeled with biotin can be loaded to the microfluidic channel. The ELISA beads that have captured the IL-2 molecules secreted form the Jurkat cells will light up in the fluorescent emission images after incubation of streptavidin fluorescent dyes. The fluorescent signal can be used to determine the IL-2 secretion level for each single cell.

Following the IL-2 detection process, the single Jurkat-cell mRNA can be directly sequenced in the same microfluidic channel. Hydrogel precursor mix that contains monomer, cleavable cross-linker and photo-initiator with cell-compatible buffer condition can be loaded to the microfluidic channel. A specific pattern of UV light can be applied to the channel to cross-link the hydrogel within the light path. A ring-shaped hydrogel can be formed around each single cell. The hydrogel functions as a hydrogel matrix. A cell lysis buffer can be introduced into the channel, and after lysis, the mRNA molecules released from the cell can be captured by the poly-T capture oligos on both top and bottom surfaces via mRNA poly-A tails hybridization. The hydrogel of the hydrogel matrix can be designed to have pore size that prevents the mRNA from leaking outside of the hydrogel matrix, so all of the mRNA molecules remain inside the hydrogel matrix until they are fully captured by the surfaces. The hydrogel cleaving reagent can then be loaded into the channel to dissolve the hydrogel without disturbing all mRNA molecules hybridized to the surface.

The captured mRNA is converted to DNA library. A reverse transcription reagent consisting of Maxima H+ reverse transcriptase in 1× buffer can be loaded into the flowcell to synthesize the complementary cDNA from the mRNA molecules captured by the poly-T capture oligo anchored on the surface. The 2nd-strand cDNA can then be synthesized. Next, Tn-5 tagmentation can fragment the cDNA and introduce the amplification primer to the 3'-end of the 1st Stranded cDNA molecule. Only the anchored cDNA fragments (close to 3' end of the original mRNA molecule) will be retained. At this step, all of the captured mRNA molecules on the surface will be converted to the cDNA library. After this, bridge amplification can be performed using the surface amplification primers present on the surface in proximity to cDNA library molecules. The resulting clusters of each cDNA molecule on the surface can then be sequenced using a sequencing by synthesis method to decode the sequence of single cell mRNA molecules within a compartment.

Figure 31A:
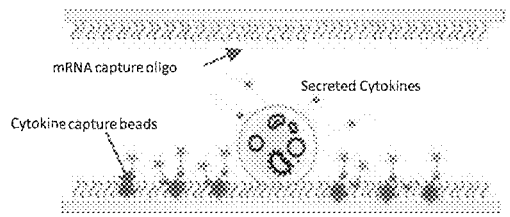
FIG. 31A shows a schematic illustration of a microfluidic device containing cytokine capture beads and mRNA capture oligos, according to some embodiments.
Figure 31B:
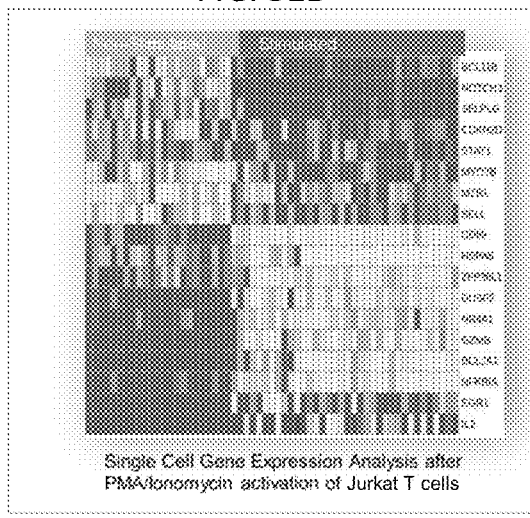
FIG. 31B shows the gene expression analysis of non-stimulated & stimulated Jurkat cells, according to some embodiments.
Figure 31C:
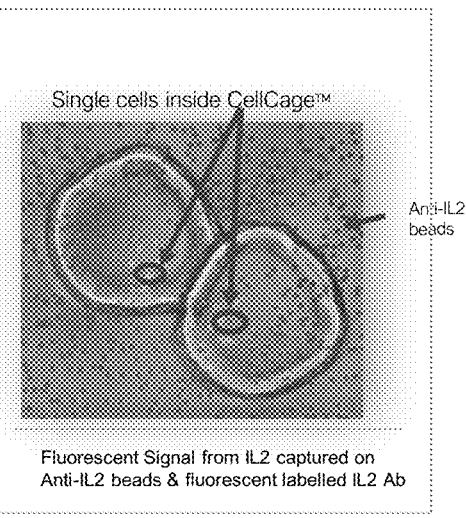
FIG. 31C shows the fluorescent signal from two hydrogel matrices, each containing a single IL-2 secreting cell, according to some embodiments.

FIG. 31B shows the gene expression analysis of non-stimulated & stimulated Jurkat cells. Upon stimulation, several of the key marker genes such as CD69, GZMB, NFKB1A, DUSP2 are upregulated and several genes such as BCL11B, NOTCH3, MYO7B are downregulated. A fraction of the stimulated cells secrete IL2. FIG. 31C shows the hydrogel matrices corresponding to IL-2 secreting cells using the secreted protein quantification based on ELISA as well as hydrogel matrices with mRNA reads mapping to IL2.

Example 13: CHO Cell Culture in Dextran Chamber

Figure 32:
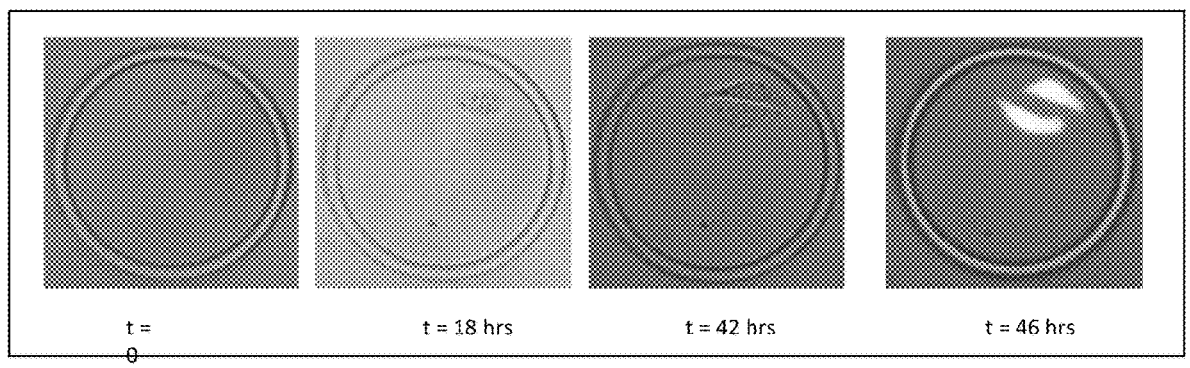
FIG. 32 shows images of a hydrogel matrix being used to culture a CHO cell at 0 hours, 18 hours, 42 hours, and 46 hours, according to some embodiments.

A hydrogel matrix can be used for cell culture if a cell-compatible hydrogel wall material is applied and there is a proper bottom surface for cell attachment. To culture CHO cells in a hydrogel matrix, a poly-L-lysine substrate can be used for microfluidic channel construction (poly-L-lysine is a positive charged layer widely used for CHO cell culture). The CHO cells can be loaded to the microfluidic channel in hydrogel precursor mix that contains monomer (dextran), cleavable cross-linker and photo-initiator with cell-compatible buffer condition. After the hydrogel matrices are patterned with UV light, the CHO cell culture media can be loaded into the microfluidic channel. The hydrogel matrix device can then be incubated at 37° C. FIG. 32 shows images of the CHO cell culture at 0 hours, 18 hours, 42 hours, and 46 hours. Fresh cell culture media was reloaded every 24 hours.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method, comprising:
   (a) introducing a plurality of cells into a fluidic device, wherein the fluidic device comprises a surface comprising one or more capture elements, and wherein a cell of the plurality of cells couples to a capture element of the one or more capture elements;
   (b) introducing one or more polymer precursors into the fluidic device; and
   (c) selectively applying light to the fluidic device to polymerize the one or more polymer precursors, thereby selectively encapsulating the cell of the plurality of cells in the fluidic device.

2. The method of claim 1, wherein the capture element comprises a physical trap.

3. The method of claim 1, wherein the capture element comprises one or more functional groups capable of interacting with the cell.

4. The method of claim 3, wherein the one or more functional groups comprise fibronectin.

5. The method of claim 3, wherein the one or more functional groups comprise arginylglycylaspartic acid (RGD) peptides.

6. The method of claim 3, wherein the one or more functional groups comprise antibodies.

7. The method of claim 1, wherein in (c), the cell is encapsulated within a chamber comprising one or more polymer matrix walls.

8. The method of claim 7, wherein the one or more polymer matrix walls extend from the surface to an additional surface opposite of the surface, thereby forming an interior of the chamber, wherein the interior of the chamber comprises the cell.

9. The method of claim 1, wherein the one or more polymer precursors comprise (i) one or more cleavable crosslinkers and (ii) a photo-initiator.

10. The method of claim 7, wherein the chamber has an annular-like cross section.

11. The method of claim 1, wherein the fluidic device further comprises one or more capture oligonucleotides configured to capture one or more analytes released from the cell.

12. The method of claim 11, wherein the one or more analytes comprise messenger ribonucleic acids (RNAs), and wherein the method further comprises capturing the messenger RNAs at the one or more capture oligonucleotides.

13. The method of claim 12, further comprising loading the fluidic device with reverse transcriptase reagents to copy the captured messenger RNAs to produce complementary deoxyribonucleic acids (DNAs).

14. The method of claim 11, wherein the one or more capture oligonucleotides are located on the surface of the fluidic device.

15. The method of claim 11, wherein the one or more capture oligonucleotides are located on an additional surface of the fluidic device, wherein the additional surface of the fluidic device is located opposite of the surface.

16. The method of claim 11, wherein the one or more capture oligonucleotides each comprise a barcode which indicates a position thereof within the fluidic device.

17. The method of claim 1, wherein the fluidic device further comprises one or more antibodies configured to capture one or more proteins secreted from the cell.

18. The method of claim 17, wherein the one or more proteins secreted from the cell comprise cytokines.

19. The method of claim 18, wherein the one or more antibodies are located on one or more cytokine capture beads.

20. The method of claim 19, wherein the fluidic device further comprises an additional surface opposite of the surface, and wherein the additional surface comprises one or more capture oligonucleotides configured to capture messenger ribonucleic acids (RNAs) released from the cell.

21. The method of claim 1, wherein the one or more capture elements are disposed in a pattern on the surface.

22. The method of claim 1, wherein the fluidic device comprises a flow channel, and wherein the surface is a bottom surface of the flow channel.

23. The method of claim 22, wherein the flow channel further comprises a top surface opposite of the bottom surface, and wherein the top surface comprises one or more capture oligonucleotides configured to capture one or more analytes released from the cell.

24. The method of claim 23, wherein the one or more analytes comprise messenger ribonucleic acids (RNAs), and wherein the method further comprises capturing the messenger RNAs at the one or more capture oligonucleotides.

25. The method of claim 24, further comprising loading the fluidic device with reverse transcriptase reagents to copy the captured messenger RNAs to produce complementary deoxyribonucleic acids (DNAs).

26. The method of claim 25, further comprising sequencing the complementary DNAs.

27. The method of claim 1, wherein the surface is planar.

28. The method of claim 1, wherein the one or more capture elements are immobilized on the surface.

* * * * *